(12) United States Patent
Razavi et al.

(10) Patent No.: US 12,186,594 B2
(45) Date of Patent: Jan. 7, 2025

(54) PULSED FOCUSED ULTRASOUND THERAPY FOR TREATMENT OF PANCREATIC DISORDERS

(71) Applicant: The Board of Trustees of the Leland Stanford Junior University, Stanford, CA (US)

(72) Inventors: Mehdi Razavi, Palo Alto, CA (US); Jeremy Dahl, Palo Alto, CA (US); Avnesh S. Thakor, Palo Alto, CA (US)

(73) Assignee: THE BOARD OF TRUSTEES OF THE LELAND STANFORD JUNIOR UNIVERSITY, Stanford, CA (US)

(*) Notice: Subject to any disclaimer, the term of this patent is extended or adjusted under 35 U.S.C. 154(b) by 380 days.

(21) Appl. No.: 17/601,194

(22) PCT Filed: Apr. 9, 2020

(86) PCT No.: PCT/US2020/027423
§ 371 (c)(1),
(2) Date: Oct. 4, 2021

(87) PCT Pub. No.: WO2020/210458
PCT Pub. Date: Oct. 15, 2020

(65) Prior Publication Data
US 2022/0331611 A1    Oct. 20, 2022

Related U.S. Application Data

(60) Provisional application No. 62/833,458, filed on Apr. 12, 2019.

(51) Int. Cl.
*A61N 7/00*    (2006.01)
*A61K 9/00*    (2006.01)
(Continued)

(52) U.S. Cl.
CPC .............. *A61N 7/00* (2013.01); *A61K 9/0009* (2013.01); *A61K 35/28* (2013.01); *A61K 35/39* (2013.01);
(Continued)

(58) Field of Classification Search
None
See application file for complete search history.

(56) References Cited

U.S. PATENT DOCUMENTS

2007/0142753 A1* 6/2007 Warlick .................. A61N 7/00
                                                       601/2
2011/0178441 A1* 7/2011 Tyler ..................... A61B 5/369
                                                       601/2
(Continued)

FOREIGN PATENT DOCUMENTS

WO    2015017772 A1    2/2015
WO    2018083700 A1    5/2015

OTHER PUBLICATIONS

Wajchenberg, "β-Cell Failure in Diabetes and Preservation by Clinical Treatment" Endocrine Reviews 28(2): 187-218 Apr. 2007 (Year: 2007).*

(Continued)

*Primary Examiner* — Colin T. Sakamoto
(74) *Attorney, Agent, or Firm* — MARSHALL, GERSTEIN & BORUN LLP

(57) ABSTRACT

Methods of using pulsed focused ultrasound (pFUS) therapy to treat pancreatic disorders such as type 1 diabetes, pancreatitis, and pancreatic cancer are provided. The methods utilize pulsed focused ultrasound (pFUS) therapy either by itself or in combination with islet transplantation and/or stem cell therapy to promote regeneration of damaged pancreatic tissue, increase insulin secretion in response to glucose, or improve engraftment and revascularization of transplanted islets or beta cells. Additionally, methods of (Continued)

using pFUS are provided for modulating paracrine secretion in the pancreas, islets, beta cells, or stem cells, or at a transplantation site to therapeutically alter levels of various factors including, without limitation, cytokines, growth factors, angiogenic factors, and cell adhesion molecules.

14 Claims, 70 Drawing Sheets

(51) Int. Cl.
| | |
|---|---|
| A61K 35/28 | (2015.01) |
| A61K 35/39 | (2015.01) |
| A61P 3/10 | (2006.01) |
| C12N 5/00 | (2006.01) |
| C12N 5/071 | (2010.01) |
| C12N 5/0775 | (2010.01) |
| C12N 13/00 | (2006.01) |
| A61K 35/12 | (2015.01) |

(52) U.S. Cl.
CPC .............. *A61P 3/10* (2018.01); *C12N 5/0012* (2013.01); *C12N 5/0667* (2013.01); *C12N 5/0676* (2013.01); *C12N 13/00* (2013.01); A61K 2035/124 (2013.01); A61N 2007/0004 (2013.01)

(56) References Cited

U.S. PATENT DOCUMENTS

| | | | |
|---|---|---|---|
| 2011/0182979 A1 | 7/2011 | Shimoda et al. | |
| 2015/0025422 A1 | 1/2015 | Tyler | |
| 2015/0313961 A1* | 11/2015 | Thurmond | C07K 14/47 604/501 |
| 2016/0236012 A1 | 8/2016 | Zderic et al. | |

OTHER PUBLICATIONS

Burks et al. (2011) "Investigation of Cellular and Molecular Responses to Pulsed Focused Ultrasound in a Mouse Model" PLoS One 6(9):e24730 (pp. 1-10).
Burks et al. (2013) Noninvasive pulsed focused ultrasound allows spatiotemporal control of targeted homing for multiple stem cell types in murine skeletal muscle and the magnitude of cell homing can be increased through repeated applications. Stem Cells 31:2551-2560.
Burks et al. (2015) Pulsed focused ultrasound pretreatment improves mesenchymal stromal cell efficacy in preventing and rescuing established acute kidney injury in mice. Stem Cells 33:1241-1253.
Strand et al. (2017) Current and future perspectives on alginate encapsulated pancreatic islet. Stem Cells Translational Medicine 6:1053-1058.
Kerby et al. (2013) Co-transplantation of islets with mesenchymal stem cells in microcapsules demonstrates graft outcome can be improved in an isolated-graft model of islet transplantation in mice. Cytotherapy 15:192-200.
Cavallari et al. (2012) Mesenchymal stem cells and islet cotransplantation in diabetic rats: improved islet graft revascularization and function by human adipose tissue-derived stem cells preconditioned with natural molecules. Cell Transplant 21:2771-2781.
Rackham et al. (2014) Preculturing islets with adipose-derived mesenchymal stromal cells is an effective strategy for improving transplantation efficiency at the clinically preferred intraportal site. Cell medicine 7:37-47.

Ludwig et al. (2012) Improvement of islet function in a bioartificial pancreas by enhanced oxygen supply and growth hormone releasing hormone agonist. Proc. Natl. Acad. Sci. 109:5022-5027.
Castellanos et al. (2017) Calcium-dependent ultrasound stimulation of secretory events from pancreatic beta cells. J. Ther. Ultrasound 5:30.
Arzouni et al. (2018) Using Mesenchymal Stromal Cells in Islet Transplantation. Stem Cells Transl Med 7(8):559-563.
Szot et al. (2007) Transplantation of Pancreatic Islets Into the Kidney Capsule of Diabetic Mice. J Vis Exp (9):404.
Ito et al. (2010) Mesenchymal stem cell and islet co-transplantation promotes graft revascularization and function. Transplantation 89:1438-1445.
Castellanos et al. (2017) Ultrasound Stimulation of Insulin Release from Pancreatic Beta Cells as a Potential Novel Treatment for Type 2 Diabetes. Ultrasound Med. Biol. 43:1210-1222.
Razavi et al. (2019) improving the function and engraftment of transplanted pancreatic islets using pulsed focused Ultrasound therapy. Sci Rep 9(1):13416.
Berman et al. (2010) Mesenchymal stem cells enhance allogeneic islet engraftment in nonhuman primates. Diabetes 59:2558-2568.
Ryan et al. (2001) Clinical outcomes and insulin secretion after islet transplantation with the Edmonton protocol. Diabetes 50:710-719.
Park et al. (2010) Trophic molecules derived from human mesenchymal stem cells enhance survival, function, and angiogenesis of isolated islets after transplantation. Transplantation 89:509-517.
Watt et al. (2013) The angiogenic properties of mesenchymal stem/stromal cells and their therapeutic potential. Br Med Bull 108:25-53.
Tuch et al. (2009) Safety and viability of microencapsulated human islets transplanted into diabetic humans. Diabetes Care 32:1887-1889.
Tao et al. (2016) Proangiogenic Features of Mesenchymal Stem Cells and Their Therapeutic Applications. Stem Cells Int 2016:1314709.
Yeung et al. (2012) Human mesenchymal stem cells protect human islets from pro-inflammatory cytokines. PLoS One 7:e38189.
Schive et al. (2017) Human adipose-derived mesenchymal stem cells respond to short-term hypoxia by secreting factors beneficial for human islets in vitro and potentiate antidiabetic effect in vivo. Cell medicine 9:103-116.
Barnett et al. (2007) Magnetic resonance-guided, real-time targeted delivery and imaging of magnetocapsules Immunoprotecting pancreatic islet cells. Nature medicine 13:986-991.
Ren et al. (2019) Adipose tissue-derived mesenchymal stem cells rescue the function of islets transplanted in sub-therapeutic numbers via their angiogenic properties. Cell and tissue research 376:353-364.
Ohmura et al. (2010) Combined transplantation of pancreatic islets and adipose tissue-derived stem cells enhances the survival and insulin function of islet grafts in diabetic mice. Transplantation 90:1366-1373.
Wang et al. (2018) Autologous Mesenchymal Stem Cell and Islet Cotransplantation: Safety and Efficacy. Stem Cells Transl Med 7:11-19.
Villa et al. (2017) Effects of composition of alginate-polyethylene glycol microcapsules and transplant site on encapsulated islet graft outcomes in mice. Transplantation 101:1025.
Del Burgo et al. (2018) 3D Printed porous polyamide macrocapsule combined with alginate microcapsules for safer cell-based therapies. Scientific Reports 8:8512.
Qi (2014) Transplantation of encapsulated pancreatic islets as a treatment for patients with type 1 diabetes mellitus. Adv Med 2014:429710.
Duprez et al. (2011) Preparatory studies of composite mesenchymal stem cell islets for application in intraportal islet transplantation. Ups J Med Sci 116(1):8-17.

* cited by examiner

Schematic

Photo

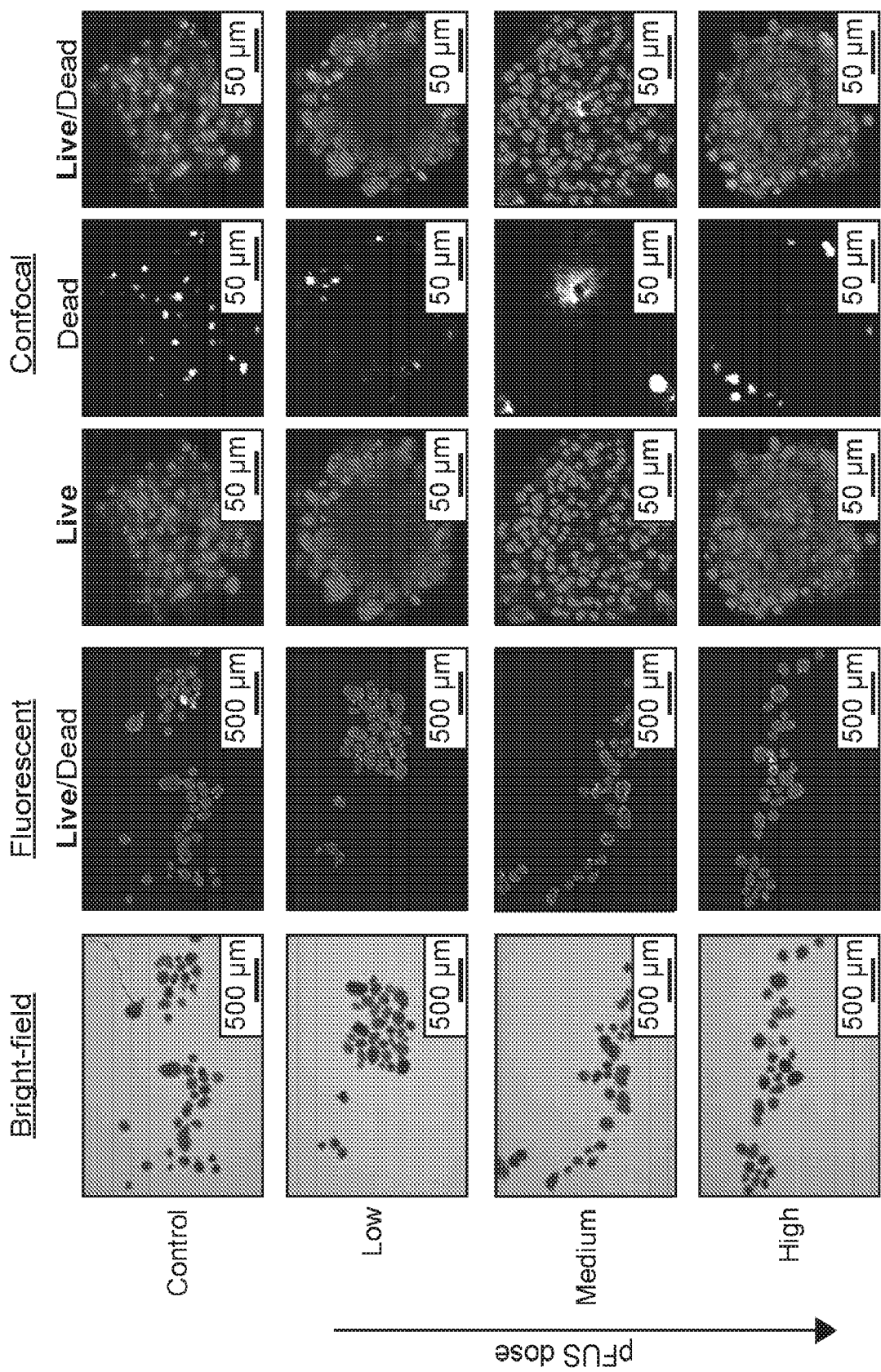

pFUS treatment on the kidney transplanted with islets

Transplated Kidney with islets at the time of sacrifice

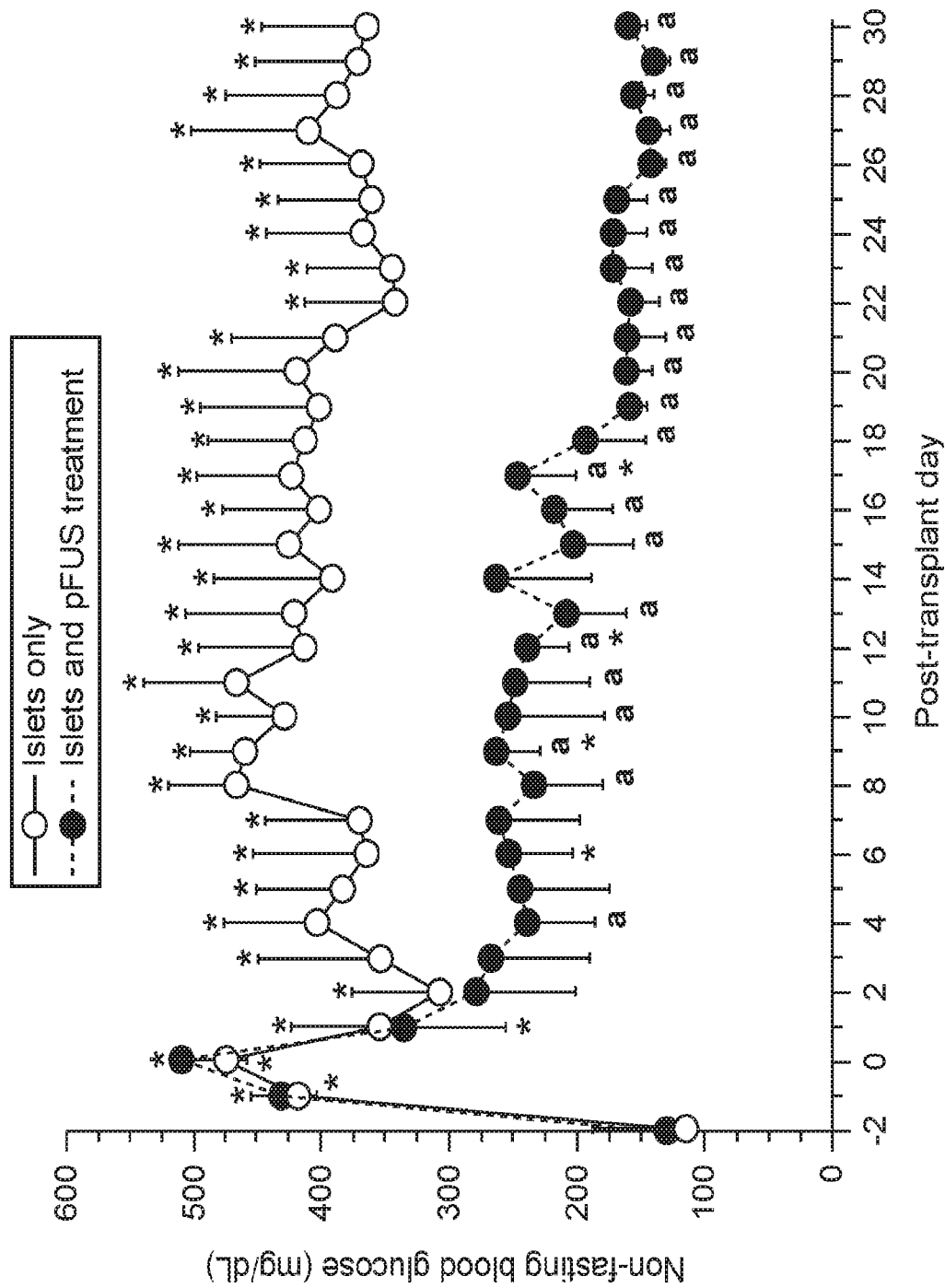

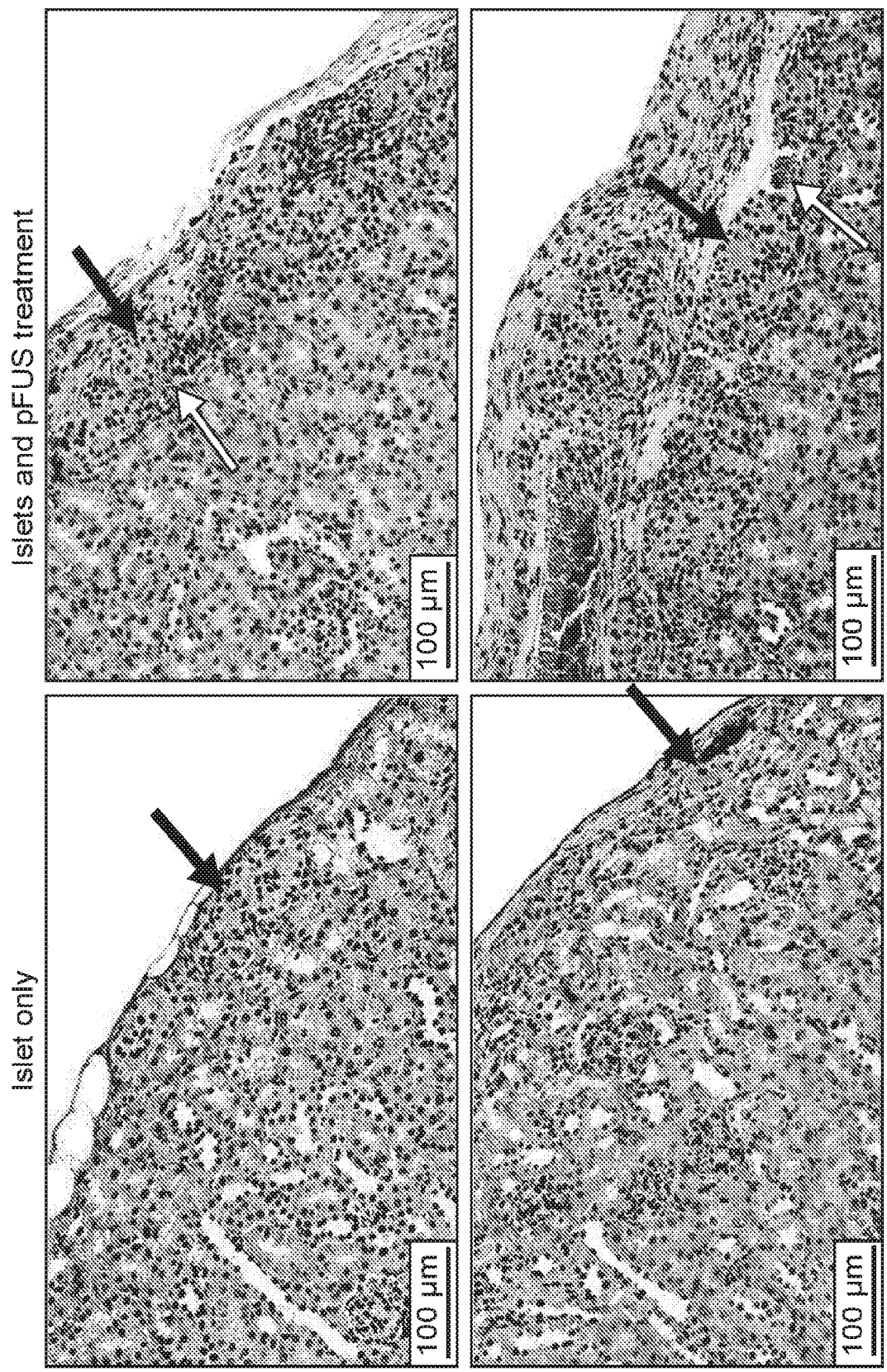

| Cell Viability | pFUS Stimulation | |
|---|---|---|
| (Relative to Control) | High Dose | Low Dose |
| BM-MSC | 1.02±1.05 | 1.01±1.00 |
| AD-MSC | 0.90±0.77 | 0.855±1.13 |
| UC-MSC | 0.91±1.02 | 0.96±0.61 |

Alginate capsule

Encapsulated islet

Islet

AD-MSCs

Islet coated with AD-MSCs

Encapsulated islet coated with AD-MSCs and pFUS treated
Alginate capsule
100 μm

Encapsulated islet coated with AD-MSCs and pFUS treated
100 μm

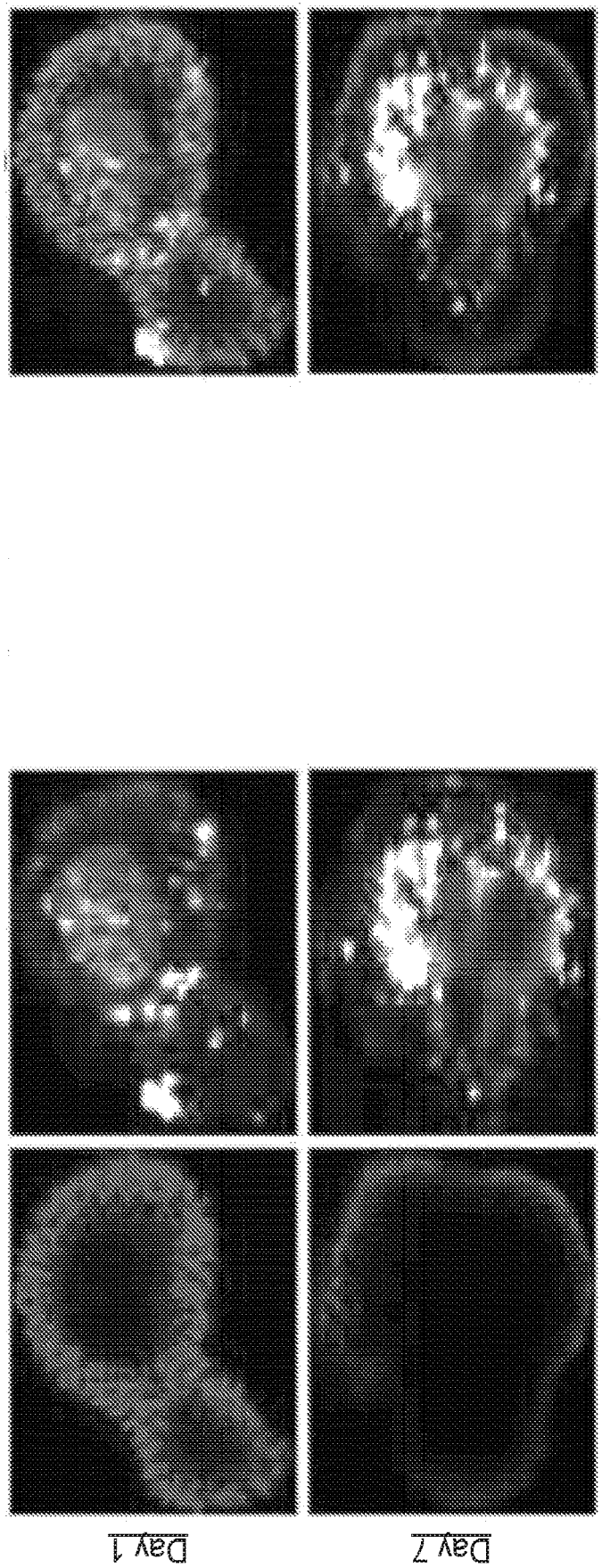

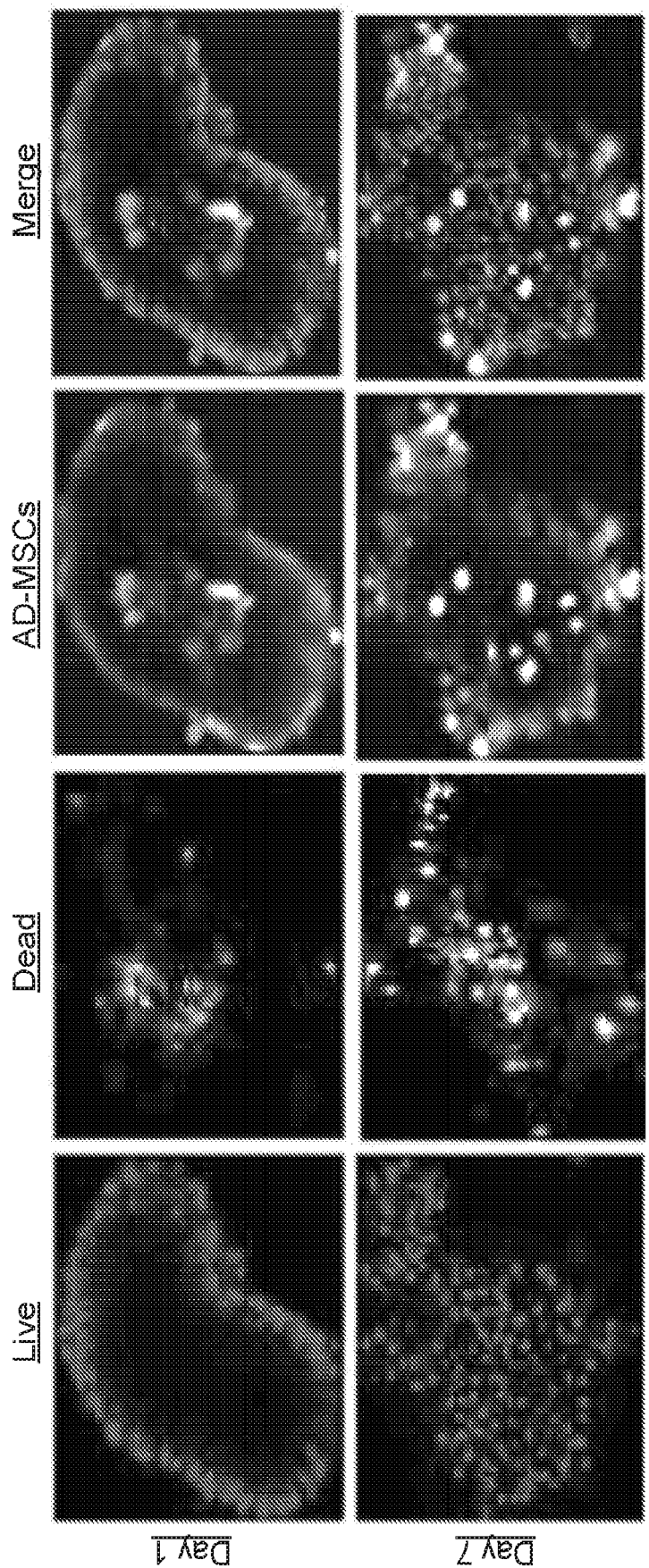

Confocal images
Step 2: Encapsulation of Islets Coated with AD-MSCs

Confocal images
Step 3: pFUS Treatment on Encapsulated Islets Coated with AD-MSCs

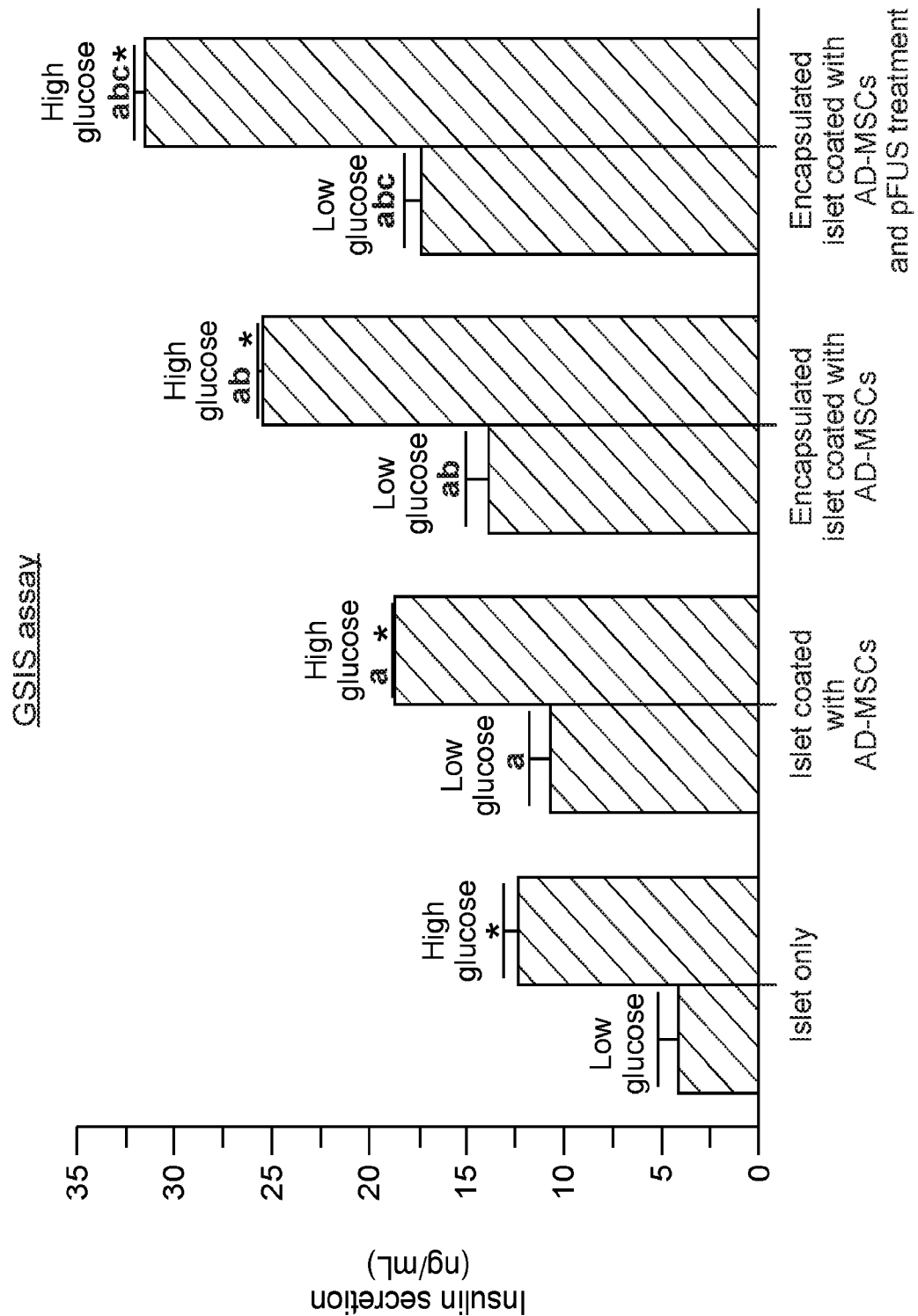

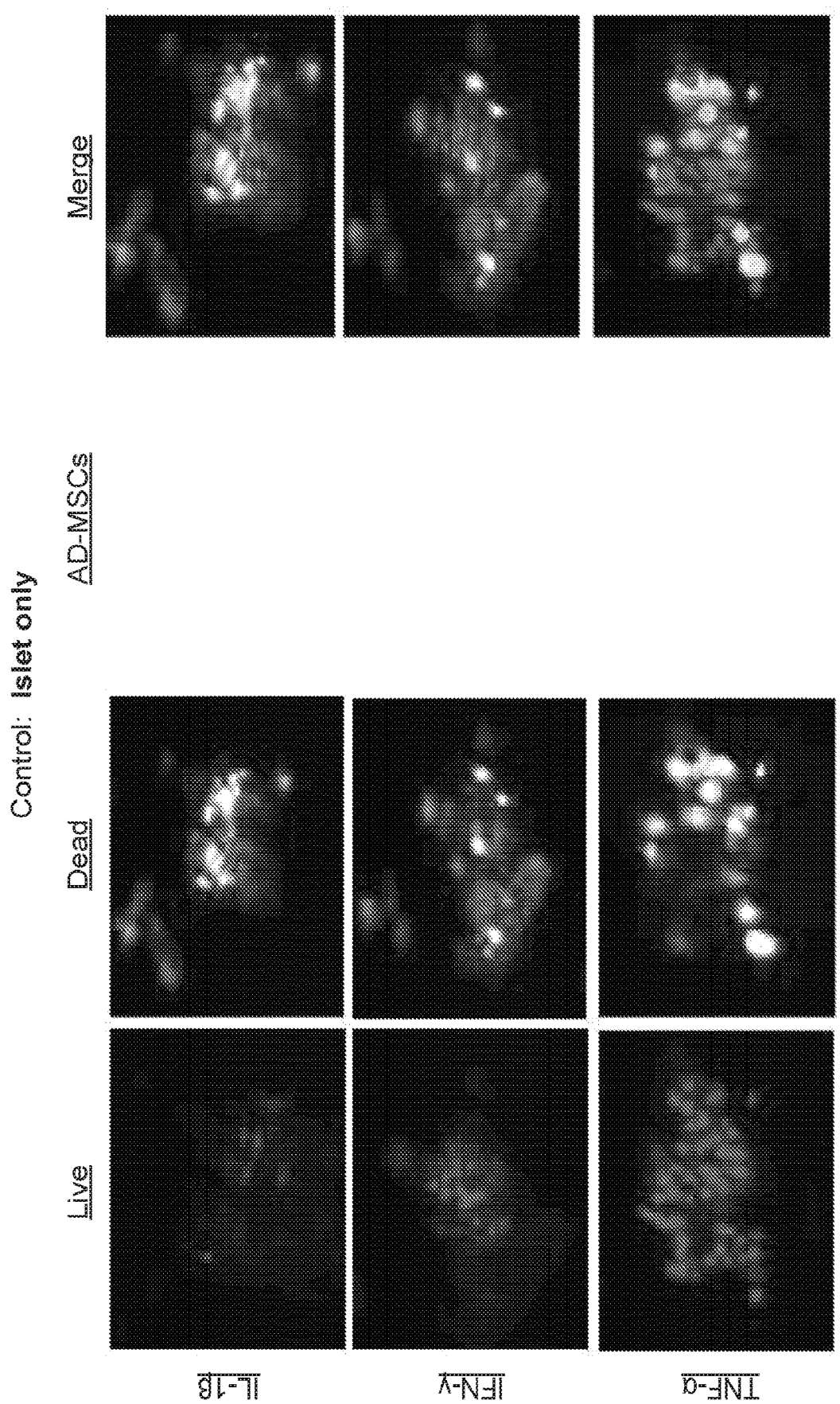

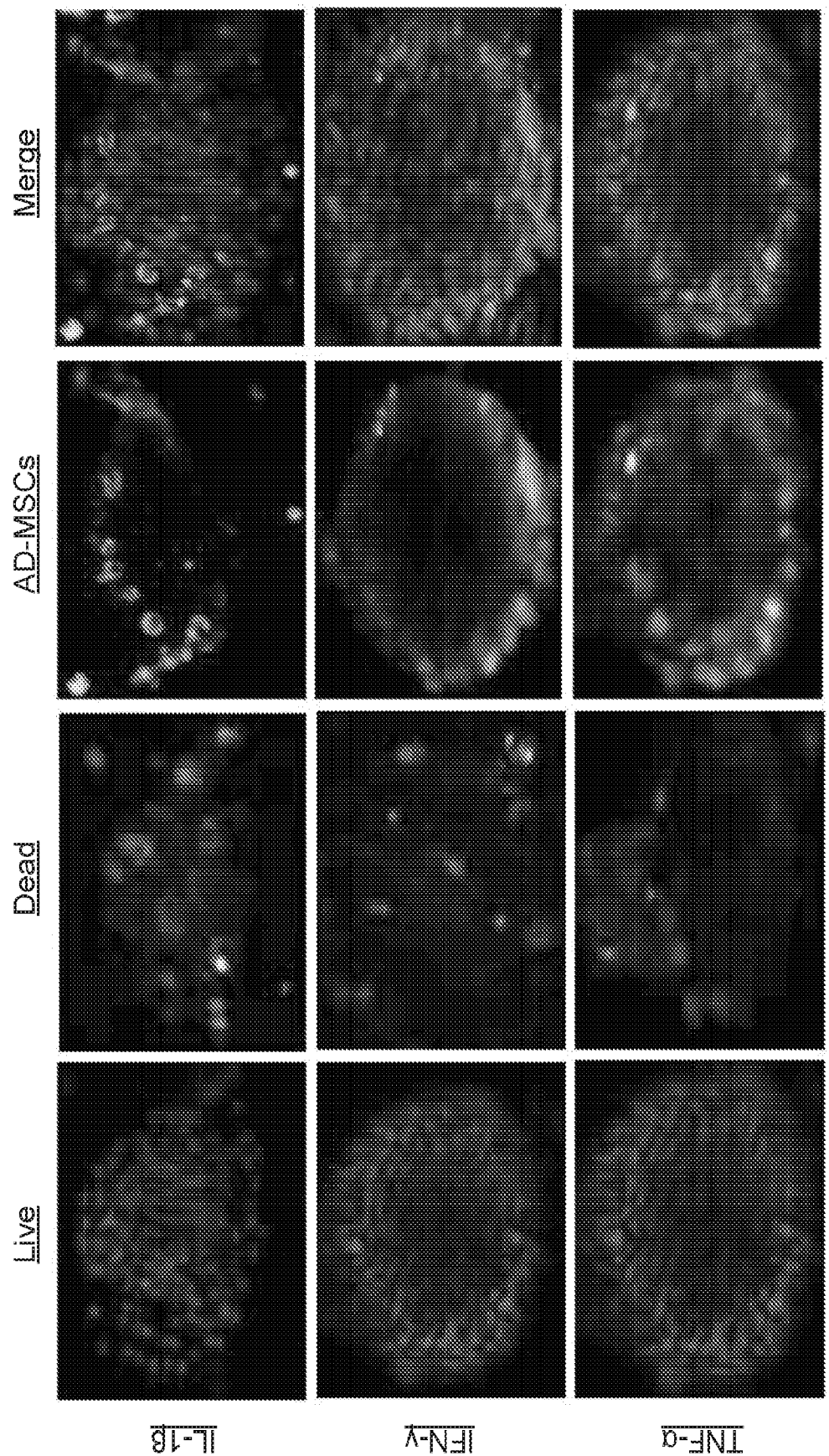
FIG. 18A (Cont.) Step 2: Encapsulation of Islets Coated with AD-MSCs

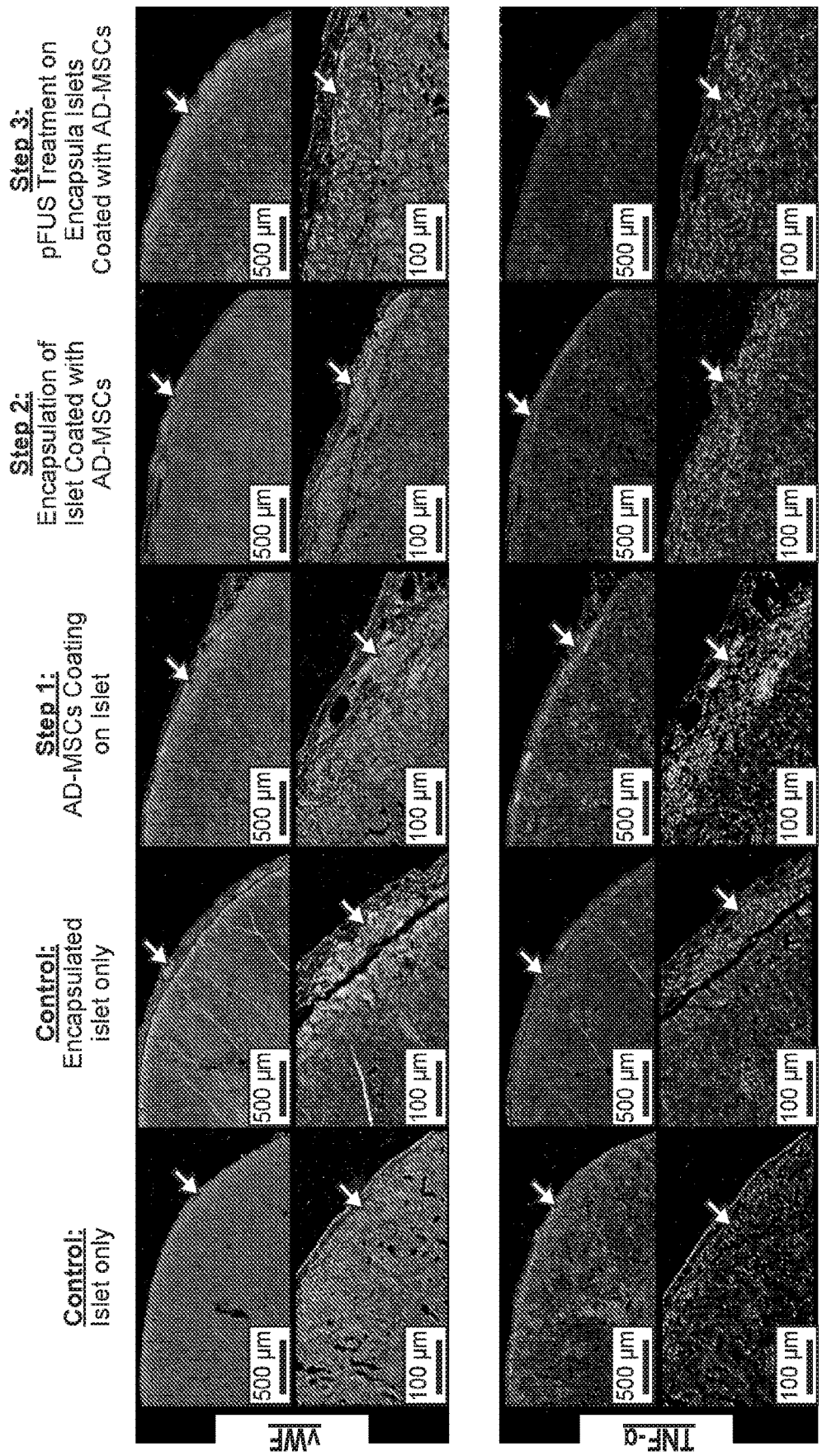

PULSED FOCUSED ULTRASOUND THERAPY FOR TREATMENT OF PANCREATIC DISORDERS

CROSS-REFERENCE TO RELATED APPLICATIONS

This application is a U.S. National Phase of International Application No. PCT/US2020/027423, filed Apr. 9, 2020, which claims priority to U.S. Provisional Application No. 62/833,458, filed Apr. 12, 2019.

STATEMENT OF GOVERNMENT INTEREST

This invention was made with Government support under contract DK119293 awarded by the National Institutes of Health. The Government has certain rights in the invention.

BACKGROUND OF THE INVENTION

Focused ultrasound (FUS) is a non-invasive therapeutic modality used for the treatment of solid tumors. It works by causing temperature elevations (>60° C.) at focal points while sparing the overlying and surrounding normal tissues (Hsiao et al. (2016) J. Cancer 7:225-231). Continuous focused ultrasound (cFUS) has therefore been utilized for thermal ablation of tumors, relying on continuous exposures to generate the heat required to induce coagulative necrosis (Burks et al. (2011) PLoS One 6:e24730). In the clinical setting, cFUS is currently being used for thermal ablation of uterine fibroids, bone tumors, desmoid tumors and prostate cancer (Golan et al. (2017) J. Urol. 198:1000-1009). In clinical trials, cFUS is also being investigated in the setting of the pancreas for the treatment of pancreatic cancer (Li et al. (2012) Hepatobiliary Pancreat Dis. Int. 11:655-660).

Although the main mechanism underlying cFUS is thermal ablation, which is achieved by converting ultrasound energy into heat, there are other additional mechanical effects of cFUS, including acoustic cavitation, radiation force and acoustic streaming. Furthermore, these effects have recently attracted much attention in the application of drug delivery, gene therapy and thrombolysis (Frenkel (2008) Adv. Drug Deliv. Rev. 60:1193-1208; Phenix et al. (2014) J. Pharm. Pharm. Sci. 17:136-153; Suo et al. (2015) Phys. Med. Biol. 60:7403-7418). However, to minimize any temperature elevations and hence allow the mechanical effects of sound waves to predominate, FUS can be applied non-continuously or pulsed (i.e., pulsed focused ultrasound [pFUS]); this lowers the rate of energy deposition and thus allows cooling to occur between pulses (Tempany et al. (2011) Radiology 259:39-56). Exposure to pFUS, despite utilizing relatively high intensities (1000-2000 W/cm$^2$), minimizes temperature elevations in tissue (no more than 4° C.-5° C.) (Frenkel et al. (2007) Radiology 239:86-93; Patel et al. (2008) Int. J. Hyperthermia 24:537-549).

Hence, studies are now indicating that pFUS can be used to increase cellular and vascular permeability and control drug release from ultrasound-responsive carriers without heat deposition in the target tissues (Tempany et al., supra). Furthermore, recent studies have investigated the molecular mechanisms and effects of pFUS in rodent muscle (Burks et al. (2011) PLoS One 2011; 6:e24730), kidney (Ziadloo et al. (2012) PLoS One; 6:e24730) and heart (Jang et al. (2017) J. Transl. Med. 15:252) and have found that it increases the activation/expression of several cytokines, growth factors and cell adhesion molecules in tissues (Burks et al. (2013) Stem Cells 31:2551-2560; Burks et al. (2015) Stem Cells 33:1241-1253; Jang et al., supra). However, what still remains unknown are the effects of pFUS on the pancreas.

The pancreas is a glandular organ comprising two distinct components: the exocrine pancreas, which is a reservoir of digestive enzymes, and the endocrine islets, which can secrete metabolism-related hormones including insulin (Zhou and Melton (2018) Nature 557:351-358). Distinct diseases can affect either the exocrine or endocrine pancreas; for instance, pancreatitis and pancreatic cancer affect predominantly the exocrine gland, whereas diabetes affects the endocrine component of the gland (i.e., the islets).

There remains a need for better methods of treating diseases of the pancreas such as pancreatitis, pancreatic cancer, and type 1 diabetes as well as regenerating pancreatic islets, particularly beta cells.

SUMMARY OF THE INVENTION

Safe and efficacious methods of using pulsed focused ultrasound (pFUS) therapy to treat pancreatic disorders such as type 1 diabetes, pancreatitis, and pancreatic cancer are provided. The methods utilize pFUS therapy either by itself or in combination with islet transplantation and/or stem cell therapy to promote regeneration of damaged pancreatic tissue, increase insulin secretion in response to glucose, or improve engraftment and revascularization of transplanted islets or beta cells. Additionally, methods of using pFUS are provided for modulating paracrine secretion in the pancreas, islets, beta cells, or stem cells, or at a transplantation site to therapeutically alter levels of various factors including, without limitation, cytokines, growth factors, angiogenic factors, and cell adhesion molecules.

In one aspect, a method of increasing insulin secretion from a population of beta cells or islets is provided, the method comprising administering a therapeutically effective amount of pulsed focused ultrasound (pFUS) therapy locally to the population of beta cells or islets, wherein insulin secretion from beta cells in the population of beta cells or islets is increased. This method can be performed, for example, on endogenous pancreatic islets within a pancreas, transplanted islets or beta cells at a transplantation site, isolated beta cells, islets in culture, beta cells in culture, or beta cells differentiated from stem cells or pancreatic progenitor cells.

In certain embodiments, the pFUS therapy is administered in vivo, ex vivo, or in vitro.

In certain embodiments, the subject is pre-diabetic or hyperglycemic. In some embodiments, the patient has mild hyperglycemia, moderate hyperglycemia, or severe hyperglycemia. In some embodiments, the pFUS therapy is administered locally to the endogenous beta cells or islets in the pancreas of the subject.

In certain embodiments, the patient has an amount of pancreatic beta cells less than 50%, less than 60%, less than 70%, or less than 80% of a reference amount of beta cells for a non-diabetic subject. In some embodiments, the patient has lost 50% to 80% of the endogenous beta cells, including any amount within this range such as 50%, 55%, 60%, 65%, 70%, 75%, or 80% of the beta cells.

In certain embodiments, sufficient pFUS is administered to increase intracellular Ca$^{2+}$ concentration and resting membrane potential (Vm) of the beta cells.

In certain embodiments, the pFUS therapy is administered with a spatial peak temporal peak intensity (ISPTP) of about 895 W/cm$^2$.

In certain embodiments, the pFUS therapy is administered with a spatial average temporal average intensity (ISATA) of about 13 W/cm$^2$.

In certain embodiments, the pFUS therapy is administered with a spatial average pulse average intensity (ISAPA) of about 272 W/cm$^2$.

In another aspect, a method of treating a subject for type 1 diabetes is provided, the method comprising: a) transplanting a therapeutically effective amount of a population of beta cells or islets to the subject at a transplantation site; and b) administering a therapeutically effective amount of pulsed focused ultrasound (pFUS) therapy locally at the transplantation site to stimulate insulin secretion from beta cells in the transplanted population of beta cells or islets.

In certain embodiments, the method further comprises administering a therapeutically effective amount of the pFUS therapy to the population of beta cells or islets before transplanting.

In certain embodiments, the method further comprises administering a therapeutically effective amount of the pFUS therapy at the transplantation site before said transplanting, after said transplanting, or before and after said transplanting to promote engraftment and revascularization of the population of beta cells or islets.

In certain embodiments, the beta cells or islets are autologous, allogeneic, or xenogeneic, or comprise beta cells derived from stem cells or pancreatic progenitor cells.

In certain embodiments, the method further comprises transplanting stem cells, wherein the stem cells are in close proximity to the beta cells at the transplantation site. In some embodiments, the stem cells are mesenchymal stem cells (MSCs). The MSCs may include, without limitation, MSCs from bone marrow (BM-MSCs), adipose tissue (AD-MSCs), or umbilical cord (UC-MSCs).

In certain embodiments, the method further comprises administering a therapeutically effective amount of pFUS therapy to the stem cells (e.g., MSCs) before, after, or before and after transplanting the stem cells to stimulate paracrine secretion from the stem cells.

In certain embodiments, the method further comprises coculturing the beta cells with the stem cells (e.g., MSCs) to coat the beta cells or islets with the stem cells; and transplanting the beta cells or islets coated with the stem cells at the transplantation site.

In certain embodiments, the beta cells or islets and stem cells (e.g., MSCs) are cocultured at a ratio ranging from about 1:100 to 1:2000 to allow the stem cells to attach to and coat the beta cells, including any ratio of beta cells/islets to stem cells in this range, such as 1:100, 1:200, 1:300, 1:500, 1:600, 1:700, 1:800, 1:900, 1:1000, 1:1100, 1:1200, 1:1300, 1:1400, 1:1500, 1:1600, 1:1700, 1:1800, 1:1900, or 1:200.

In certain embodiments, the method further comprises encapsulating the beta cells or islets and stem cells (e.g., MSCs) in a biocompatible conformal coating capable of allowing nutrients, oxygen, and glucose to diffuse to the beta cells or islets in vivo.

In certain embodiments, the conformal coating has a thickness ranging from about 25 μm to about 100 μm, including any thickness within this range such as 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, or 100 μm.

In certain embodiments, the conformal coating comprises a hydrogel. In some embodiments, the hydrogel comprises alginate. The alginate concentration in the hydrogel may range, e.g., from about 2 percentage by weight (wt %) to about 10 wt %, including any wt % within this range, such as 2, 2.5, 3, 3.5, 4, 4.5, 5, 5.5, 6, 6.5, 7, 7.5, 8, 8.5, 9, 9.5, or 10 wt %. In one embodiment, the alginate concentration in the hydrogel is 2 wt %.

In certain embodiments, the pFUS therapy is administered multiple times for at least 2 weeks after said transplanting.

In certain embodiments, sufficient pFUS is administered to enhance vascularization, reduce inflammation, and improve survival of the beta cells or islets.

In certain embodiments, sufficient pFUS is administered to increase expression of one or more pro-angiogenic factors, including, without limitation, MCSF, VEGF-A, TGF-β, and IL5.

In certain embodiments, sufficient pFUS is administered to increase expression of one or more anti-inflammatory cytokines including, for example, without limitation, TGF-β, IL4, IL22, and IL5.

In certain embodiments, sufficient pFUS is administered to decrease expression of one or more pro-inflammatory cytokines, including, for example, without limitation, IL17A.

In certain embodiments, sufficient pFUS is administered to increase intracellular Ca$^{2+}$ concentration and resting membrane potential (Vm) of the transplanted beta cells.

In certain embodiments, the transplantation site is in a kidney, liver, omentum, peritoneum, or subcutaneous tissue of the subject.

In certain embodiments, the pFUS therapy is administered with a spatial peak temporal peak intensity (ISPTP) of about 895 W/cm$^2$.

In certain embodiments, the pFUS therapy is administered with a spatial average temporal average intensity (ISATA) of about 13 W/cm$^2$.

In certain embodiments, the pFUS therapy is administered with a spatial average pulse average intensity (ISAPA) of about 272 W/cm$^2$.

In another aspect, a method of stimulating paracrine secretion of cytokines from a stem cell is provided, the method comprising performing pulsed focused ultrasound (pFUS) on the stem cell.

In certain embodiments, the stem cell is a mesenchymal stem cell (MSC). For example, the MSC may be from bone marrow (BM-MSC), adipose tissue (AD-MSC), or umbilical cord (UC-MSC).

In certain embodiments, the method is performed in vivo, ex vivo, or in vitro.

In certain embodiments, the method further comprises adjusting an acoustic dose of the pFUS to adjust amounts of immunomodulatory cytokines, anti-inflammatory cytokines, and angiogenic cytokines that are secreted from the stem cell.

In certain embodiments, the pFUS is performed at an acoustic dose with a spatial average temporal average intensity (ISATA) of about 0.45 W/cm$^2$ and a negative peak pressure (NPP) of about 310 kPa, or an acoustic dose with an ISATA of about 1.3 W/cm$^2$ and an NPP of about 540 kPa.

In certain embodiments, the acoustic dose is selected to increase expression of one or more immunomodulatory cytokines selected from the group consisting of IL31, SCF, RANTES, IFNG, MIP1B, IFNA, TNFB, GROA, IL1A, IL12P40, IL15, IL18, MCP3, ICAM1, VCAM1, IL22, and ENA78; one or more anti-inflammatory cytokines selected from the group consisting of FASL, IL1B, TGFB, IL1RA, TGFB, IL9, BDNF, TRAIL, IL10, and IFNB; and one or more angiogenic cytokines selected from the group consisting of VEGFG, VEGF, FGFB, IL2, and EOTAXIN from BM-MSCs.

In certain embodiments, the acoustic dose is selected to increase expression of one or more immunomodulatory cytokines selected from the group consisting of one or more immunomodulatory cytokines selected from the group consisting of IL31, TNFA, MCP3, LEPTIN, and CD40L; one or more anti-inflammatory cytokines selected from the group consisting of FASL, MIP1A, IL1B, IL6, IL8, IL9, BDNF, IFNB, and LIF; and one or more angiogenic cytokines selected from the group consisting of VEGFG, VEGF, TGFA, FGFB, and PAI1 from BM-MSCs.

In certain embodiments, the acoustic dose is selected to increase expression of one or more immunomodulatory cytokines selected from the group consisting of IL15, MCP3, VCAM1, and IL17F; one or more anti-inflammatory cytokines selected from the group consisting of MIP1A, IL1RA, and IFNB; and one or more angiogenic cytokines selected from the group consisting of TGFA, IL7, IL2, and EOTAXIN from AD-MSCs.

In certain embodiments, the acoustic dose is selected to increase expression of one or more immunomodulatory cytokines selected from the group consisting of MCP3, ICAM1, VCAM1, LEPTIN, and IL17F; the anti-inflammatory cytokine, IFNB; and one or more angiogenic cytokines selected from the group consisting of TGFA, SDF1A, IL7, IL2, and EOTAXIN from AD-MSCs.

In certain embodiments, the acoustic dose is selected to increase expression of one or more immunomodulatory cytokines selected from the group consisting of GMCSF, TNFA, MCP1, IL12P40, RESISTIN, VCAM1, LEPTIN, CD40L, IL17F; one or more anti-inflammatory cytokines selected from the group consisting of MIP1A, IL6, IL8, LIF, IFNB; and one or more angiogenic cytokines selected from the group consisting of HGF, VEGFG, PDGFBB, VEGF, TGFA, IL7, IL2, and EOTAXIN from UC-MSCs.

In certain embodiments, the acoustic dose is selected to increase expression of one or more immunomodulatory cytokines selected from the group consisting of SCF, RANTES, TNFA, MCP1, GROA, IL1A, IL12P40, IL18, MCP3, MIG, RESISTIN, IL21, ICAM1, VCAM1, LEPTIN, CD40L, EN78, and IL17F; one or more anti-inflammatory cytokines selected from the group consisting of MIP1A, IL6, IL8, IL9, NGF, EGF, GCSF, LIF, and IFNB; and one or more angiogenic cytokines selected from the group consisting of HGF, VEGFG, PDGFBB, TGFA, SDF1A, IL5, IL7, IL2, and EOTAXIN from UC-MSCs.

In certain embodiments, the pFUS therapy is administered with an ultrasound duty cycle of about 20%.

In another aspect, a method of modulating cytokine levels in pancreatic tissue using pulsed focused ultrasound (pFUS) therapy is provided, the method comprising: a) administering pulsed focused ultrasound (pFUS) therapy locally to the pancreatic tissue at a sufficiently low acoustic intensity to decrease cytokine expression in the pancreatic tissue; or b) administering pulsed focused ultrasound (pFUS) therapy locally to the pancreatic tissue at a sufficiently high acoustic intensity to increase cytokine expression in the pancreatic tissue.

In certain embodiments, the pFUS therapy is administered in vivo, ex vivo, or in vitro.

In certain embodiments, the pFUS therapy is administered at a sufficiently low acoustic intensity to decrease cytokine expression of one or more cytokines selected from the group consisting of granulocyte colony-stimulating factor (GCSF), granulocyte-macrophage colony-stimulating factor (GM-CSF), interferon-α (IFN-α), interferon-γ (IFN-γ), interleukin-10 (IL-10), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-27 (IL-27), interleukin-28 (IL-28), interleukin-3 (IL-3), interleukin-31 (IL-31), interleukin-4 (IL-4), interleukin-5 (IL-5), interleukin-6 (IL-6), interleukin-9 (IL-9), IFN-γ-induced protein 10 (IP-10), leptin, leukemia inhibitory factor (LIF), lipopolysaccharide-induced CXC chemokine (LIX: −56±1%), macrophage colony-stimulating factor (MCSF), monocyte chemotactic protein-3 (MCP-3), macrophage inflammatory protein-1α (MIP-1α), macrophage inflammatory protein-1β (MIP-1β), macrophage inflammatory protein-2 (MIP-2), transforming growth factor β1 (TGF-β1), tumor necrosis factor α (TNF-α), and vascular endothelial growth factor (VEGF).

In certain embodiments, the pFUS therapy is administered at a sufficiently low acoustic intensity to decrease cytokine expression of at least IL-6, IL-1β, and TNF-α. Such pFUS therapy may be administered in vivo, for example, to a subject to treat pancreatitis or pancreatic cancer.

In certain embodiments, the pFUS therapy is administered at a sufficiently low acoustic intensity to decrease cytokine expression of at least, IP-10, IFN-γ and IL-2. Such pFUS therapy may be administered in vivo to a subject, for example, to slow or halt progression of type 1 diabetes.

In certain embodiments, the pFUS therapy is administered at a sufficiently low acoustic intensity to decrease cytokine expression of granulocyte colony-stimulating factor (GCSF), granulocyte-macrophage colony-stimulating factor (GM-CSF), interferon-α (IFN-α), interferon-γ (IFN-γ), interleukin-10 (IL-10), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-27 (IL-27), interleukin-28 (IL-28), interleukin-3 (IL-3), interleukin-31 (IL-31), interleukin-4 (IL-4), interleukin-5 (IL-5), interleukin-6 (IL-6), interleukin-9 (IL-9), IFN-γ-induced protein 10 (IP-10), leptin, leukemia inhibitory factor (LIF), lipopolysaccharide-induced CXC chemokine (LIX), macrophage colony-stimulating factor (MCSF), monocyte chemotactic protein-3 (MCP-3), macrophage inflammatory protein-1α (MIP-1α), macrophage inflammatory protein-1β (MIP-1β), macrophage inflammatory protein-2 (MIP-2), transforming growth factor β1 (TGF-β1), tumor necrosis factor α (TNF-α), and vascular endothelial growth factor (VEGF).

In certain embodiments, the pFUS therapy is administered to the pancreatic tissue with a spatial average temporal average intensity (ISATA) of 11.5 W/cm$^2$ and a negative peak pressure (NPP) of 3 MPa.

In certain embodiments, the pFUS therapy is administered to the pancreatic tissue with a sufficiently high acoustic intensity to increase cytokine expression of one or more cytokines selected from the group consisting of granulocyte colony-stimulating factor (GCSF), granulocyte-macrophage colony-stimulating factor (GM-CSF), growth-regulated oncogene α (GRO-α, interferon-γ (IFN-γ), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-28 (IL-28), IL-3, IL-31, IL-4, IL-5, IL-6, IL-9, leptin, leukemia inhibitory factor (LIF), lipopolysaccharide-induced CXC chemokine (LIX), macrophage inflammatory protein-2 (MIP-2), regulated on activation, normal T cell expressed and secreted (RANTES), transforming growth factor-β (TGF-β), and tumor necrosis factor α (TNF-α).

In certain embodiments, the pFUS is administered at a sufficiently high acoustic intensity to increase expression of one or more angiogenic growth factors including, without limitation, TGF-β and MCP-1. In some embodiments, such pFUS therapy is administered in vivo to a subject to promote vascularization of pancreatic tissue. In some embodiments, such pFUS therapy is administered in vivo to a subject to promote homing of mesenchymal stem cells (MSCs).

In certain embodiments, the pFUS is administered at a sufficiently high acoustic intensity to increase expression of at least TNF-α, IFN-γ and IL-1β. In some embodiments, such pFUS therapy is administered in vivo to a subject to promote regeneration or replacement of pancreatic tissue.

In certain embodiments, the pFUS is administered at a sufficiently high acoustic intensity to increase cytokine expression of granulocyte colony-stimulating factor (GCSF), granulocyte-macrophage colony-stimulating factor (GM-CSF), growth-regulated oncogene α (GRO-α, interferon-γ (IFN-γ), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-28 (IL-28), IL-3, IL-31, IL-4, IL-5, IL-6, IL-9, leptin, leukemia inhibitory factor (LIF), lipopolysaccharide-induced CXC chemokine (LIX), macrophage inflammatory protein-2 (MIP-2), regulated on activation, normal T cell expressed and secreted (RANTES), transforming growth factor-β (TGF-β), and tumor necrosis factor α (TNF-α).

In certain embodiments, the pFUS therapy is administered with a spatial average temporal average intensity (ISATA) of 18.5 W/cm$^2$ and a negative peak pressure (NPP) of 4 MPa.

In certain embodiments, the pancreatic tissue is damaged from diabetes, pancreatitis, pancreatic cancer, surgery, or a traumatic physical injury.

In the practice of the subject methods, pFUS may be administered, for example, with an ultrasound frequency ranging from about 20 kHz to about 5.0 MHz, about 0.7 MHz to about 3.0 MHz, or about 1.0 MHz to about 1.1 MHz, including any ultrasound frequency within these ranges, such as 0.2, 0.4, 0.6, 0.8, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 3.0, 3.2, 3.4, 3.6, 3.8, 4.0, 4.2, 4.4, 4.6, 4.8, or 5.0 MHz.

In the practice of the subject methods, pFUS may be administered, for example, with a pulse repetition frequency (PRF) ranging from 0.1 Hz to 1000 Hz, 1 Hz to 100 Hz, or about 5 Hz to 20 Hz, or any PRF with these ranges, such as 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, or 1000 Hz.

In the practice of the subject methods, pFUS may be administered, for example, with an ultrasound duty cycle ranging from 0.01% to 100% or 1% to 20%, including any ultrasound duty cycle within these ranges such as 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 90%, 95%, or 100%. In some embodiments, the pFUS is administered with an ultrasound duty cycle of about 5%. In some embodiments, the pFUS therapy is administered with an ultrasound duty cycle of less than 1%.

In the practice of the subject methods, pFUS may be administered, for example, with a negative peak pressure (NPP) ranging from 0.1 MPa to 10 MPa, including any NPP within this range such as 0.1, 0.2, 0.3, 0.4, 0.5, 0.6, 0.7, 0.8, 0.9, 1, 2, 3, 4, 5, 6, 7, 8, 9, or 10 MPa. In some embodiments, the pFUS is administered with a negative peak pressure (NPP) of up to 3 MPa. In some embodiments, the NPP is about 2.9 MPa.

In the practice of the subject methods, pFUS may be administered to the subject, for example, for a time ranging from about 20 seconds to about 7 minutes, including any amount of time within this range, such as 20 seconds, 25 seconds, 30 seconds, 35 seconds, 40 seconds, 45 seconds, 50 seconds, 55 seconds, 1 minute, 1.25 minutes, 1.5 minutes, 1.75 minutes, 2 minutes, 2.25 minutes, 2.5 minutes, 2.75 minutes, 3 minutes, 3.25 minutes, 3.5 minutes, 3.75 minutes, 4 minutes, 4.25 minutes, 4.5 minutes, 4.75 minutes, 5 minutes, 5.25 minutes, 5.5 minutes, 5.75 minutes, 6 minutes, 6.25 minutes, 6.5 minutes, 6.75 minutes, or 7 minutes. In some embodiments, the pFUS therapy is administered to the subject for at least 20 seconds. In some embodiments, the pFUS therapy is administered to the subject for a period ranging from about 1 minute to about 5 minutes. In one embodiment, the pFUS therapy is administered to the subject for about 160 seconds.

In the practice of the subject methods, pFUS may be administered, for example, with a pulse length of about 10 milliseconds.

In the practice of the subject methods, multiple cycles of treatment may be administered to the subject.

BRIEF DESCRIPTION OF THE DRAWINGS

(FIGS. 1A, 1B) Pulsed FUS guidance of the mouse pancreas using a therapeutic transducer fitted in a custom cone and filled with degassed water: (FIG. 1A) side view, (FIG. 1B) top view. The transmitted ultrasound waves are produced by a function generator, amplified through the amplifier at a constant gain and emitted from the transducer face to eight evenly distributed foci throughout the mouse pancreas. (FIG. 1C) Typical waveform and (FIG. 1D) 2-D pressure map measured (full width at half-maximum area for pressure) at a focal area (10 mm long×1.5 mm diameter).

FIGS. 6A-6C. In vitro analysis of islet survival and function: (FIG. 6A) Bright-field, fluorescent and confocal images of control (i.e. non-pFUS treated islets) and islets treated with pFUS at low, medium and high acoustic intensities; (FIG. 6B) Results of live/dead assay; and (FIG. 6C) GSIS assay. Significant differences: $^a$P<0.05: control vs. low or medium or high dose; $^b$P<0.05: low vs. medium or high dose; $^c$P<0.05: medium vs. high dose; *P<0.05: low vs. high glucose (Two (c) or one (b)-way ANOVA post-hoc Tukey Test).

(FIG. 7A) Results of calcium imaging during 2 low-high glucose challenges and representative confocal images of the peak calcium response to glucose challenges; and (FIG. 7B) the insulin content within control (i.e. non-pFUS treated islets) and islets treated with pFUS at low, medium and high intensities and (FIG. 7C) the amount of insulin released from control (i.e. non-pFUS treated islets) and islets treated with pFUS at low, medium and high intensities. $^a$P<0.05: control vs. low or medium or high dose; $^b$p<0.05: low vs. medium or high dose; $^c$P<0.05: medium vs. high dose; *P<0.05: low vs. high glucose (Two (a) or one (b,c)-way ANOVA post-hoc Tukey Test).

(FIG. 8A) A microscopic view of a MEA; Islet placed on top of a MEA electrode (shown by arrow); (FIG. 8B) The characteristic pattern of the electrical activity in islets obtained at 16.7 mM glucose stimulation following pFUS treatment.

FIGS. 9A-9H. In vivo analysis following islet transplantation: (FIG. 9A) In vivo experimental details; (FIG. 9B) An example of an islet transplant (both control and islets treated with pFUS) using the kidney sub-capsule space as the site of transplantation: islets before, during and after transplantation (black circle=transplanted islets); pFUS treatment on the kidney containing the transplanted islets (red circle=site of pFUS targeting). Results of (FIG. 9C) blood glucose measurements, (FIG. 9D) normoglycemia percentage, (FIG. 9E) body weight, (FIG. 9F) IPGTT, (FIG. 9G) area under the IPGTT curve ($AUC_{0-120min}$), and (FIG. 9H) blood glucose clearance rates calculated from the slope of IPGTT curves from 30 to 90 min. Significant differences: (FIGS. 9C-9H) $^a$p<0.05: islets only vs. islets treated with pFUS; *P<0.05: baseline vs. all other time-points (Two (FIGS. 9C, 9E, 9F) or one (FIG. 9B)-way ANOVA with post-hoc Tukey Test or unpaired Student's t-test (FIGS. 9G, 9H).

(FIG. 10A) Representative images following H&E, insulin, vWF and TNF-α immunohistochemical staining of islets that were transplanted under the kidney capsule. Black arrows=islets; Red arrow=positive (dark brown) staining; (FIG. 10B) Quantification of the surface area occupied by islets; (FIGS. 10C-10E) Quantification of positive (FIG. 10C) insulin, (FIG. 10D) vWF and (FIG. 10E) TNF-α staining. For all figures, control samples (non-treated islets) are compared to islets treated with pFUS. Significant differences: *P<0.05 for islets only vs. islets treated with pFUS (Student's unpaired t-test).

FIGS. 11A-11B. H&E histological assessment of transplanted islets: (FIG. 11A) Representative H&E histological staining of islets that were transplanted under the kidney capsule. Black arrows=islets; Green arrows=blood vessels; (FIG. 11B) Quantification of microvessel density within islets. In this figure, control samples (transplanted islets with no treatment) are compared to transplanted islets treated with pFUS. Significant differences: *P<0.05 for transplanted islets only vs. islets treated with pFUS (Student's unpaired t-test).

(FIG. 12A) Cytokine expression profile and (FIG. 12B) insulin content within the kidney tissue of animals receiving an islet transplant. (FIG. 12C) Blood serum levels in animals receiving an islet transplant. For all figures, control samples (non-treated islets) are compared to islets treated with pFUS. Significant differences: *P<0.05 for islets only vs. islets treated with pFUS (Student's unpaired t-test).

FIG. 14A shows that stimulation of all three types of MSCs i.e. BM-MSCs, AD-MSCs and UC-MSCs with low or high dose pFUS resulted in cytokine secretion compared to control; cytokines which have immunomodulatory, anti-inflammatory, and angiogenic effects. FIG. 14B shows a heat map with upregulation represented as a red color gradient and downregulation represented as a green color gradient.

(FIG. 16A) Schematic representation of our three-step approach i.e. step 1: AD-MSCs coating, step 2: encapsulation and step 3: pFUS treatment; Characterizations of (FIGS. 16B-16E) AD-MSCs ((FIG. 16B) confocal image and (FIGS. 16C-16E) FACS analysis), (FIGS. 16F-16I) alginate capsule (photographic, SEM images and XPS scans) and (FIGS. 16J-16N) confocal images of: an (FIG. 16J) islet, (FIG. 16K) AD-MSCs.

FIGS. 17A-17D. In vitro analysis of islet survival and function in normal conditions: (FIG. 17A) Representative confocal images, and results of (FIG. 17B) Live/Dead, (FIG. 17C) MTT and (FIG. 17D) GSIS assays of tested groups (i.e. islets only, islet coated with AD-MSCs, encapsulated islets coated with AD-MSCs, and encapsulated islets coated with AD-MSCs and pFUS treatment). Confocal images and Live/Dead assay have been performed at day 1 and 7, and MTT and GSIS assays at day 7, in culture. Significant differences: (FIGS. 17B-17D) $^a$P<0.05: islets only vs. islets coated with AD-MSCs or encapsulated islets coated with AD-MSCs or encapsulated islets coated with AD-MSCs and pFUS treatment; $^b$P<0.05: islets coated with AD-MSCs vs. encapsulated islets coated with AD-MSCs or encapsulated islets coated with AD-MSCs and pFUS treatment; $^c$P<0.05: encapsulated islets coated with AD-MSCs vs. encapsulated islets coated with AD-MSCs and pFUS treatment; (FIG. 17B) *P<0.05: Day 1 vs. Day 7; (FIG. 17D) *P<0.05: High glucose vs. Low glucose (Two (FIGS. 17B, 17D) or one (FIG. 17C)-way ANOVA post-hoc Tukey Test).

(FIG. 18A) Representative confocal images, and results of (FIG. 18B) Live/Dead, (FIG. 18C) MTT and (FIG. 18D) GSIS assays of tested groups (i.e. islets only, islet coated with AD-MSCs, encapsulated islets coated with AD-MSCs, and encapsulated islets coated with AD-MSCs and pFUS treatment). Significant differences: (FIGS. 18B-18D) $^a$P<0.05: islets only vs. islets coated with AD-MSCs or encapsulated islets coated with AD-MSCs or encapsulated islets coated with AD-MSCs and pFUS treatment; $^b$P<0.05: islets coated with AD-MSCs vs. encapsulated islets coated with AD-MSCs or encapsulated islets coated with AD-MSCs and pFUS treatment; $^c$P<0.05: encapsulated islets coated with AD-MSCs vs. encapsulated islets coated with AD-MSCs and pFUS treatment (One-way ANOVA post-hoc Tukey Test).

(FIG. 19A) Islet transplantation using a kidney subcapsular approach; pFUS treatment on the kidney transplanted with islets; Transplanted kidney with different experimental groups (i.e. islets only, encapsulated islets only, islets coated with AD-MSCs, encapsulated islets coated with AD-MSCs, and encapsulated islets coated with AD-MSCs and pFUS treatment) at the time of euthanasia (black arrows indicate transplanted islets); Results of (FIGS. 19B-19E) BG measurements, (FIGS. 19F-19I normoglycemia percentage, (FIGS. 19J-19M) IPGTT, (FIG. 19N-19O) area under the IPGTT curve ($AUC_{0-120min}$), (FIGS. 19R-19U) BG clearance rates calculated from slope of IPGTT curves from 30 to 90 min and (FIGS. 19V-19Y) body weight of mice post-transplant measured at various time points over 30 days. Results shows the effect of (FIGS. 19B, 19F, 19J, 19N, 19R, 19V) islet encapsulation by comparing islets only with encapsulated islets only, (FIGS. 19C, 19G, 19K, 19O, 19S, 19W) AD-MSCs coating on islets by comparing islets only with islets coated with AD-MSCs, (FIGS. 19D, 19H, 19L, 19P, 19T, 19X) encapsulating islets with AD-MSCs by comparing encapsulated islets only with encapsulated islets coated with AD-MSCs, (FIGS. 19E, 19I, 19M, 19O, 19U, 18Y) and pFUS treatment by comparing encapsulated islets coated with AD-MSCs with encapsulated islets coated with AD-MSCs and pFUS treatment groups. Significant differences: (FIG. 19B-19Y) $^a$P<0.05: encapsulated islets only vs. islets only; $^b$P<0.05: islets coated with AD-MSCs vs. islets only; $^c$P<0.05: islets coated with AD-MSCs vs. encapsulated islets only; $^d$P<0.05: encapsulated islets coated with AD-MSCs vs. encapsulated islets only; $^e$P<0.05: encapsulated islets coated with AD-MSCs vs. islets coated with AD-MSCs; $^f$P<0.05: encapsulated islets coated with AD-MSCs vs. islets only; $^g$P<0.05: encapsulated islets coated with AD-MSCs and pFUS treatment vs. encapsulated islets coated with AD-MSCs; $^h$P<0.05: encapsulated islets coated with AD-MSCs and pFUS treatment vs. islets coated with AD-MSCs; $^i$P<0.05: encapsulated islets coated with AD-MSCs and pFUS treatment vs. encapsulated islets only; $^j$P<0.05: encapsulated islets coated with AD-MSCs and pFUS treatment vs. islets only; *P<0.05: baseline vs. all other time-points (Two (FIGS. 19B, 19H, 19N, 19T, 19D, 19J, 19P, 19V, 19G, 19M, 19S, 19Y) or one (FIGS. 19K, 19Q, 19W, 19L, 19R, 19X)-way ANOVA post-hoc Tukey Test or unpaired Student's t-test (FIGS. 19E, 19F)).

(FIG. 20A) Representative images following H&E, insulin, vWF and TNF-α immunohistochemical staining of islets in tested groups (i.e. islets only, encapsulated islets only, islets coated with AD-MSCs, encapsulated islets coated with AD-MSCs, and encapsulated islets coated with AD-MSCs and pFUS treatment) that were transplanted under the kidney capsule. Black arrows indicate islets present within the representative images and red arrows indicate blood vessels within the islets; (FIG. 20B) Quantification of surface area occupied by islets; (FIGS. 20C-20E) Quantification of positive (FIG. 20C) insulin, (FIG. 20D) vWF and (FIG. 20E) TNF-α staining. Significant differences: (FIG. 20B-20E) $^a$P<0.05: islets only vs. encapsulated islets only or islets coated with AD-MSCs or encapsulated islets coated with AD-MSCs or encapsulated islets coated with AD-MSCs and pFUS treatment; $^b$P<0.05: encapsulated islets only vs. islets coated with AD-MSCs or encapsulated islets coated with AD-MSCs or encapsulated islets coated with AD-MSCs and pFUS treatment; $^c$P<0.05: islets coated with AD-MSCs vs. encapsulated islets coated with AD-MSCs or encapsulated islets coated with AD-MSCs and pFUS treatment; $^d$P<0.05: encapsulated islets coated with AD-MSCs vs. encapsulated islets coated with AD-MSCs and pFUS treatment (One-way ANOVA post-hoc Tukey Test).

DETAILED DESCRIPTION

Figure 1A:
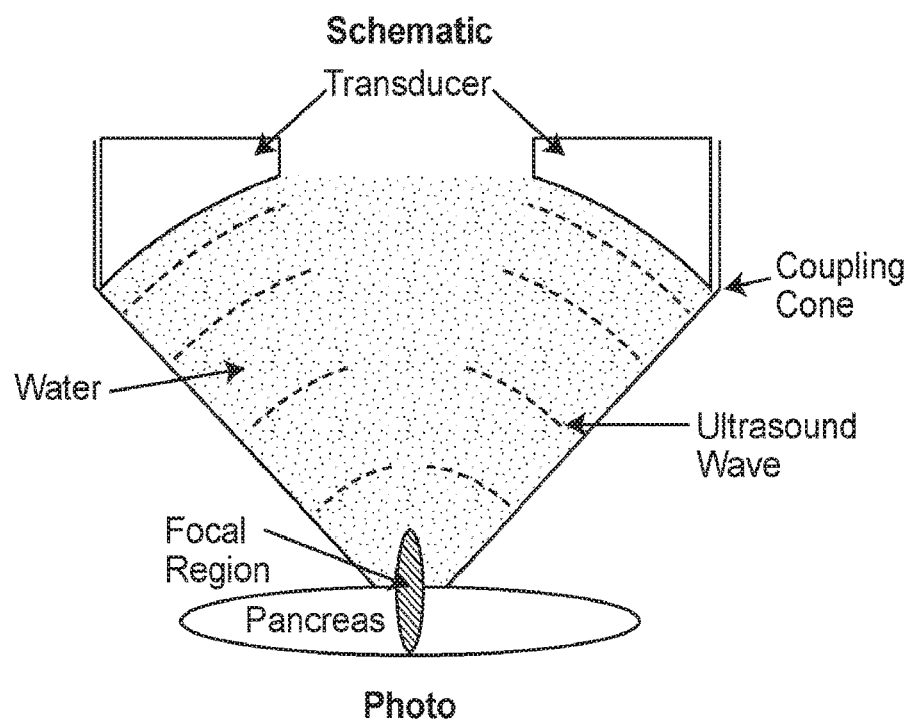
FIGS. 1A-1D. Pulsed focused ultrasound (pFUS) treatment of the pancreas.

Methods of using pulsed focused ultrasound (pFUS) therapy to treat pancreatic disorders such as type 1 diabetes, pancreatitis, and pancreatic cancer are provided. The methods utilize pulsed focused ultrasound (pFUS) therapy either by itself or in combination with islet transplantation and/or stem cell therapy to promote regeneration of damaged pancreatic tissue, increase insulin secretion in response to glucose, or improve engraftment and revascularization of transplanted islets or beta cells. Additionally, methods of using pFUS are provided for modulating paracrine secretion in the pancreas, islets, beta cells, or stem cells, or at a transplantation site to therapeutically alter levels of various factors including, without limitation, cytokines, growth factors, angiogenic factors, and cell adhesion molecules.

Before the methods of using pFUS for treatment of pancreatic disorders, islet transplantation, and modulating paracrine secretion in tissue, islets, beta cells, and stem cells are further described, it is to be understood that this invention is not limited to a particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As used herein the singular forms "a", "an", and "the" include plural referents unless the context clearly dictates otherwise. Thus, for example, reference to "a cell" includes a plurality of such cells and reference to "the cytokine" includes reference to one or more cytokines and equivalents thereof, e.g., chemokines, interferons, interleukins, lymphokines, and tumor necrosis factors, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The term "about," particularly in reference to a given quantity, is meant to encompass deviations of plus or minus five percent.

The term "stem cell" refers to a cell that retains the ability to renew itself through mitotic cell division and that can differentiate into a diverse range of specialized cell types. Mammalian stem cells can be divided into three broad categories: embryonic stem cells, which are derived from blastocysts, adult stem cells, which are found in adult tissues, and cord blood stem cells, which are found in the umbilical cord. In a developing embryo, stem cells can differentiate into all of the specialized embryonic tissues. In adult organisms, stem cells and progenitor cells act as a repair system for the body by replenishing specialized cells. Totipotent stem cells are produced from the fusion of an egg and sperm cell. Cells produced by the first few divisions of the fertilized egg are also totipotent. These cells can differentiate into embryonic and extraembryonic cell types. Pluripotent stem cells are the descendants of totipotent cells and can differentiate into cells derived from any of the three germ layers. Multipotent stem cells can produce only cells of a closely related family of cells (e.g., hematopoietic stem cells differentiate into red blood cells, white blood cells, platelets, etc.). Unipotent cells can produce only one cell type, but have the property of self-renewal, which distinguishes them from non-stem cells. Induced pluripotent stem cells are a type of pluripotent stem cell derived from adult cells that have been reprogrammed into an embryonic-like pluripotent state. Induced pluripotent stem cells can be derived, for example, from adult somatic cells such as skin or blood cells.

As used herein, the terms "mesenchymal stromal cells" and "mesenchymal stem cells" are used interchangeably and refer to multipotent cells derived from connective tissue. The terms encompass MSCs derived from various sources including, without limitation, bone marrow, adipose tissue, umbilical cord tissue, molar tooth bud tissue, and amniotic fluid.

"Substantially purified" generally refers to isolation of a substance (e.g., compound, polynucleotide, protein, polypeptide, antibody, aptamer) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide or peptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom but has not yet been diagnosed as having it; (b) inhibiting the disease and/or symptom(s), i.e., arresting their development;

or (c) relieving the disease symptom(s), i.e., causing regression of the disease and/or symptom(s). Those in need of treatment include those already inflicted (e.g., those with hyperglycemia or pre-diabetic) as well as those in which prevention is desired (e.g., those with increased susceptibility to diabetes, those having a genetic predisposition to developing diabetes, etc.).

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

By "therapeutically effective dose or amount" of pulsed focused ultrasound (pFUS) therapy, islets, beta cells, stem cells (e.g., MSCs), or islets or beta cells co-encapsulated with stem cells (e.g., islets or beta cells coated with MSCs and conformally co-encapsulated in an alginate hydrogel) is intended an amount that, when the pFUS, islets, beta cells, stem cells (e.g., MSCs), or islets or beta cells co-encapsulated with stem cells (e.g., MSCs) are administered, as described herein, brings about a positive therapeutic response, such as promoting regeneration of pancreatic tissue and/or improved engraftment and revascularization of islets or beta cells, and/or restoring beta cell/islet function (e.g., stimulating insulin production and secretion in response to glucose), and/or improving survival of transplanted beta cells or islets. Additionally, a "therapeutically effective dose or amount" may increase intracellular calcium ($Ca^{2+}$) concentration in beta cells, increase resting membrane potential (Vm) in beta cells, which reduces the threshold required to trigger depolarization, stimulate calcium transients, and/or enhance the influx of calcium following glucose stimulation (i.e., entry of $Ca^{2+}$ into beta cells results in membrane depolarization and insulin secretion). A "therapeutically effective dose or amount" of pFUS may also modulate paracrine secretion in the pancreas and/or at a transplantation site and/or of beta cells and/or stem cells (e.g., MSCs) to therapeutically alter levels of various factors including, without limitation, cytokines, growth factors, angiogenic factors, and cell adhesion molecules. A therapeutically effective dose or amount can be administered in one or more administrations "Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like.

"Biocompatible" refers to a material that is non-toxic to a cell or tissue.

As used herein, the term "cell viability" refers to a measure of the number of cells that are living or dead, based on a total cell sample. High cell viability, as defined herein, refers to a cell population in which greater than 80% of all cells are viable, preferably greater than 90-95%, and more preferably a population characterized by high cell viability containing more than 97-99% viable cells.

Use of pFUS to Modulate Expression of Cytokines and Other Factors in Pancreatic Tissue Pulsed focused ultrasound utilizes shorter pulsed exposures than conventional focused ultrasound, which decreases energy deposition and allows cooling between pulses, thereby minimizing temperature elevations in tissue and allowing non-thermal effects such as acoustic cavitation and acoustic radiation forces to predominate. Applying pFUS with short cycles of sound waves mechanically "shakes" cells within tissues, which induces transient local changes in gene expression. The acoustic intensity can be adjusted to control levels of gene expression in the pancreas. For example, performing pFUS on the pancreas at low acoustic intensities turns off the expression of multiple cytokines, whereas performing pFUS at high intensities turns on the expression of cytokines. Accordingly, pFUS can be used to modulate levels of cytokines in the pancreas as well as other factors, including, without limitation, growth factors, angiogenic factors, and cell adhesion molecules (see Example 1). The ability to non-invasively manipulate the microenvironment of the pancreas using sound waves is useful for selectively modulating expression of particular factors for treatment of damaged pancreatic tissue and the application of cellular therapies for treating pancreatic disorders in the context of both regenerative medicine (e.g., diabetes and pancreatitis) and oncology (e.g., pancreatic cancer).

In certain embodiments, pFUS therapy is administered at a sufficiently low acoustic intensity to decrease cytokine expression of one or more cytokines selected from the group consisting of granulocyte colony-stimulating factor (GCSF), granulocyte-macrophage colony-stimulating factor (GM-CSF), interferon-α (IFN-α), interferon-γ (IFN-γ), interleukin-10 (IL-10), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-27 (IL-27), interleukin-28 (IL-28), interleukin-3 (IL-3), interleukin-31 (IL-31), interleukin-4 (IL-4), interleukin-5 (IL-5), interleukin-6 (IL-6), interleukin-9 (IL-9), IFN-γ-induced protein 10 (IP-10), leptin, leukemia inhibitory factor (LIF), lipopolysaccharide-induced CXC chemokine (LIX: −56±1%), macrophage colony-stimulating factor (MCSF), monocyte chemotactic protein-3 (MCP-3), macrophage inflammatory protein-1α (MIP-1α), macrophage inflammatory protein-1β (MIP-1β), macrophage inflammatory protein-2 (MIP-2), transforming growth factor β1 (TGF-β1), tumor necrosis factor α (TNF-α), and vascular endothelial growth factor (VEGF). In some embodiments, the pFUS therapy is administered at a sufficiently low acoustic intensity to decrease cytokine expression of at least IL-6, IL-1β, and TNF-α. Such pFUS therapy may be administered in vivo to a subject, for example, to treat pancreatitis or pancreatic cancer. In some embodiments, the pFUS therapy is administered at a sufficiently low acoustic intensity to decrease cytokine expression of at least, IP-10, IFN-γ and IL-2. Such pFUS therapy may be administered in vivo to a subject, for example, to slow or halt progression of type 1 diabetes.

In certain embodiments, pFUS therapy is administered at a sufficiently low acoustic intensity to decrease cytokine expression of granulocyte colony-stimulating factor (GCSF), granulocyte-macrophage colony-stimulating factor (GM-CSF), interferon-α (IFN-α), interferon-γ (IFN-γ), interleukin-10 (IL-10), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-27 (IL-27), interleukin-28 (IL-28), interleukin-3 (IL-3), interleukin-31 (IL-31), interleukin-4 (IL-4), interleukin-5 (IL-5), interleukin-6 (IL-6), interleukin-9 (IL-9), IFN-γ-induced protein 10 (IP-10), leptin, leukemia inhibitory factor (LIF), lipopolysaccharide-induced CXC chemokine (LIX), macrophage colony-stimulating factor (MCSF), monocyte chemotactic protein-3 (MCP-3), macrophage inflammatory protein-1α (MIP-1α), macrophage inflammatory protein-1β (MIP-1β), macrophage inflammatory protein-2 (MIP-2), transforming growth factor β1 (TGF-β1), tumor necrosis factor α (TNF-α), and vascular endothelial growth factor (VEGF).

In certain embodiments, pFUS therapy is administered to the pancreatic tissue with a sufficiently high acoustic intensity to increase cytokine expression of one or more cytokines selected from the group consisting of granulocyte colony-stimulating factor (GCSF), granulocyte-macrophage colony-stimulating factor (GM-CSF), growth-regulated oncogene α (GRO-α, interferon-γ (IFN-γ), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-28 (IL-28), IL-3, IL-31, IL-4, IL-5, IL-6, IL-9, leptin, leukemia inhibitory factor (LIF), lipopolysaccharide-induced CXC chemokine (LIX), macrophage inflammatory protein-2 (MIP-2), regulated on activation, normal T cell expressed and secreted (RANTES), transforming growth factor-β (TGF-β), and tumor necrosis factor α (TNF-α).

In certain embodiments, pFUS therapy is administered at a sufficiently high acoustic intensity to increase expression of one or more angiogenic growth factors including, without limitation, TGF-β and MCP-1. In some embodiments, such pFUS therapy is administered in vivo to a subject to promote vascularization of pancreatic tissue. In some embodiments, such pFUS therapy is administered in vivo to a subject to promote homing of mesenchymal stem cells (MSCs).

In certain embodiments, pFUS therapy is administered at a sufficiently high acoustic intensity to increase expression of at least TNF-α, IFN-γ and IL-1β. In some embodiments, such pFUS therapy is administered in vivo to a subject to promote regeneration or replacement of pancreatic tissue.

In certain embodiments, pFUS therapy is administered at a sufficiently high acoustic intensity to increase cytokine expression of granulocyte colony-stimulating factor (GCSF), granulocyte-macrophage colony-stimulating factor (GM-CSF), growth-regulated oncogene α (GRO-α, interferon-γ (IFN-γ), interleukin-12 (IL-12) p70, interleukin-13 (IL-13), interleukin-15 (IL-15), interleukin-17α (IL-17α), interleukin-18 (IL-18), interleukin-1α (IL-1α), interleukin-1β (IL-1β), interleukin-2 (IL-2), interleukin-23 (IL-23), interleukin-28 (IL-28), IL-3, IL-31, IL-4, IL-5, IL-6, IL-9, leptin, leukemia inhibitory factor (LIF), lipopolysaccharide-induced CXC chemokine (LIX), macrophage inflammatory protein-2 (MIP-2), regulated on activation, normal T cell expressed and secreted (RANTES), transforming growth factor-β (TGF-β), and tumor necrosis factor α (TNF-α).

In certain embodiments, low-intensity pFUS is administered to the pancreas with a spatial average temporal average intensity (ISATA) of 11.5 W/cm$^2$ and a negative peak pressure (NPP) of 3 MPa. In other embodiments, high-intensity pFUS is administered to the pancreas with an ISATA of 18.5 W/cm$^2$ and an NPP of 4 MPa. In some embodiments, sufficient pFUS is administered to increase intracellular Ca$^2$ concentration and resting membrane potential (Vm) of pancreatic beta cells. In certain embodiments, the pFUS therapy is administered to beta cells with a spatial peak temporal peak intensity (ISPTP) of about 895 W/cm$^2$, a spatial average temporal average intensity (ISATA) of about 13 W/cm$^2$, and a spatial average pulse average intensity (ISAPA) of about 272 W/cm$^2$.

Use of pFUS for Stimulation and Homing of Stem Cells

Pulsed focused ultrasound therapy can also be used non-invasively for stimulation and homing of stem cells in cellular therapy applications. Stimulation of stem cells with pFUS can be performed in vivo, ex vivo, or in vitro. For example, pFUS can be used to stimulate endogenous stem cells in vivo or transplanted stem cells in vivo or ex vivo. Transplanted stem cells may be autologous, allogeneic, or xenogeneic. The pFUS may be administered to the stem cells before or after transplant or both before and after transplant. Alternatively, pFUS can be used to stimulate stem cells grown in culture in vitro.

In certain embodiments, pFUS is performed on MSCs. The MSCs may be derived from any source including, without limitation, bone marrow, adipose tissue, umbilical cord tissue, molar tooth bud tissue, and amniotic fluid.

In certain embodiments, pFUS is used to stimulate paracrine secretion of cytokines from a stem cell. The acoustic dose can be adjusted to modulate the levels of immunomodulatory cytokines, anti-inflammatory cytokines, and angiogenic cytokines that are secreted from the stem cell. In some embodiments, the acoustic dose is selected to increase expression of one or more immunomodulatory cytokines selected from the group consisting of IL31, SCF, RANTES, IFNG, MIP1B, IFNA, TNFB, GROA, IL1A, IL12P40, IL15, IL18, MCP3, ICAM1, VCAM1, IL22, and ENA78; one or more anti-inflammatory cytokines selected from the group consisting of FASL, IL1B, TGFB, IL1RA, TGFB, IL9, BDNF, TRAIL, IL10, and IFNB; and one or more angiogenic cytokines selected from the group consisting of VEGFG, VEGF, FGFB, IL2, and EOTAXIN from BM-MSCs.

In some embodiments, the acoustic dose is selected to increase expression of one or more immunomodulatory cytokines selected from the group consisting of IL31, TNFA, MCP3, LEPTIN, and CD40L; and/or one or more anti-inflammatory cytokines selected from the group consisting of FASL, MIP1A, IL1B, IL6, IL8, IL9, BDNF, IFNB, and LIF; and/or one or more angiogenic cytokines selected from the group consisting of VEGFG, VEGF, TGFA, FGFB, and PAI1 from BM-MSCs.

In some embodiments, the acoustic dose is selected to increase expression of one or more immunomodulatory cytokines selected from the group consisting of IL15, MCP3, VCAM1, and IL17F; one or more anti-inflammatory cytokines selected from the group consisting of MIP1A, IL1RA, and IFNB; and one or more angiogenic cytokines selected from the group consisting of TGFA, IL7, IL2, and EOTAXIN from AD-MSCs.

In some embodiments, the acoustic dose is selected to increase expression of one or more immunomodulatory cytokines selected from the group consisting of MCP3, ICAM1, VCAM1, LEPTIN, and IL17F; the anti-inflammatory cytokine, IFNB; and one or more angiogenic cytokines selected from the group consisting of TGFA, SDF1A, IL7, IL2, and EOTAXIN from AD-MSCs.

In some embodiments, the acoustic dose is selected to increase expression of one or more immunomodulatory cytokines selected from the group consisting of GMCSF, TNFA, MCP1, IL12P40, RESISTIN, VCAM1, LEPTIN, CD40L, and IL17F; one or more anti-inflammatory cytokines selected from the group consisting of MIP1A, IL6, IL8, LIF, and IFNB; and one or more angiogenic cytokines selected from the group consisting of HGF, VEGFG, PDGFBB, VEGF, TGFA, IL7, IL2, and EOTAXIN from UC-MSCs.

In some embodiments, the acoustic dose is selected to increase expression of one or more immunomodulatory cytokines selected from the group consisting of SCF, RANTES, TNFA, MCP1, GROA, IL1A, IL12P40, IL18, MCP3, MIG, RESISTIN, IL21, ICAM1, VCAM1, LEPTIN, CD40L, EN78, and IL17F; one or more anti-inflammatory cytokines selected from the group consisting of MIP1A, IL6, IL8, IL9, NGF, EGF, GCSF, LIF, and IFNB; and one or more angiogenic cytokines selected from the group consisting of HGF, VEGFG, PDGFBB, TGFA, SDF1A, IL5, IL7, IL2, and EOTAXIN from UC-MSCs.

In certain embodiments, the pFUS is administered to the stem cells at a low acoustic dose with a spatial average temporal average intensity (ISATA) of about 0.45 W/cm$^2$ and a negative peak pressure (NPP) of about 310 kPa. In other embodiments, the pFUS is administered to the stem cells at a high acoustic dose with an ISATA of about 1.3 W/cm$^2$ and an NPP of about 540 kPa. The effect of pFUS acoustic dose on cytokines is dependent on the source of MSCs. Bone marrow-derived MSCs show increased cytokine secretion at lower acoustic doses. Umbilical cord-derived MSCs show increased cytokine secretion at higher doses, and adipose-derived MSCs show less sensitivity to sound waves at any dose. Thus, MSCs respond to pFUS in a source-dependent manner, with each source producing a distinct cytokine profile (e.g., see Example 3 showing that under the conditions tested, the cytokine produced at the highest level by BM-MSCs was IL-15, by AD-MSCs was TGF-α and by UC-MSCs was LIF).

Use of pFUS to Stimulate Insulin Secretion and Improve Engraftment of Transplanted Beta Cells or Islets Pulsed focused ultrasound therapy can be used to stimulate insulin secretion from endogenous or transplanted beta cells. Additionally, pFUS therapy can be used non-invasively to enhance the function and engraftment of beta cells or islets following transplantation. In particular, methods are provided for treating endogenous or transplanted beta cells or islets with pFUS to stimulate insulin secretion and improve survival. Although not wishing to be bound by a particular theory, the improvement in islet function may be the result of pFUS treatment increasing the intracellular concentration of Ca$^{2+}$, which triggers the release of insulin granules by exocytosis from beta cells. In addition, treatment of tissue in the vicinity of a transplantation site with pFUS increases levels of angiogenic factors and anti-inflammatory cytokines, which enhances engraftment of transplanted beta cells or islets by facilitating islet revascularization and reducing inflammation.

For example, the pancreas and endogenous pancreatic beta cells or islets can be treated with pFUS to restore pancreatic function and improve insulin secretion from beta cells in a prediabetic or hyperglycemic subject that retains some beta cell function. The patient undergoing treatment with pFUS may have mild hyperglycemia, moderate hyperglycemia, or severe hyperglycemia. In some embodiments, the subject has lost 20% to 90% of the endogenous beta cells, including any amount of beta cells within this range, such as 20%, 25%, 30%, 35%, 40%, 45%, 50%, 55%, 60%, 65%, 70%, 75%, 80%, 85%, or 90% of the endogenous beta cells.

Alternatively, pFUS can be used to enhance engraftment and improve insulin secretion of transplanted beta cells or islets in a diabetic subject. For example, beta cells or islets can be treated with pFUS before transplantation and/or after transplantation. In some embodiments, an isolated population of islets comprising one or more types of islet cells selected from the group consisting of β-cells secreting insulin, α-cells secreting glucagon, δ-cells secreting somatostatin, ε-cells secreting ghrelin, and pancreatic polypeptide (PP) cells is treated with pFUS before and/or after transplantation. In some embodiments, a population of isolated beta cells is treated with pFUS before and/or after transplantation.

Additionally, the transplantation site can be treated with pFUS before and/or after transplantation to modulate levels of cytokines, growth factors, angiogenic factors, and cell adhesion molecules to improve vascularization and engraftment of the transplanted beta cells or islets. The transplantation site may be located, for example, in various organs or tissues including, without limitation, in the kidney, liver, omentum, peritoneum, or subcutaneous tissue of the subject.

In some embodiments, the beta cells or islets used for transplantation are obtained from the pancreas of a donor or multiple donors, a culture of beta cells or islets from a donor, or from established cell culture lines. Beta cells or islets may be obtained from the same or a different species than the subject to be treated, but preferably are of the same species, and more preferably of the same immunological profile as the subject. Such cells can be obtained, for example, by biopsy from a close relative or matched donor.

In other embodiments, the beta cells or islets used for transplantation are derived from stem cells including, without limitation, embryonic stem cells, adult stem cells (e.g., mesenchymal stem cells), or induced pluripotent stem cells, or pancreatic progenitor cells. In some embodiments, induced pluripotent stem cells are produced from a patient's own somatic cells and subsequently differentiated into beta cells or islets. Somatic cells including, without limitation, fibroblasts, keratinocytes, epithelial cells, and peripheral blood cells can be induced into forming pluripotent stem cells, for example, by treating them with reprograming factors such as Yamanaka factors, including but not limited to, OCT3, OCT4, SOX2, KLF4, c-MYC, NANOG, and LIN28 (see, e.g., Takahashi et al. (2006) Cell 126 (4):663-676, herein incorporated by reference).

Methods for introducing a cell reprogramming factor into somatic cells are not limited in particular, and known procedures can be selected and used as appropriate. For example, when a cell reprogramming factor as described above is introduced into somatic cells of the above-mentioned type in the form of proteins, such methods include ones using protein introducing reagents, fusion proteins with protein transfer domains (PTDs), electroporation, and microinjection. When a cell reprogramming factor as described above is introduced into somatic cells of the above-mentioned type in the form of nucleic acids encoding the cell reprogramming factor, a nucleic acid(s), such as cDNA(s), encoding the cell reprogramming factor can be inserted in an appropriate expression vector comprising a promoter that functions in somatic cells, which then can be introduced into somatic cells by procedures such as infection, lipofection, liposomes, electroporation, calcium phosphate coprecipitation, DEAE-dextran, microinjection, and electroporation.

Examples of an "expression vector" include viral vectors, such as lentiviruses, retroviruses, adenoviruses, adeno-associated viruses, and herpes viruses; and expression plasmids for animal cells. For example, retroviral or Sendai virus (SeV) vectors are commonly used to introduce a nucleic acid(s) encoding a cell reprogramming factor as described above into somatic cells.

After in vitro expansion, the induced pluripotent stem cells can be differentiated into beta cells in a step-wise manner by culturing the induced pluripotent stem cells in the presence of an activator of protein kinase C (PKC) signaling (e.g., phorbol 12,13-dibutyrate), growth factors (e.g., keratinocyte growth factor), a hedgehog inhibitor (e.g., SANT1), and retinoic acid to promote differentiation into pancreatic progenitors, which are subsequently treated with an inhibitor of the BMP signaling pathway (e.g., LDN193189) to generate insulin-producing cells. For beta cell differentiation protocols, see, e.g., Rezania et al. (2014) Nat. Biotechnol. 32:1121-1133, Ghazizadeh et al. (2017) Nat Commun 8:298, Velazco-Cruz et al. (2019) Stem Cell Reports 12:351-365, Nair et al. (2019) Nat Cell Biol 21:263-274, Pagliuca et al. (2014) Cell 159:428-439, Kieffer et al. (2016) Cell Stem Cell 18:699-702, Dadheech et al. (2019) Adv. Exp. Med. Biol. 1144:25-35, Millman et al. (2016) Nat. Commun. 7:11463, Tremmel et al. (2019) Curr. Opin. Organ Transplant. 24(5): 574-581; herein incorporated by reference in their entireties.

In some embodiments, stem cells are co-transplanted with beta cells or islets to further improve beta cell or islet function and viability. In order for the beta cells to benefit from the stem cells, the two cell types need to be in proximity to each other at the transplantation site. Without being bound by a particular theory, islets or beta cells transplanted in proximity to stem cells may benefit from paracrine factors secreted by the stem cells. In some embodiments, the beta cells or islets are cocultured with stem cells prior to transplantation to allow the stem cells to attach to and coat the beta cells or islets. The beta cells or islets coated with the stem cells can then be implanted together at the transplantation site to ensure there is sufficiently close contact with the stem cells for the beta cells or islets to benefit from the stem cell paracrine factors.

The stem cells are chosen for their ability to promote insulin production and engraftment of transplanted beta cells or islets. The ability of the stem cells to assist the beta cells or islets in this manner can be improved by treating the stem cells with pFUS before and/or after transplantation to stimulate paracrine secretion of various factors including, without limitation, cytokines, growth factors, angiogenic factors, and cell adhesion molecules. The stem cells may be obtained directly from the patient to be treated, a donor, a culture of cells from a donor, or from established cell culture lines. In some embodiments, the stem cells are mesenchymal stem cells (MSCs). The MSCs may be derived from any source including, without limitation, bone marrow, adipose tissue, umbilical cord tissue, molar tooth bud tissue, and amniotic fluid.

In some embodiments, the beta cells or islets and/or stem cells (e.g., MSCs) are encapsulated in a biocompatible carrier, matrix, or scaffold that can be implanted in a subject. The carrier, matrix, or scaffold can be predominantly non-immunogenic and biodegradable. In some embodiments, the matrix is biodegradable over a time period of less than a year, less than six months, less than a month, or two to ten weeks. Compositions comprising encapsulated beta cells or islets and/or stem cells are suitable for local delivery to a transplantation site, for example, in the kidney, liver, omentum, peritoneum, or subcutaneous tissue of the subject.

Preferably, the beta cells and/or stem cells are encapsulated in a very thin membrane or conformal coating to minimize capsule size and graft volume. A conformal coating is used to minimize capsule thickness, which allows the beta cells or islets to engraft in smaller spaces. Using a conformal coating also helps to sustain beta cell and islet function by facilitating the rapid diffusion of oxygen and nutrients into the capsule through the thin coating, as well as allowing the insulin, secreted by the beta cells in response to glucose, to be readily released from the capsule. In certain embodiments, the conformal coating has a thickness ranging from about 25 μm to about 100 μm, including any thickness within this range such as 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, or 100 μm. For a description of techniques for applying a conformal coating to islets, see, e.g., Tomei et al. (2014) Proc Natl Acad Sci U.S.A. 111(29): 10514-10519, Kizilel et al. (2010) Tissue Eng Part A 16(7): 2217-2228, Teramura et al. (2007) Biomaterials 28(32): 4818-4825, Hill et al. (1997) Ann N Y Acad Sci. 831:332-343; herein incorporated by reference.

In some embodiments, beta cells/islets and stem cells (e.g., MSCs) are co-encapsulated by coating the cells with a hydrogel-based conformal coating. A hydrogel is defined as a substance formed when an organic polymer (natural or synthetic) is cross-linked via covalent, ionic, or hydrogen bonds to create a three-dimensional open-lattice structure, which entraps water molecules to form a gel. In general, the polymers used to form hydrogels are at least partially soluble in aqueous solutions, such as water, buffered salt solutions, or aqueous alcohol solutions that have charged side groups, or a monovalent ionic salt thereof. Exemplary hydrogel-forming molecules include glycoproteins, carbohydrates, and other macromolecules, including, but not limited to, alginate, collagen, fibrin, fibronectin, chitosan, laminin, hyaluronic acid, chondroitin sulfate, heparan sulfate, dermatan sulfate, agarose, gelatin, cellulose, and carboxymethyl cellulose; and synthetic macromolecules such as polyethylene glycol, polyvinyl pyrrolidone, polyvinyl alcohol, polyacrylates, polylactic acid, polyglycolic acid, and poly(lactic-co-glycolic acid. Collagen I, elastin and engineered elastin-like proteins, and fibrin can be used for producing protein hydrogels.

In certain embodiments, the hydrogel used for encapsulation of cells comprises alginate. Alginate is a linear copolymer containing blocks of (1,4)-linked β-D-mannuronate and α-L-guluronate residues. Alginates extracted from various sources may be used for encapsulation of cells, including, without limitation, alginates from algae (e.g., seaweeds and kelps) such as *Laminaria, Macrocystis* (e.g., *Macrocystis pyrifera*), Ascophyllum (e.g., Ascophyllum *nodosum*), *Ecklonia, Lessonia*, and Durvillea; and bacterial alginates from *Pseudomonas* and *Azotobacter*. Depending on the source, the alginate copolymer may differ in the amounts of the (1,4)-linked β-D-mannuronate and α-L-guluronate present and the length of each polymer block. The molecular weight of the alginate copolymer may range between 32,000 g/mol and 400,000 g/mol. The alginate in the hydrogel can be ionically cross-linked with divalent cations (e.g., calcium ($Ca^{2+}$) crosslinked alginate hydrogel encapsulating beta cells or islets and MSCs). In some embodiments, the alginate concentration in the hydrogel ranges from about 2 to about 10 percentage by weight (wt %), including any wt % within this range, such as 2, 2.5, 3, 3.5, 4, 4.5, 5, 5.5, 6, 6.5, 7, 7.5, 8, 8.5, 9, 9.5, or 10 wt %. In some embodiments, the alginate is partially oxidized. For example, about 2% to about 10% of the alginate may be oxidized, including any percent in this range, such as 2%, 2.5%, 3%, 3.5%, 4%, 4.5%, 5%, 5.5%, 6%, 6.5%, 7%, 7.5%, 8%, 8.5%, 9%, 9.5%, or 10%.

A medical practitioner may locate the site to be implanted or treated with pFUS, for example, by medical imaging (e.g. ultrasound, radiography, or MRI). In some embodiments, a contrast agent is included in the composition comprising the encapsulated beta cells or islets and/or stem cells to allow confirmation of the location of the transplanted cells by medical imaging after implantation. In some embodiments, the contrast agent is a microbubble (e.g., for use in ultrasound) or a radiopaque contrast agent (e.g., for use in radiography). The contrast agent may be contained in the same composition as the beta cells or islets or in a different composition and used prior to or after transplantation.

In some embodiments, sufficient pFUS is administered to increase intracellular $Ca^{2+}$ concentration and resting membrane potential (Vm) of the beta cells. In certain embodiments, the pFUS therapy is administered to beta cells or islets with a spatial peak temporal peak intensity (ISPTP) of about 895 W/cm$^2$, a spatial average temporal average intensity (ISATA) of about 13 W/cm$^2$, and a spatial average pulse average intensity (ISAPA) of about 272 W/cm$^2$.

Multiple cycles of pFUS therapy may be administered to beta cells or islets. In some embodiments, pFUS therapy is administered for at least 1 week, at least 2 weeks, at least 3 weeks, or at least 4 weeks following transplantation of beta cells or islets, or longer until the subject establishes glycemic control.

Administration

At least one therapeutically effective dose of pFUS therapy will be administered, to pancreatic tissue, and/or beta cells, and/or islets, and/or stem cells (e.g., MSCs), and/or beta cells or islets co-encapsulated with stem cells (e.g., alginate hydrogel co-encapsulating beta cells or islets and MSCs), and/or tissue in the vicinity of a transplantation site for beta cells or islets (e.g., in the kidney, liver, omentum, peritoneum, or subcutaneous tissue of the subject). By "therapeutically effective dose or amount" of pFUS therapy is intended an amount that when administered brings about a positive therapeutic response with respect to treatment of an individual for a pancreatic disorder or pancreatic damage, such as caused by acute pancreatic injury or chronic pancreatic diseases such as diabetes, pancreatitis, and pancreatic cancer. Of particular interest is an amount of pFUS therapy that promotes regeneration of damaged pancreatic tissue, and/or improves insulin secretion by endogenous or transplanted beta cells or islets in response to glucose, or promotes engraftment and revascularization of transplanted beta cells or islets. Additionally, administering pFUS, as described herein, may be used to modulate gene expression and/or paracrine secretion (e.g., alter levels of pro-inflammatory cytokines, anti-inflammatory cytokines, growth factors, angiogenic factors, cell adhesion factors, and the like) or for homing of stem cells.

Thus, for example, a "positive therapeutic response" would be an improvement in pancreatic function or beta cell or islet function in association with the pFUS therapy, and/or an improvement in one or more symptoms of a pancreatic disease in association with the pFUS therapy. In patients with type 1 diabetes, such improvements may include increased insulin content within beta cells or islets and improved ability of beta cells or islets to release insulin in response to glucose. Such improvements in islet function may result from pFUS stimulating insulin secretion from endogenous or transplanted beta cells or islets, which, in turn, will improve maintenance of blood glucose levels within normal limits.

In certain embodiments, multiple therapeutically effective doses of pFUS therapy will be administered to the pancreatic tissue, and/or beta cells, and/or islets, and/or stem cells (e.g., MSCs), and/or beta cells or islets co-encapsulated with stem cells (e.g., alginate hydrogel co-encapsulating beta cells or islets and MSCs), and/or tissue in the vicinity of a transplantation site for beta cells or islets (e.g., in the kidney, liver, omentum, peritoneum, or subcutaneous tissue of the subject). For example, a therapeutically effective dose can be administered, one day a week, two days a week, three days a week, four days a week, or five days a week, and so forth. By "intermittent" administration is intended the therapeutically effective dose can be administered, for example, every other day, every two days, every three days, and so forth. For example, in some embodiments, pFUS will be administered twice-weekly or thrice-weekly for an extended period of time, such as for 1, 2, 3, 4, 5, 6, 7, 8 . . . 10 . . . 15 . . . 24 weeks, and so forth. By "twice-weekly" or "two times per week" is intended that two therapeutically effective doses of pFUS is administered to the subject within a 7-day period, beginning on day 1 of the first week of administration, with a minimum of 72 hours, between doses and a maximum of 96 hours between doses. By "thrice weekly" or "three times per week" is intended that three therapeutically effective doses are administered to the subject within a 7-day period, allowing for a minimum of 48 hours between doses and a maximum of 72 hours between doses. For purposes of the present disclosure, this type of dosing is referred to as "intermittent" therapy. In accordance with the methods of the present invention, a subject can receive intermittent therapy (i.e., twice-weekly or thrice-weekly administration of a therapeutically effective dose) for one or more weekly cycles until the desired therapeutic response is achieved.

In some embodiments, pFUS is administered in combination with transplantation of beta cells or islets, stem cell therapy, or administration of therapeutic agents. Thus, pFUS in combination with transplantation of beta cells or islets and/or stem cell therapy and/or therapeutic agents can be presented to the individual by way of concurrent therapy. By "concurrent therapy" is intended administration to a human subject such that the therapeutic effect of the combination of pFUS with other agents is caused in the subject undergoing therapy. For example, one or more therapeutically effective doses of pFUS may be administered after transplantation (e.g., within the first 2 weeks after transplantation of beta cells or islets) to promote engraftment and vascularization of beta cells or islets. In some embodiments, pFUS therapy is administered prior to, concurrent with, or subsequent to administration of therapeutic agents.

Multiple cycles of pFUS may be performed on a single region of a target organ (e.g., pancreas or other organ where beta cells or islets are transplanted (e.g., kidney or liver) or two or more different regions of the target organ. For example, multiple overlapping or non-overlapping regions in the pancreas or in the vicinity of a transplantation site for beta cells or islets can be treated with pFUS. In some embodiments, non-overlapping adjacent regions in the target organ are treated with pFUS.

The pFUS may be coupled with imaging guidance (e.g., ultrasound or magnetic resonance imaging) to correctly position the delivery of sound waves and to avoid causing effects on intervening tissues. In some embodiments, imaging is used to focus sound waves within a relatively small focal zone (e.g., typically 1 mm×1 mm×10 mm) to treat particular cells (e.g., beta cells, islets, or stem cells) or structures within the body. For example, imaging can be used to focus sound waves at the site of transplantation of beta cells or islets. Additionally, imaging can be used to select damaged regions in the pancreas in need of treatment with pFUS.

In certain embodiments, pFUS is administered with an ultrasound frequency ranging from about 20 kHz to about 5.0 MHz, about 0.7 MHz to about 3.0 MHz, or about 1.0 MHz to about 1.1 MHz, including any ultrasound frequency within these ranges, such as 0.2, 0.4, 0.6, 0.8, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 3.0, 3.2, 3.4, 3.6, 3.8, 4.0, 4.2, 4.4, 4.6, 4.8, or 5.0 MHz.

In certain embodiments, pFUS is administered with a PRF ranging from 0.1 Hz to 1000 Hz, 1 Hz to 100 Hz, or about 5 Hz to 20 Hz, or any PRF with these ranges, such as 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, or 1000 Hz.

In certain embodiments, pFUS is administered with an ultrasound duty cycle ranging from 0.01% to 100% or 1% to 20%, including any ultrasound duty cycle within these ranges such as 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 90%, 95%, or 100%. In some embodiments, the pFUS is administered with an ultrasound duty cycle of about 5%. In some embodiments, the pFUS therapy is administered with an ultrasound duty cycle of less than 1%.

In certain embodiments, pFUS may be administered with a negative peak pressure (NPP) ranging from 0.1 MPa to 10 MPa, including any NPP within this range such as 0.1, 0.2, 0.3, 0.4, 0.5, 0.6, 0.7, 0.8, 0.9, 1, 2, 3, 4, 5, 6, 7, 8, 9, or 10 MPa. In some embodiments, the pFUS is administered with a negative peak pressure (NPP) of up to 3 MPa. In some embodiments, the NPP is about 2.9 MPa.

In certain embodiments, pFUS is administered to the subject for a time ranging from about 20 seconds to about 7 minutes, including any amount of time within this range, such as 20 seconds, 25 seconds, 30 seconds, 35 seconds, 40 seconds, 45 seconds, 50 seconds, 55 seconds, 1 minute, 1.25 minutes, 1.5 minutes, 1.75 minutes, 2 minutes, 2.25 minutes, 2.5 minutes, 2.75 minutes, 3 minutes, 3.25 minutes, 3.5 minutes, 3.75 minutes, 4 minutes, 4.25 minutes, 4.5 minutes, 4.75 minutes, 5 minutes, 5.25 minutes, 5.5 minutes, 5.75 minutes, 6 minutes, 6.25 minutes, 6.5 minutes, 6.75 minutes, or 7 minutes. In some embodiments, the pFUS therapy is administered to the subject for at least 20 seconds. In some embodiments, the pFUS therapy is administered to the subject for a period ranging from about 1 minute to about 5 minutes. In one embodiment, the pFUS therapy is administered to the subject for about 160 seconds.

In certain embodiments, pFUS is administered with a pulse length of about 10 milliseconds.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Effect of Pulsed Focused Ultrasound on the Native Pancreas

Pulsed focused ultrasound (pFUS) utilizes short cycles of sound waves to mechanically shake cells within tissues which, in turn, causes transient local increases in cytokines, growth factors and cell adhesion molecules. Although the effect of pFUS has been investigated in several different organs including the kidney, muscle and heart, its effect on the pancreas has not been investigated. In the present work, we applied pFUS to the rodent pancreas with the following parameters: 1.1-MHz frequency, 5-Hz pulse repetition frequency, 5% duty cycle, 10-ms pulse length, 160-s duration. Low-intensity pFUS had a spatial average temporal average intensity of 11.5 W/cm$^2$ and a negative peak pressure of 3 MPa; high-intensity pFUS had a spatial average temporal average intensity of 18.5 W/cm$^2$ and negative peak pressure of 4 MPa. Here we found that pFUS changed the expression of several cytokines while having no effect on the underlying tissue histology or health of pancreatic cells (as reflected by no significant change in plasma levels of amylase and lipase). Furthermore, we found that this effect on cytokine expression in the pancreas was acoustic intensity dependent; while pFUS at low intensities turned off the expression of several cytokines, at high intensities, it had the opposite effect and turned on the expression of these cytokines. The ability to non-invasively manipulate the microenvironment of the pancreas using sound waves could have profound implications for priming and modulating this organ for the application of cellular therapies in the context of both regenerative medicine (i.e., diabetes and pancreatitis) and oncology (i.e., pancreatic cancer).

Methods pFUS on the Pancreas

Figure 1B:
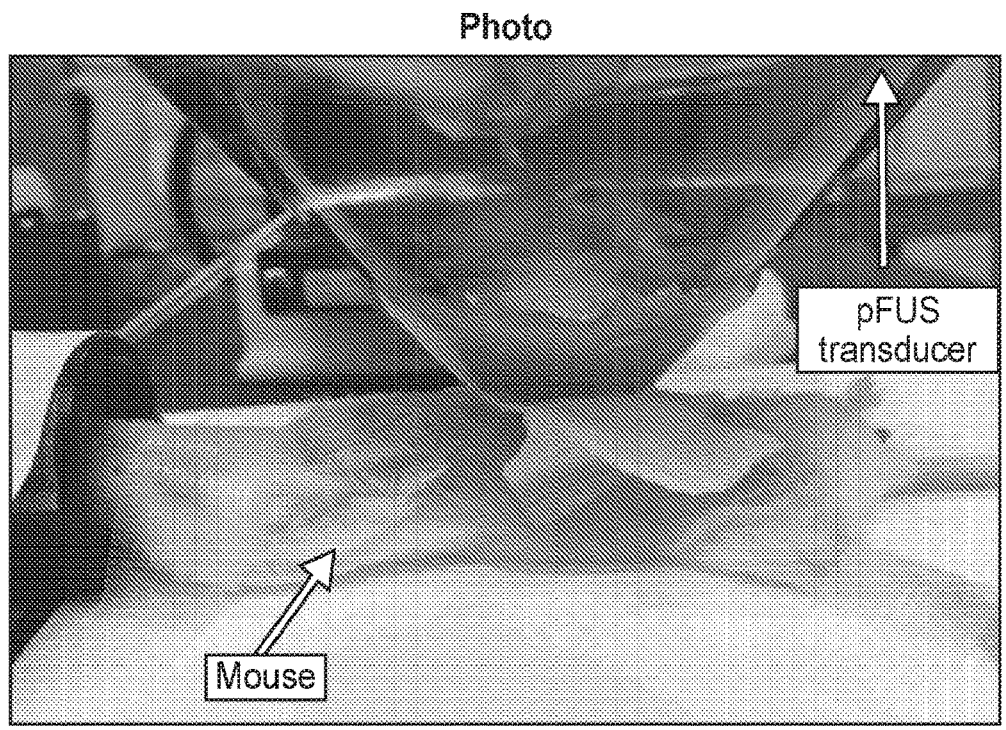
Figure 1C:
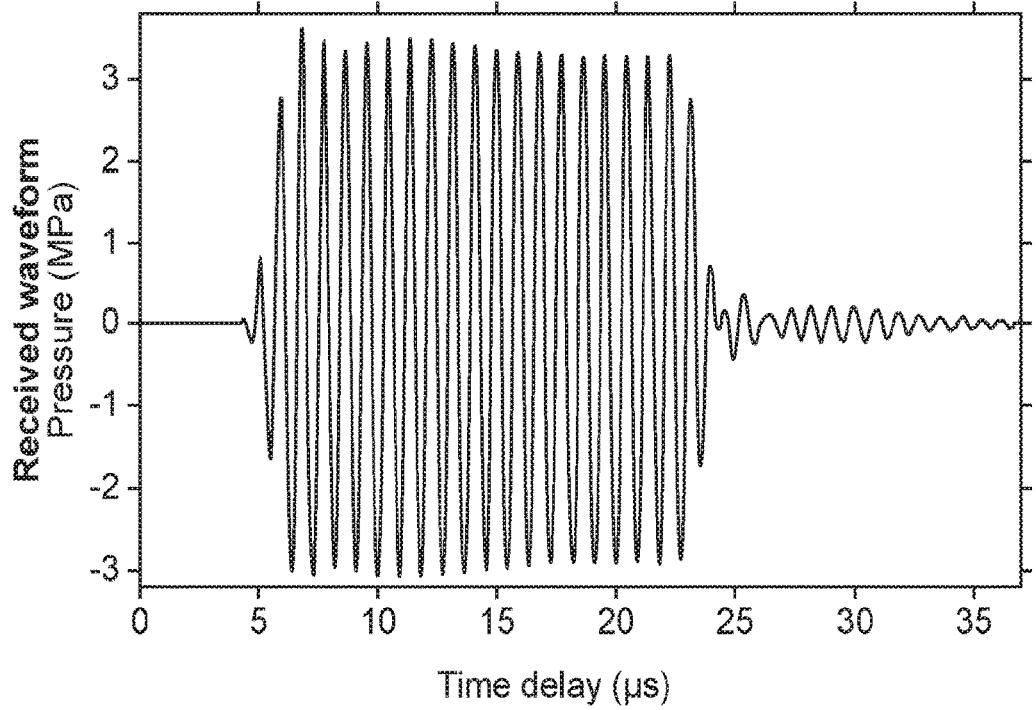
Figure 1D:
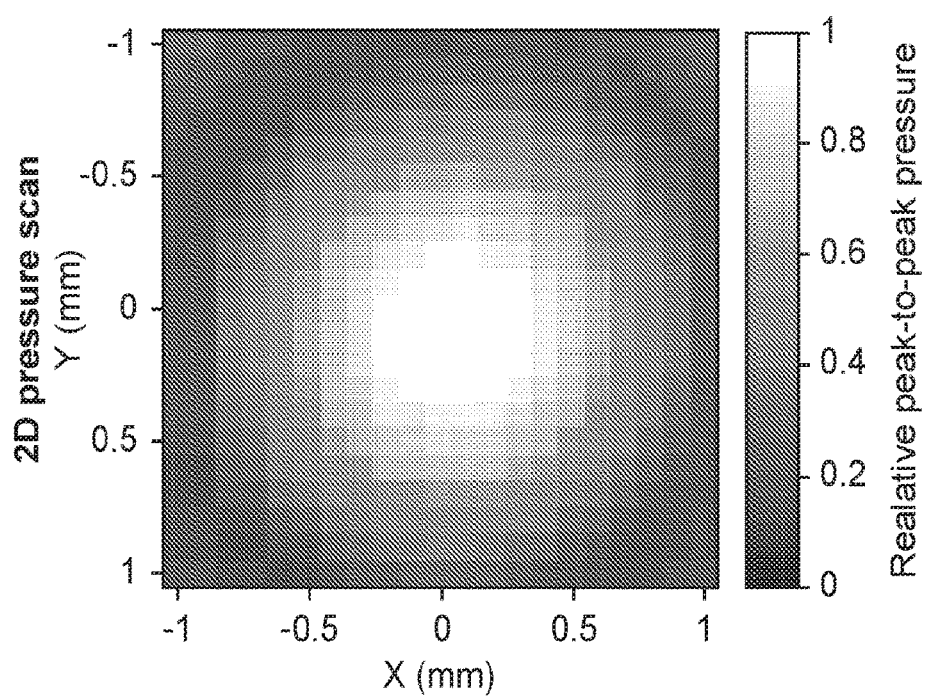

Setup. A therapeutic pFUS transducer (H-102 NRE, Sonic Concepts, Bothell, WA, USA) with a central frequency of 1.1 MHz, focal length of 55 mm, aperture diameter of 64 mm and central opening of 49 mm was used. This transducer was driven by a function generator (Agilent 33250 A, Santa Clara, CA, USA), which was connected to a 50-dB linear power amplifier (ENI 525 LA, Rochester, NY, USA) and an impedance matching circuit (Sonic Concepts). The transducer was then calibrated in a water tank filled with degassed water. To excite the transducer during calibration, a "burst" mode consisting of a 1.1-MHz frequency with 20 cycles at a 100-Hz pulse repetition frequency (PRF) was used. A hydrophone (HNR-0500, Onda, Sunnyvale, CA, USA) was placed in the focal spot of the transducer, and an Acoustic Intensity Measurement System (AIMS III, Onda) was used for precise movement and positioning of the hydrophone as well as to obtain digitized waveforms from the oscilloscope (Agilent DSO6012 a). To guide pFUS, the therapeutic transducer was fitted in a custom coupling cone filled with degassed water (FIGS. 1A, 1B). The coupling cone (Sonic Concepts) was made of light transparent plastic to provide acoustic coupling between the pFUS transducer and pancreas. The cone dimensions were matched with the size and form of the H102-NRE transducer. In all experiments, the coupling cone was filled with degassed, deionized water. The measured beam profile (full width half-maximum area for pressure) at the focal area was 10 mm long and 1.5 mm in diameter. Intensity and pressure measurements were performed for negative peak pressures (NPPs) up to 3 MPa to reduce the risks of hydrophone damage. The obtained intensities and NPP values were then scaled to the desired PRF and duty cycle and extrapolated to higher pressures/intensities. A typical waveform and 2-D pressure map are provided in FIGS. 1C and 1D. The temperature rise during pFUS was estimated by measuring the thermal index ($T_1$) in degassed, deionized water using a hydrophone.

Treatment. Female CD1 mice (7-9 weeks of age, 28-36 g) were used in all of our studies. Animals were housed under conventional conditions having access to food and water ad libitum. The care for all mice within the study was in accordance with the guidelines approved by the Institutional Animal Care and Use Committee at Stanford University. During the procedure, mice were anesthetized with isoflurane (2.5% in $O_2$) and placed in the supine position. Body hair of mice was then removed with depilatory cream, and the skin was disinfected. A transverse incision was made on the left upper abdomen to expose the stomach and spleen, which were covered with sterile phosphate-buffered saline-wetted gauze immediately after exposure. The tip of the transducer was then placed above the pancreas and coupled to the organ with ultrasound gel (Aquasonic, Bio-Medical Instruments, Clinton Charter Township, MI, USA). Eight evenly distributed foci throughout the pancreas were treated with pFUS. The duration of each sonication was 20 s with less than 5 s between sonications. The distance between spots was kept at 1 mm in both the x- and y-directions. The following ultrasound parameters were used: 1.1-MHz frequency, 5-Hz pulse repetition frequency, 5% duty cycle, 10-ms pulse length, 160-s duration, low-intensity pFUS having a spatial average temporal average intensity (ISATA) of 11.5 W/cm$^2$ and 3 MPa negative peak pressure (NPP) of 3 MPa, and high-intensity pFUS having an ISATA of 18.5 W/cm$^2$ and a NPP of 4 MPa. For control animals, the pancreas was exposed and coupled to the transducer with ultrasound gel in the same way, but these animals received sham pFUS with no power delivered to the transducer. The selection of our pFUS parameters was based on previous literature indicating these parameters were tolerable and effective on mouse muscle (Burks et al. 2011), mouse kidney (Ziadloo et al. 2012) and rat heart (Jang et al. 2017). After pFUS treatment, the skin incision was sutured, and animals were left to recover.

Mice were randomly allocated to a total of six experimental groups (n=6 per group) consisting of three groups (group 1: sham/control; group 2: low-intensity pFUS; group 3: high-intensity pFUS) at two time points (4 and 24 h). At each time point, mice were euthanized by $CO_2$ inhalation, and pancreases harvested for histologic and molecular analyses.

Histologic Analysis of pFUS-Treated Pancreases

After harvesting of the pancreas, a section of the treated gland was fixed in 10% (v/v) neutral buffered formalin, embedded in paraffin, sectioned (5 mm thick) using a HM 355 S automatic microtome (ThermoFisher Scientific, Waltham, MA, USA) and stained with hematoxylin and eosin (H&E). Immunohistochemistry was also undertaken on pancreatic tissue sections using primary antibodies (Ab-Cam) including guinea pig polyclonal antibodies to insulin (1:50) and mouse monoclonal antibodies to glucagon (1:50). All stained sections were then scanned using a NanoZoomer (Hamamatsu Photonics, Hamamatsu, Japan). To detect apoptotic cells, terminal deoxynucleotidyl transferase deoxyuridine triphosphate (dUTP) nick end labeling (TUNEL) staining was also performed using a fluorescein-based in situ cell death detection kit (Roche Applied Science, Penzberg, Germany) according to the manufacturer's protocol.

Molecular Analysis of pFUS-Treated Pancreases

After harvesting of the pancreas, a section of the treated pancreas was frozen using liquid nitrogen and homogenized using a tissue protein extraction reagent (ThermoFisher Scientific) containing a protease inhibitor cocktail (Sigma-Aldrich, St. Louis, MO, USA) and phenylmethanesulfonyl fluoride (PMSF, Sigma-Aldrich). Homogenized tissues were then centrifuged at 15,000 rpm for 20 min at 4° C., and the supernatants collected. To determine the total protein content, the supernatants were analyzed using bicinchoninic acid assay (ThermoFisher Scientific). Supernatants with a total protein content of 3 mg/mL were then analyzed with multiplex enzyme-linked immunosorbent assays (ELISAs). For multiplex ELISAs, mouse 39 plex kits (ThermoFisher Scientific) were used according to the manufacturer's protocol.

Serum Markers of Pancreatic Damage after pFUS

At the time of euthanasia, blood samples were collected from all groups of animals and centrifuged, and the supernatants collected. Serum levels of amylase and lipase were then measured as indicators of pancreatic enzyme activity using the AMY Flex reagent cartridge and LIPL Flex reagent cartridge (Sigma-Aldrich), respectively. Animals that did not undergo any operation were used as the control group for time 0 h.

Statistical Analysis

All experiments were performed with 4-6 animals, and the results are expressed as means § standard errors of the mean. Statistical analysis of all quantitative data was performed using a one- or two-way analysis of variance with post hoc Tukey tests (Prism GraphPad Software, San Diego, CA, USA, or Astatsa.com; Online Web Statistical Calculators, Mountain View, CA, USA) with any differences considered statistically significant when p<0.05.

Results

Histologic Analysis of pFUS-Treated Pancreases

Figure 2:
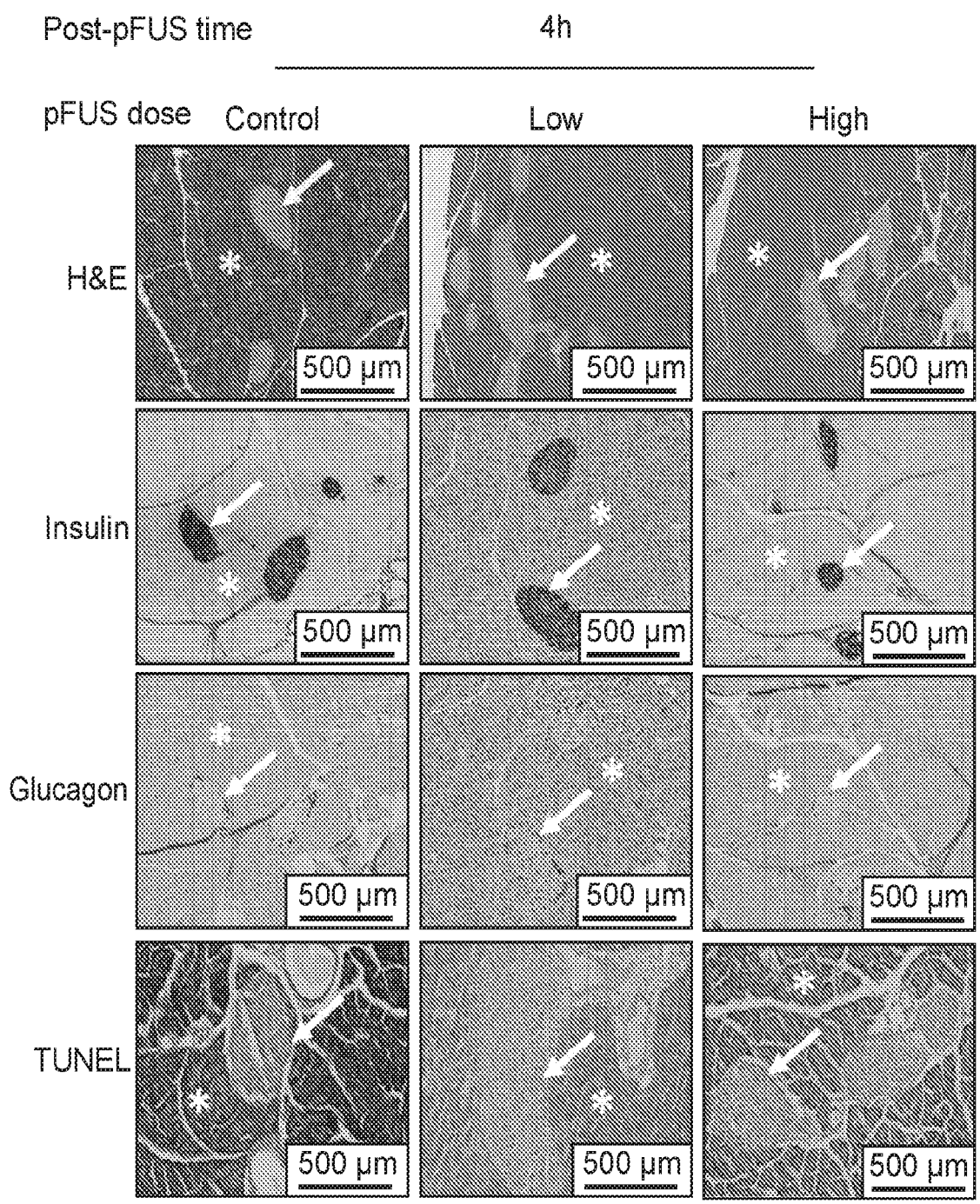
FIG. 2. Histologic analysis of pulsed focused ultrasound (pFUS)-treated pancreases. Samples of pFUS-treated pancreases stained with hematoxylin and eosin, insulin, glucagon and TUNEL (terminal deoxynucleotidyl transferase dUTP nick end labeling). Asterisks indicate the exocrine, and arrows the endocrine (i.e., islets), components of the pancreas.
Figure 2:
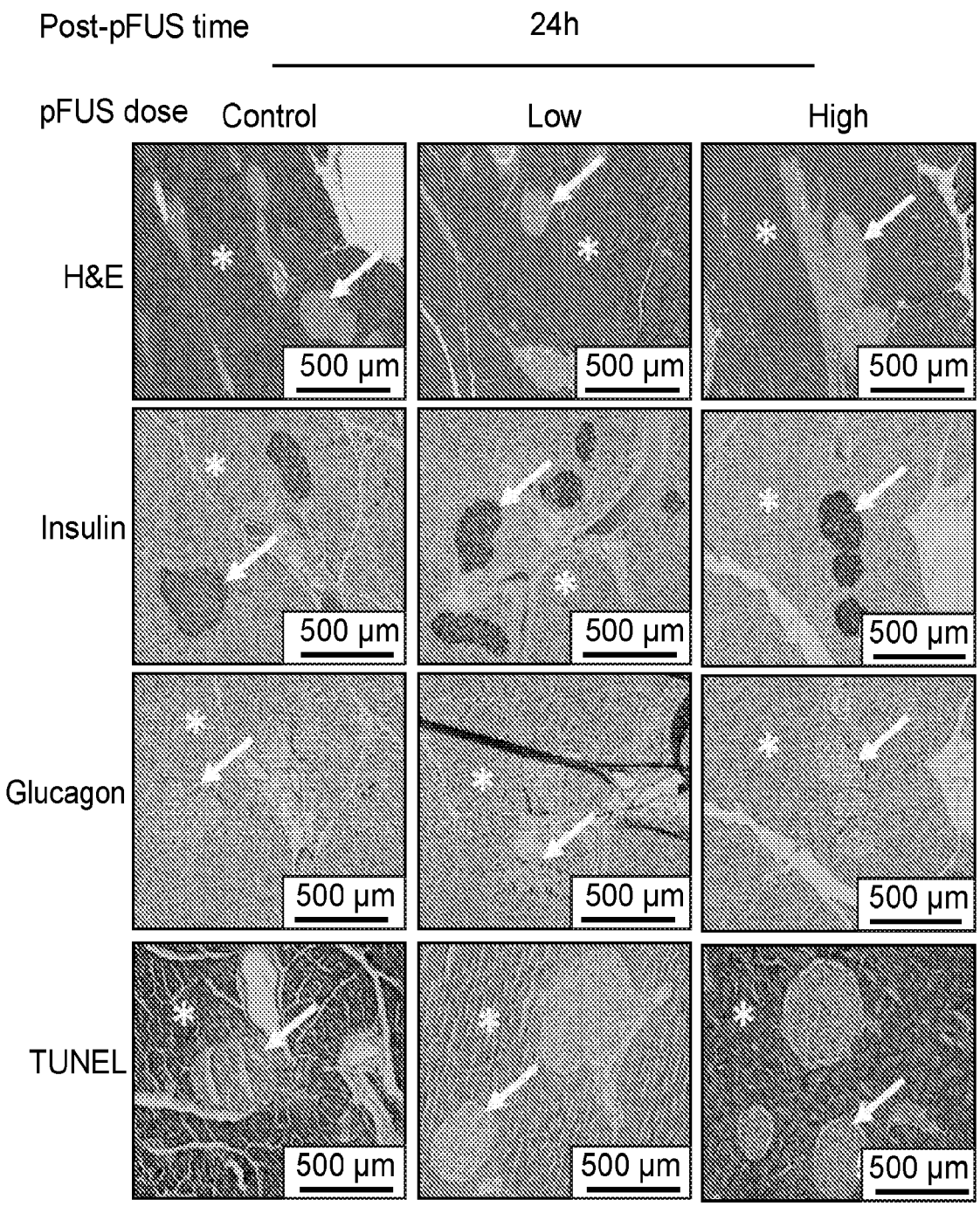

No significant changes were seen after histologic analysis of either the exocrine or endocrine (i.e., islets) component of the pancreas after pFUS treatment. In mice exposed to low and high acoustic intensities of pFUS, the morphologic integrity of pancreatic islets was highly preserved. After pFUS, islets manifested expression of insulin and glucagon similar to control animals. According to the TUNEL assay, there was also no evidence of any increased apoptosis in pancreatic tissue samples after pFUS treatment at both low and high acoustic intensities (FIG. 2).

Molecular Analysis of pFUS-Treated Pancreases

Figure 3:
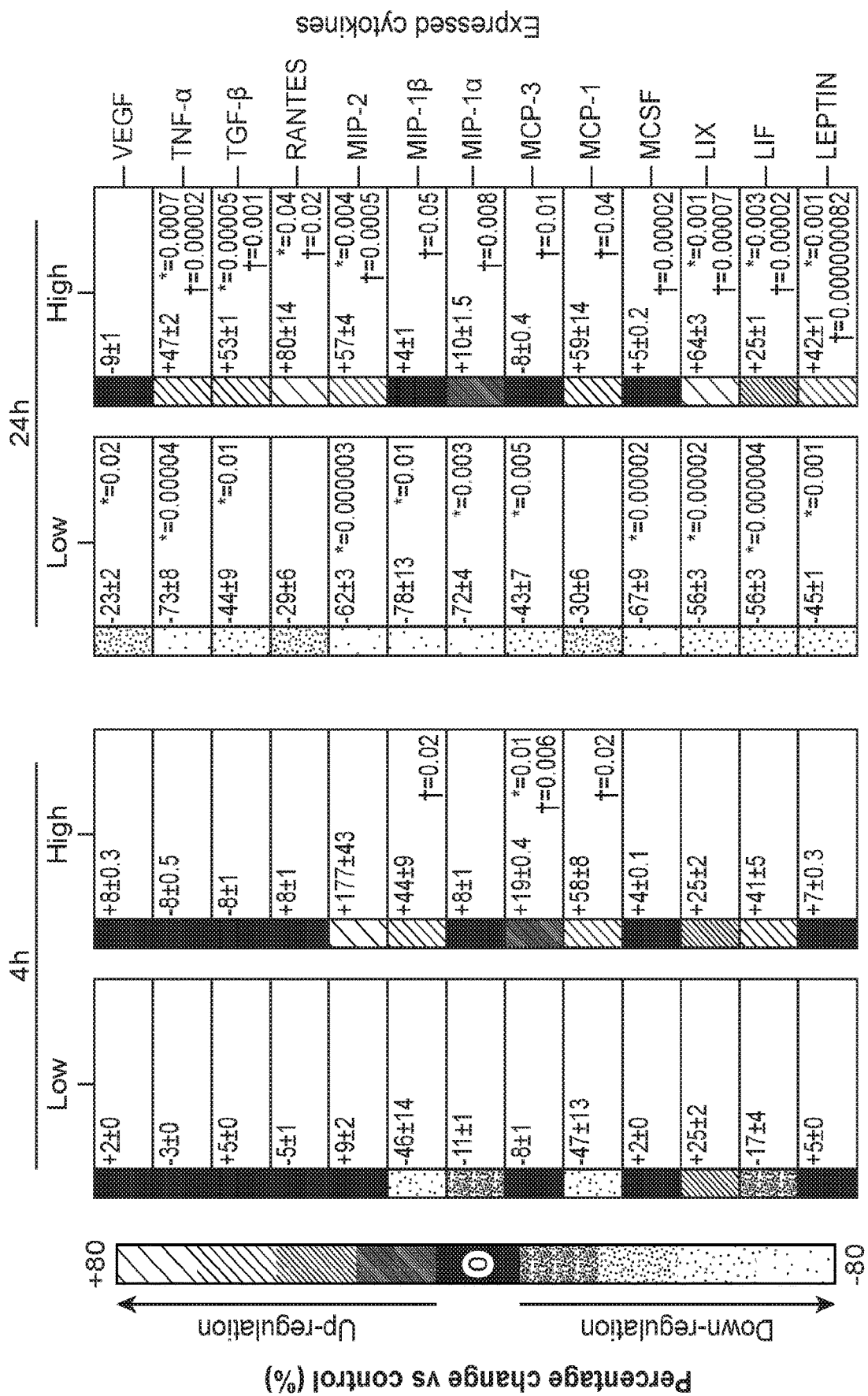
FIG. 3. Molecular analysis of pulsed focused ultrasound (pFUS)-treated pancreases. Molecular expression profile of the pancreas after pFUS treatment relative to that of control mice. In each box, the left-side values are means±standard errors of the mean, and right-side values are p values. Significant differences: *$p<0.05$: pFUS-treated pancreas versus control. †$p<0.05$: high dose versus low dose (two-way analysis of variance post hoc Tukey test).
Figure 3:
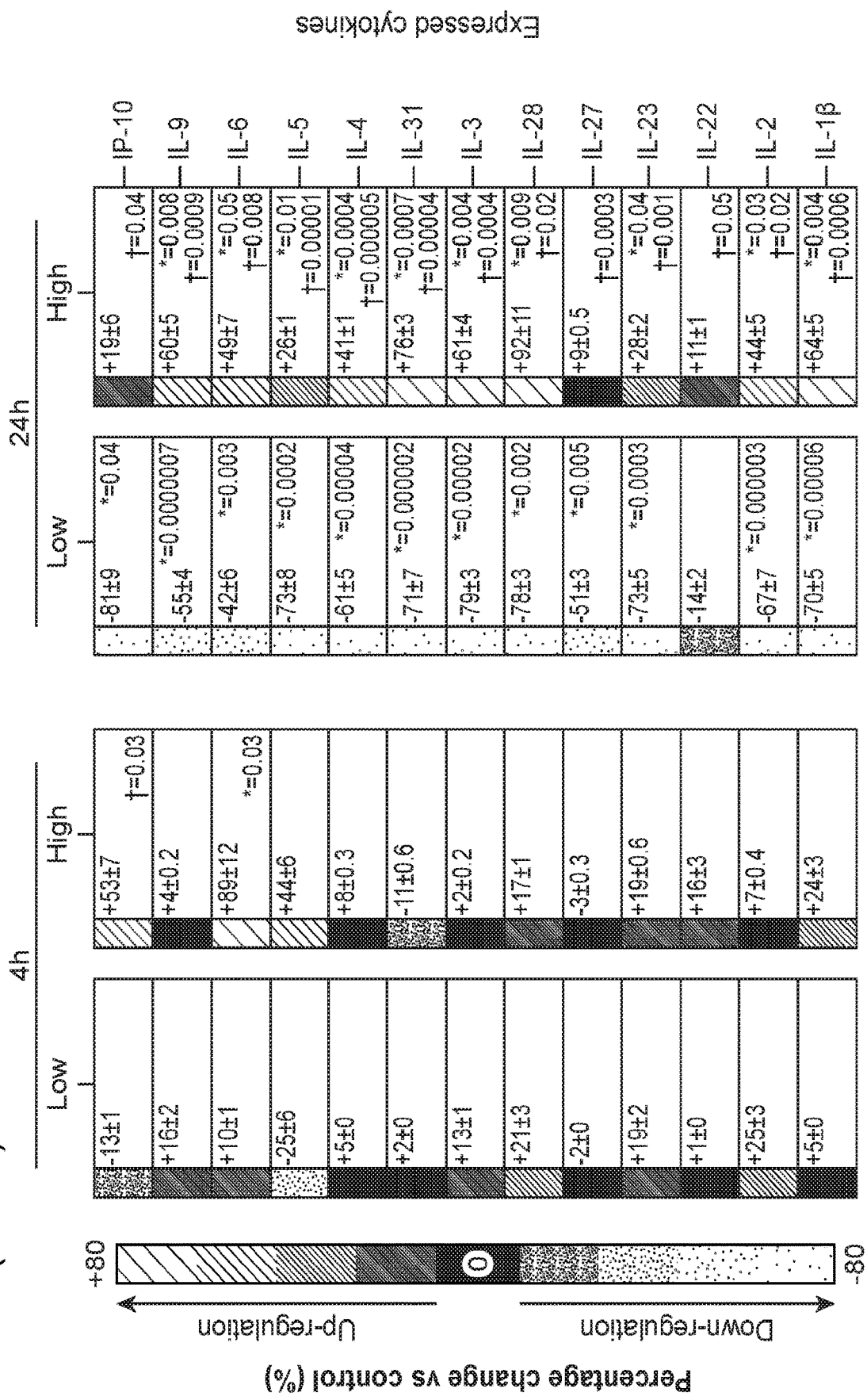
Figure 3:
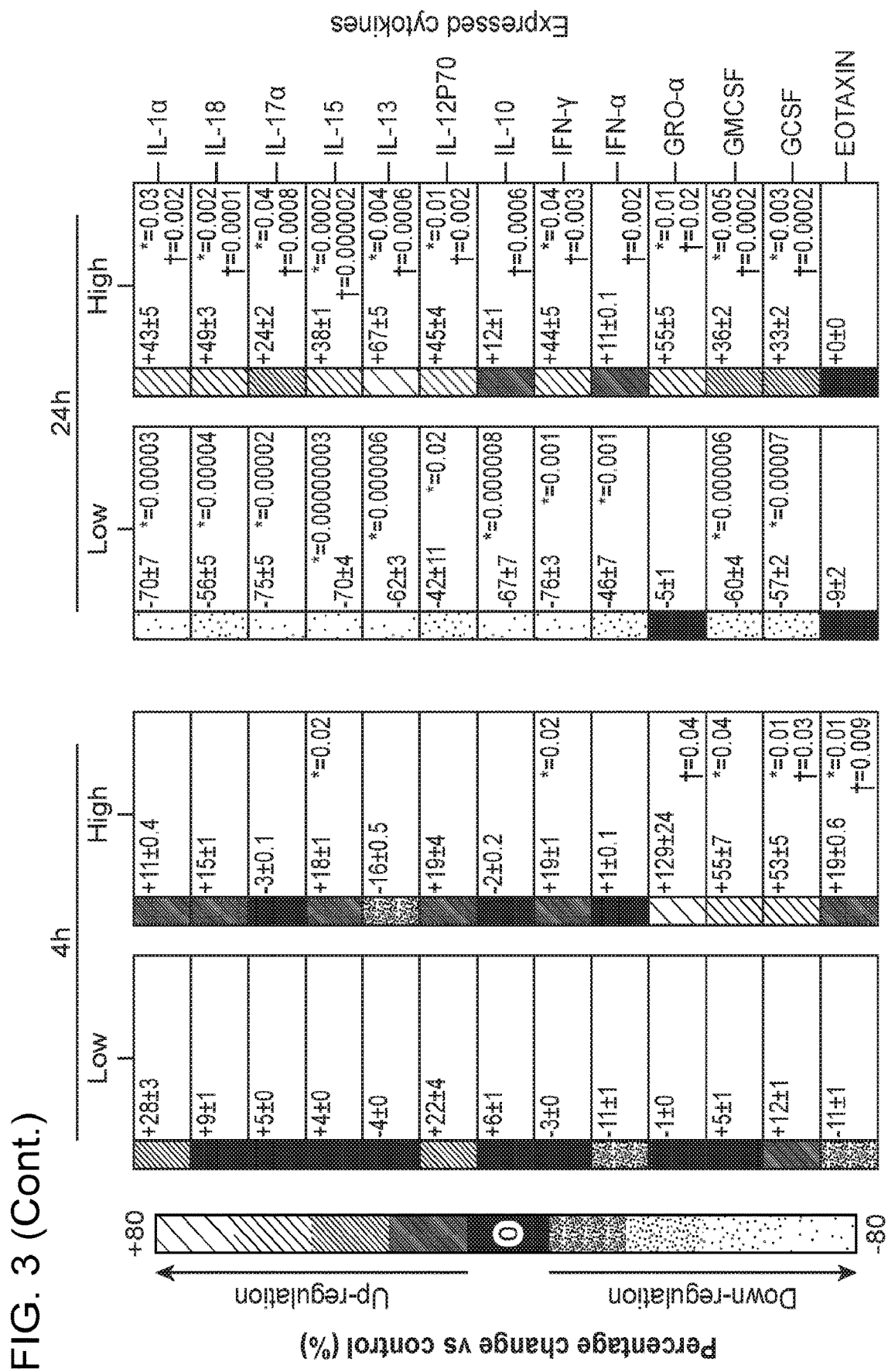

Low-intensity pFUS. Compared with those of control animals, pancreases treated with low-intensity pFUS did not exhibit any changes in cytokine expression at 4 h (p>0.05). However, at 24 h, pancreases exhibited a significant downregulation in expression of granulocyte colony-stimulating factor (GCSF: −57±1%), granulocyte-macrophage colony-stimulating factor (GM-CSF: −60±2%), interferon-α (IFN-α: −46±1%), IFN-γ(−76±1%), interleukin-10 (IL-10: −67±1%), IL-12 P70 (−42±4%), IL-13 (−62±2%), IL-15 (−70±1%), IL-17α (−75±1%), IL-18 (−56±2%), IL-1α (−70±2%), IL-1β (−70±4%), IL-2 (−67±3%), IL-23 (−73±3%), IL-27 (−51±1%), IL-28 (−78±6%), IL-3 (−79±1%), IL-31 (−71±2%), IL-4 (−61±2%), IL-5 (−73±1%), IL-6 (−42±5%), IL-9 (−55±2%), IFN-γ-induced protein 10 (IP-10: −81±13%), leptin (−45±1%), leukemia inhibitory factor (LIF: −56±1%), lipopolysaccharide-induced CXC chemokine (LIX: −56±1%), macrophage colony-stimulating factor (MCSF: −67±3%), Monocyte chemotactic protein-3 (MCP-3) (−43±8%), macrophage inflammatory protein 1α (MIP-1α: −72±3%), MIP-1β (−78±9%), MIP-2 (−62±2%), transforming growth factor β1 (TGF-β1: −44±7%), tumor necrosis factor α (TNF-α: −73±2%) and vascular endothelial growth factor (VEGF: −23±1%) (FIG. 3, p<0.05).

High-intensity pFUS. Increasing the intensity of pFUS from low to high led to a significant increase in expression of eotaxin, GCSF, GM-CSF, IFN-γ, IL-15, IL-6 and MCP-3 at 4 h after pFUS treatment compared with control animals. After 24 h, the expression of multiple cytokines in treated pancreases significantly increased compared with that in control animals: GCSF (+33±2%), GM-CSF (+36±2%), growth-regulated oncogene α (GRO-α: +55±5), IFN-γ (44±5%), IL-12 P70 (45±4%), IL-13 (67±5%), IL-15 (38±1%), IL-17α (24±2%), IL-18 (49±3%), IL-1α (43±5%), IL-1μ (64±5%), IL-2 (44±5%), IL-23 (28±3%), IL-28 (92±10%), IL-3 (61±4%), IL-31 (76±4%), IL-4 (41±2%), IL-5 (26±1%), IL-6 (49±7%), IL-9 (60±5%), leptin (42±1%), LIF (+25±1), LIX (64±3%), MIP-2 (57±4%), regulated on activation, normal T cell expressed and secreted (RANTES: 80±14%), TGF-β (53±2%) and TNF-α (47±2%) (FIG. 3, p<0.05).

Serum Markers of Pancreatic Damage after pFUS

Figure 4A:
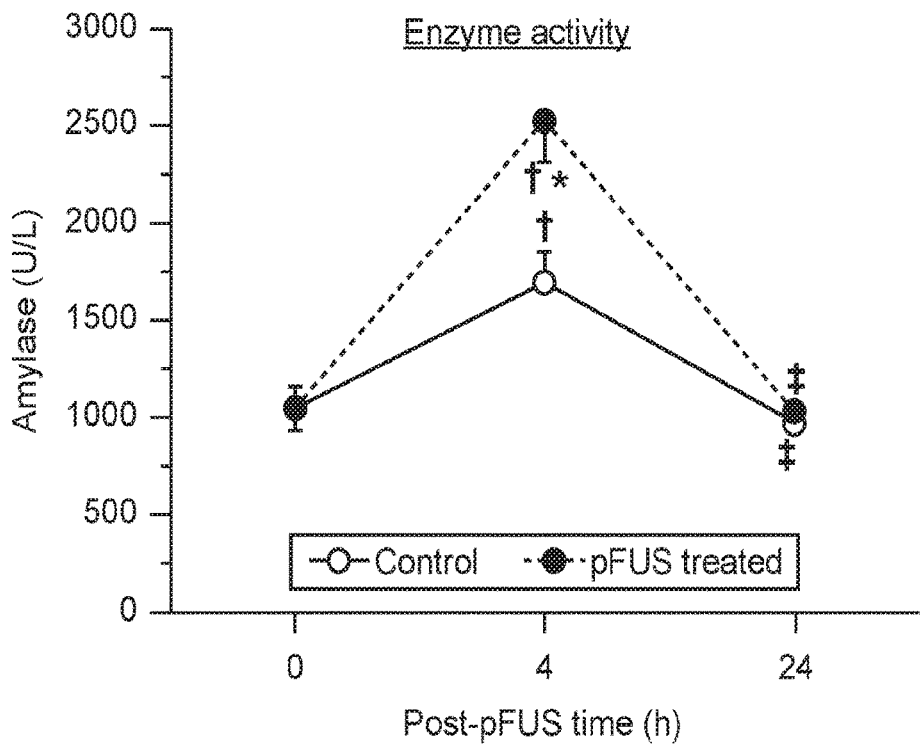
FIGS. 4A-4B. Serum markers of pancreatic damage after pulsed focused ultrasound (pFUS): Serum levels of (FIG. 4A) amylase and (FIG. 4B) lipase as indicators of pancreatic enzyme activity measured in normal mice (i.e., time point 0 h), mice whose pancreases were treated with pFUS and control mice that underwent a sham surgical procedure. Significant differences: †$p<0.05$: 4 h versus 0 h and 24 h versus 0 h; ‡$p<0.05$: 24 h versus 4 h; *$p<0.05$: pFUS-treated pancreas versus control (unpaired t-test).

Amylase. The serum amylase level in mice whose pancreases were treated with high pFUS was 2526±210 U/L at 4 h after treatment; however, this significantly decreased to 1029±72 U/L at 24 h. Control mice (i.e., mice that underwent a sham procedure—surgery alone with no pFUS) had an amylase level of 1697±155 U/L at 4 h, which significantly decreased to 975±55 U/L at 24 h (p<0.05). Compared with normal animals (i.e., mice that did not undergo any sham surgery or pFUS), both pFUS-treated and control animals had a slightly higher serum amylase level at 4 h (2526±210 and 1697±155 U/L vs. 1045±115 U/L). Although this difference was statistically significant (p<0.05), this was not the case by 24 h as levels of both pFUS-treated and control animals had returned to normal (FIG. 4A; 1029±72 and 975±55 U/L vs. 1045±115 U/L; p>0.05).

Figure 4B:
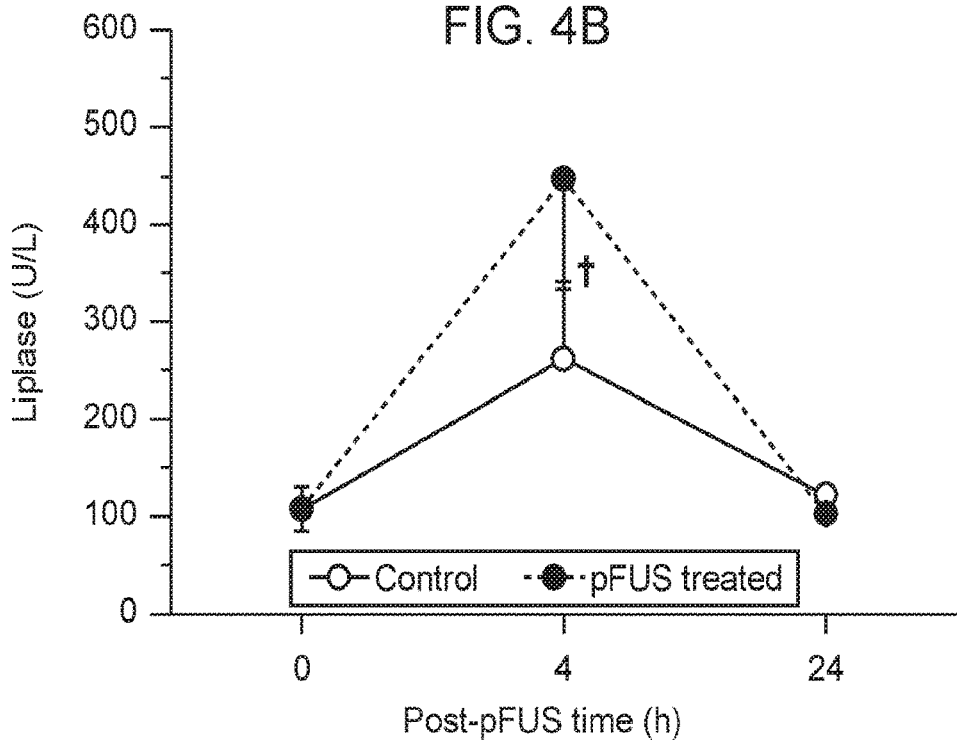

Lipase. The serum lipase level in mice whose pancreases were treated with high pFUS was 447±113 U/L at 4 h after treatment; however, this significantly decreased to 103±8 U/L at 24 h. Control mice (i.e., mice that underwent a sham procedure—surgery alone with no pFUS) had an amylase level of 263±79 U/L at 4 h, which significantly decreased to 122±11 U/L at 24 h (p<0.05). No significant difference was found between the lipase level of mice treated with pFUS and control mice at both time points (p>0.05). Compared with normal animals (i.e., mice that did not undergo sham surgery or pFUS), both pFUS-treated and control animals had a slightly higher serum amylase level at 4 h (447±113 and 263±79 U/L vs. 108±10 U/L). Although this difference was statistically significant (p<0.05), this was not the case by 24 h as levels of both pFUS-treated and control animals had returned to normal (FIG. 4B; 103±8 and 122±11 U/L vs. 108±10 U/L; p>0.05).

Discussion

In our study, we used a frequency and duty cycle similar to those reported in prior studies (Burks et al. 2011, 2015; Ziadloo et al. 2012; Jang et al. 2017); however, we utilized a lower ISATA. Previous studies investigating the molecular mechanisms and effects of pFUS in rodent muscle (Burks et al. 2011), kidney (Ziadloo et al. 2012) and heart (Jang et al. 2017) have indicated that pFUS increases the activation/expression of several cytokines, growth factors and cell adhesion molecules. Here, we applied pFUS to the mouse pancreas and analyzed the corresponding histologic and molecular effects within this organ. The pancreas is unusually sensitive to mechanical injury, and it has long been recognized that manipulation of the pancreas at the time of surgery can induce acute pancreatitis, complicating postoperative recovery; hence, manipulation of the pancreas is minimized whenever possible during surgery (Romac et al. 2018). Therefore, we selected a lower ISATA (i.e., 11.5 W/cm$^2$ for low pFUS and 18.5 W/cm$^2$ for high pFUS) compared with the ISATA used in by Burks et al. (2011), that is, 133 W/cm$^2$, to minimize the possibility of mechanical or thermal injury.

Our goal was to administer pFUS to the pancreas with no adverse effects. Our results indicate that pFUS, at the intensities used in this study, can be administered to the pancreas with no adverse histologic effects. Interestingly, pFUS was found to modulate the microenvironment of the pancreas, and these effects were dependent on the acoustic intensity of pFUS; at low intensities, there was downregulation of the expression of several cytokines/molecular markers, while at high intensities this effect was reversed, with upregulation of the expression of several cytokines/molecular markers.

FUS is a non-invasive treatment modality that can be coupled with imaging guidance (e.g., ultrasound or magnetic resonance imaging) to accurately focus sound waves with a relatively small focal zone (typically 1×1×10 mm) to structures deep within the body without causing effects on the intervening tissues (Clement 2004; Jiang et al. 2009; N'Djin et al. 2011). Although cFUS causes thermal ablation of tissue, pFUS uses shorter pulsed exposures (10-50 ms/s) to provide lower energy deposition and allow cooling to occur between pulse intervals, thereby minimizing temperature elevations in tissue (Frenkel et al. 2007; Patel et al. 2008). Instead, this allows the non-thermal effects of FUS (i.e., acoustic cavitation and acoustic radiation forces) to predominate. An estimate of the temperature increase, based on the TI measured in water using the hydrophone setup, was 1.2 and 2.1 for low- and high-dose pFUS, respectively.

Previous characterizations of the cellular and molecular responses to pFUS have not exhibited significant long-term deleterious effects. For example, although exposure of the brain to pFUS has been found to produce indiscrete lesions (McDannold et al. 2005; Sheikov et al. 2008), and even though there was limited extravasation of red blood cells and infiltration of macrophages, which persisted up to 4 wk, these effects did not appear to induce neuronal damage, necrosis or apoptosis (McDannold et al. 2005). Pulsed FUS exposures of the muscle also suggest that pFUS, unlike FUS, can be applied to tissues without causing cellular destruction (Burks et al. 2011). Currently, clinical trials are ongoing to investigate the application of cFUS in the treatment of pancreatic cancer; initial results indicate that cFUS is tolerable and can be applied non-invasively to the pancreas despite its sensitive nature, deep location and intricate relationship to major blood vessels. This is important as minor trauma to the pancreas can result in the release of pancreatic enzymes that can cause life-threatening pancreatitis (Sung et al. 2011). In keeping with this, we also confirmed that pFUS, at both low and high acoustic intensities, had no detrimental effect on the pancreas as determined histologically (i.e., preservation of the morphology of both the exocrine and endocrine components of the pancreas), using TUNEL assays (i.e., to measure markers of cellular apoptosis within the pancreas) and after analysis of the serum (i.e., levels of amylase and lipase, which are key indicators used to diagnose pancreatitis [Lin et al. 2006]). For the latter variable, the levels of both amylase and lipase were raised at 4 h but then decreased by 24 h. However, this effect is not likely attributable to pFUS given that even control animals experienced this trend; instead, it is likely owing to the effect of having to minimally invasively expose the pancreas in order to apply pFUS to the gland. Although this effect was seen in our study, it would not be seen in humans given that pFUS can target the pancreas non-invasively. Unfortunately, this was not possible in our study given that the native pancreas in small animal models, such as the mouse, cannot be easily visualized and identified in vivo using either ultrasound or magnetic resonance imaging.

After the application of pFUS to the pancreas, we observed molecular changes in the pancreas as reflected by alterations in the expression of various cytokines, growth factors and cell adhesion molecules. Previous studies have also found that pFUS is able to modulate the microenvironment of other tissues/organs including muscle (Burks et al. 2011), kidney (Burks et al. 2015) and heart (Jang et al. 2017). Indeed, pFUS has been reported to trigger acute and short-lived cascades of cytokines and growth factors that are involved in macrophage infiltration, wound healing and anti-inflammatory responses (Burks et al. 2011). However, what is interesting is that we observed a differential effect on the molecular profile of the pancreas depending on whether low or high acoustic intensities of pFUS were employed. In general, our results indicated that when pFUS was applied at low acoustic intensities, it down-regulated cytokine expression in the pancreas, and at high intensities, it upregulated cytokine expression. However, the differential effect we have observed can possibly be explained by either direct effects of sound waves on the cells of the pancreas (i.e., their ability to exert mechanical effects, which are then translated into molecular changes via a process of mechanotransduction [Burks et al. 2011]) or indirect effects of sound waves on the neuronal supply to cells (i.e., the ability to modulate the activity of autonomic or peripheral neurons via a process of neuromodulation [Kubanek 2018; Sato et al. 2018]).

At low acoustic intensities, pFUS induced a downregulation of the expression of angiogenic growth factors (i.e., MCSF, VEGF and TGF-$\beta$), as well as several key pro-inflammatory cytokines (i.e., IP-10, IL-6, IL-1 $\beta$, TNF-$\alpha$, IFN-$\gamma$ and IL-2) at 24 h post-pFUS. In the setting of the pancreas, MCSF, VEGF and TGF-$\beta$ have been reported to induce proliferation of hematopoietic and cancer cells while also promoting angiogenesis (Vinals and Pouyssegur 2001; Eubank et al. 2003; Holmes and Zachary 2005); hence downregulation of these factors could play a key role in modulating the tumor microenvironment and hence pancreatic tumor growth. In the setting of diabetes, IP-10, IFN-$\gamma$ and IL-2 have been found to participate in the auto-immune response that leads to destruction of beta cells within the pancreatic islets; hence downregulation of these cytokines after pFUS at low acoustic intensities could have a role in slowing the progression of diabetes. Finally, IL-6, IL-1$\beta$ and TNF-$\alpha$ have been found to play a key role in acute pancreatitis and pancreatic tumor progression (Viedma et al. 1992; Lewis et al. 2006; Zhao et al. 2016) so their downregulation could be important in attenuating the progression of both of these diseases.

At high acoustic intensities, pFUS induced an upregulation of the expression of angiogenic growth factors (i.e., TGF-$\beta$ and MCP-1) as well as pro-inflammatory cytokines (i.e., TNF-$\alpha$, IFN-$\gamma$ and IL-1$\beta$), at 24 h post-pFUS. This effect could be very important in the setting of tissue regeneration, where TGF-$\beta$ has been reported to accelerate vascularization (Krafts 2010) and MCP-1 can provide an important signal for mesenchymal stem cell (MSC) homing (Belema-Bedada et al. 2008; Nitzsche et al. 2017). In the latter scenario, pFUS could be applied to enable spatiotemporal control over the homing of unmodified MSCs (Burks et al. 2015). In support of this, Burks et al. (2011, 2013) and Ziadloo et al. (2012) previously characterized homing of intravenous MSCs after pFUS to healthy skeletal muscle and kidney. Similar to our study, they found that pFUS can create a transient molecular zip code consisting of localized changes in the levels of different cytokines (Burks et al. 2013). The evidence therefore suggests that pFUS can elicit local molecular responses through mechanotransduction, which can promote the homing of circulating MSCs. For instance, given that our study has found that pro-inflammatory cytokines (i.e., TNF-$\alpha$, IFN-$\gamma$ and IL-1 $\beta$) are also upregulated after high pFUS, this may prove advantageous for creating an environment that can facilitate the homing of MSCs to the pancreas for organ regeneration. Another consideration would be that pFUS-induced changes to the organ microenvironment can alter MSC function after homing occurs. Several studies have found that treating MSCs with various factors in vitro (before infusion) enhances their therapeutic capabilities in vivo. For example, pre-treating MSCs with IFN-$\gamma$ resulted in both increased production of IL-10 and reduced levels of TNF-$\alpha$ in a mouse model of inflammatory bowel disease (Duijvestein et al. 2011). Another study pre-treated MSCs with IFN-$\gamma$ and then either TNF-$\alpha$, IL-1$\alpha$, or IL-1$\beta$ and found that all three combinations improved outcomes in mouse models of graft-versus-host disease and delayed-type hypersensitivity (Kavanagh et al. 2014). Interestingly, studies have also found that the cocktail of TNF-$\alpha$, IL-1$\beta$ and IFN-$\gamma$ can direct the differentiation of pancreatic ductal cells toward the endocrine lineage (Valdez et al. 2016), and this may be important in the setting of regenerating the pancreas after its destruction in the setting of either diabetes or pancreatitis. Hence, pFUS could either pre-condition the target organ both to enhance MSC homing and/or to stimulate different cell signaling pathways (Burks et al. 2011, 2013, 2015).

In summary, pFUS is able to induce changes in the molecular microenvironment of the pancreas without adversely affecting the pancreatic gland. These changes are dependent on the acoustic intensity, and future studies will be undertaken to fully evaluate the mechanisms responsible for these changes as well as the implications of these changes in different disease states.

REFERENCES

Belema-Bedada F, Uchida S, Martire A, Kostin S, Braun T. Efficient homing of multipotent adult mesenchymal stem cells depends on FROUNT-mediated clustering of CCR2. Cell Stem Cell 2008; 2:566-575.

Burks S R, Ziadloo A, Hancock H A, Chaudhry A, Dean D D, Lewis B K, Frenkel V, Frank J A. Investigation of cellular and molecular responses to pulsed focused ultrasound in a mouse model. PLoS One 2011; 6:e24730.

Burks S R, Ziadloo A, Kim S J, Nguyen B A, Frank J A. Noninvasive pulsed focused ultrasound allows spatiotemporal control of targeted homing for multiple stem cell types in murine skeletal muscle and the magnitude of cell homing can be increased through repeated applications. Stem Cells 2013; 31:2551-2560.

Burks S R, Nguyen B A, Tebebi P A, Kim S J, Bresler M N, Ziadloo A,

Street J M, Yuen P S T, Star R A, Frank J A. Pulsed focused ultrasound pretreatment improves mesenchymal stromal cell efficacy in preventing and rescuing established acute kidney injury in mice. Stem Cells 2015; 33:1241-1253.

Clement G T. Perspectives in clinical uses of high-intensity focused ultrasound. Ultrasonics 2004; 42:1087-1093.

Duijvestein M, Wildenberg M E, Welling M M, Hennink S, Molendijk I, Van Zuylen V L, Bosse T, Vos A C W, De Jonge-Muller E S M, Roelofs H, Van Der Weerd L, Verspaget H W, Fibbe W E, Te Velde AA, Van Den Brink G R, Hommes D W. Pretreatment with interferon-γ enhances the therapeutic activity of mesenchymal stromal cells in animal models of colitis. Stem Cells 2011; 29:1549-1558.

Eubank T D, Galloway M, Montague C M, Waldman W J, Marsh C B. M-CSF induces vascular endothelial growth factor production and angiogenic activity from human monocytes. J Immunol 2003; 171:2637-2643.

Frenkel V. Ultrasound mediated delivery of drugs and genes to solid tumors. Adv Drug Deliv Rev 2008; 60:1193-1208.

Frenkel V, Oberoi J, Stone M J, Park M, Deng C, Wood B J, Neeman Z, Home M, Li K C P. Pulsed high-intensity focused ultrasound enhances thrombolysis in an in vitro model. Radiology 2007; 239:86-93.

Golan R, Bernstein A N, McClure T D, Sedrakyan A, Patel N A, Parekh D J, Marks L S, Hu J C. Partial gland treatment of prostate cancer using high-intensity focused ultrasound in the primary and salvage settings: A systematic review. J Urol 2017; 198:1000-1009.

Holmes D I R, Zachary I. The vascular endothelial growth factor (VEGF) family: Angiogenic factors in health and disease. Genome Biol 2005; 6209.

Hsiao Y H, Kuo S J, Tsai H D, Chou M C, Yeh G P. Clinical application of high-intensity focused ultrasound in cancer therapy. J Cancer 2016; 7:225-231.

Jang K W, Tu T W, Nagle M E, Lewis B K, Burks S R, Frank J A. Molecular and histological effects of MR-guided pulsed focused ultrasound to the rat heart. J Transl Med 2017; 15 252.

Jiang Z, Holyoak G R, Bartels K E, Ritchey J W, Xu G, Bunting C F, Slobodov G, Piao D. In vivo trans-rectal ultrasound-coupled optical tomography of a transmissible venereal tumor model in the canine pelvic canal. J Biomed Opt 2009; 14 030506.

Kavanagh D P J, Robinson J, Kalia N. Mesenchymal stem cell priming: Fine-tuning adhesion and function. Stem Cell Rev Rep 2014; 10: 587-599.

Krafts K P. Tissue repair: The hidden drama. Organogenesis 2010; 6: 225-233.

Kubanek J. Neuromodulation with transcranial focused ultrasound. Neurosurg Focus 2018; 44:E14.

Lewis A M, Varghese S, Xu H, Alexander H R. Interleukin-1 and cancer progression: The emerging role of interleukin-1 receptor antagonist as a novel therapeutic agent in cancer treatment. J Transl Med 2006; 4:48.

Li P Z, Zhu S H, He W, Zhu L Y, Liu S P, Liu Y, Wang G H, Ye F. High-intensity focused ultrasound treatment for patients with unresectable pancreatic cancer. Hepatobiliary Pancreat Dis Int 2012; 11:655-660.

Lin X Z, Wang S S, Tsai Y T, Lee S D, Shiesh S C, Pan H B, Su C H, Lin C Y. Serum amylase, isoamylase, and lipase in the acute abdomen. J Clin Gastroenterol 2006; 11:47-52.

McDannold N, Vykhodtseva N, Raymond S, Jolesz F A, Hynynen K. MRI-guided targeted blood-brain barrier disruption with focused ultrasound: Histological findings in rabbits. Ultrasound Med Biol 2005; 31:1527-1537.

N'Djin W A, Melodelima D, Schenone F, Rivoire M, Chapelon J Y. Assisted hepatic resection using a toroidal HIFU device: An in vivo comparative study in pig. Med Phys 2011; 38:1769-1778.

Nitzsche F, Müller C, Lukomska B, Jolkkonen J, Deten A, Boltze J. Concise review: MSC adhesion cascade—Insights into homing and transendothelial migration. Stem Cells 2017; 35:1446-1460.

Patel P R, Luk A, Durrani A, Dromi S, Cuesta J, Angstadt M, Dreher M R, Wood B J, Frenkel V. In vitro and in vivo evaluations of increased effective beam width for heat deposition using a split focus high intensity ultrasound (HIFU) transducer. Int J Hyperthermia 2008; 24:537-549.

Phenix C P, Togtema M, Pichardo S, Zehbe I, Curiel L. High intensity focused ultrasound technology, its scope and applications in therapy and drug delivery. J Pharm Pharm Sci 2014; 17:136-153.

Romac J M J, Shahid R A, Swain S M, Vigna S R, Liddle R A. Piezo1 is a mechanically activated ion channel and mediates pressure induced pancreatitis. Nat Commun 2018; 9 1715.

Sato T, Shapiro M G, Tsao D Y. Ultrasonic neuromodulation causes widespread cortical activation via an indirect auditory mechanism. Neuron 2018; 98:1031-1041.e5.

Sheikov N, McDannoki N, Sharma S, Hynynen K. Effect of focused ultrasound applied with an ultrasound contrast agent on the tight junctional integrity of the brain microvascular endothelium. Ultrasound Med Biol 2008; 34:1093-1104.

Sung H Y, Jung S E, Cho S H, Zhou K, Han J Y, Han S T, Kim J I, Kim J K, Choi J Y, Yoon S K, Yang J M, Han C W, Lee Y S. Long-term outcome of high-intensity focused ultrasound in advanced pancreatic cancer. Pancreas 2011; 40:1080-1086.

Suo D, Guo S, Lin W, Jiang X, Jing Y. Thrombolysis using multi-frequency high intensity focused ultrasound at MHz range: An in vitro study. Phys Med Biol 2015; 60:7403-7418.

Tempany C M C, McDannoki N J, Hynynen K, Jolesz F A. Focused ultrasound surgery in oncology: Overview and principles. Radiology 2011; 259:39-56.

Valdez I A, Dirice E, Gupta M K, Shirakawa J, Teo A K K, Kulkarni R N. Proinflammatory cytokines induce endocrine differentiation in pancreatic ductal cells via STAT3-dependent NGN3 activation. Cell Rep 2016; 15:460-470.

Viedma J A, P'erez-Mateo M, Dom'inguez JE, Carballo F. Role of interleukin-6 in acute pancreatitis comparison with C-reactive protein and phospholipase A. Gut 1992; 33:1264-1267.

Vinals F, Pouyss'egur J. Transforming growth factor beta1 (TGF-beta1) promotes endothelial cell survival during in vitro angiogenesis via an autocrine mechanism implicating TGF-alpha signaling. Mol Cell Biol 2001; 21:7218-7230.

Zhao X, Fan W, Xu Z, Chen H, He Y, Yang G, Yang G, Hu H, Tang S, Wang P, Zhang Z, Xu P, Yu M. Inhibiting tumor necrosis factor-alpha diminishes desmoplasia and inflammation to overcome chemoresistance in pancreatic ductal adenocarcinoma. Oncotarget 2016; 7:81110-81122.

Zhou Q, Melton D A. Pancreas regeneration. Nature 2018; 557:351-358.

Ziadloo A, Burks S R, Gold E M, Lewis B K, Chaudhry A, Merino M J, Frenkel V, Frank J A. Enhanced homing permeability and retention of bone marrow stromal cells by noninvasive pulsed focused ultrasound. Stem Cells 2012; 30:1216-1227.

Example 2

Improving the Function and Engraftment of Transplanted Pancreatic Islets Using Pulsed Focused Ultrasound Therapy Introduction Type 1 diabetes (T1D) is a chronic autoimmune disease caused by the selective destruction of insulin producing β cells within pancreatic islets[1]. Currently, T1D affects 1.4 million people in the United States and 30 million people globally, and its incidence is increasing at an alarming rate[2]. In order for patients with T1D to maintain glucose homeostasis and prevent long-term complications of hyperglycemia, the current standard of care is daily self-administered injections of insulin[3]. However, this can only keep blood glucose levels within a broad range and cannot respond dynamically to second-by-second changes in blood glucose variability. Although whole pancreas transplantation is an effective approach to restore the physiological control of blood glucose levels without the need for exogenous insulin injections, it is a major surgical procedure and is rarely indicated as a treatment for T1D[4]. An alternative is islet transplantation, where islets are extracted from a donor pancreas and then minimally invasively administered into the liver of a diabetic patient. However, islets need to be harvested from a donor pancreas during which time their vascular connections are severed. Furthermore, compared to solid organ transplantation, islet transplantation is unusual in that a surgical vascular anastomosis is not created[5]. Hence, for islets to survive following engraftment, they need to rebuild their network of blood vessels, derived from the host microvascular bed, to ensure they receive an adequate supply of oxygen and nutrients; a process which takes 2-4 weeks. As a result, up to 60% of islets are lost within the first 2 weeks following transplantation, mainly due to hypoxia from an underdeveloped blood supply as well as the instant blood-mediated inflammatory reaction (IBMIR) towards islets[6]. Together, this reduces the number of viable islets which ultimately jeopardizes the long-term success of any islet transplant.

Figure 5:
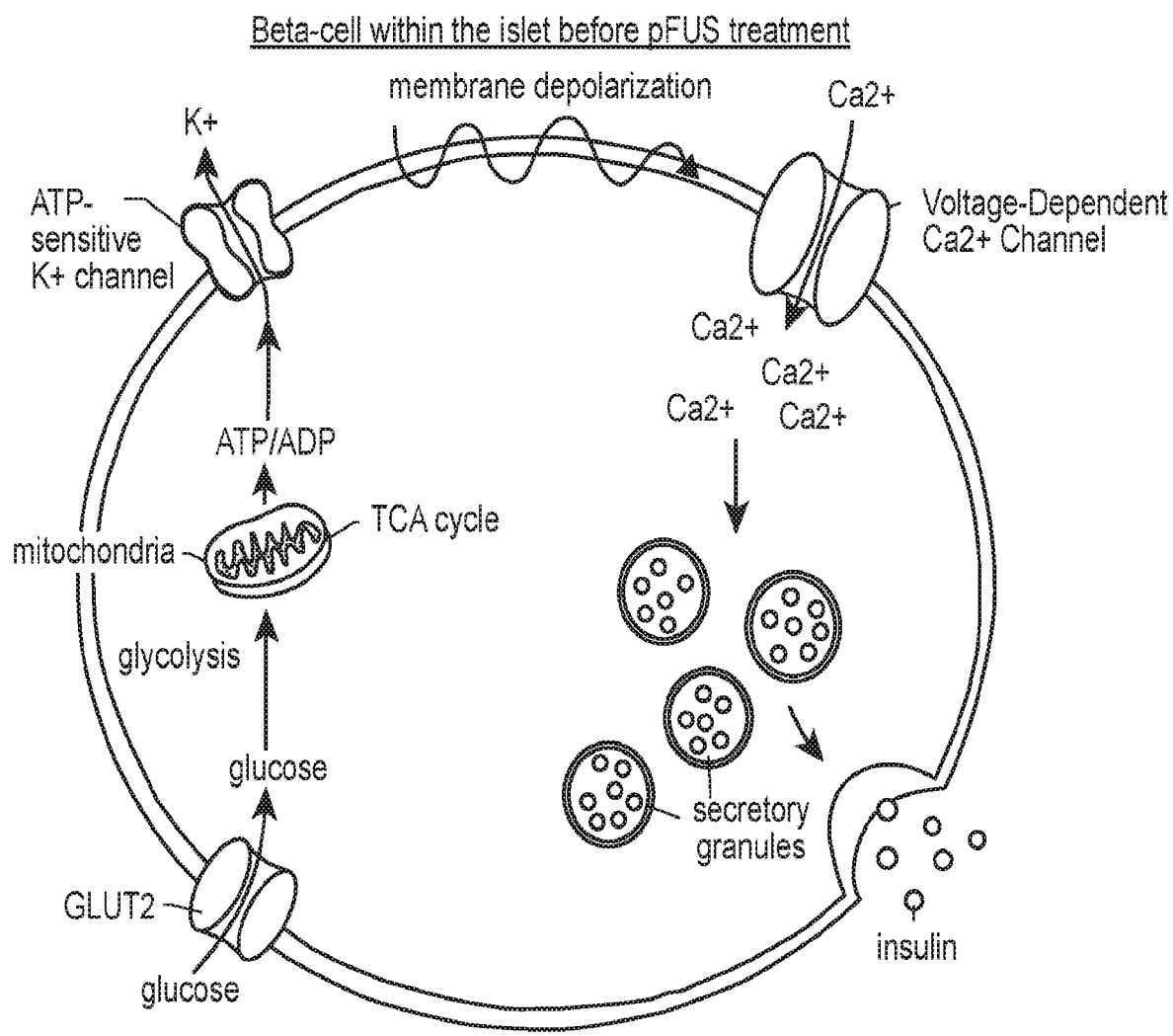
FIG. 5. Schematic representation of how pFUS can stimulate insulin secretion: pFUS enhances insulin secretion from islets by enhancing intracellular calcium levels within β-cells which then triggers the release of insulin granules via exocytosis.
Figure 5:
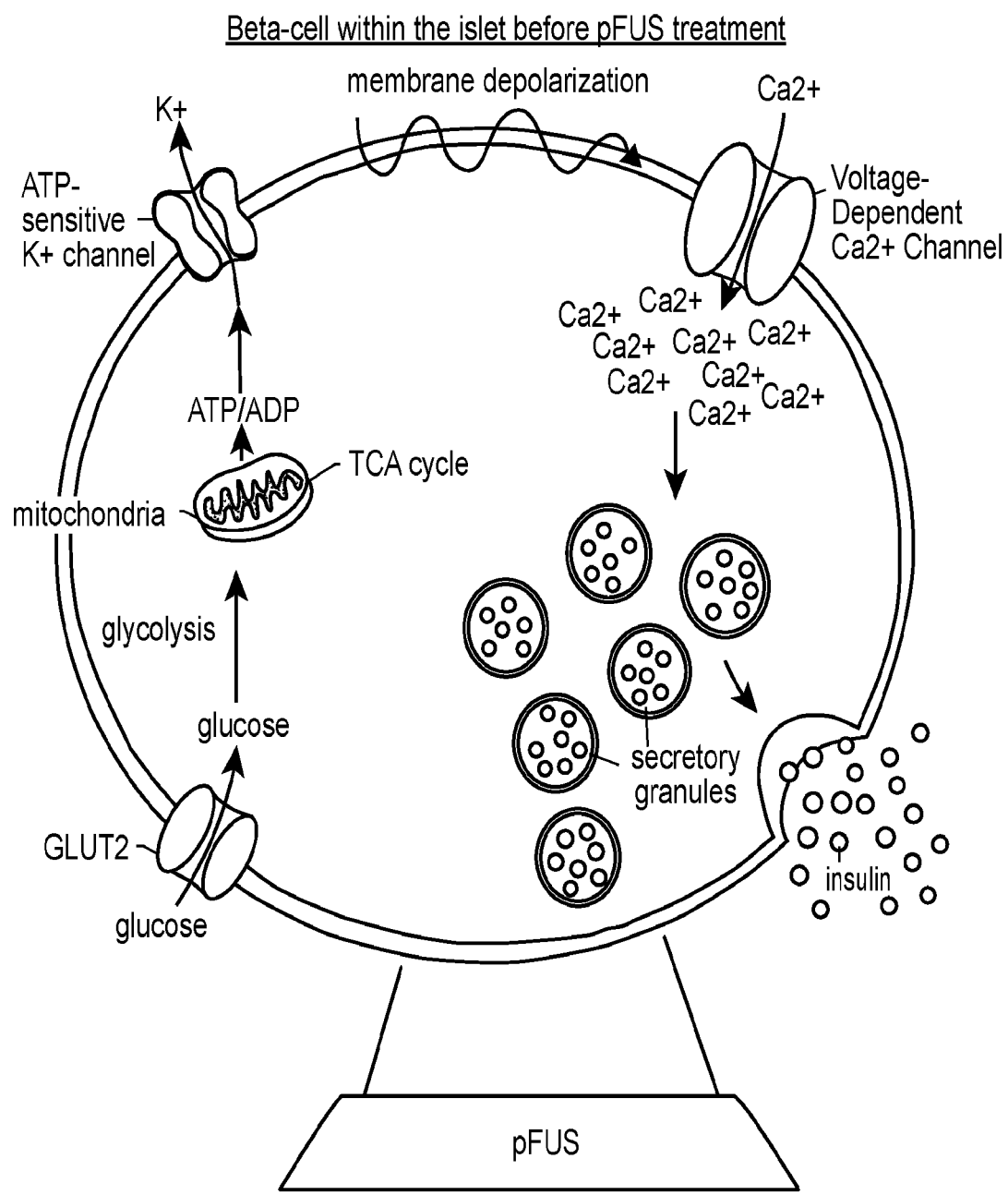

Once islets engraft following their transplantation, they then need to be able to function to release insulin from β cells. In response to elevated blood glucose levels, adenosine triphosphate (ATP)-sensitive potassium channels in β cells close, causing membrane depolarization thereby increasing intracellular free $Ca^{2+}$ ($[Ca^{2+}]i$). In turn, this triggers the exocytosis of insulin granules from β cells[7] (FIG. 5). However, following islet transplantation, patients require immunosuppression therapy (i.e. tacrolimus and sirolimus), which has been shown to impair insulin secretion from islets[8,9]. Hence, a significant proportion of transplanted islets become "glucose-blind", wherein β cells still contain insulin granules but cannot effectively release them in response to elevated glucose levels[10]. Interestingly, recent studies have shown that ultrasound, in certain conditions, can have several biological effects including an increase in calcium influx into cells[11], including insulinoma β cells[10]. Furthermore, ultrasound has been shown in vivo to induce the formation of new blood vessels[12]. Hence, it is plausible that ultrasound could be used therapeutically in the setting of islet transplantation, not only to facilitate islet function, but also to help with islet engraftment and revascularization.

Currently, focused ultrasound (FUS) is used as a clinically available modality that applies acoustic waves at specific locations within the body to induce a therapeutic effect without affecting overlying tissues[13,14]. For example, high intensity focused ultrasound (HIFU), a form of FUS, is now used to treat various conditions such as uterine fibroids, bone and prostate tumors by ablating the diseased tissue[15]. Pulsed focused ultrasound (pFUS) is a variation of this technology that uses short duty-cycles to minimize temperature elevations, thereby allowing the mechanical effects of ultrasound to predominate[16]. Hence, in the present study, we will explore whether pFUS can stimulate insulin secretion from pancreatic islets by increasing $[Ca^{2+}]i$ within β cells. Next, we will examine in vivo whether applying pFUS to the site of islet transplantation can improve the function, viability and engraftment of transplanted islets within recipient diabetic animals. We will induce diabetes in mice using streptozocin (STZ) and then transplant islets under the renal capsule, which is a well-established technique for islet transplantation in small animal models[17].

Results

Figure 6B:
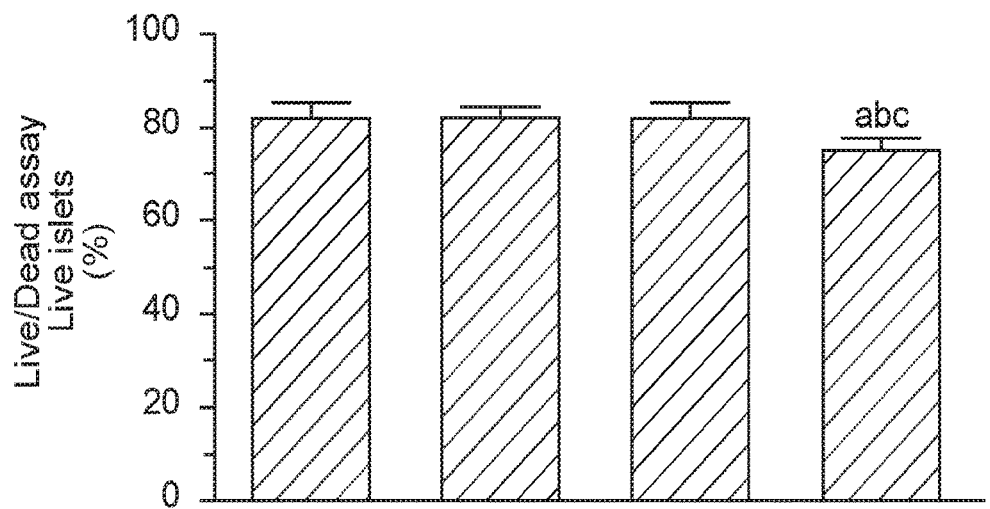
Figure 6C:
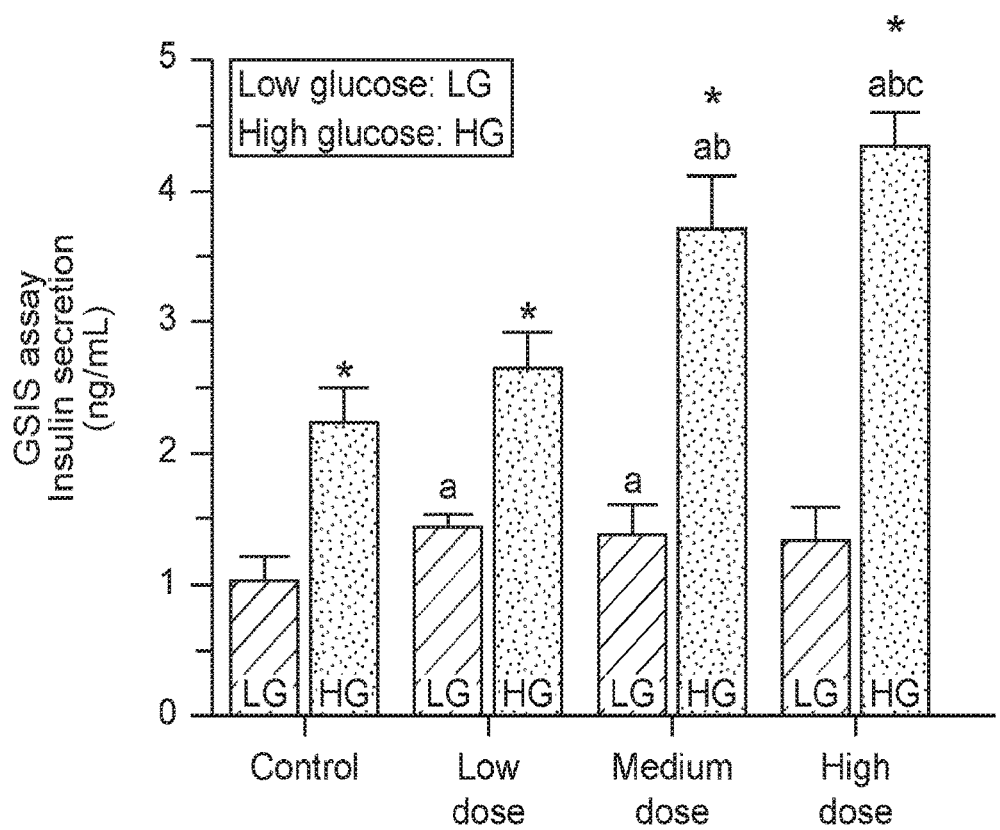

In Vitro analysis of Islet survival and function. Following sonication with pFUS at low, medium and high intensities, islets maintained their spherical shape and kept their integrity, thereby confirming that pFUS does not adversely affect islet quality (FIG. 6A). Using a live/dead assay, the percentage of live islets in the control group (i.e. non-pFUS treated islets) was 82.00±3.21% which was similar to islets treated with pFUS at low (82.33±2.00%, P>0.05) and medium (82.00±3.05%, P>0.05) intensities after 7 days of culture. However, there was a significant reduction in viability when islets were treated with pFUS at high intensities (FIG. 6B; 75.33±2.08%, P<0.05). Following stimulation of islets at both low and high glucose concentrations, the concentration of insulin secreted by islets significantly increased when pFUS was applied to islets, in an acoustic intensity-dependent manner: (Low glucose stimulation=control: 1.03±0.18; low intensity: 1.44±0.09; medium intensity: 1.38±0.22; high intensity: 1.32±0.26 ng/ml. High glucose stimulation=control: 1.23±0.23; low intensity: 2.64±0.27; medium intensity: 3.71±0.40; high intensity: 4.35±0.24 ng/ml) (FIG. 6C; P<0.05).

Figure 7A:
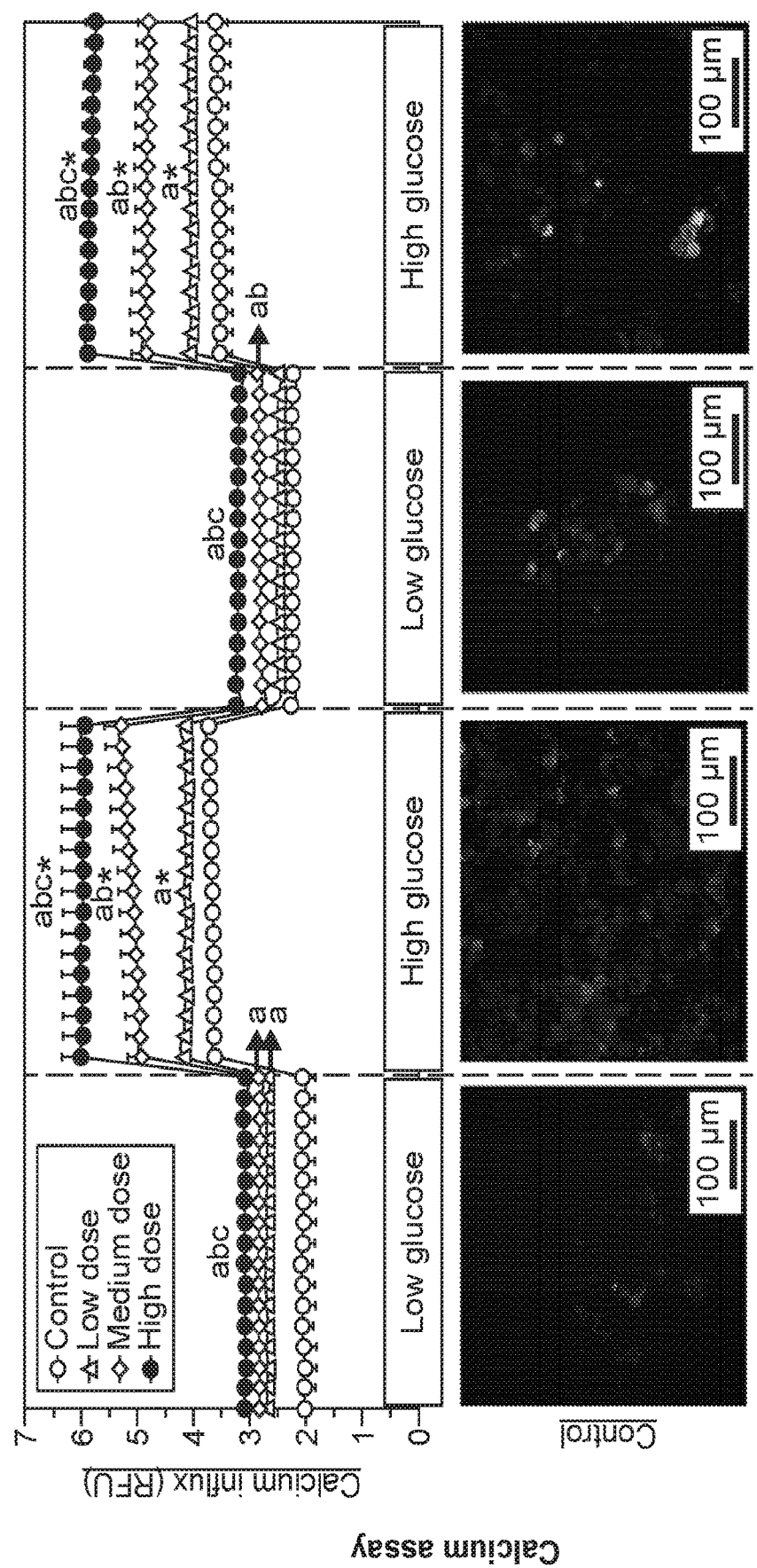
FIGS. 7A-7C. Calcium imaging and insulin assessment of islets.
Figure 7A:
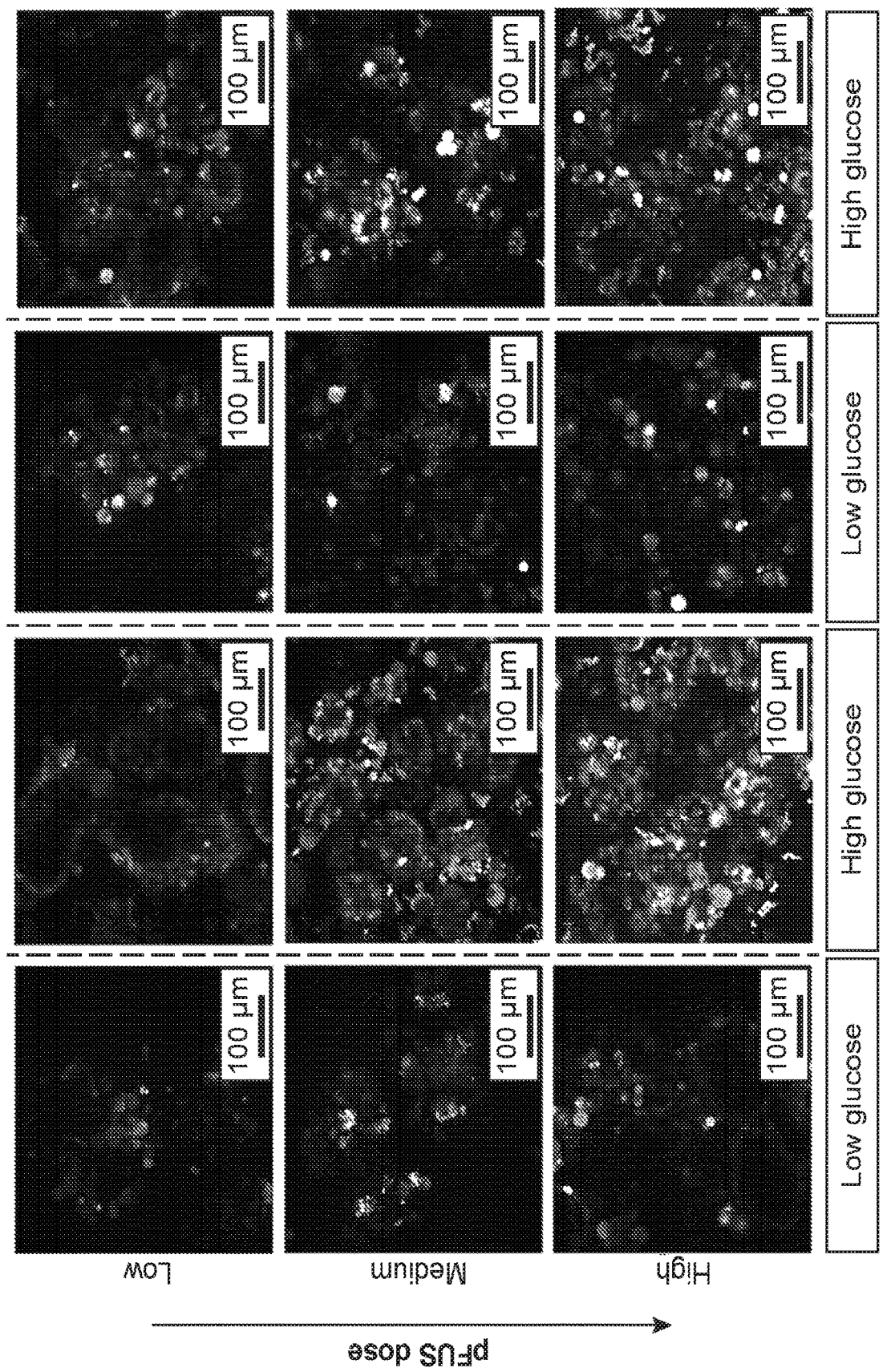
Figure 7B:
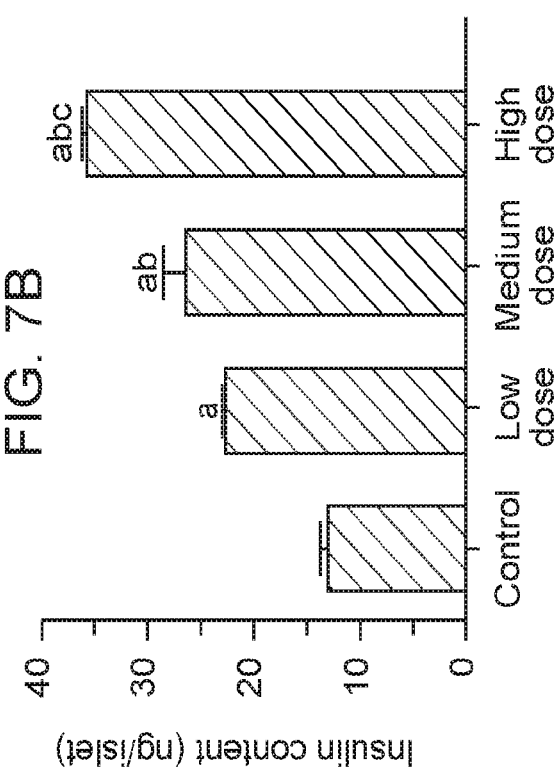
Figure 7C:
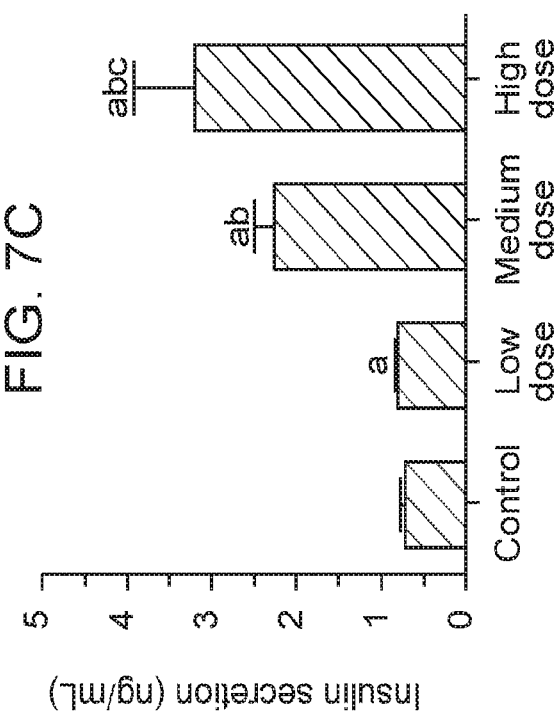

Following glucose stimulation, there was an increase in fluorescence signal intensity in islets thereby indicating an increase in intracellular calcium concertation. In control non-pFUS treated islets, the fluorescence signal intensity was dependent on the amount of glucose present (Low glucose: 2.04±0.21 vs. High glucose: 3.62±0.07 relative fluorescence unit (RFU); p<0.05) and this response pattern was maintained over two consecutive low-high glucose challenge cycles. Furthermore, this fluorescence signal intensity, and hence the amount of intracellular calcium within islets, was significantly increased at both low and high levels of glucose stimulation when islets were treated with pFUS in an acoustic-intensity dependent manner (Low glucose stimulation=control: 2.04±0.21; low intensity: 2.70±0.09; medium intensity: 2.82±0.08; high intensity: 3.09±0.04 RFU. High glucose stimulation=control: 3.62±0.07; low intensity: 4.17±0.0; medium intensity: 4.91±0.26; high intensity: 5.99±0.34 RFU; p<0.05) (FIG. 7A). Under basal conditions (i.e. culture in RPMI medium at 37° C. and 5% $CO_2$), control non-pFUS treated islets contained 13.14±0.72 ng of insulin per islet and this concentration significantly increased when islets were treated with pFUS in an acoustic-intensity dependent manner: low intensity: 22.69±0.24; medium intensity: 26.50±2.03 and high intensity: 35.87±0.33 ng (FIG. 7B; P<0.05). Similarly, control non-pFUS treated islets secreted 0.71±0.03 ng/ml of insulin into the surrounding medium and this concentration significantly increased when islets were treated with pFUS in an intensity-dependent manner: low intensity: 0.81±0.02; medium intensity: 2.27±0.21 and high intensity: 3.20±0.71 ng/ml (FIG. 7C; P<0.05).

Figure 8A:
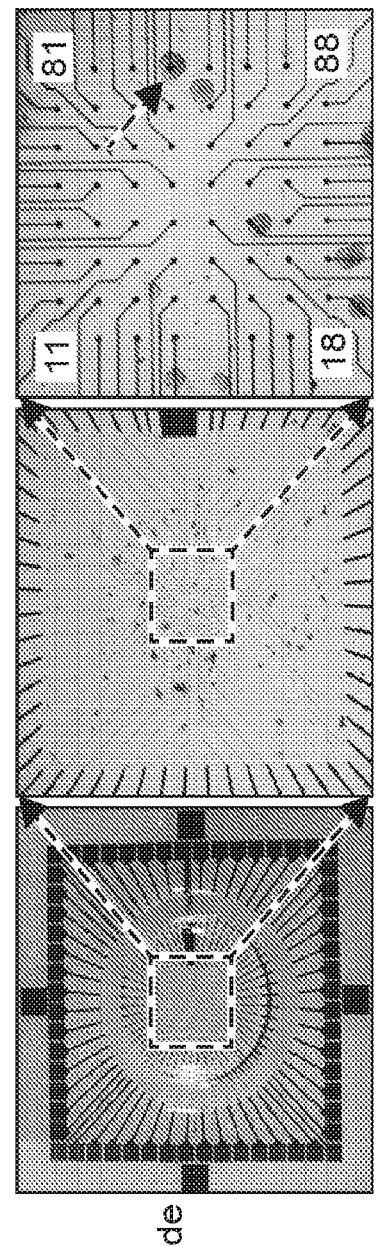
FIGS. 8A-8B. Recordings of membrane potential oscillations.
Figure 8B:
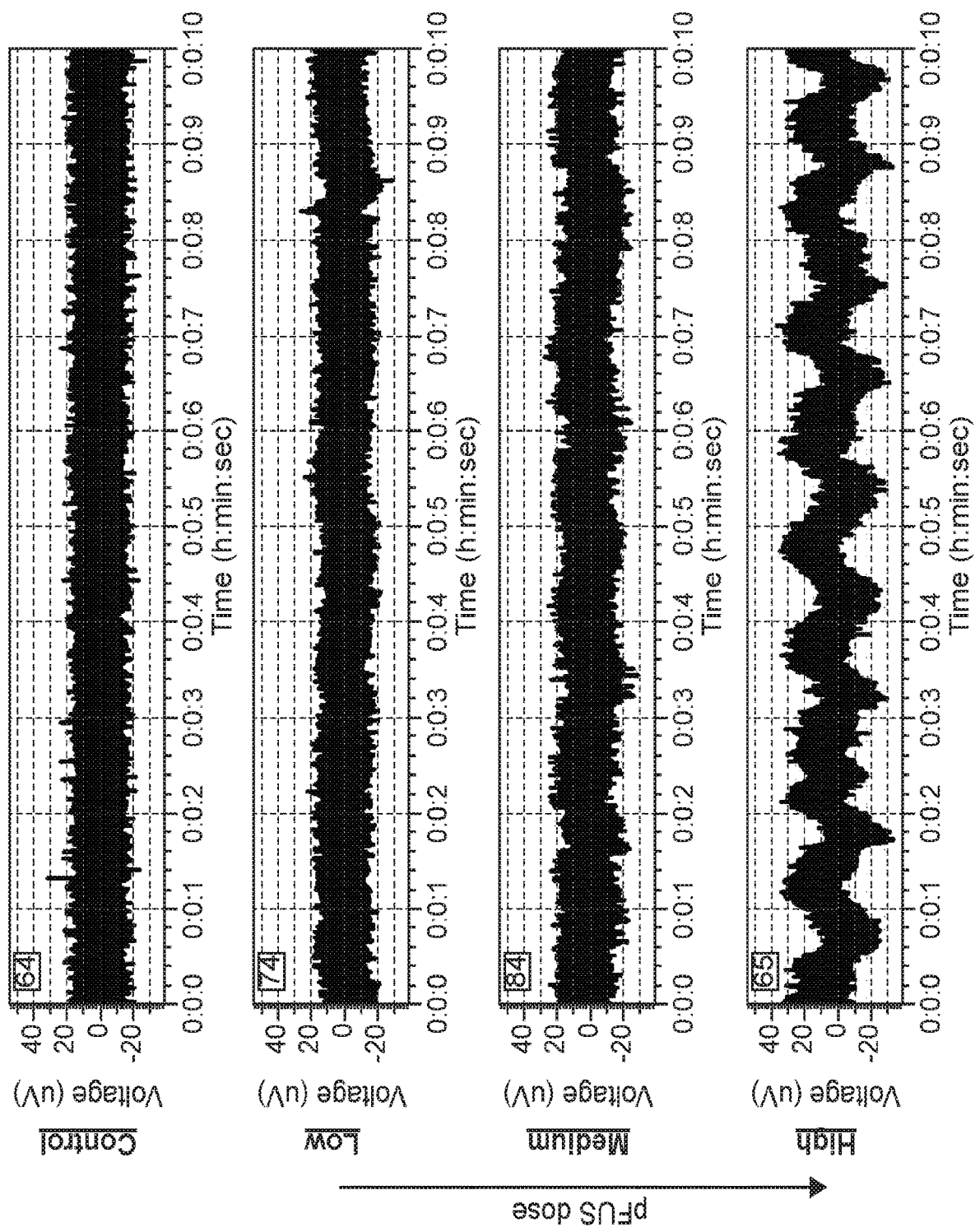

Under control conditions, islets showed no electrical activity (i.e. membrane potential oscillations), however, following pFUS stimulation there was an increase in electrical activity with a continuous spiking of membrane potential. Furthermore, our results showed that the membrane voltage of islets increased when they were treated with pFUS in an acoustic-intensity dependent manner (change in membrane voltage: control: 0; low intensity: 5±2, medium intensity: 10±3 and high intensity: 25±5 µV, FIG. 8).

Figure 9A:
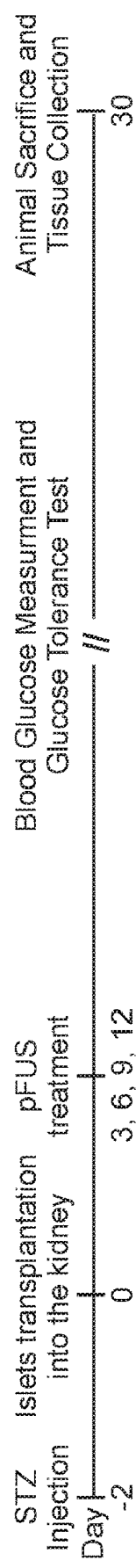
Figure 9B:
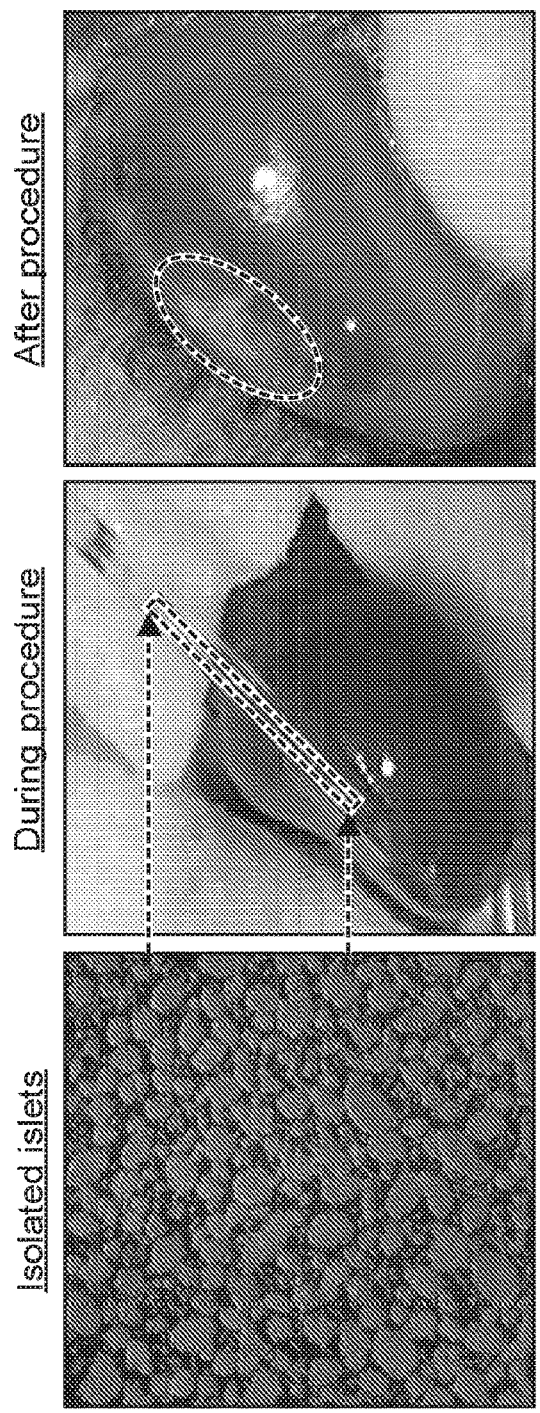
Figure 9B:
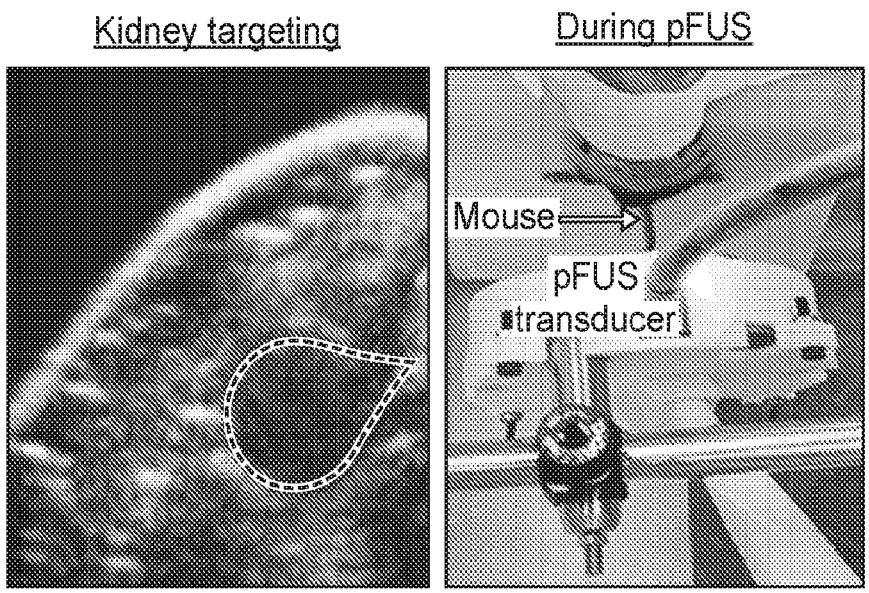
Figure 9B:
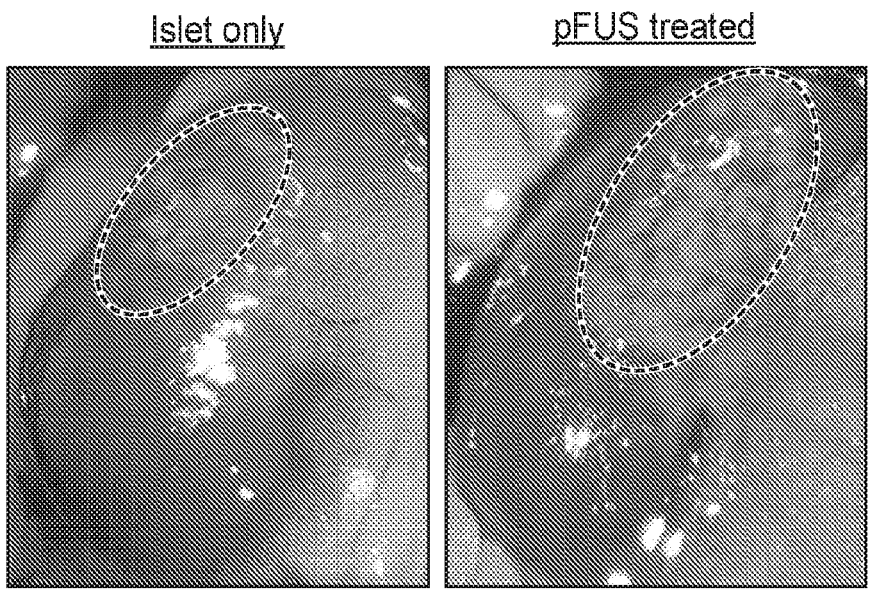
Figure 9E:
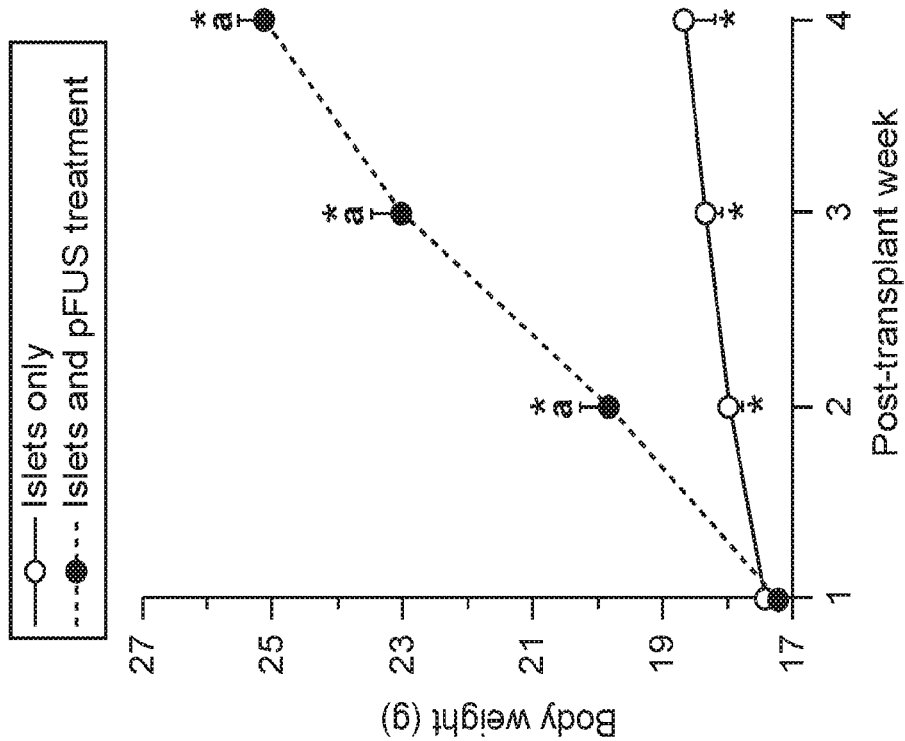
Figure 9D:
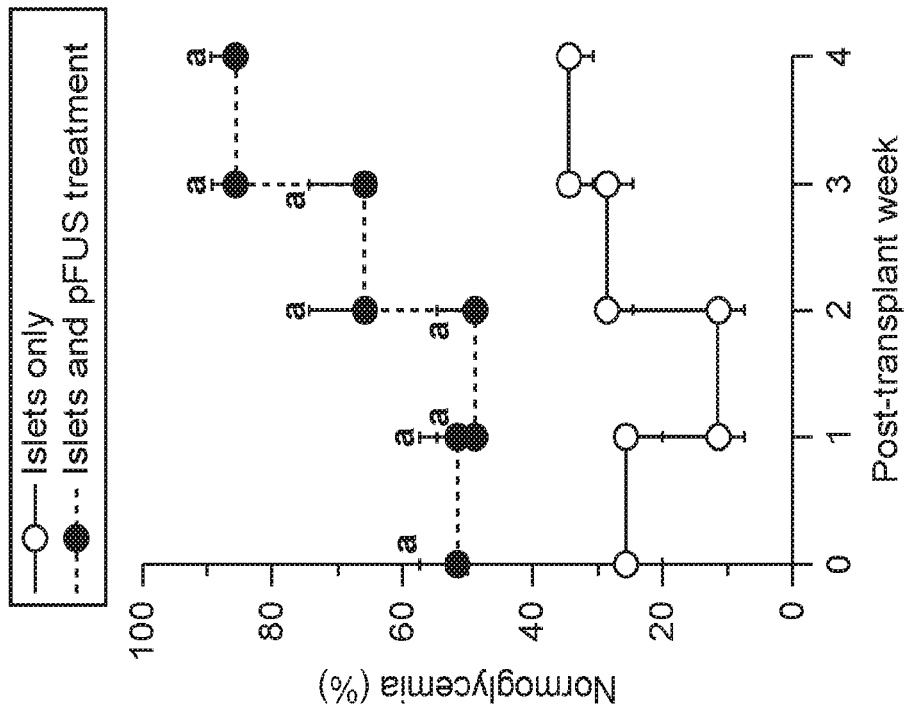

In Vivo analysis of transplanted Islets treated with pFUS. Experimental details of our in vivo experiment are outlined in FIGS. 9A, 9B. Following ip injection of STZ, all mice became hyperglycemic with their non-fasting blood glucose values increasing from 122±8 mg/dl (baseline, day −2) to 492±17 mg/dl (post-STZ treatment, day 0). Following islet transplantation, both experimental groups showed a significant decrease in their non-fasting blood glucose levels within the first 48 h (islet transplantation alone: 307±67 mg/dl and islet transplantation with pFUS treatment: 277±76 mg/dl). However, after 48 h the blood glucose levels began to rise again in animals which were transplanted with islets alone, and this persisted for the duration of the experimental protocol (day 30: 364±82 mg/dl). In contrast, in animals which were transplanted with islets that were then treated with pFUS, there was a continual drop in non-fasting blood glucose levels such that by the end of the experimental protocol all animals had become normoglycemic and had thus re-established glycemic control (day 30:159±15 mg/dL; FIG. 9C). Indeed, in this group of animals 51±6% became normoglycemic in the first week post-transplantation with this number increasing to 86±4% at week 4 post-transplantation (FIG. 9D). This was accompanied by mice progressively increasing their body weight from 17.2±0.2 g (week 1) to 25.1±0.4 g (week 4); an effect which was not seen in animals that were transplanted with islets alone which remained hyperglycemic throughout the experimental protocol (week 1: 17.4±0.2 g to week 4:18.7±0.5 g; FIG. 9E).

Figure 9F:
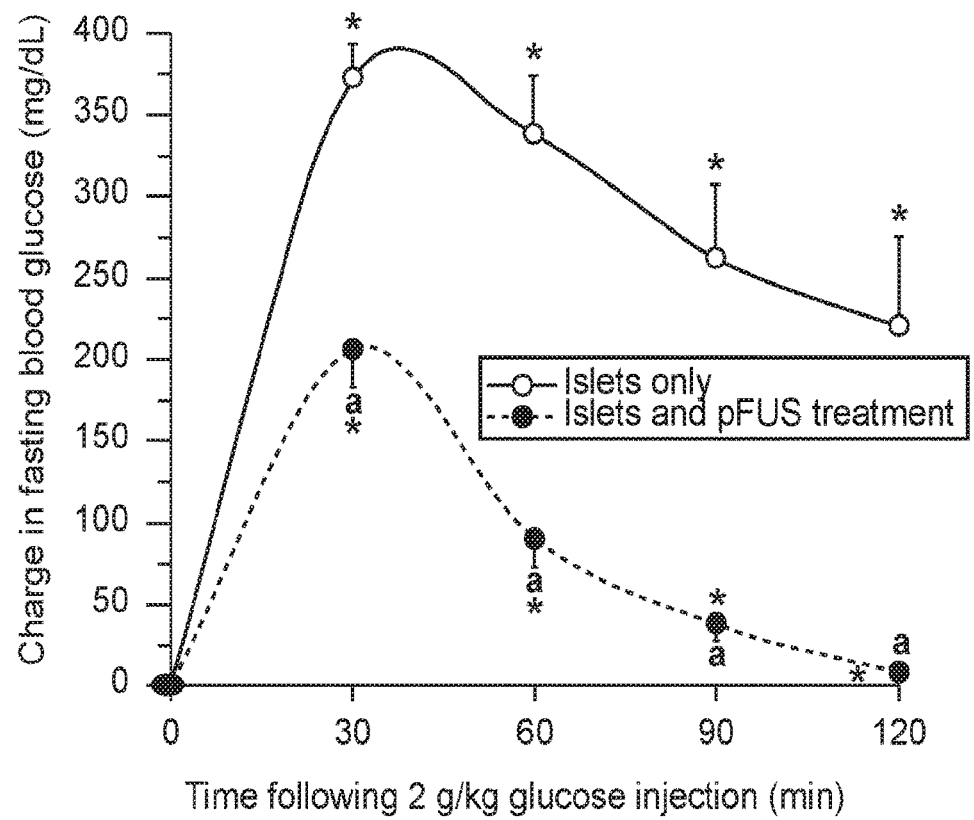
Figure 9G:
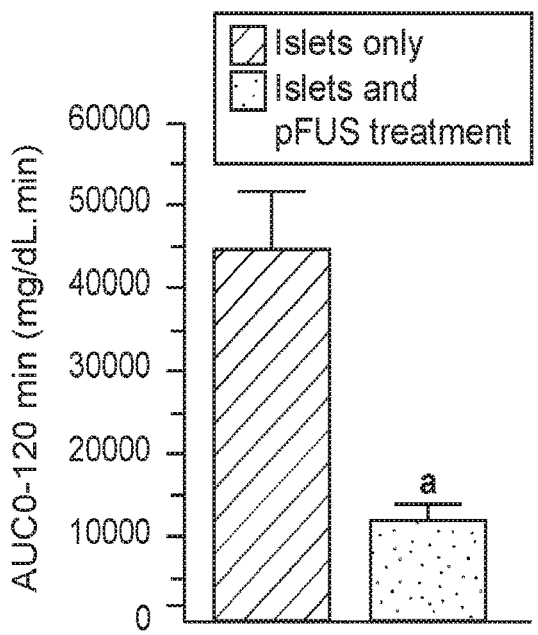
Figure 9H:
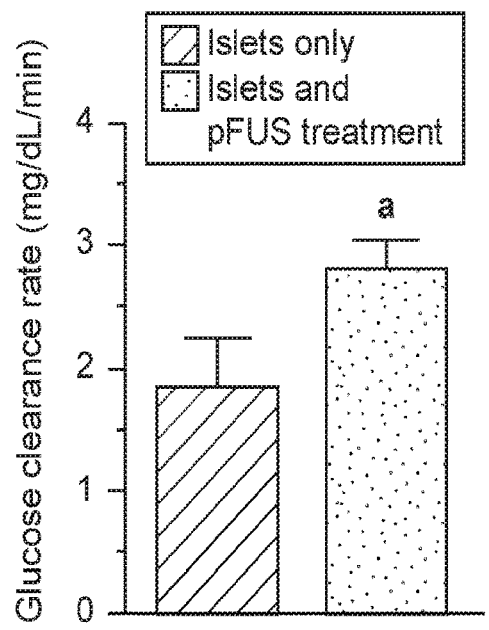

In both experimental groups, blood glucose levels significantly increased following intraperitoneal glucose administration with a peak-value seen at 30 min at 2 weeks following transplantation (P<0.05). However, in the animals treated with pFUS the change from baseline to the peak glucose value was significantly lower for the same glucose challenge (206±23 vs 371±23 mg/dL; p<0.05) and by 120 min, these animals had restored their glucose values back to baseline levels unlike those animals which received islet transplantation alone (FIG. 9F). Accordingly, the AUC0-120 min (11,988±1,881 vs 44,345±7,315 mg/dl·min; FIG. 9G) was significantly lower and the glucose clearance rate (2.8±0.2 vs 1.9±0.4 mg/dl/min; FIG. 9H) was significantly faster in animals which had received islet transplantation and were treated with pFUS, compared to those animals which received islet transplantation alone (P<0.05).

Figure 10A:
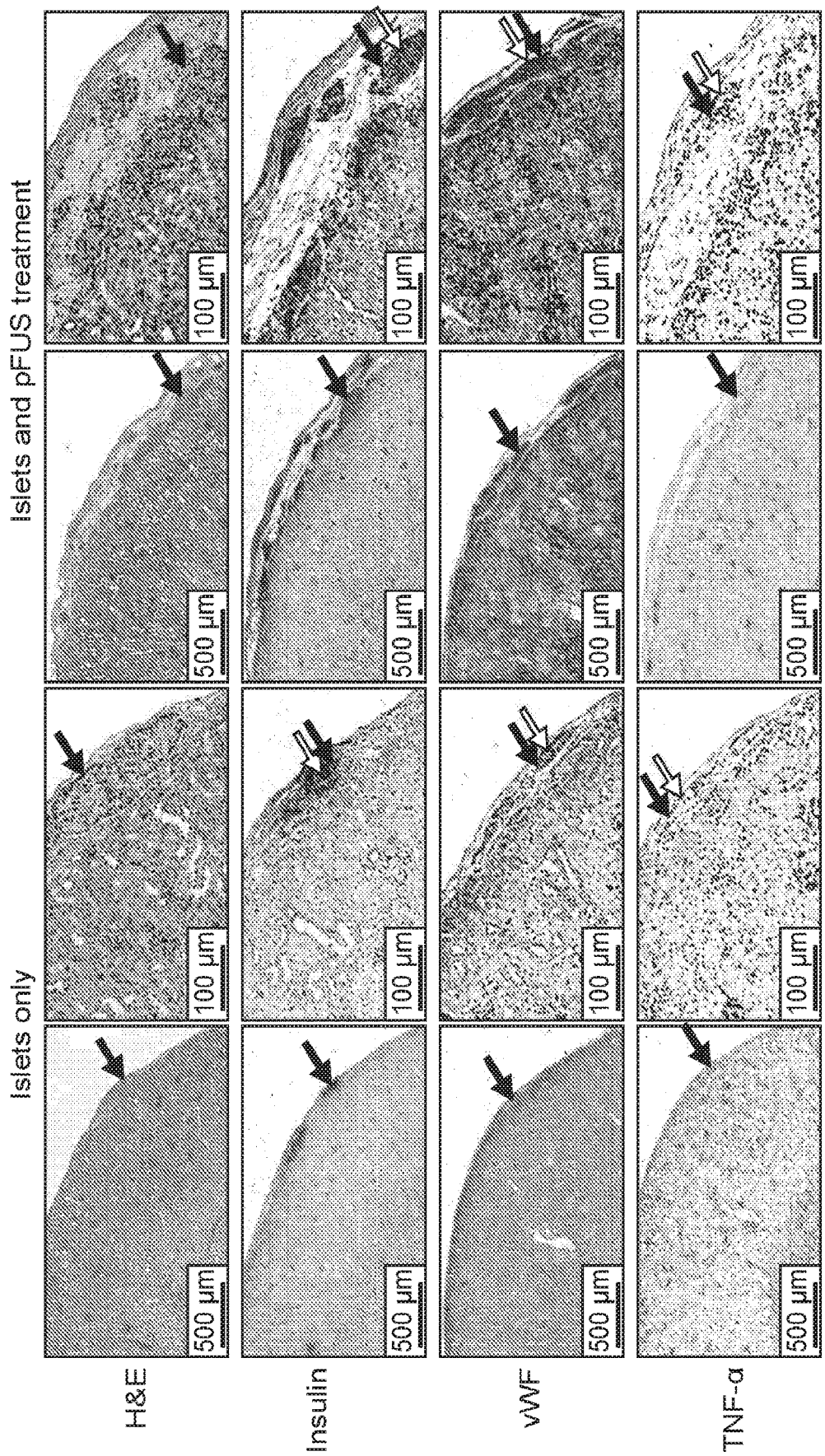
FIGS. 10A-10E. Histological assessment of transplanted islets.
Figure 10C:
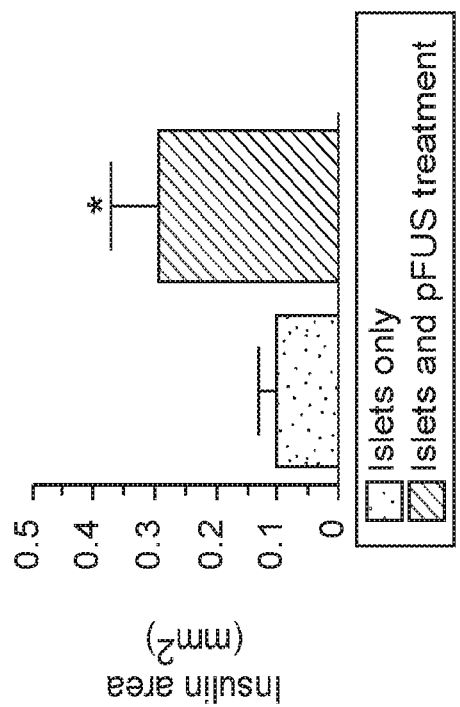
Figure 10E:
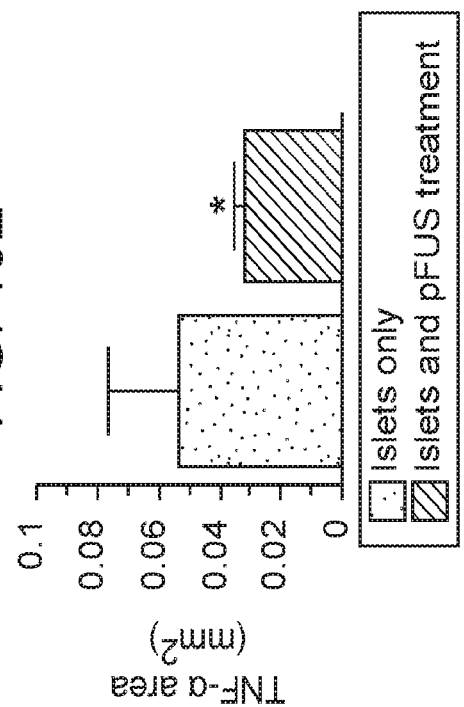
Figure 10B:
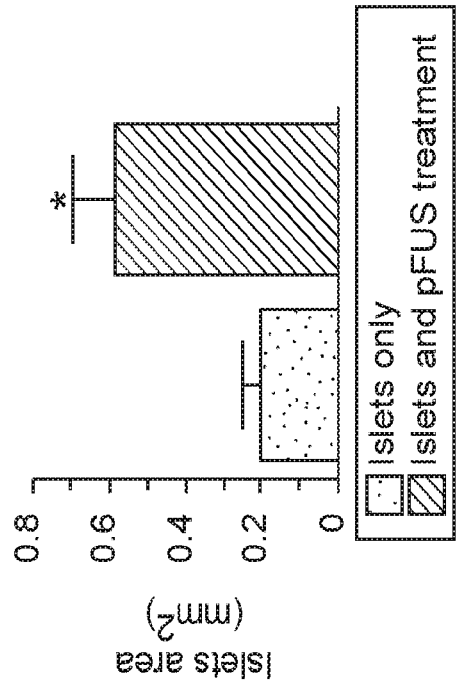
Figure 10D:
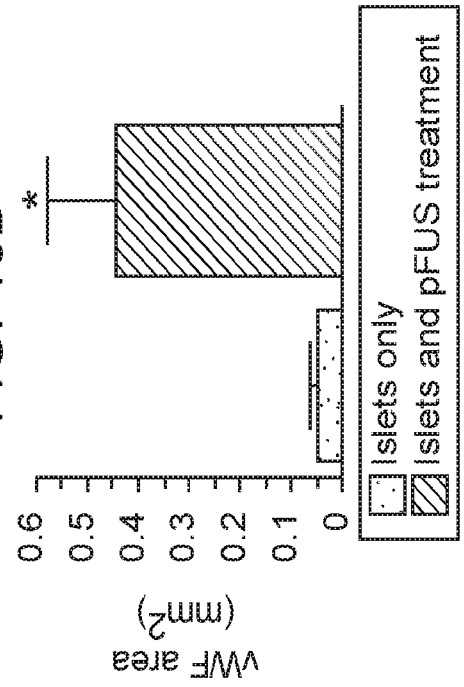

In animals treated with pFUS, there was a significantly greater number of viable transplanted islets in histological specimens compared to those animals which did not receive any pFUS treatment (total islet area: 0.58±0.11 vs 0.20±0.05 $mm^2$, P<0.05; FIGS. 10A, 10B). Transplanted islets treated with pFUS retained their native size, spherical morphology, and maintained their intrinsic architecture with β cells (positive insulin staining) located in the center of the islets; findings which were not found in islets transplanted alone (FIG. 10A). There was a significant increase in insulin staining in pFUS treated islets compared to islets only (insulin-positive area per section: 0.28±0.08 vs 0.10±0.03 mm2; P<0.05; FIGS. 10A, 10C). Following treatment with pFUS, transplanted islets demonstrated a greater degree of vascularity. This was confirmed using immunohistochemical analysis which showed a significantly higher expression of vWF in pFUS treated islets (vWF-positive area per $mm^2$ section: 0.44±0.14 vs 0.05±0.01; P<0.05; FIGS. 10A, 10D). Transplanted islets treated with pFUS also demonstrated reduced inflammation as evidenced by a reduction in the presence of TNF-α (TNF-α-positive area per section: 0.05±0.02 vs 0.03±0.003 mm2; P<0.05; FIGS. 10A, 10E).

Figure 11B:
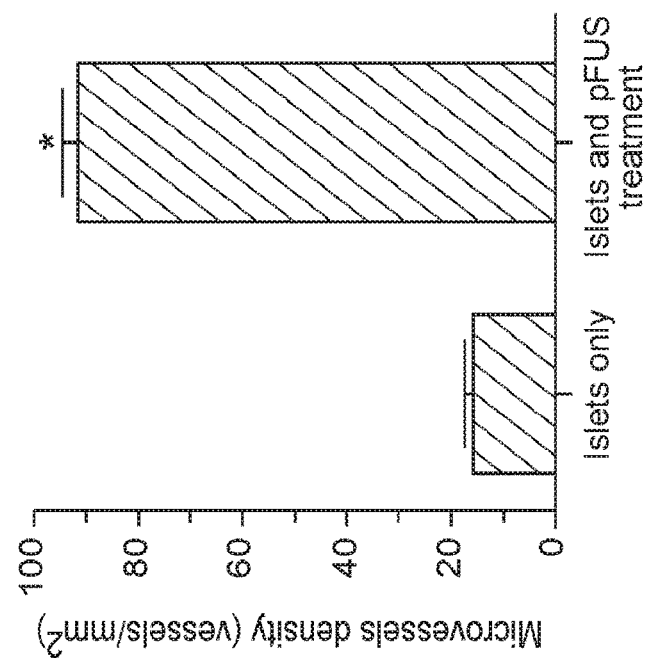

The greater degree of vascularity both surrounding, and within, transplanted islets treated with pFUS was further confirmed by H&E staining. Results showed significantly increased microvessel density for transplanted islets treated with pFUS compared to islets transplanted alone (92±3 vs 16±2 vessels/$mm^2$; FIG. 11).

Figure 12A:
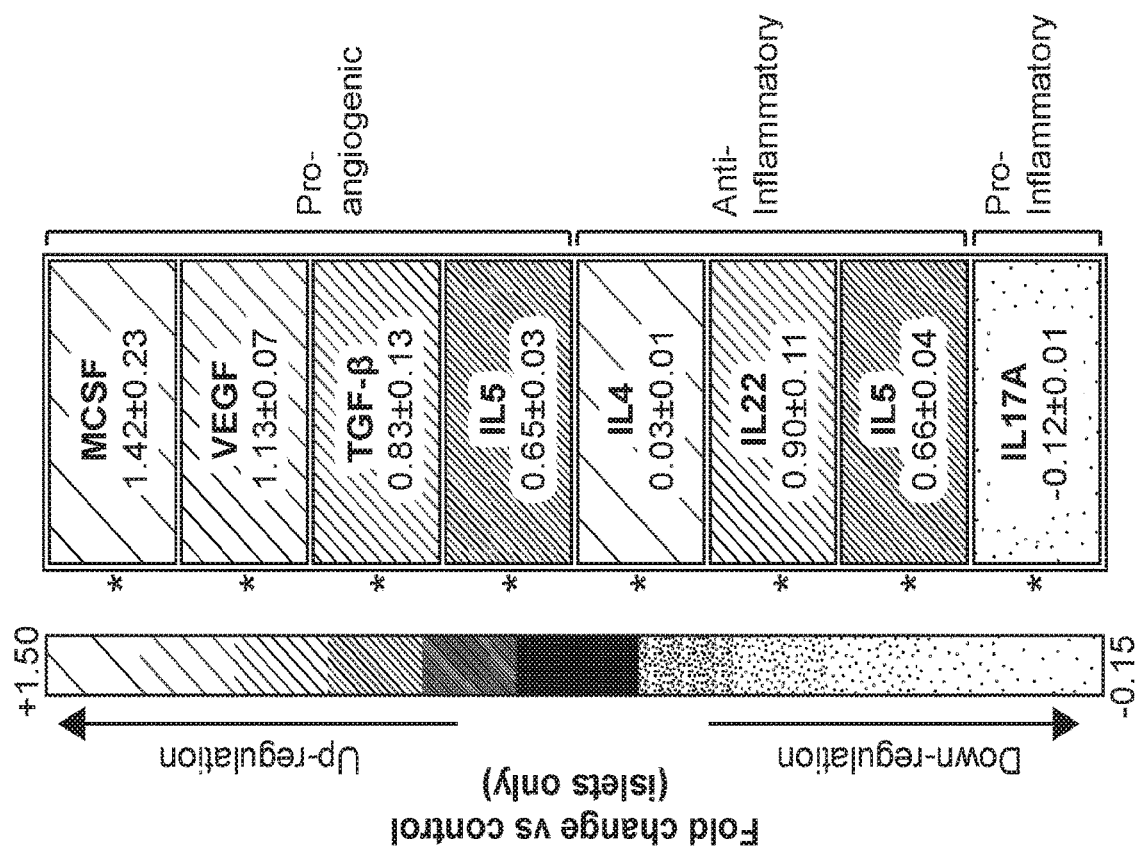
FIGS. 12A-12C. Tissue and Blood analysis following islet transplantation.
Figure 12B:
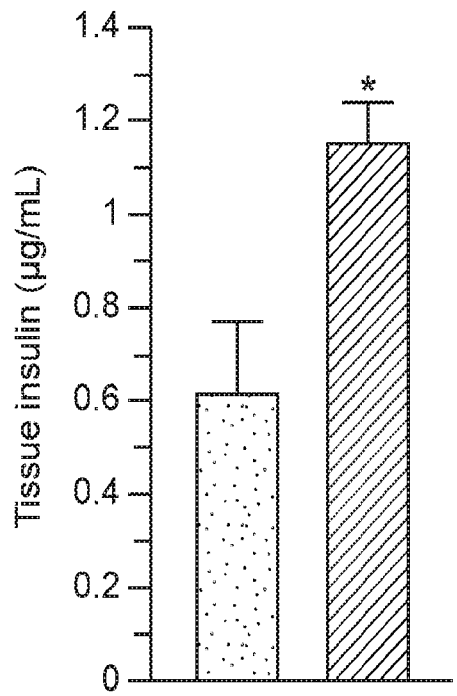
Figure 12C:
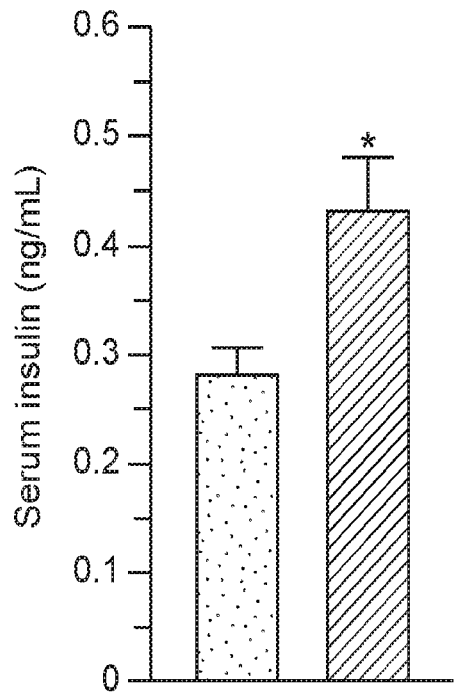

Within the kidneys which contained the transplanted islets that were treated with pFUS, we also noted an up-regulation of macrophage colony-stimulating factor (MCSF: 1.42±0.23 fold increase), vascular endothelial growth factor (VEGF: 1.13±0.07 fold increase), transforming growth factor beta (TGF-β: 0.83±0.13 fold increase), Interleukin 5 (IL5: 0.65±0.03 fold increase), 4 (IL4: 0.03±0.01 fold increase), 22 (IL22: 0.90±0.11 fold increase), 5 (IL5: 0.66±0.04 fold increase), and down-regulation of Interleukin 17 A (IL17A: 0.12±0.01 fold decrease) when compared to the untreated kidneys which contained the transplanted islets alone (FIG. 12A; P<0.05). Analysis of the explanted kidneys containing the islet transplant from animals treated with pFUS demonstrated a significantly higher amount of insulin compared with untreated animals (1.15±0.09 vs 0.61±0.16 µg/mL; P<0.05; FIG. 12B). Similarly, the insulin content within the serum of animals treated with pFUS was significantly higher (0.43±0.05 vs 0.28±0.02 ng/ml; P<0.05; FIG. 12C).

Discussion

In the present work, we found that pFUS can (i) safely stimulate insulin secretion from islets via a voltage dependent mechanism which stimulated calcium influx into cells that was acoustic intensity dependent and (ii) be used in vivo to facilitate the function, engraftment and survival of transplanted islets by promoting islet revascularization as well as reducing inflammation. In the latter case, diabetic mice treated with pFUS not only demonstrated an improved ability to re-establish glycemic control, but they also showed a faster dynamic response to glucose challenges.

Although the discovery of insulin has changed the outlook and survival for diabetic patients for almost a century[18], they are still not exempt from developing diabetic complications[19]. In part, this is due to the lack of tight regulation of glucose resulting in patients often having higher than normal blood glucose concentrations for sustained periods of time. Although islet transplantation aims to address this problem by establishing a functional islet mass in diabetic patients, it has encountered hurdles related to not enough islets surviving and engrafting following transplantation in addition to the surviving islets being able to function normally. Both of these issues can potentially be addressed with pFUS, which is a non-invasive technology that can target transplanted islets with acoustic waves, through imaging guidance. Indeed, our results show that when islets are treated with pFUS, their ability to release insulin from β cells in response to glucose is enhanced. Furthermore, this effect was acoustic intensity-dependent with higher intensities resulting in higher amounts of insulin released from islets. This is in keeping with studies from Castellanos et al. who also showed that ultrasound could be used to stimulate insulin from INS-1 pancreatic β cells[20]. However, in contrast to that study which showed that INS-1 pancreatic β cells were able to maintain their viability when stimulated with pFUS, we demonstrated that at high acoustic intensities (i.e. PNP of 212 kPa and ISPTP of 2.86 W/cm$^2$), there was a significant decrease in islet viability when compared to non-pFUS treated islets. This is likely due to the sensitive nature of islets compared to immortalized INS-1 pancreatic β cells, thereby potentially making them more susceptible to the mechanical effects of acoustic waves[21].

In addition, studies have shown that high ultrasound exposures can induce apoptosis in cells via mitochondria-caspase pathways and through inducing inertial cavitation[22]. Nevertheless, at medium intensities (i.e. PNP of 150 kPa, ISPTP of 1.43 W/cm$^2$), we observed an enhancement in islet function in vitro, with no decrease in viability.

Glucose enters β cells through the glucose transporter 2 (GLUT2) where it is then converted to pyruvate in the glycolysis pathway[23]. This results in an increase in the ATP/ADP ratio, which causes closure of ATP-sensitive K$^+$ channels[24] and thus membrane depolarization. In turn, this opens voltage-activated Ca$^{2+}$ channels resulting in an influx of calcium, which then increases intracellular calcium ([Ca$^{2+}$]i) that results in the release of insulin granules[23]. In the present study, when islets were treated with pFUS they demonstrated improved function; this can be attributed to pFUS-stimulating an increase in [Ca$^{2+}$]i which subsequently can trigger insulin granule exocytosis[25,26]. This can be due to pFUS either (i) increasing resting membrane potential (Vm) in β cells and hence reducing the threshold required to trigger depolarization and/or (ii) enhancing the influx of calcium following glucose stimulation. Furthermore, ultrasound has also been shown to stimulate calcium transients within cells[27] as well as transiently induce cell membrane permeabilization by creating re-sealable pores on cell membranes as a result of acoustic cavitation (both stable and inertial)[28,29]. Together, these effects can enable ions (including Ca$^{2+}$) to enter into β cells resulting in membrane depolarization and insulin secretion[27]. Future studies will aim to determine the relative contributions of each of the above effects in facilitating the Ca$^{2+}$-dependent enhancement in insulin release following pFUS observed in the present study.

When 175 islets alone were transplanted into diabetic animals, hyperglycemia could not be reversed; this is in keeping with other studies which have shown similar results using this sub-therapeutic number of islets alone[30,31]. However, when islets were sonicated with pFUS over the first 2 weeks following transplantation, diabetic animals could now re-establish glycemic control which was sustained for 30 days following transplantation. In addition, these animals also showed faster dynamic responses to glucose challenges compared to animals that were not treated with pFUS.

Elevated levels of glucose in the body (glucotoxicity) have been shown to contribute to the worsening functioning of both native and transplanted islets[32]. Here, we demonstrated how pFUS can change the insulin content within islets as well their ability to release insulin in response to glucose. The improvement in islet function observed in this study could be attributed to pFUS stimulating insulin secretion from transplanted islets; in turn, this will ensure that the blood glucose levels within the body are maintained within normal limits thereby facilitating islet engraftment and function[33]. Histological examination of the islet graft after 1 month demonstrated that islets treated with pFUS had better morphology (insulin staining noted within the center of islets), enhanced vascularization (increased vWF staining and microvessel density on H&E staining) and reduced evidence of inflammation (decrease in TNF-α staining). Previous studies have shown that the architecture, organization and morphology of islets play a crucial role in their function and outcome following transplantation. When islets aggregate, the diffusion of oxygen and nutrients to cells within the center of larger aggregates will be limited compared to smaller aggregates or separated islets, thereby affecting their function and ultimately their survival[34]. Furthermore, the revascularization of smaller islets (and hence aggregates) has also been shown to be more efficient when compared to larger islets[35].

Following islet transplantation, islets need to rapidly re-establish their vascular supply to ensure that they receive an adequate supply of nutrients and oxygen for survival[36]. If their revascularization is either delayed or is insufficient, islets will not survive and this will ultimately affect the overall function of the transplant[37,38]. Given that von Willebrand Factor (vWF) acts as a regulator of angiogenesis by controlling vessel proliferation and maturation[39], our data shows that pFUS increases vWF immunoreactivity in transplanted islets suggesting that soundwaves can help to promote vessel proliferation and maturation, thereby helping islets to form a more functional microcirculation. In addition, within the kidneys containing the transplanted islets, we also found the following pro-angiogenic factors to be upregulated: MCSF[40], VEGF-A[41], TGF-β[42], and IL5[43-]; Studies have shown that MCSF induces monocytes to produce and release VEGF-A which promotes endothelial cell (EC) proliferation and new blood vessel formation[40]. In addition, multiple studies have shown that VEGF-A is crucial for the revascularization of islets following transplantation[44] and β-cells themselves have been shown to secrete large amounts of VEGF-A, which is mitogenic for ECs and crucial for maintaining the density and specialty phenotype of fenestrated intra-islet ECs[45]. Similarly, TGF-β has been shown to enhance islet survival and function by inducing islet neogenesis[46] as well as promoting EC survival during angiogenesis[42]. While the role of IL-5 is less well defined, studies have shown that it has both pro-angiogenic[43] and anti-inflammatory[47] attributes. Hence, the observed increase in pro-angiogenic factors within the kidneys containing transplanted islets can potentially be attributed to these factors being secreted by islets following their treatment with pFUS; this is further supported by improved vascularization of transplanted islet as demonstrated by histological (i.e. H&E) and immunohistochemical (i.e. vWF staining) analysis of tissue samples. Taken together, is therefore plausible that pFUS is able to increase the release of these factors either indirectly (via its effect on the engraftment site—i.e. kidney) or directly (via stimulating individual cells within the transplanted islets).

In addition to the pro-angiogenic factors that were upregulated, pFUS also increased other cytokines such as TGF-β[48], IL4[49], IL22[48], and IL5[50], which have been shown to have anti-inflammatory properties, while decreasing cytokines such as IL17A[51], which have been shown to have pro-inflammatory properties. In keeping with this, we also observed a reduction in TNF-α staining within the transplanted islets that were treated with pFUS. This is important as the inflammatory response mounted by the recipient to transplanted islets has been shown to play a significant role in poor islet engraftment and survival[52].

The clinical translation of this pFUS to T1D patients is relatively feasible given that the equipment necessary to accomplish pFUS is identical to that used for HIFU treatments. Thus, it is only necessary to adjust the acoustic parameters to achieve the PNPs and acoustic intensities reported here. However, it should be noted that the PNPs and intensities measured here are non-derated values because the coupling medium (water) is non-attenuating and the depth at which the pFUS was applied in the animals was non-significant for the frequency utilized. For humans, it will be necessary to utilize acoustic parameters that achieve the reported PNPs and intensities after deration. Derating the PNPs and intensities will be necessary because, for clinical treatment, the transducer will be coupled directly to the individual (via acoustic coupling gel) and the acoustic pressure and intensities will be attenuated by the intervening tissue between the transducer and the target tissue region.

In summary, our results show that pFUS is safe and can stimulate the function of islets, via a $Ca^{2+}$-dependent mechanism. Furthermore, pFUS can enhance the engraftment (through facilitating islet revascularization and reducing inflammation), function and survival of islets following transplantation. Given that FUS is an FDA approved technology, pFUS therefore has the potential to be easily clinically translated as a completely non-invasive and drug-free therapeutic approach which can be utilized in the setting of islet transplantation.

Methods

Isolation and culture of Islets. Pancreatic islets were isolated from C57/B6 mice (male, 6-8 week-old, Charles River Laboratories, USA), as previously described (see *Supplemental Information*)[53].

In Vitro treatment of Islets with pFUS. For each pFUS treatment, experiments were performed using a 12 well-plate (Corning, USA) containing 100 islets/well. Given that the ultrasound beam width (16 mm) was close to the diameter of an individual well, this allowed the simultaneous sonication of all the islets since they were predominantly seeded in the center of a well. Ultrasound gel was applied on the surface of the piston transducer to couple it with the bottom of the well plate. For the in vitro experiments, the transducer was used with the following parameters: 1 MHz, 2000 cycle, sinusoidal pulses at a pulse repetition frequency (PRF) of 100 Hz for a 20% duty cycle (DC) and voltages of 12, 16.5, and 23.2 Vpk-pk to achieve three different acoustic intensities: low, medium and high, with a total pFUS exposure time of 1 min (Table 1). The selection of pFUS parameters was based on previous literature showing that these parameters could improve cellular function with no adverse effect on cell growth and/or viability[20,54].

In Vitro analysis of Islets treated with pfUS. Islet viability, glucose stimulated insulin secretion (GSIS) assay, calcium assay, and recording of membrane potential oscillations were performed as described in the Supplemental Information. All experiments were performed in triplicate where each individual experiment contained 30 islets in a 96 well plate (30 islets/well). As required, pFUS treated islets were selected from a 12 well-plate which contained 100 islets per well. There were 4 experimental groups tested: Group 1=no pFUS stimulation of islets (control); Group 2=islets stimulated with pFUS at a low intensity (PNP: 106 kPa, ISPTP: 0.71 $W/cm^2$); Group 3=islets stimulated with pFUS at a medium intensity (PNP: 150 kPa, ISPTP: 1.43 $W/cm^2$); and Group 4=islets stimulated with pFUS at a high intensity (PNP: 212 kPa, ISPTP: 2.86 $W/cm^2$).

Islet transplantation and treatment with pfUS. All experiments were approved by the Institutional Animal Care and Use Committee (IACUC) at Stanford University and all experiments were performed in accordance with relevant guidelines and regulations. Male C57BL/6 mice, at 6-8 weeks age (Charles River Laboratories, USA), were used as both donors and recipients. All animals were maintained on a 12 h:12 h light:dark cycle with ad libitum access to food and water. Recipient mice were matched for their body weight and baseline blood glucose levels and then randomly assigned into 2 experimental groups: Group 1: mice transplanted with islets only (n=5; Control Group) and Group 2: mice transplanted with islets followed by treatment with pFUS at days 3, 6, 9, and 12 post-transplantation (n=5). Prior to islet transplantation, all recipient mice were made diabetic (i.e. determined by 2 consecutive non-fasting blood glucose levels>350 mg/dl, as previously documented-) by an intraperitoneal injection of streptozotocin (STZ; 180 mg/kg). Isolated islets from C57BL/6 mice were cultured overnight before transplantation to allow the islets to rest following the isolation procedure prior to being transplanted as well as to enable quality control testing of the islets. Each diabetic mouse then received 175 handpicked islets, which were implanted under the right kidney capsule, before being randomly allocated to an experimental group.

Islets were then treated with pFUS as described in the Supplemental Information. To treat the whole kidney, 8 non-overlapping adjacent regions through the kidney were targeted for 30 sec per region. The time to treat one kidney with these parameters was approximately 4 min. In order to deliver pFUS therapy to the animal, the HIFU transducer was used with the following parameters: 5% DC, 5 Hz PRF, 2.9 MPa PNP, and 272 $W/cm^2$ ISAPA, which has been shown in previous studies to be safe in small animals (Table 2)[56]. After pFUS treatment, each mouse was removed from the water bath, dried, and placed in a recovery cage.

Statistical analysis. All values were expressed as the mean±standard error of the mean (SEM). Statistical analysis of all quantitative data was performed using a one or two-way ANOVA (Analysis of Variance) with post-hoc Tukey test (Astatsa.com; Online Web Statistical Calculators, USA) or unpaired Student's t-test with any differences considered statistically significant when P<0.05.

REFERENCES

1. Bluestone, J. A. et al. Type 1 diabetes immunotherapy using polyclonal regulatory T cells. *Sci. Transl. Med.* 7 (2015).
2. Skyler, J. S. & Ricordi, C. Stopping type 1 diabetes: Attempts to prevent or cure type 1 diabetes in man. *Diabetes* 60, 1-8 (2011).
3. El-khatib, F. H., Russell, S. J., Nathan, D. M., Sutherlin, R. G. & Damiano, E. R. A bihormonal closed-loop artificial pancreas for type 1 diabetes. *Sci. Transl. Med.* 2 (2010).
4. Dominguez-Bendala, J. & Ricordi, C. Present and future cell therapies for pancreatic beta cell replenishment. *World J. Gastroenterol.* 18, 6876-6884 (2012).
5. Misler, S. The isolated pancreatic islet as a micro-organ and its transplantation to cure diabetes: Celebrating the legacy of Paul Lacy. *Islets* 2, 210-224 (2010).
6. Nilsson, B., Ekdahl, K. N. & Korsgren, O. Control of instant blood-mediated inflammatory reaction to improve islets of Langerhans engraftment. *Current Opinion in Organ Transplantation* 16, 620-626 (2011).
7. Henquin, J. C. Regulation of insulin secretion: A matter of phase control and amplitude modulation. *Diabetologia* 52, 739-751 (2009).
8. Barton, F. B. et al. Improvement in outcomes of clinical islet transplantation: 1999-2010. *Diabetes Care* 35, 1436-1445 (2012).
9. Ludwig, B. et al. Improvement of islet function in a bioartificial pancreas by enhanced oxygen supply and growth hormone releasing hormone agonist. *Proc. Nat. Acad. Sci.* 109, 5022-5027 (2012).
10. Castellanos, I. S. et al. Calcium-dependent ultrasound stimulation of secretory events from pancreatic beta cells. *J. Ther. Ultrasound* 5 (2017).
11. Juffermans, L. J. M., Kamp, O., Dijkmans, P. A., Visser, C. A. & Musters, R. J. P. Low-Intensity Ultrasound-Exposed Microbubbles Provoke Local Hyperpolarization of the Cell Membrane Via Activation of BKCa Channels. *Ultrasound Med. Biol.* 34, 502-508 (2008).
12. Mizrahi, N., Seliktar, D. & Kimmel, E. Ultrasound-Induced Angiogenic Response in Endothelial Cells. *Ultrasound Med. Biol.* 33, 1818-1829 (2007).
13. Clement, G. T. Perspectives in clinical uses of high-intensity focused ultrasound. *Ultrasonics* 42, 1087-1093 (2004).
14. Carpentier, A. et al. Clinical trial of blood-brain barrier disruption by pulsed ultrasound. *Sci. Transl. Med.* 8 (2016).
15. Kennedy, J. E. High-intensity focused ultrasound in the treatment of solid tumours. *Nature Reviews Cancer* 5, 321-327 (2005).
16. Frenkel, V. Ultrasound mediated delivery of drugs and genes to solid tumors. *Advanced Drug Delivery Reviews* 60, 1193-1208 (2008).
17. Szot, G. L., Koudria, P. & Bluestone, J. A. Transplantation of Pancreatic Islets Into the Kidney Capsule of Diabetic Mice. *J. Vis. Exp.*, doi: 10.3791/404 (2008).
18. Bai, Y. Stem cell therapy for type 1 diabetes mellitus. *Chinese J. Tissue Eng. Res.* 19, 3096-3101 (2015).
19. Nathan, D. M. Finding New Treatments for Diabetes—How Many, How Fast . . . How Good? *N. Engl. J. Med.* 356, 437-440 (2007).
20. Suarez Castellanos, I., Jeremic, A., Cohen, J. & Zderic, V. Ultrasound Stimulation of Insulin Release from Pancreatic Beta Cells as a Potential Novel Treatment for Type 2 Diabetes. *Ultrasound Med. Biol.* 43, 1210-1222 (2017).
21. Shenkman, R. M., Godoy-Silva, R., Papas, K. K. & Chalmers, J. J. Effects of energy dissipation rate on islets of langerhans: Implications for isolation and transplantation. *Biotechnol. Bioeng.* 103, 413-423 (2009).
22. Honda, H., Kondo, T., Zhao, Q. L., Feril, L. B. & Kitagawa, H. Role of intracellular calcium ions and reactive oxygen species in apoptosis induced by ultrasound. *Ultrasound Med. Biol.* 30, 683-692 (2004).
23. Wollheim, C. B. Beta-cell mitochondria in the regulation of insulin secretion: A new culprit in Type II diabetes. *Diabetologia* 43, 265-277 (2000).
24. Schulze, D. U., Düfer, M., Wieringa, B., Krippeit-Drews, P. & Drews, G. An adenylate kinase is involved in KATP channel regulation of mouse pancreatic beta cells. *Diabetologia* 50, 2126-2134 (2007).
25. Hassan, M. A., Campbell, P. & Kondo, T. The role of Ca2+ in ultrasound-elicited bioeffects: Progress, perspectives and prospects. *Drug Discovery Today* 15, 892-906 (2010).
26. Tsukamoto, A. et al. Stable cavitation induces increased cytoplasmic calcium in L929 fibroblasts exposed to 1-MHz pulsed ultrasound. *Ultrasonics* 51, 982-990 (2011).
27. Suarez Castellanos, I. M., Balteanu, B., Singh, T. & Zderic, V. Therapeutic modulation of calcium dynamics using ultrasound and other energy-based techniques. *IEEE Rev. Biomed. Eng.* 9, 177-191 (2016).
28. Yudina, A. & Moonen, C. Ultrasound-induced cell permeabilisation and hyperthermia: Strategies for local delivery of compounds with intracellular mode of action. *Int. J. Hyperth.* 28, 311-319 (2012).
29. Mitragotri, S. Healing sound: The use of ultrasound in drug delivery and other therapeutic applications. *Nat. Rev. Drug Discov.* 4, 255-260 (2005).
30. Kim, S. J., Nian, C., Doudet, D. J. & Mcintosh, C. H. S. Dipeptidyl peptidase IV inhibition with MK0431 improves islet graft survival in diabetic NOD mice partially via T-cell modulation. *Diabetes* 58, 641-651 (2009).
31. Deng, S. et al. Insulin gene transfer enhances the function of human islet grafts. *Diabetologia* 46, 386-393 (2003).
32. Poitout, V. et al. Regulation of the insulin gene by glucose and fatty acids. *J. Nutr.* 136, 873-6 (2006).
33. Tanaka, Y., Gleason, C. E., Tran, P. O. T., Harmon, J. S. & Robertson, R. P. Prevention of glucose toxicity in HIT-T15 cells and Zucker diabetic fatty rats by antioxidants. *Proc. Nat. Acad. Sci.* 96, 10857-10862 (1999).
34. Carlsson, P. O., Liss, P., Andersson, A. & Jansson, L. Measurements of oxygen tension in native and transplanted rat pancreatic islets. *Diabetes* 47, 1027-1032 (1998).
35. Kampf, C., Mattsson, G. & Carlsson, P. O. Size-dependent revascularization of transplanted pancreatic islets. *Cell Transplant.* 15, 205-209 (2006).
36. Vajkoczy, P., Menger, M. D., Simpson, E. & Messmer, K. Angiogenesis and Vascularization of Murine Pancreatic Islet Isografts. *Transplantation* 60, 123-126 (2007).
37. Del Toro-Arreola, A., Robles-Murillo, A. K., Daneri-Navarro, A. & Rivas-Carrillo, J. D. The role of endothelial cells on islet function and revascularization after islet transplantation. *Organogenesis* 12, 28-32 (2016).

38. Vlahos, A. E., Cober, N. & Sefton, M. V. Modular tissue engineering for the vascularization of subcutaneously transplanted pancreatic islets. *Proc. Natl. Acad. Sci.* 114, 9337-9342 (2017).
39. Randi, A. M. & Laffan, M. A. Von Willebrand factor and angiogenesis: basic and applied issues. *Journal of Thrombosis and Haemostasis* 15, 13-20 (2017).
40. Eubank, T. D., Galloway, M., Montague, C. M., Waldman, W. J. & Marsh, C. B. M-CSF Induces Vascular Endothelial Growth Factor Production and Angiogenic Activity From Human Monocytes. *J. Immunol.* 171, 2637-2643 (2003).
41. Holmes, D. I. R. & Zachary, I. The vascular endothelial growth factor (VEGF) family: Angiogenic factors in health and disease. *Genome Biology* 6 (2005).
42. Viñals, F. & Pouyssegur, J. Transforming growth factor beta1 (TGF-beta1) promotes endothelial cell survival during in vitro angiogenesis via an autocrine mechanism implicating TGF-alpha signaling. *Mol. Cell. Biol.* 21, 7218-30 (2001).
43. Park, S. L. et al. HSP70-1 is required for interleukin-5-induced angiogenic responses through eNOS pathway. *Sci. Rep.* 7 (2017).
44. Brissova, M. et al. Pancreatic islet production of vascular endothelial growth factor-A is essential for islet vascularization, revascularization, and function. *Diabetes* 55, 2974-2985 (2006).
45. Peiris, H., Bonder, C. S., Coates, P. T. H., Keating, D. J. & Jessup, C. F. The β-cell/EC axis: How do islet cells talk to each other? *Diabetes* 63, 3-11 (2014).
46. Han, B., Qi, S. Hu, B., Luo, H. & Wu, J. TGF-i Promotes Islet-Cell Function and Regeneration. *J. Immunol.* 186, 5833-5844 (2011).
47. El-Wakkad, A., Hassan, N. E. M., Sibaii, H. & El-Zayat, S. R. Proinflammatory, anti-inflammatory cytokines and adiponkines in students with central obesity. *Cytokine* 61, 682-687 (2013).
48. Sanjabi, S., Zenewicz, L. A., Kamanaka, M. & Flavell, R. A. Anti-inflammatory and pro-inflammatory roles of TGF-β, IL-10, and IL-22 in immunity and autoimmunity. *Current Opinion in Pharmacology* 9, 447-453 (2009).
49. Woodward, E. A., Prêle, C. M., Nicholson, S. E., Kolesnik, T. B. & Hart, P. H. The anti-inflammatory effects of interleukin-4 are not mediated by suppressor of cytokine signalling-1 (SOCS1). *Immunology* 131, 118-127 (2010).
50. Pripp, A. H. & Stanišić, M. The correlation between pro- and anti-inflammatory cytokines in chronic subdural hematoma patients assessed with factor analysis. *PLoS One* 9 (2014).
51. Dong, C. Regulation and pro-inflammatory function of interleukin-17 family cytokines. *Immunological Reviews* 226, 80-86 (2008).
52. Citro, A., Cantarelli, E. & Piemonti, L. Anti-inflammatory strategies to enhance islet engraftment and survival. *Curr. Diab. Rep.* 13, 733-744 (2013).
53. Neuman, J. C., Truchan, N. A., Joseph, J. W. & Kimple, M. E. A Method for Mouse Pancreatic Islet Isolation and Intracellular CAMP Determination. *J. Vis. Exp.* e50374, 10.3791/50374 (2014).
54. Zhou, X. et al. Improved Human Bone Marrow Mesenchymal Stem Cell Osteogenesis in 3D Bioprinted Tissue Scaffolds with Low Intensity Pulsed Ultrasound Stimulation. *Sci. Rep.* 6 (2016).
55. Molven, A. et al. The hypoglycemic phenotype is islet cell-autonomous in short-chain hydroxyacyl-CoA dehydrogenase-deficient mice. *Diabetes* 65, 1672-1678 (2016).
56. Burks, S. R. et al. Pulsed focused ultrasound pretreatment improves mesenchymal stromal cell efficacy in preventing and rescuing established acute kidney injury in mice. *Stem Cells* 33, 1241-1253 (2015).

TABLE 1

Acoustic Output of pFUS used for in vitro treatment of islets

| Acoustic Output | DC (%) | PRF (Hz) | PNP (kPa) | MI (MPa/MHz$^{1/2}$) | TI (° C.) | Isata (W/cm$^2$) | Isapa (W/cm$^2$) | Isptp (W/cm$^2$) | Time (min) |
|---|---|---|---|---|---|---|---|---|---|
| Low | 20 | 100 | 106 | 0.11 | 0.37 | 0.05 | 0.14 | 0.71 | 1 |
| Medium | 20 | 100 | 150 | 0.15 | 0.74 | 0.10 | 0.27 | 1.43 | 1 |
| High | 20 | 100 | 212 | 0.21 | 1.48 | 0.20 | 0.55 | 2.86 | 1 |

TABLE 2

Acoustic Output of pFUS used for in vivo treatment of islets*.

| | DC (%) | PRF (Hz) | PNP (MPa) | MI (MPa/MHz$^{1/2}$) | TI (° C.) | $I_{sata}$ (W/cm$^2$) | $I_{sapa}$ (W/cm$^2$) | $I_{sptp}$ (W/cm$^2$) | Time (min) |
|---|---|---|---|---|---|---|---|---|---|
| Acoustic Output | 5 | 5 | 2.9 | 2.8 | 1.6 | 13 | 272 | 895 | 4 |

*The values presented in Tables 1 and 2 are non-derated values. DC: Duty Cycle. PRF: Pulse Repetition Frequency. PNP: Peak Negative Pressure. MI: Mechanical Index at 1.1 MHz. TI: Thermal Index. Isata: Spatial Average Temporal Average Intensity. Isapa: Spatial Average Pulse Average Intensity. Isptp: Spatial Peak Temporal Peak Intensity.

Example 3

The Paracrine Function of Mesenchymal Stem Cells in Response to Pulsed Focused Ultrasound Introduction Mesenchymal stem cells (MSCs) are multipotent stem cells[1] that can be isolated from various tissues[2-10]. Although bone marrow derived MSCs (BM-MSCs) have traditionally been used as the main source of MSCs in clinical practice, MSCs derived from adipose tissue (AD-MSCs) and umbilical cord (UC-MSCs) have emerged as new and readily available sources with well documented regenerative and immunomodulatory properties[11-14]. While AD-MSCs can be easily isolated with high yield from adipose tissue obtained during routine liposuction/lipoplasty procedures[15], UC-MSCs are retrieved from the umbilical cord which is considered a medical waste at the time of birth.

MSCs actively secrete cytokines and growth factors that act either on themselves (autocrine function) or neighboring cells (paracrine function) to modulate the immune system, inflammatory response, as well as stimulate neo-angiogenesis[16]. For instance, MSC-secreted cytokines have been implicated in the repair and regeneration of the central nervous system (CNS)[17], heart[18-21], bone[16,22], and other damage tissues[23]. Given that MSCs have the ability to sense and respond to various stimuli[24-26], several groups have investigated preconditioning MSCs (i.e. intentionally exposing them to a controlled amount of stimulus for a defined period of time in order to produce a desired response) to enhance their secretion of trophic factors[16]; these stimuli include hypoxia[27], thermal shock inductions[28], pharmacologic treatment[29] and pro-inflammatory (IFN-γ or TNF-α) cytokine exposure[30,31]. However, following their administration into the patients, there is currently no way in which MSCs can actively and controllably be stimulated.

One approach to non-invasively stimulate MSCs in a controlled and systematic way outside of the body, as well as inside the body following their administration, is to sonicate them using waves. Focused ultrasound (FUS) is a novel technology, which can focus sound waves at specific locations deep in the body, with pin-point accuracy, without the use of any incisions. Pulsed focused ultrasound (pFUS) is a variation of this technology that uses short duty-cycles to minimize temperature elevations, thereby allowing the biomechanical effects of ultrasound to predominate[32]. We have recently shown that pFUS can stimulate pancreatic islets to increase in their function and release of insulin[33]. Hence, we hypothesized that pFUS can also stimulate MSCs and modulate their paracrine function by changing their profile of secreted cytokines. We therefore examined the effect of pFUS on the viability and function (determined by their paracrine function) of MSCs derived from various sources (i.e. BM, AD and UC-MSCs).

Materials and Methods

MSC Isolation and In Vitro Expansion

Human AD- and UC-MSCs were kindly donated from the University of Miami (from Drs Ricordi and Patel) (refs) and Human BM-MSCs were kindly donated from the laboratory of diagnostic research at the NIH (from Dr Frank) (ref). All MSCs were full characterized as previously described (refs). BM- and AD-MSCs were cultured in Mesenchymal Stem Cell Growth Medium (Lonza, NJ, US), supplemented with 10% FBS with additional supplements (MSCGM hMSC SingleQuot Kit, Lonza, NJ, US). UC-MSCs were cultured in low glucose DMEM (Fisher Scientific, Grand Island, NY, US) supplemented with 10% XcytepLUS (ibiologics), 1% glutamax (Gibco, Grand Island, NY, US), 1% non-essential amino acids solution (NEAA; Gibco, Grand Island, NY, US) and 1% penicillin and streptomycin (Life Technologies, Grand Island, NY, US). All cells were cultured in an incubator at 37° C. with 5% $CO_2$, and the culture media changed every 3 days.

MSC Stimulation with Pulsed-Focus Ultrasound (pFUS)

pFUS was performed on MSCs as described previously[34]. For each pFUS treatment, experiments were performed using a 6 well-plate (Corning, USA) containing $10^5$ MSCs/well. MSCs were first cultured in the well-plates for 24 h; the plate was then immersed in an autoclaved water bath and placed above the pFUS transducer at the transducer's focal spot (i.e. 50 mm away from the transducer surface). For sound waves to cover all the MSCs cultured in each well-plate, each well was divided into 25 spots (5×5 mesh, 5.75 mm distance between each point). The culture plates were then held still, while the 1 MHz transducer was attached to the AIMS system for precise positioning and moving of the pFUS transducer to cover all 25 spots. The following pFUS parameters were fixed: 1 MHz frequency, 20% duty cycle, 100 Hz PRF, with the total duration time of 6 min (i.e. 14.4 sec per spot). MSCs were then divided into 3 groups: Group 1: MSCs stimulated with low dose pFUS (i.e. 0.45 W/cm$^2$ $I_{SATA}$; 310 kPa NPP); Group 2: MSCs stimulated with high dose pFUS (i.e. 1.3 W/cm$^2$ $I_{SATA}$; 540 kPa NPP); and Group 3: MSCs with no pFUS stimulation (controls). Each treatment was repeated in duplicate.

Analysis of MSC-Secreted Cytokines

Following pFUS stimulation, MSCs were incubated at 37° C. and 5% $CO_2$ for 48 h, after which time their culture media was collected for multiplex immunoassay analysis (human multiplex ELISA; eBiosciences/Affymetrix/Fisher) to assess and measure the levels of secreted cytokines. In brief, beads were first added to a 96 well plate and washed (Biotek ELx405). Samples were then added to the plate containing the mixed antibody-linked beads and incubated at room temperature for 1 h followed by overnight incubation at 4° C. on a plate shaker (500 rpm). A biotinylated detection antibody was then added, after which the plates were incubated at room temperature for 75 min on a plate shaker (500 rpm). Next, the samples were washed and streptavidin-PE added followed by incubation of the plate for 30 min at room temperature on the plate shaker (500 rpm). The plate was then washed and a reading buffer added to the wells. Finally, a Luminex Flex 3D instrument was used to read the plates with a lower bound of 50 beads per sample per cytokine. Control assay beads (Radix Biosolutions) were added to wells. Multiplex ELISA assays were performed on all 3 sources of MSCs (i.e. BM-, AD-, and UC-MSCs), which was sampled twice and the average cytokine value was taken from 2 separate readings. The percentage change in cytokine expression from pFUS stimulated MSCs relative to control (i.e. non-stimulated) MSCs was then calculated (Eq. 1):

$$\text{Percentage change vs. control} = \frac{OD_{sample} - OD_{control}}{OD_{control}} \times 100$$

$OD_{sample}$: optical density (absorbance) of MSCs stimulated with pFUS; $OD_{control}$: optical density of control MSCs. Data was compiled as a heat map with upregulation represented as a red color gradient and downregulation represented as a green color gradient. We then categorized the secreted cytokines to three subgroups: immunomodulatory, anti-inflammatory, and angiogenic cytokines.

Determination of MSCs Morphology and Viability

Following pFUS stimulation, MSCs were incubated at 37° C. and 5% $CO_2$ for 48 h and then harvested and counted using a hemocytometer[35]. Cell numbers were compared with the cell number at time point 0 and the results expressed as the fold change vs. control. Cell morphology was also observed under a confocal microscope (Zeiss LSM710).

Statistical Analysis

All experimental data is expressed as the mean±standard error of the mean. Statistical analysis of all quantitative data was performed using One-way ANOVA (Analysis of variance) with post hoc Tukey test (Astatsa.com; Online Web Statistical Calculators, USA) with any differences considered statistically significant when P<0.05.

Results

Analysis of MSC-Secreted Cytokines

BM-MSCs

Figure 13A:
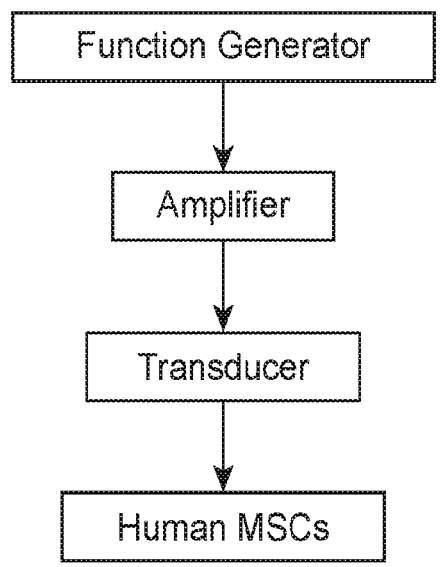
FIGS. 13A-13E. Set-up (FIG. 13A), schematic (FIG. 13B), photo (FIG. 13C) and field distribution of pFUS used in our study for MSCs stimulation (FIGS. 13D-13E): MSCs were first cultured in the well-plates; the plate was then immersed in an autoclaved water and placed above the pFUS transducer at the transducer's focal spot. The transmitted ultrasound waves were produced by a function generator, amplified through a power amplifier at a constant gain and emitted from a focused piston transducer face. In order for sound waves to cover whole MSCs cultured in well-plate, each well was graded into 25 spots (5×5 mesh, 5.75 mm distance between each points).
Figure 13C:
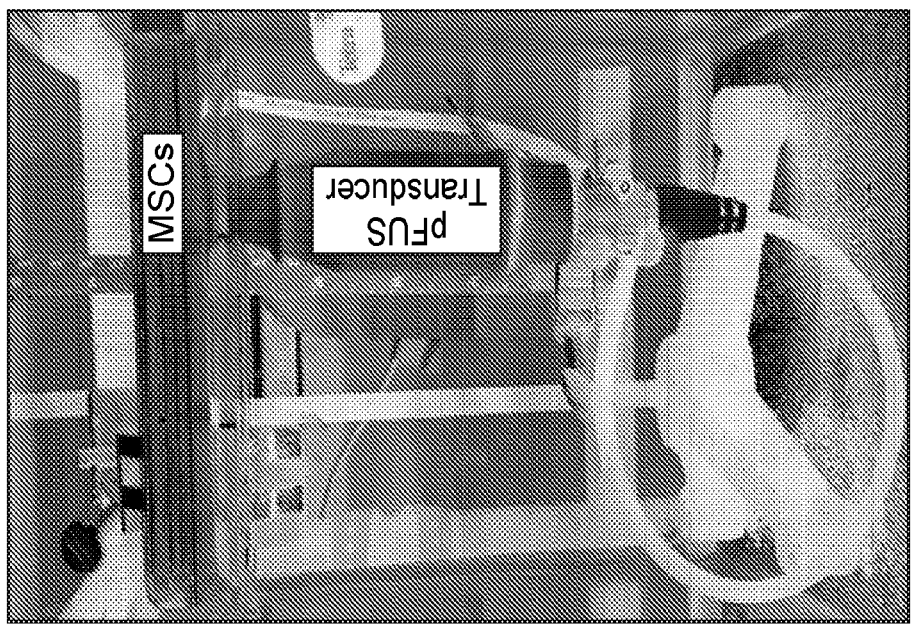
Figure 13B:
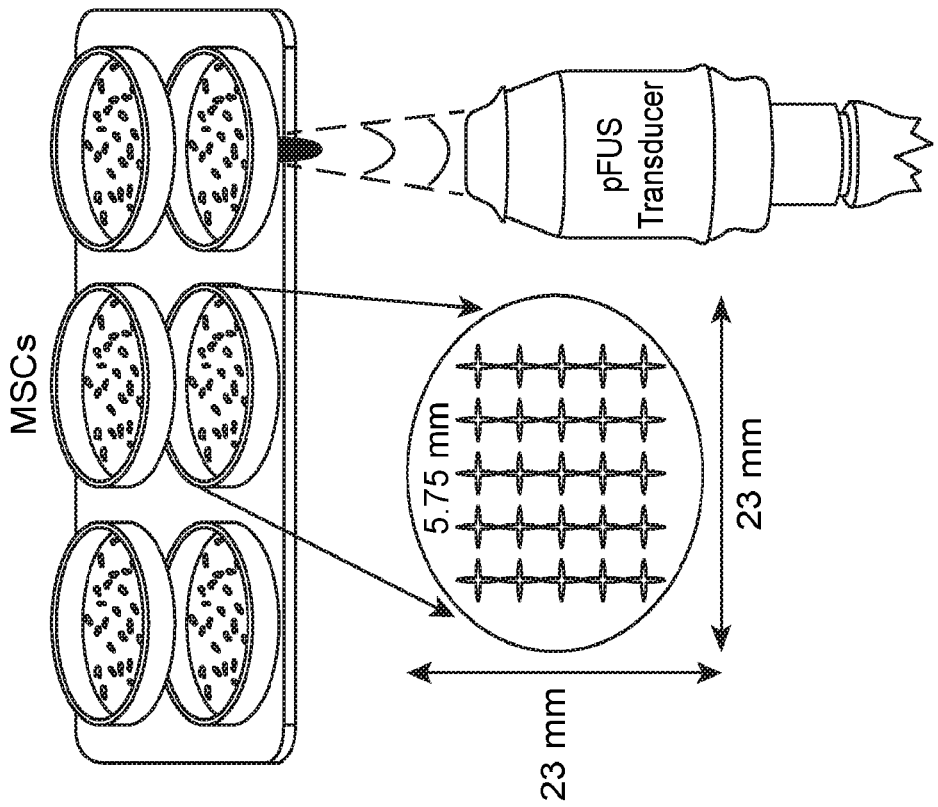
Figure 13D:
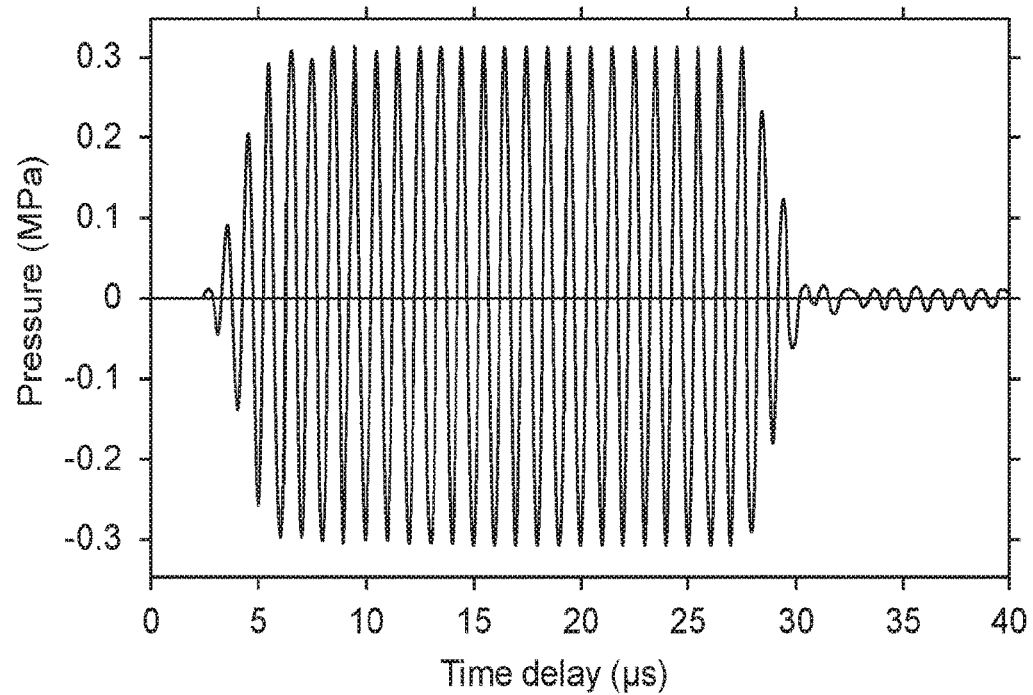
Figure 13E:
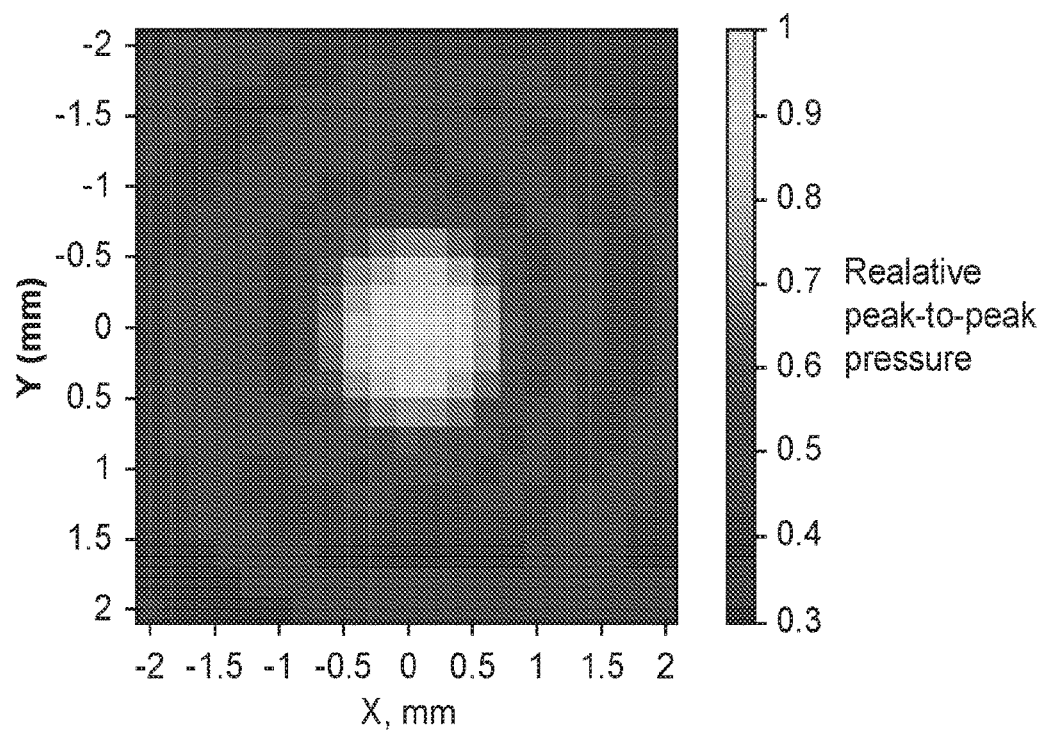
Figure 14A:
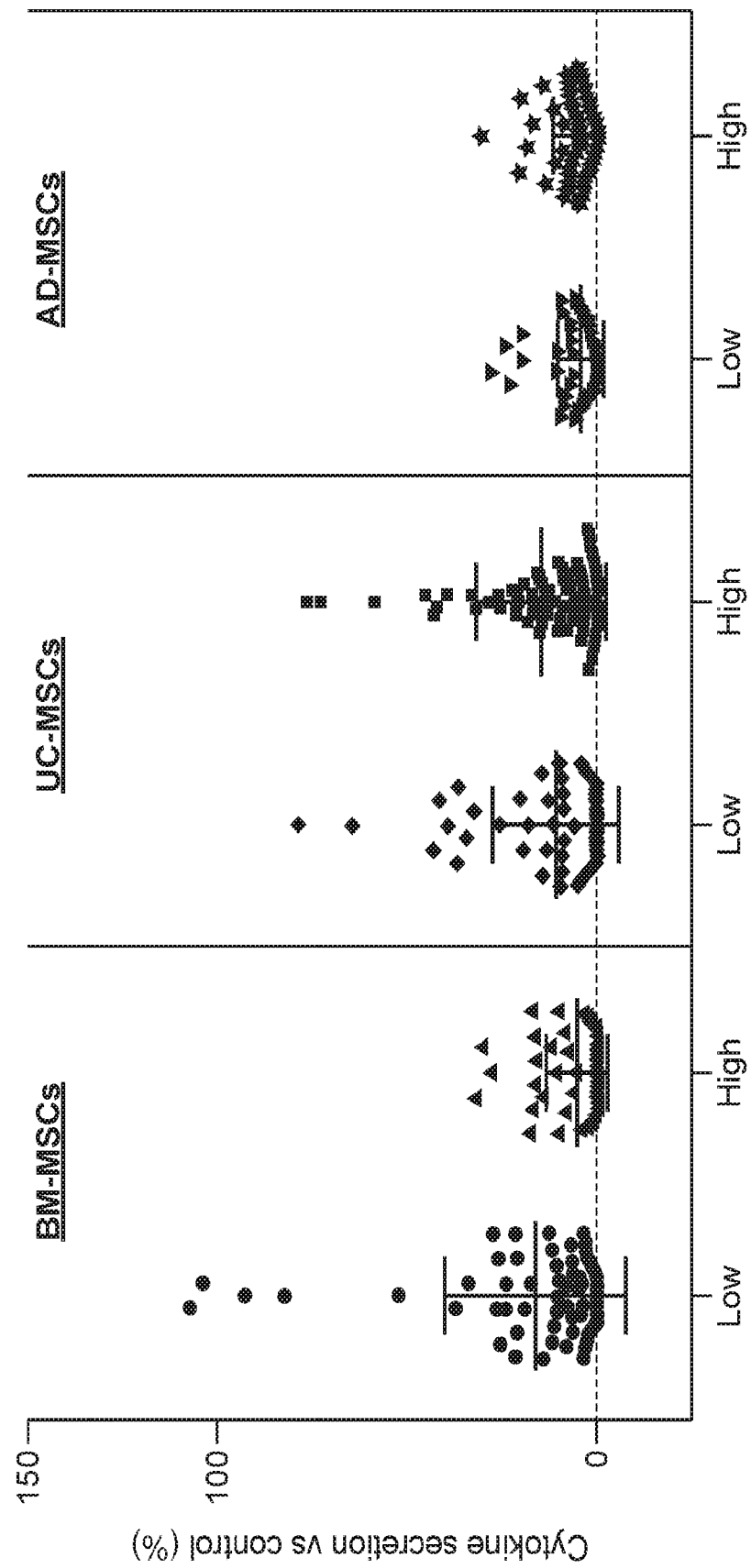
FIGS. 14A-14B. Analysis of MSCs secreted paracrine cytokines.
Figure 14B:
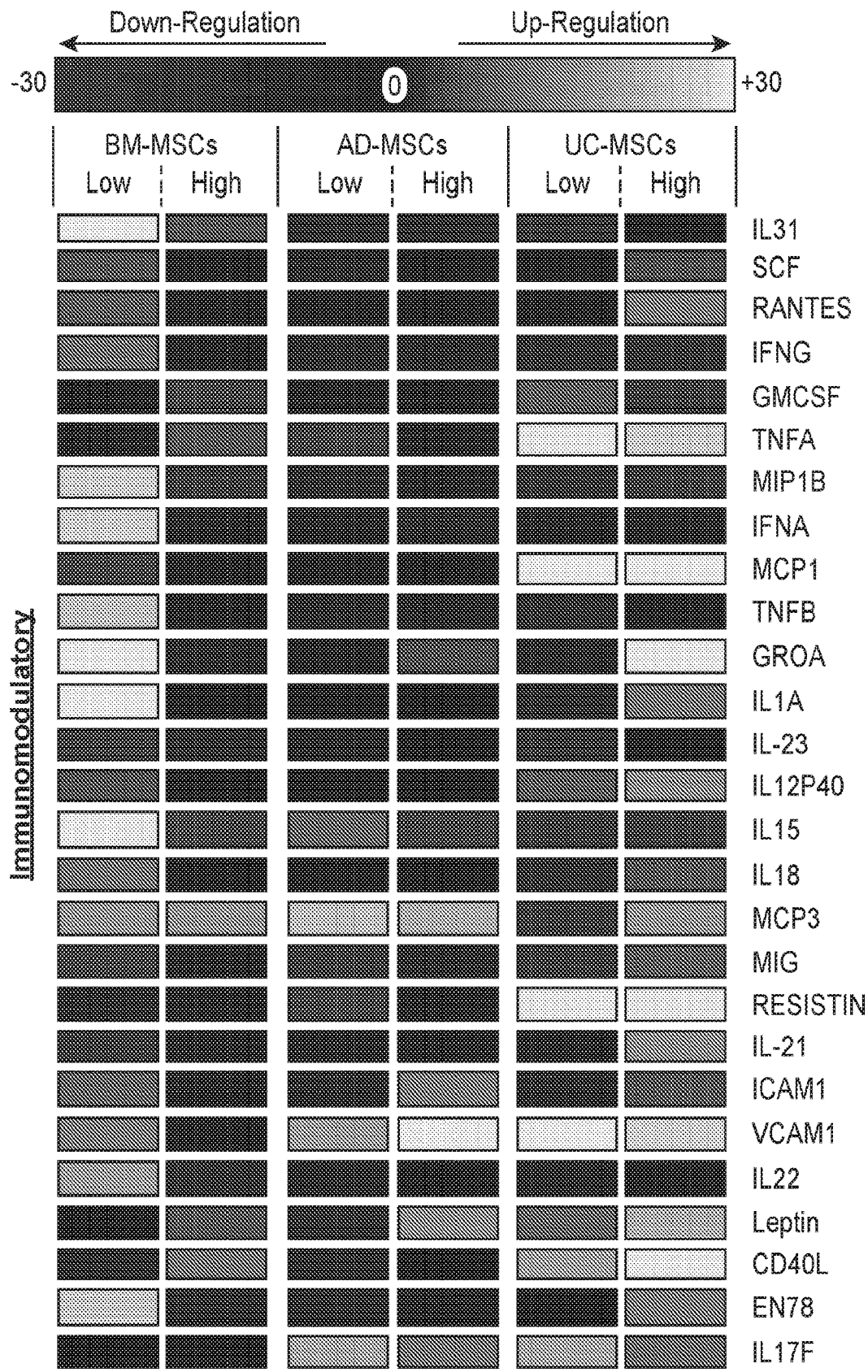
Figure 14B:
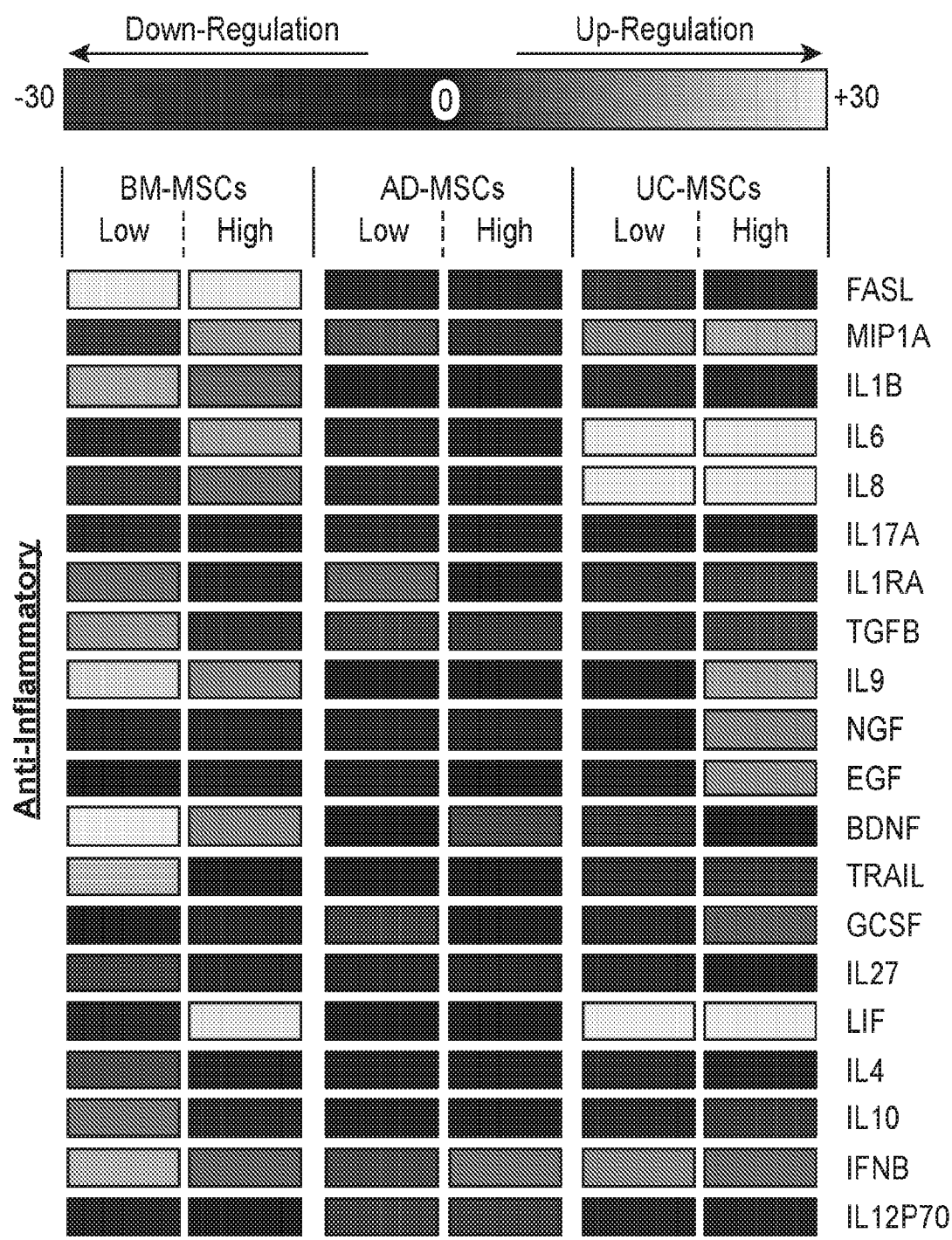
Figure 14B:
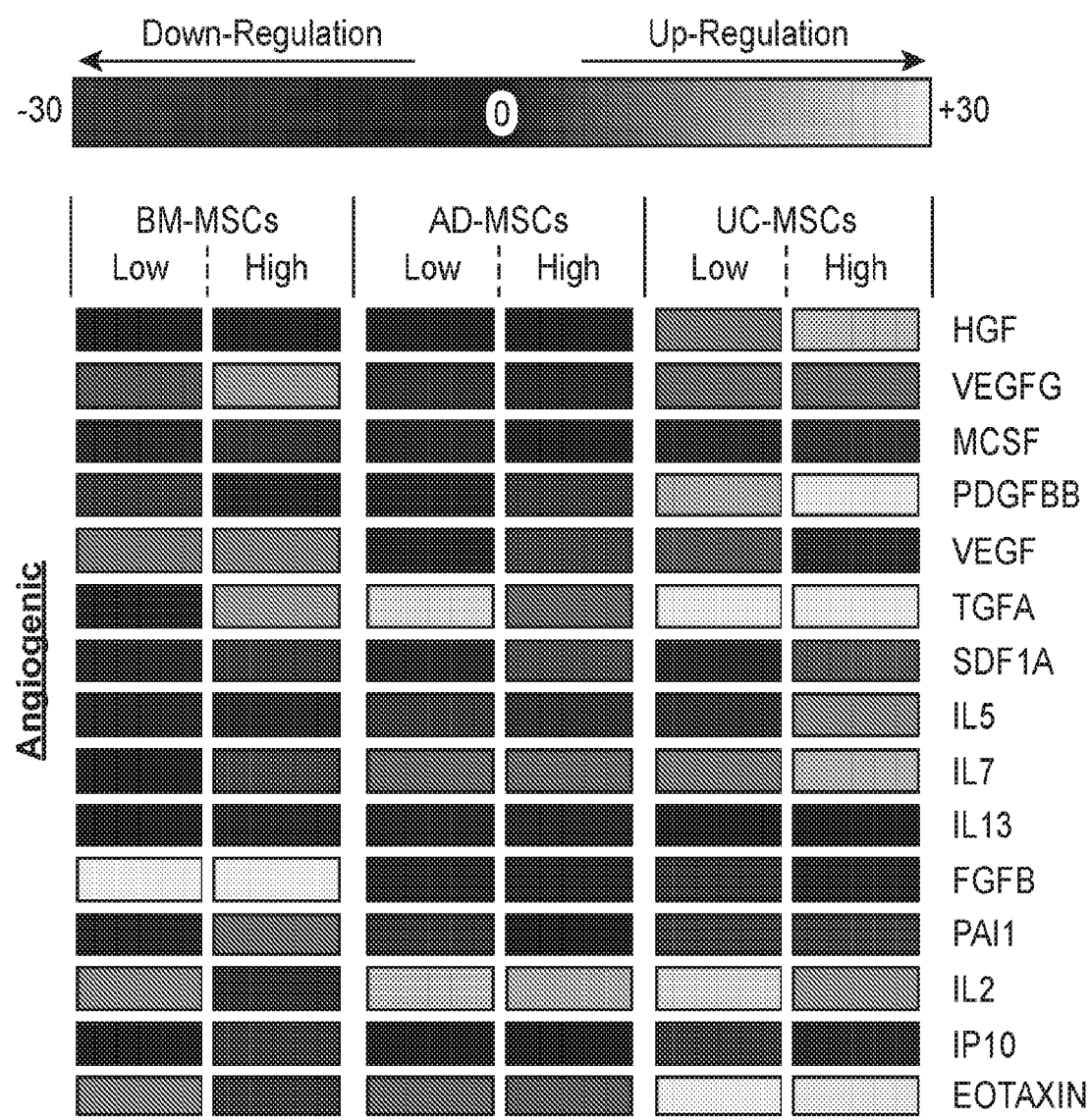
Figures 15A, 15B:
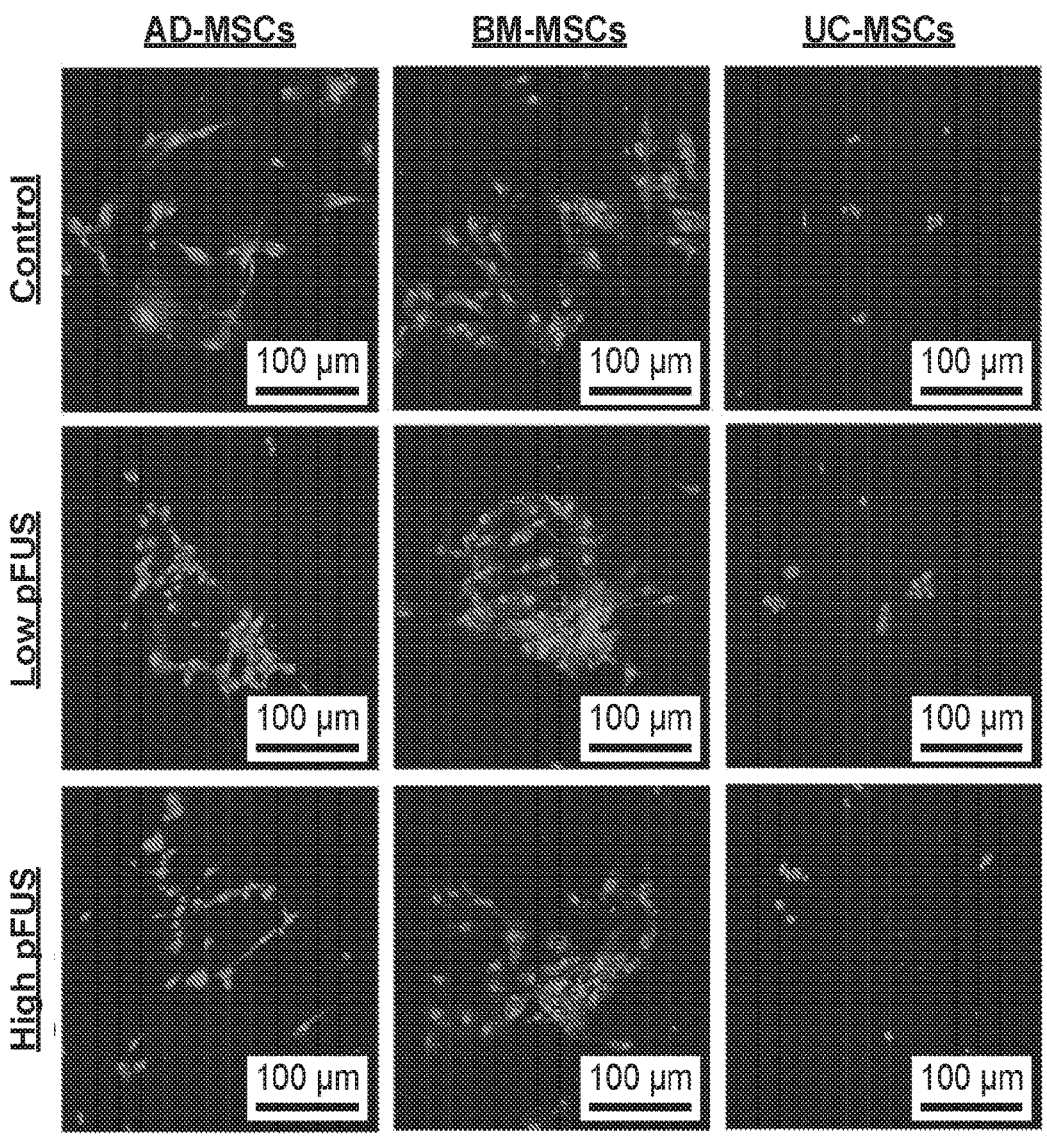
FIGS. 15A-15B. Determination of MSCs Morphology and Viability: Stimulation of all three types of MSCs i.e. BM-MSCs, AD-MSCs and UC-MSCs with pFUS in both low and high dose did not significantly change the morphology (FIG. 15A) and viability (FIG. 15B) of MSCs compared to their control.

Stimulation of BM-MSCs with low or high dose pFUS resulted in a 15±20% or 5±10% increase in cytokine secretion, respectively when compared to control BM-MSCs (FIG. 13A, P<0.05). Stimulation of BM-MSCs with low dose pFUS upregulated the expression of a subset of immunomodulatory (IL31, SCF, RANTES, IFNG, MIP1B, IFNA, TNFB, GROA, IL1A, IL12P40, IL15, IL18, MCP3, ICAM1, VCAM1, IL22, and ENA78), anti-inflammatory (FASL, IL1B, TGFB, IL1 RA, TGFB, IL9, BDNF, TRAIL, IL10, and IFNB), and angiogenic (VEGFG, VEGF, FGFB, IL2, and EOTAXIN) cytokines, while also downregulating the expression of the angiogenic cytokine PDGFBB, when compared to control BM-MSCs (FIG. 13B, P<0.05). Stimulation with high dose pFUS caused upregulation of immunomodulatory (1L31, TNFA, MCP3, LEPTIN, and CD40L); anti-inflammatory (FASL, MIP1A, IL1B, IL6, IL8, IL9, BDNF, IFNB, and LIF); and angiogenic (VEGFG, VEGF, TGFA, FGFB, and PAI1) cytokines, while also downregulating select immunomodulatory (IL23); anti-inflammatory cytokine (TGFB) and angiogenic (IL2, and IP10) cytokines, when compared to control BM-MSCs (FIG. 13B, P<0.05).

AD-MSCs

Stimulation of AD-MSCs with low or high dose pFUS resulted in an 3±5% or 5±7% increase in cytokine secretion, respectively when compared to control AD-MSCs (FIG. 13A, P<0.05). Stimulation of AD-MSCs with low dose pFUS upregulated the expression of a subset of immunomodulatory (I-15, MCP3, VCAM1, and IL17F); anti-inflammatory (MIP1A, IL1RA, and IFNB); and angiogenic (TGFA, IL7, IL2, and EOTAXIN) cytokines, while also downregulating the expression of the immunomodulatory cytokine IL31, when compared to control AD-MSCs (FIG. 13B, P<0.05). Stimulation of AD-MSCs with high dose pFUS also caused upregulation of immunomodulatory (MCP3, ICAM1, VCAM1, LEPTIN, and IL17F); an anti-inflammatory (IFNB); and angiogenic (TGFA, SDF1A, IL7, IL2, and EOTAXIN) cytokines, when compared to control AD-MSCs (FIG. 13B, P<0.05).

UC-MSCs

Stimulation of UC-MSCs with low or high dose pFUS resulted in an 10±15% or 15±17% increase cytokine secretion, respectively when compared to control UC-MSCs (FIG. 13A, P<0.05). Stimulation of UC-MSCs with low dose pFUS upregulated the expression of a subset of immunomodulatory (GMCSF, TNFA, MCP1, IL12P40, RESISTIN, VCAM1, LEPTIN, CD40L, IL17F); anti-inflammatory (MIP1A, IL6, IL8, LIF, IFNB); and angiogenic (HGF, VEGFG, PDGFBB, VEGF, TGFA, IL7, IL2, EOTAXIN) cytokines, while also downregulating the expression of immunomodulatory (IL31, MIP1B, TNFB, IL1A, IL23, IL15, IL18); anti-inflammatory (FASL, IL1B, IL1RA, BDNF, TRAIL); and the angiogenic cytokine IP10, when compared to control UC-MSCs (FIG. 13B, P<0.05). Stimulation of UC-MSCs with high dose pFUS caused upregulation of a subset of immunomodulatory (SCF, RANTES, TNFA, MCP1, GROA, IL1A, IL12P40, IL18, MCP3, MIG, RESISTIN, IL21, ICAM1, VCAM1, LEPTIN, CD40L, EN78, and IL17F); anti-inflammatory (MIP1A, IL6, IL8, IL9, NGF, EGF, GCSF, LIF, and IFNB); and angiogenic (HGF, VEGFG, PDGFBB, TGFA, SDF1A, IL5, IL7, IL2, and EOTAXIN) cytokines. High dose pFUS also caused downregulation of the immunomodulatory cytokine IL15 when compared to control UC-MSCs (FIG. 13B, P<0.05).

Determination of MSCs Morphology and Viability

Stimulation of all three types of MSCs (i.e. BM-MSCs, AD-MSCs and UC-MSCs) with pFUS, at both low and high doses, did not significantly change the morphology and viability of MSCs compared to their control (FIG. 14; BM-MSCs: low dose=1.01±1.00 fold change vs control, high dose=1.02±1.05, control=1±0.5; AD-MSCs: low dose=0.85±1.13, high dose=0.90±0.77, control=1±0.5; UC-MSCs: low dose=0.96±0.6, high dose=0.91±1.02, control=1±0.5; P>0.05).

Discussion

MSCs are a promising regenerative cellular therapy which have been shown to have a significant benefit in multiple preclinical models[16-23]. In addition to BM-MSCs, AD-MSCs and UC-MSCs are now being used in clinical trials to treat multiple conditions[36-37]. In this study, we investigated (i) whether pFUS (i.e. sound waves) can safely be used to biomechanically stimulate MSCs and if this is dependent on the acoustic dose employed and (ii) whether different sources of MSCs respond differently to pFUS, as determined by their cytokine profile.

Our results show that pFUS can be used in vitro, at low and high doses, with no adverse effect on MSC morphology or viability. The effect of acoustic dose on cytokines is dependent on the source of MSCs with BM-MSCs showing increased secretion at lower doses, UC-MSCs showing increased secretion at higher doses and AD-MSCs demonstrating the least amount of sensitivity to sound waves at any dose. Finally, our results show MSCs respond to pFUS in a source-dependent manner, with each source producing a distinct cytokine profile (i.e. the highest level of a cytokine produced by BM-MSCs was IL-15, for AD-MSCs was TGF-α and for UC-MSCs was LIF).

Given that pFUS can produce a different profile of cytokines depending on the source of MSC, this will become important for choosing a specific MSC for a particular disease indication, especially if pFUS is used for pre-conditioning MSCs. In terms of the cytokine produced at highest level for each MSC, IL-15 has been shown to induces the differentiation and proliferation of T, B and natural killer (NK) cells and induces maturation of dendritic cells, thereby highlighting is important immunomodulatory function[38-39]; TGF-α has been shown to initiate multiple cell proliferation events that play a role in wound healing as well as promoting angiogenesis[40]; LIF has been shown to promote growth and cell differentiation as well as modulate embryonic stem cell self-renewal and differentiation[41-43].

Taken together, it is clear that pFUS can be used to stimulate MSCs. While, the present study did not investigate the mechanisms underlying this effect, possible pathways include the mitogen-activated protein kinase (MAPK)[44], focal adhesion kinase activates-extracellular signal-regulated kinase 1/2 (FAK-ERK1/2)[45], and stromal cell-derived factor-1/C-X-C chemokine receptor type 4 (SDF-1/CXCR4)[46]. These pathways have already been shown to be activated following stimulation of stem cells with low intensity pulsed ultrasound (LIPUS)[44-46]. Future work will aim to systematically investigate these mechanisms, and the effect of different acoustic parameters on these pathways, in order to better determine how to efficiently modulate the function of MSCs. Furthermore, our data clearly shows that different sources of MSCs respond differently to the same stimulus (i.e. sound waves) which is in keeping with other studies which have compared their secretory profile in response to pro-inflammatory cytokines[47-48]. Additional studies will aim to both better understand the underlying molecular biology governing these changes as well as other regenerative outputs of MSCs (i.e. contents of their extracellular vesicles). Finally, we will aim to better understand the ability of translating this approach of using pFUS from the in vitro setting (to precondition MSCs) to the in vivo setting (where we can stimulate MSCs after they have been given into living subjects). Once the pFUS parameters have been optimized and validated, clinical application of pFUS would only require that the derated pFUS parameters match the optimized determined pFUS parameters.

In summary, we found that pFUS cannot only stimulate MSCs but that this stimulation was dependent on the source of MSC studied. These important findings should set the foundation for additional mechanistic and validation studies using this non-invasive and translatable technology in regenerative medicine.

REFERENCES

1. Nagamura-Inoue T, He H. Umbilical cord-derived mesenchymal stem cells: Their advantages and potential clinical utility. *World journal of stem cells*. 2014; 6(2): 195.
2. Gnecchi M, Melo L G. Bone marrow-derived mesenchymal stem cells: isolation, expansion, characterization, viral transduction, and production of conditioned medium. In: *Stem cells in regenerative medicine*. Springer; 2009:281-294.
3. Gruber H E, Deepe R, Hoelscher G L, et al. Human adipose-derived mesenchymal stem cells: direction to a phenotype sharing similarities with the disc, gene expression profiling, and coculture with human annulus cells. *Tissue engineering Part A*. 2010; 16(9):2843-2860.
4. Ishige I, Nagamura-Inoue T, Honda M J, et al. Comparison of mesenchymal stem cells derived from arterial, venous, and Wharton's jelly explants of human umbilical cord. *International journal of hematology*. 2009; 90(2): 261-269.
5. Tondreau T, Meuleman N, Delforge A, et al. Mesenchymal stem cells derived from CD133-positive cells in mobilized peripheral blood and cord blood: proliferation, Oct4 expression, and plasticity. *Stem cells*. 2005; 23(8): 1105-1112.
6. Bieback K, Kluter H. Mesenchymal stromal cells from umbilical cord blood. *Current stem cell research & therapy*. 2007; 2(4):310-323.
7. Scherjon S A, Kleijburg-van der Keur C, de Groot-Swings G M, Claas F H, Fibbe W E, Kanhai H H. Isolation of mesenchymal stem cells of fetal or maternal origin from human placenta. *Stem cells*. 2004; 22(7):1338-1345.
8. Ponnaiyan D, Bhat K, Bhat G. Comparison of immunophenotypes of stem cells from human dental pulp and periodontal ligament. *International journal of immunopathology and pharmacology*. 2012; 25(1):127-134.
9. Joshi M, Patil P B, He Z, Holgersson J, Olausson M, Sumitran-Holgersson S. Fetal liver-derived mesenchymal stromal cells augment engraftment of transplanted hepatocytes. *Cytotherapy*. 2012; 14(6):657-669.
10. Noort W, Scherjon S, Kleijburg-Van Der Keur C, et al. Mesenchymal stem cells in human second-trimester bone marrow, liver, lung, and spleen exhibit a similar immunophenotype but a heterogeneous multilineage differentiation potential. *haematologica*. 2003; 88(8):845-852.
11. Sun Z, Wang S, Zhao R C. The roles of mesenchymal stem cells in tumor inflammatory microenvironment. *J Hematol Oncol*. 2014; 7:14.
12. Kono $T_M$, Sims E K, Moss D R, et al. Human adipose-derived stromal/stem cells protect against STZ-induced hyperglycemia: analysis of hASC-derived paracrine effectors. *Stem Cells*. 2014; 32(7):1831-1842.
13. Dave S D, Vanikar A V, Trivedi H L. Extrinsic factors promoting in vitro differentiation of insulin-secreting cells from human adipose tissue-derived mesenchymal stem cells. *Appl Biochem Biotechnol*. 2013; 170(4):962-971.
14. Bartolucci J, Verdugo F J, González P L, et al. Safety and Efficacy of the Intravenous Infusion of Umbilical Cord Mesenchymal Stem Cells in Patients With Heart Failure: A Phase 1/2 Randomized Controlled Trial (RIMECARD Trial [Randomized Clinical Trial of Intravenous Infusion Umbilical Cord Mesenchymal Stem Cells on Cardiopathy]). *Circ Res*. 2017; 121(10):1192-1204.
15. Via A G, Frizziero A, Oliva F. Biological properties of mesenchymal Stem Cells from different sources. *Muscles, ligaments and tendons journal*. 2012; 2(3):154.
16. Baraniak P R, McDevitt T C. Stem cell paracrine actions and tissue regeneration. *Regenerative medicine*. 2010; 5(1):121-143.
17. Crigler L, Robey R C, Asawachaicham A, Gaupp D, Phinney D G. Human mesenchymal stem cell subpopulations express a variety of neuro-regulatory molecules and promote neuronal cell survival and neuritogenesis. *Exp Neurol*. 2006; 198(1):54-64.
18. Takahashi M, Li T S, Suzuki R, et al. Cytokines produced by bone marrow cells can contribute to functional improvement of the infarcted heart by protecting cardiomyocytes from ischemic injury. *Am J Physiol Heart Circ Physiol*. 2006; 291(2):H886-893.
19. Xu M, Uemura R, Dai Y, Wang Y, Pasha Z, Ashraf M. In vitro and in vivo effects of bone marrow stem cells on cardiac structure and function. *J Mol Cell Cardiol*. 2007; 42(2):441-448.
20. Kubal C, Sheth K, Nadal-Ginard B, Galiñanes M. Bone marrow cells have a potent anti-ischemic effect against myocardial cell death in humans. *J Thorac Cardiovasc Surg*. 2006; 132(5):1112-1118.
21. Korf-Klingebiel M, Kempf T, Sauer T, et al. Bone marrow cells are a rich source of growth factors and cytokines: implications for cell therapy trials after myocardial infarction. *Eur Heart J*. 2008; 29(23):2851-2858.
22. Lin W, Xu L, Zwingenberger S, Gibon E, Goodman S B, Li G. Mesenchymal stem cells homing to improve bone healing. *Journal of orthopaedic translation*. 2017; 9:19-27.
23. Fu X, Li H. Mesenchymal stem cells and skin wound repair and regeneration: possibilities and questions. *Cell Tissue Res*. 2009; 335(2):317-321.
24. Arnsdorf E J, Tummala P, Kwon R Y, Jacobs C R. Mechanically induced osteogenic differentiation—the role of RhoA, ROCKII and cytoskeletal dynamics. *J Cell Sci*. 2009; 122(Pt 4):546-553.
25. Li Y J, Batra N N, You L, et al. Oscillatory fluid flow affects human marrow stromal cell proliferation and differentiation. *J Orthop Res*. 2004; 22(6):1283-1289.
26. Kasper G, Glaeser J D, Geissler S, et al. Matrix metalloprotease activity is an essential link between mechanical stimulus and mesenchymal stem cell behavior. *Stem Cells*. 2007; 25(8):1985-1994.
27. Sharp F R, Ran R, Lu A, et al. Hypoxic preconditioning protects against ischemic brain injury. *NeuroRx*. 2004; 1(1):26-35.

28. Creagh E, Sheehan D, Cotter T. Heat shock proteins-modulators of apoptosis in tumour cells. *Leukemia.* 2000; 14(7):1161.
29. Niagara M I, Haider H K, Jiang S, Ashraf M. Pharmacologically preconditioned skeletal myoblasts are resistant to oxidative stress and promote angiomyogenesis via release of paracrine factors in the infarcted heart. *Circulation research.* 2007; 100(4):545-555.
30. Ren G, Zhang L, Zhao X, et al. Mesenchymal stem cell-mediated immunosuppression occurs via concerted action of chemokines and nitric oxide. *Cell stem cell.* 2008; 2(2):141-150.
31. Yang C, Chen Y, Li F, et al. The biological changes of umbilical cord mesenchymal stem cells in inflammatory environment induced by different cytokines. *Mol Cell Biochem.* 2018.
32. Frenkel V. Ultrasound mediated delivery of drugs and genes to solid tumors. *Advanced drug delivery reviews.* 2008; 60(10):1193-1208.
33. Razavi M, Zheng F, Telichko A, et al. Improving the function and engraftment of transplanted pancreatic islets using pulsed focused ultrasound therapy. *Scientific Reports* DOI: 101038/s41598-019-49933-02019.
34. Razavi M, Zheng F, Telichko A, et al. improving the function and engraftment of transplanted pancreatic islets Using pulsed focused Ultrasound therapy. *Scientific reports.* 2019; 9(1):1-12.
35. Pelekanos R A, Sardesai V S, Futrega K, Lott W B, Kuhn M, Doran M R. Isolation and Expansion of Mesenchymal Stem/Stromal Cells Derived from Human Placenta Tissue. *J Vis Exp.* 2016(112).
36. Squillaro T, Peluso G, Galderisi U. Clinical Trials With Mesenchymal Stem Cells: An Update. *Cell Transplant.* 2016; 25(5):829-848.
37. Couto P S, Shatirishvili G, Bersenev A, Verter F. First decade of clinical trials and published studies with mesenchymal stromal cells from umbilical cord tissue. *Regen Med.* 2019; 14(4):309-319.
38. Waldmann T A, Tagaya Y. The multifaceted regulation of interleukin-15 expression and the role of this cytokine in NK cell differentiation and host response to intracellular pathogens. *Annu Rev Immunol.* 1999; 17:19-49.
39. Fehniger T A, Caligiuri M A. Interleukin 15: biology and relevance to human disease. *Blood.* 2001; 97(1):14-32.
40. Schultz G, Rotatori D S, Clark W. EGF and TGF-alpha in wound healing and repair. *J Cell Biochem.* 1991; 45(4):346-352.
41. Buecker C, Chen H H, Polo J M, et al. A murine ESC-like state facilitates transgenesis and homologous recombination in human pluripotent stem cells. *Cell Stem Cell.* 2010; 6(6):535-546.
42. Chan Y S, Göke J, Ng J H, et al. Induction of a human pluripotent state with distinct regulatory circuitry that resembles preimplantation epiblast. *Cell Stem Cell.* 2013; 13(6):663-675.
43. Gafni O, Weinberger L, Mansour A A, et al. Derivation of novel human ground state naive pluripotent stem cells. *Nature.* 2013; 504(7479):282-286.
44. Gao Q, Walmsley A D, Cooper P R, Scheven B A. Ultrasound stimulation of different dental stem cell populations: role of mitogen-activated protein kinase signaling. *Journal of endodontics.* 2016; 42(3):425-431.
45. Chen J, Jiang J, Wang W, et al. Low intensity pulsed ultrasound promotes the migration of bone marrow-derived mesenchymal stem cells via activating FAK-ERK1/2 signalling pathway. *Artificial cells, nanomedicine, and biotechnology.* 2019; 47(1):3603-3613.
46. Wei F-Y, Leung K-S, Li G, et al. Low intensity pulsed ultrasound enhanced mesenchymal stem cell recruitment through stromal derived factor-1 signaling in fracture healing. *PLoS One.* 2014; 9(9).
47. Mizukami A, Caliari-Oliveira C, Cominal J G, et al. Priming approaches to improve the efficacy of mesenchymal stromal cell-based therapies. *Stem cell research & therapy.* 2019; 10(1):131.
48. Prasanna S J, Gopalakrishnan D, Shankar S R, Vasandan A B. Pro-inflammatory cytokines, IFNγ and TNFα, influence immune properties of human bone marrow and Wharton jelly mesenchymal stem cells differentially. *PloS one.* 2010; 5(2).

TABLE 1

Secreted cytokines from MSCs that play immunomodulatory, anti-inflammatory, and angiogenic roles.

| Cytokine | Reference |
|---|---|
| IL31 | [34] |
| SCF | [35] |
| RANTES | [36] |
| IFNG | [37] |
| GMCSF | [38] |
| TNFA | [37] |
| MIP1B | [39] |
| IFNA | [40] |
| MCP1 | [41] |
| TNFB | [42] |
| GROA | [43] |
| IL1A | [40] |
| IL23 | [44] |
| IL12P40 | [45] |
| IL15 | [46] |
| IL18 | [47] |
| MCP3 | [48] |
| MIG | [49, 50] |
| RESISTIN | [51] |
| IL21 | [52] |
| ICAM1 | [53, 54] |
| VCAM1 | [55] |
| IL22 | [56] |
| Leptin | [57] |
| CD40L | [58] |
| EN78 | [59] |
| IL17F | [60] |
| FASL | [61] |
| MIP1A | [62] |
| IL1B | [63] |
| IL6 | [64] |
| IL8 | [64] |
| IL17A | [60] |
| IL1RA | [65] |
| TGFB | [66] |
| IL9 | [67] |
| NGF | [68] |
| EGF | [69] |
| BDNF | [70] |
| TRAIL | [40] |
| GCSF | [71] |
| IL27 | [72] |
| LIF | [73] |
| IL4 | [74] |
| IL10 | [64] |
| IFNB | [64] |
| IL12P70 | [75] |
| HGF | [76] |
| VEGFD | [77] |
| MCSF | [78] |
| ICAM | [53, 54] |
| PDGFBB | [79] |
| VEGF | [80] |
| TGFA | [81] |
| SDF1A | [82] |
| IL5 | [83] |
| IL7 | [84] |

TABLE 1-continued

Secreted cytokines from MSCs that play immunomodulatory, anti-inflammatory, and angiogenic roles.

| Cytokine | Reference |
|---|---|
| Il13 | [64] |
| PAI1 | [85] |
| IL2 | [86] |
| IP10 | [87] |
| EOTAXIN | [87] |

Example 4

Facilitating Islet Transplantation Using a Three-Step Approach with Mesenchymal Stem Cells, Encapsulation, and Pulsed Focused Ultrasound Introduction Type 1 diabetes (T1D) affects more than 1.5 million individuals in the United States and 20 million worldwide (1). T1D is a chronic autoimmune disease caused by the selective destruction of insulin producing β cells within pancreatic islets resulting in patients requiring exogenous insulin to maintain blood glucose control (2). One solution to restore glycemic control in patients with T1D is pancreatic islet transplantation whereby healthy donor islets are infused into the liver of a patient with T1D (3, 4). However, over 60% of islets are lost in the immediate period following transplantation as a result of the instant blood-mediated inflammatory reaction (IBMIR) towards islets, as well as the lack of a dedicated blood supply to islets given that they get devascularized during their isolation procedure (5).

One strategy to improve islet survival and engraftment following transplantation is to co-transplant them with mesenchymal stem cells (MSCs). Mesenchymal stem cells are self-renewable, multi-potent non-hematopoietic progenitor cells that are ubiquitously found in a number of tissues throughout the body, including adipose tissue (AD-MSCs). MSCs can secrete soluble trophic factors (i.e. angiogenic, anti-inflammatory, anti-apoptotic, immunomodulatory and anti-fibrotic factors (6, 7)) into their surrounding microenvironment that can modulate the immune system and stimulate the endogenous regeneration of damaged tissues (8). Interestingly, the culture medium collected from MSCs has been shown to contain soluble factors that can orchestrate interactions within the microenvironment to facilitate tissue regeneration, thereby suggesting that the protective and regenerative effects of MSCs are predominantly mediated via paracrine actions. Hence, MSCs appear to be an ideal candidate to be co-transplanted with islets, given that they could help islets establish their own vasculature (via angiogenic factors) and protect islets from the IBMIR and any toxicity related issues related to immunosuppressive medications (via anti-inflammatory and immunomodulatory factors). Furthermore, recent studies have shown that AD-MSCs can increase islet survival and function, in vitro as well as in vivo following transplantation (9-12).

In the clinical setting, when MSCs have been co-transplanted with pancreatic islets, the MSCs were administered into the liver after the islets had been infused (13). Given the large volume of the liver, and the anatomical branching pattern of the portal vein (i.e. the vessel in which both islets and MSCs are infused into), it is almost impossible to ensure that MSCs would be spatially located next to islets using this approach. Hence, for MSCs to be effective, they need to be in close proximity to islets to both sample the surrounding microenvironment as well as then release the appropriate paracrine factors, which can then reach and help the transplanted islets. One way to ensure that MSCs are "spatially coupled" next to islets at the time of transplantation is to encapsulate them together. This approach will ensure that each islet will have its own cohort of MSCs within its immediate proximity, thereby enhancing their protective and supportive effects on islets. In the present study, we therefore used a high-throughput, reproducible and scalable co-axial airflow technique to conformally encapsulate islets and MSCs with an ultrapure formulation of alginate. Given that the alginate capsule is semi-permeable and thin (i.e. conformal coating ranges from 50-100 μm (14, 15)), it will allow nutrients, oxygen and glucose to diffuse to islets while concurrently enabling waste products to diffuse away from islets (16). Furthermore, it also provides a physical barrier around islets to protect them from any immune mediated attack (17).

However, once islets and MSCs have been administered into patients, there is currently no existing method to non-invasively stimulate either of them in vivo. One interesting solution to this problem is to sonicate them with sound waves. Focused ultrasound (FUS) is a novel technology, available at many institutions across the world, which can focus sound waves at specific locations deep in the body, with pin-point accuracy, without the use of any incisions. Pulsed focused ultrasound (pFUS) is a variation of this technology that uses short duty-cycles to minimize temperature elevations, thereby allowing the mechanical effects of ultrasound to predominate (18). Potentially, this would enable, for the first time, a completely non-invasive approach to rescue struggling islets and/or stimulate the regenerative function of MSCs, after these cells have been delivered into patients. Hence, the present study examined the effect of pFUS on helping the engraftment and function of islets encapsulated with AD-MSCs. We used an STZ-induced diabetic mouse model and the kidney capsule was chosen as the site of transplantation given that it is a well-established and accessible site for islet transplantation in small animals (19-21).

Materials and Methods

1. Islet and AD-MSCs Isolation and Characterization

All mice in this study were treated in accordance with the guidelines approved by the Institutional Animal Care and Use Committee (IACUC) at Stanford University. Animals were housed under conventional conditions having access to food and water ad libitum. Pancreatic islets were isolated from C57/B6 mice (male, 6-8 week-old, Charles River Laboratories, USA), as previously described (see *Supplemental Information*) (22). AD-MSCs were also obtained from the mouse adipose tissue of male C57BL/6 mice at 6-8 weeks of age, and characterized as previously described (see *Supplemental Information*) (23).

2. Step 1: AD-MSCs Coating on Islets

In a 50 mm low adherence culture dish (Corning, USA), 500 islets and 250,000 AD-MSCs (i.e. islet:AD-MSCs ratio of 1:500) were added and gently mixed together by pipetting up-and-down 5× before being incubated for 24 h at 37° C. and 5% $CO_2$. These parameters were chosen to ensure islets were optimally coated with AD-MSCs (24). Islets coated with AD-MSCs were then manually picked under a bright-field microscope and transferred into a 15 mL falcon tube where they were allowed to settle for 0.5 h at 37° C. and 5% $CO_2$ before the supernatant was decanted.

3. Step 2: Encapsulation of Islets Coated with AD-MSCs

Encapsulation of islets coated with AD-MSCs was performed by suspending the cell pellet in a sodium alginate solution (2 wt. %, Sigma Aldrich, USA) containing mannose (1 wt. %, Sigma Aldrich, USA) in 4-(2-hydroxyethyl)-1-piperazineethanesulfonic acid (HEPES; 10 mM, ThermoFisher Scientific, USA). The solution was transferred to a cell strainer (70 μm, Fischer Scientific, USA) to collect the encapsulated islets. The cell strainer was then inverted in order to spray these encapsulated cells into a $CaCl_2$ (150 mM, Sigma Aldrich, USA) solution which contained a surfactant—pluronic F-127 (0.04 wt. %, Sigma Aldrich, USA) in HEPES (10 mM, ThermoFisher Scientific, USA). Pressurized ultrapure nitrogen (speed: 2 $mm^3/s$) was then used to spray the encapsulated cells out of the cell strainer. The synthesized alginate capsules were then characterized.

4. Step 3: pFUS Treatment on Encapsulated Islets Coated with AD-MSCs 4.1. In Vitro For each pFUS treatment, experiments were performed using a 12 well-plate (Corning, USA) containing 100 islets/well. Given that the ultrasound beam width (16 mm) was close to the diameter of an individual well, this allowed the simultaneous sonication of all the islets since they were predominantly seeded in the center of a well. Ultrasound gel was applied on the surface of the piston transducer to couple it with the bottom of the well plate. For the in vitro experiments, following pFUS parameters were used: 1 MHz frequency, 2000 sin cycles per pulse, with a pulse repetition frequency (PRF) of 100 Hz, 20% duty cycle (DC), 150 kPa peak negative pressure (PNP), 1.43 $W/cm^2$ spatial average pulse average intensity ($I_{sptp}$), and 1 min exposure time. The selection of our pFUS parameters was based on previous literature showing that these parameters could improve cellular function with no adverse effect on cell growth and/or viability (25, 26).

4.2. In Vivo

Islets were transplanted under the kidney capsule of diabetic mice (see Islet Survival and Function In Vivo). Transplanted islets were then treated with pFUS in vivo. To treat the whole kidney, 8 non-overlapping adjacent regions through the kidney were targeted for 30 s per region. The time to treat one kidney with these parameters was approximately 4 min. In order to deliver pFUS therapy to the animal, following pFUS parameters were used: 5 Hz PRF, 5% DC, 2.9 MPa PNP, and 895 $W/cm^2$ $I_{sptp}$, which has been shown in previous studies to be safe in small animals (27). After pFUS treatment, each mouse was removed from the water bath, dried, and placed in a recovery cage.

5. In Vitro Analysis of Islet Survival and Function

There were 4 experimental groups tested: Group 1=Islets only (n=5; Control Group); Group 2=Islets coated with AD-MSCs (n=5; Step 1); Group 3=Encapsulated islets coated with AD-MSCs (n=5; Step 2); Group 4=Encapsulated islets coated with AD-MSCs followed by treatment with pFUS (n=5; Step 3). MTT, Live/Dead, and glucose stimulated insulin secretion (GSIS) assays were performed. Each experiment contained 30 islets in a 96 well plate (30 islets/well). As required, pFUS treated islets were selected from a 12 well-plate which contained 100 islets per well.

6. In Vivo Analysis of Islet Survival and Function

Figure 19A:
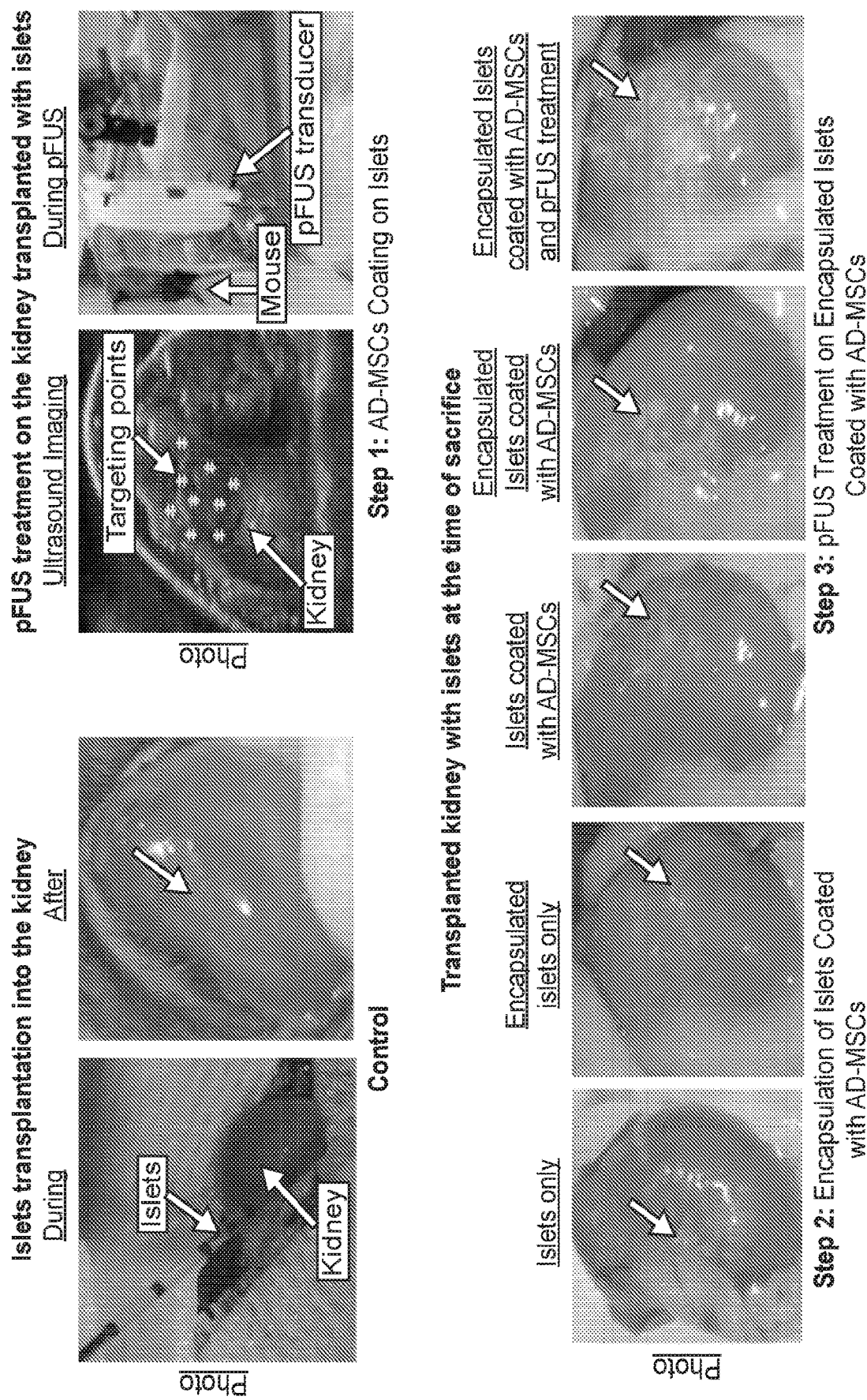
FIGS. 19A-19Y. In vivo analysis of islet survival and function (Metabolic Analysis)

There were 5 experimental groups tested: Group 1=Mice transplanted with islets only (n=5; Control Group); Group 2=Mice transplanted with encapsulated islets only (n=5; Control Group); Group 3=Mice transplanted with islets coated with AD-MSCs (n=5; Step 1); Group 4=Mice transplanted with encapsulated islets coated with AD-MSCs (n=5; Step 2); and Group 5=Mice transplanted with encapsulated islets coated with AD-MSCs followed by treatment with pFUS (n=5; Step 3). All experiments were approved by the Institutional Animal Care and Use Committee (IACUC) at Stanford University. Male C57BL/6 mice, at 6-8 weeks age (Charles River Laboratories, USA), were used as both donor and recipient animals. All animals were maintained on a 12 h:12 h light:dark cycle with ad libitum access to food and water. Recipient mice were matched for their body weight and baseline blood glucose levels. Prior to islet transplantation, all recipient mice were made diabetic (i.e. determined by 2 consecutive non-fasting blood glucose levels>350 mg/dl, as previously documented (28)) by an intraperitoneal injection of streptozotocin (STZ; 180 mg/kg). Each diabetic mouse then received 175 handpicked islets under the right kidney capsule before being randomly allocated to an experimental group. Mice transplanted with encapsulated islets coated with AD-MSCs were then treated with pFUS at days 3, 6, 9, and 12 post-transplantation (see Step 3: pFUS Treatment on Encapsulated Islets Coated with AD-MSCs). Experimental details of our in vivo experiment are outlined in FIG. 19A. Metabolic, histological and molecular analyses were then performed as described in Supplemental Information.

7. Statistical Analysis

All values were expressed as the mean±standard error of the mean (SEM). Statistical analysis of all quantitative data was performed using a one or two-way ANOVA (Analysis of Variance) with post-hoc Tukey test (Astatsa.com; Online Web Statistical Calculators, USA) or unpaired Student's t-test with any differences considered statistically significant when P<0.05.

Results

1. Characterizations

Figure 16A:
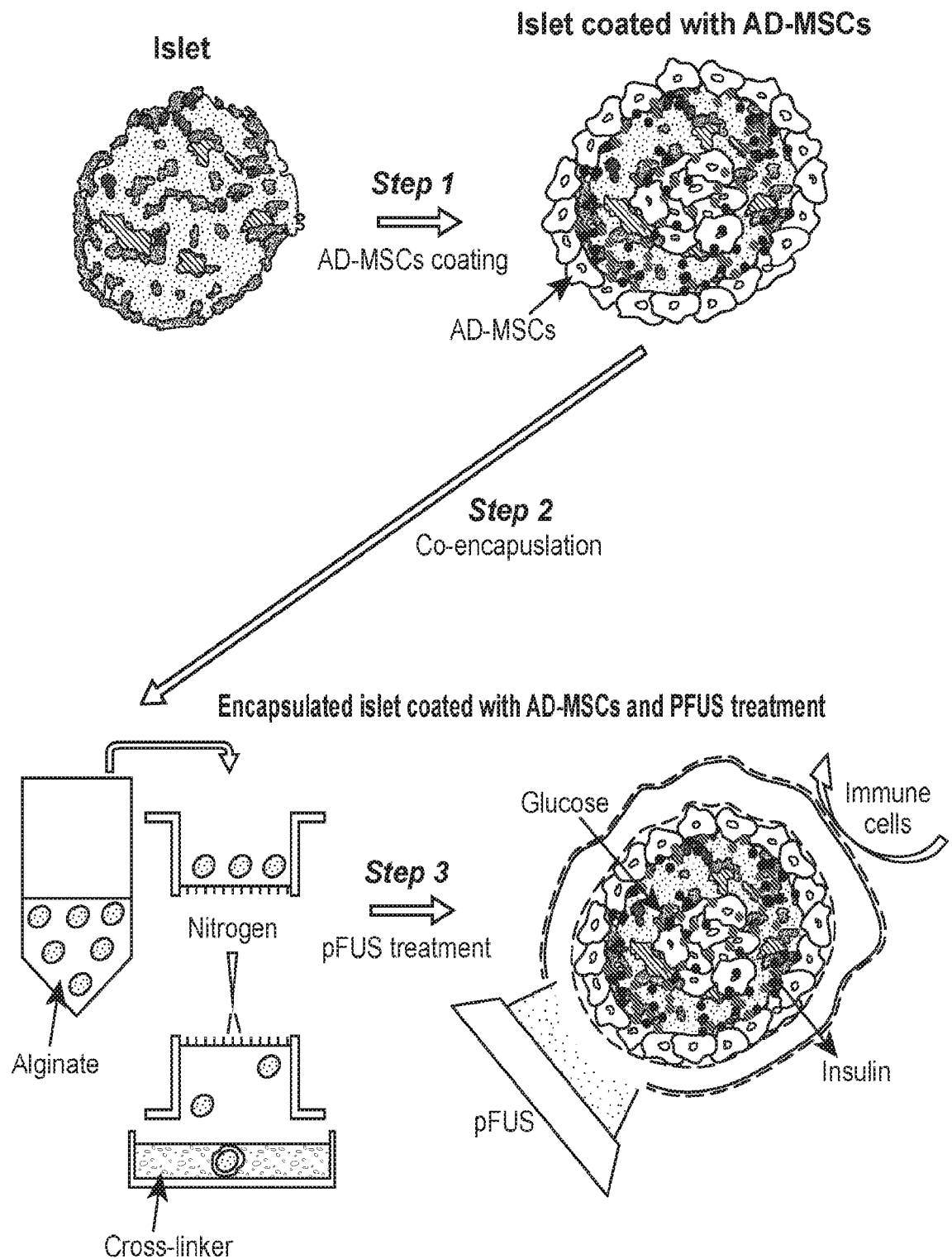
FIGS. 16A-16N. Experimental overview and characterization of islets encapsulated with AD-MSCs.
Figure 16B:
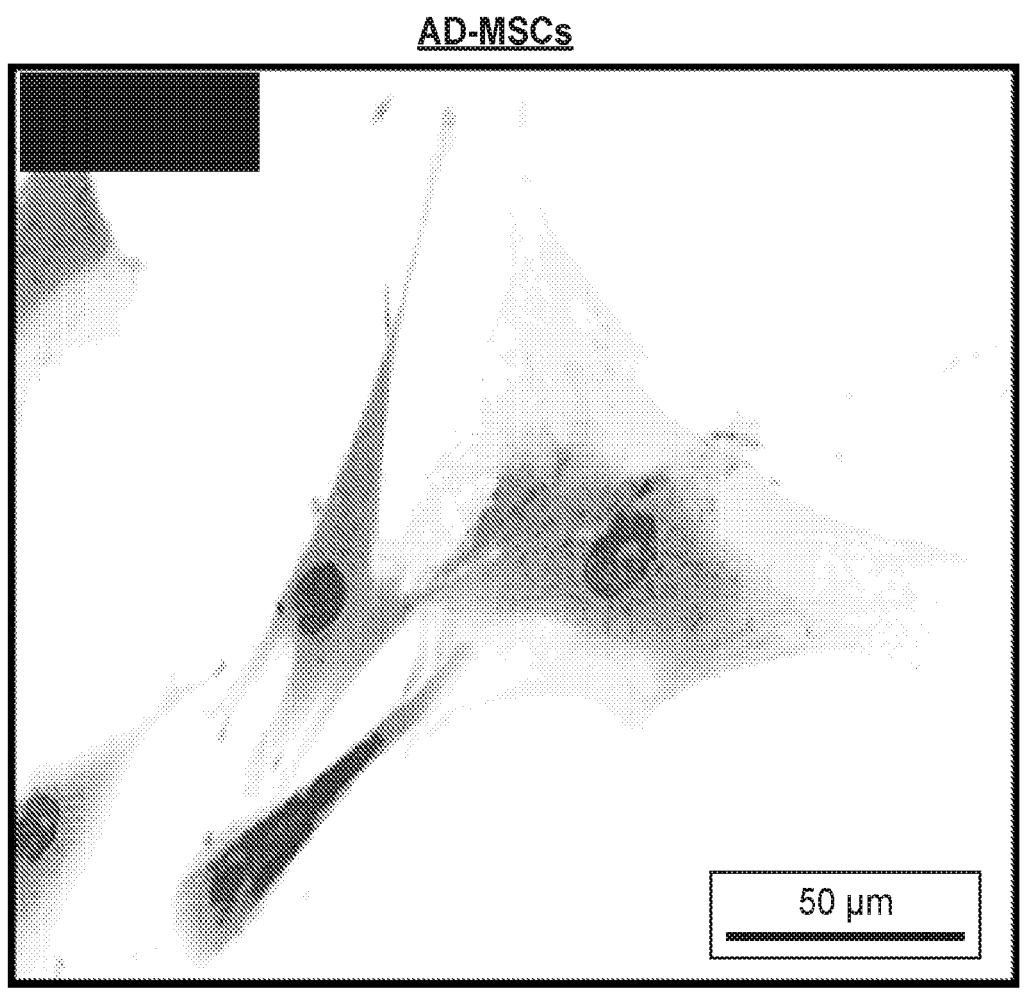
(FIG. 16L) islet coated with AD-MSCs and (FIGS. 16M-16N) encapsulated with alginate followed by pFUS treatment. Blue: live cells. Green: AD-MSCs.
Figure 16C:
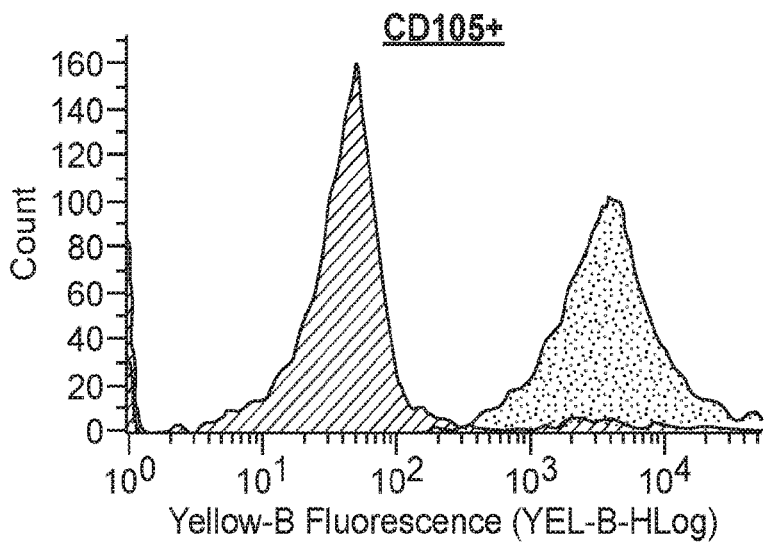
Figure 16D:
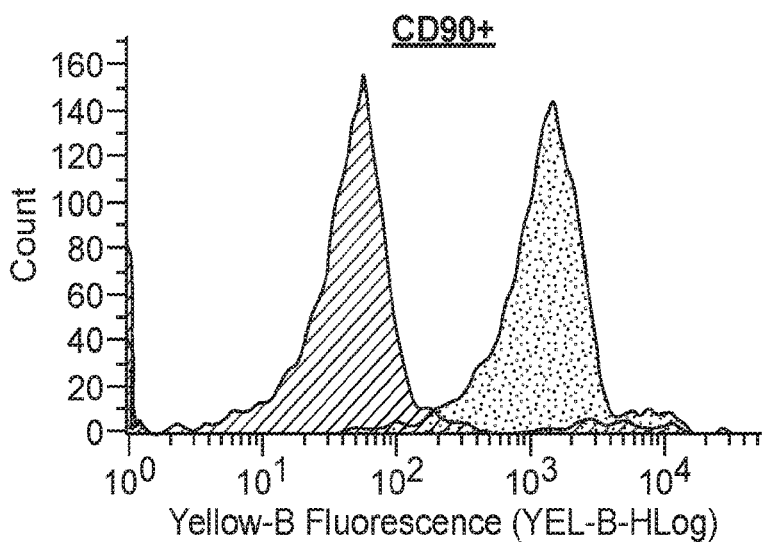
Figure 16E:
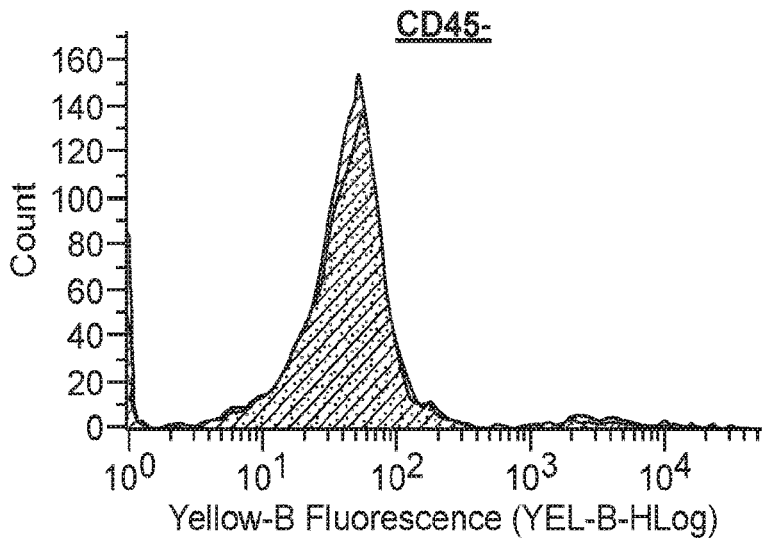
Figure 16H:
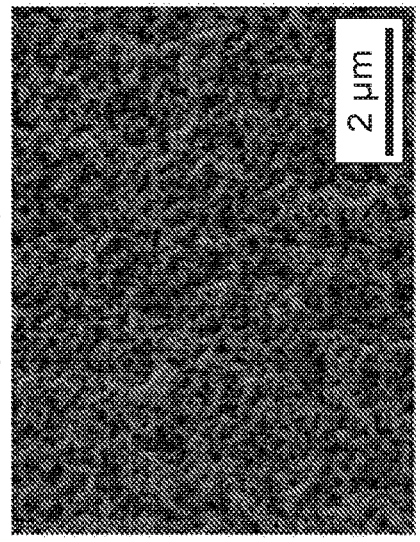
Figure 16G:
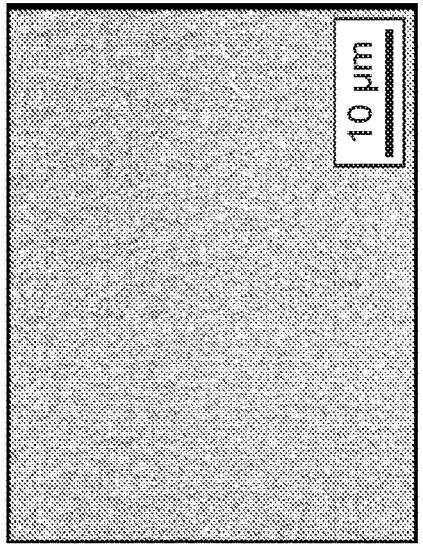
Figure 16F:
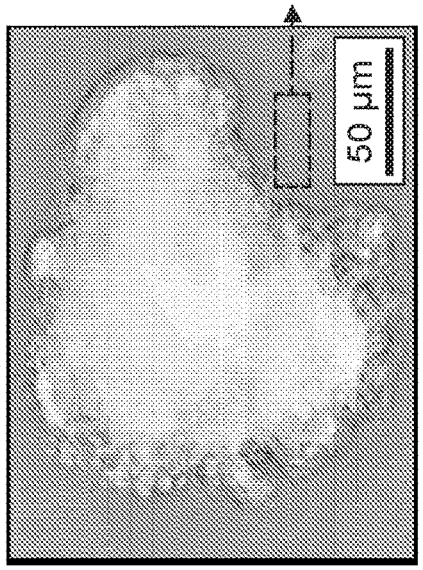
Figure 16I:
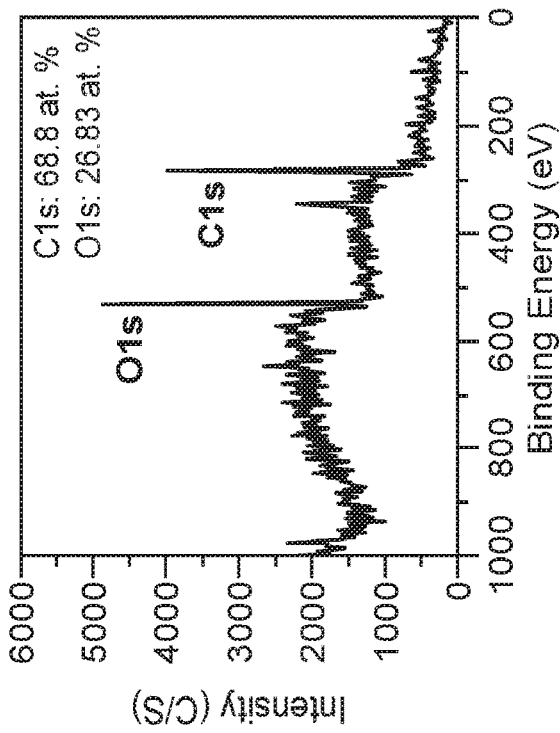
Figure 16J:
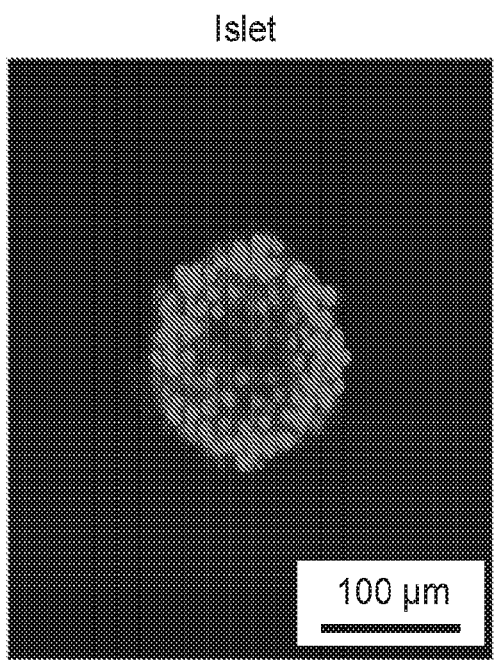
Figure 16K:
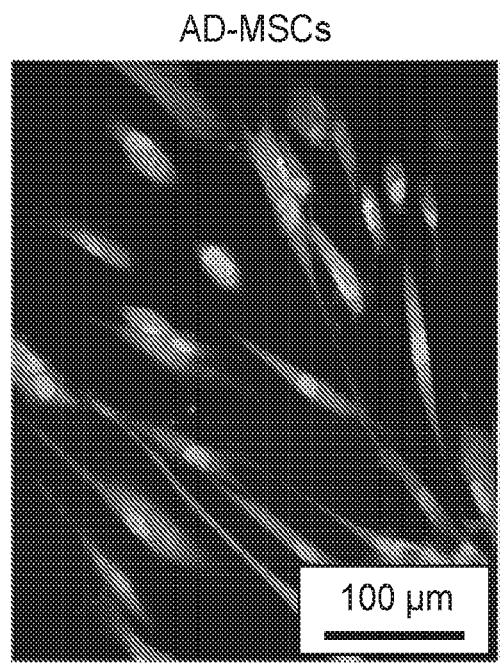
Figure 16L:
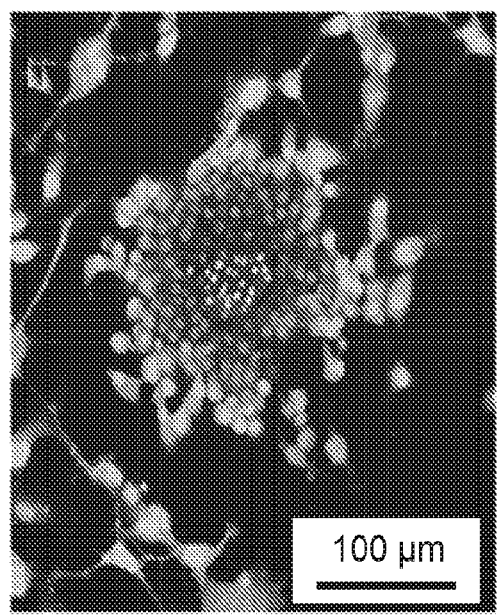
Figure 16N:
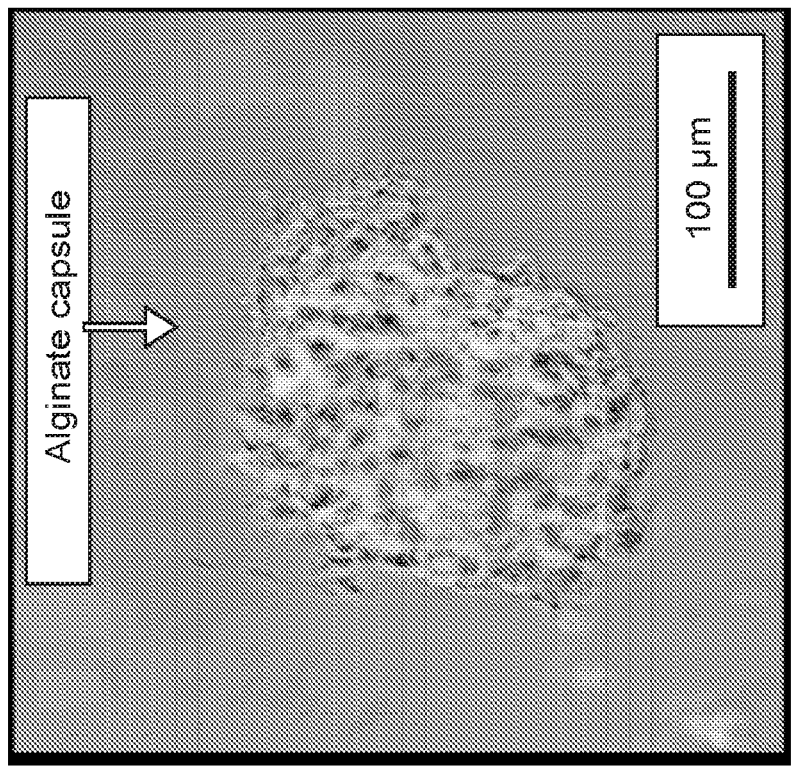
Figure 16M:
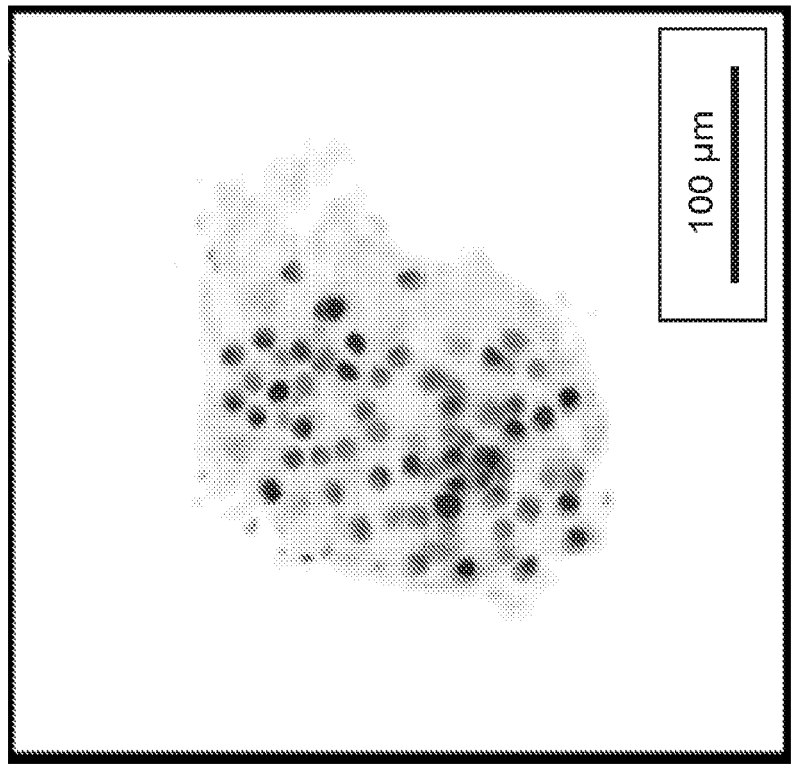

AD-MSCs had a long and thin morphology with widely dispersed filopodia and flattened polygonal extensions (FIG. 16B). Analysis of surface antigen expression showed that AD-MSCs expressed CD105 (90.53±5.45), CD90 (92.41±3.62) markers (positive) with no expression of the CD45 (2.43±0.72) marker (negative) (FIGS. 16C-16E). Characterization studies showed that alginate capsule had a porous structure with the pore size of 200±50 nm (FIG. 16F-16H). In XPS spectra, alginate showed peaks corresponding to the elements of carbon (C) and oxygen (O) which are the basic elements of alginate (FIG. 16I). When islets were co-cultured with AD-MSCs with the ratio of 1:500 for 24 h, AD-MSCs attached to islets and coated their surfaces. Following encapsulation, an alginate layer in a 50±10 μm thick was formed on islet coated with AD-MSCs. Results of confocal imaging confirmed that pFUS treatment did not adversely affect islets quality since islets could maintain their spherical shape and kept their integrity (FIG. 16J-16N).

2. In Vitro Analysis of Islet Survival and Function

Figure 17A:
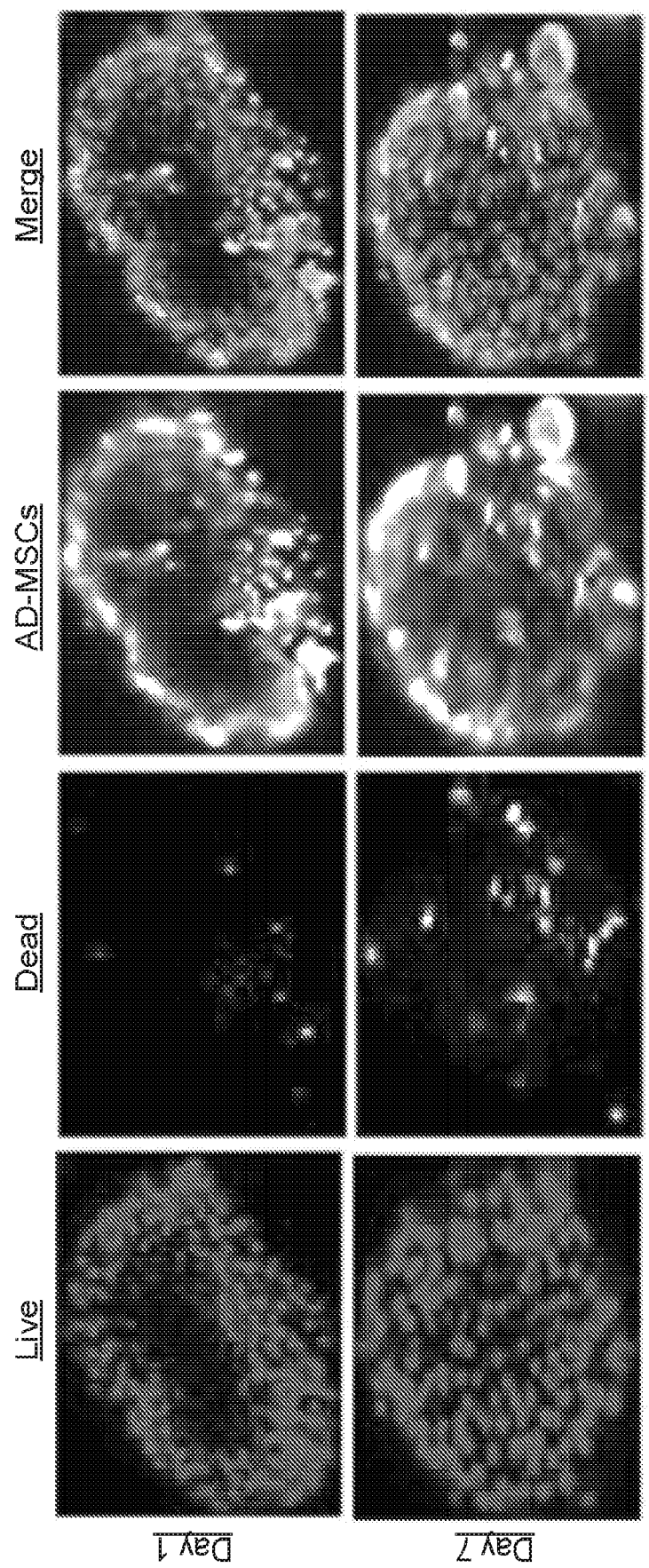
Figure 17A:
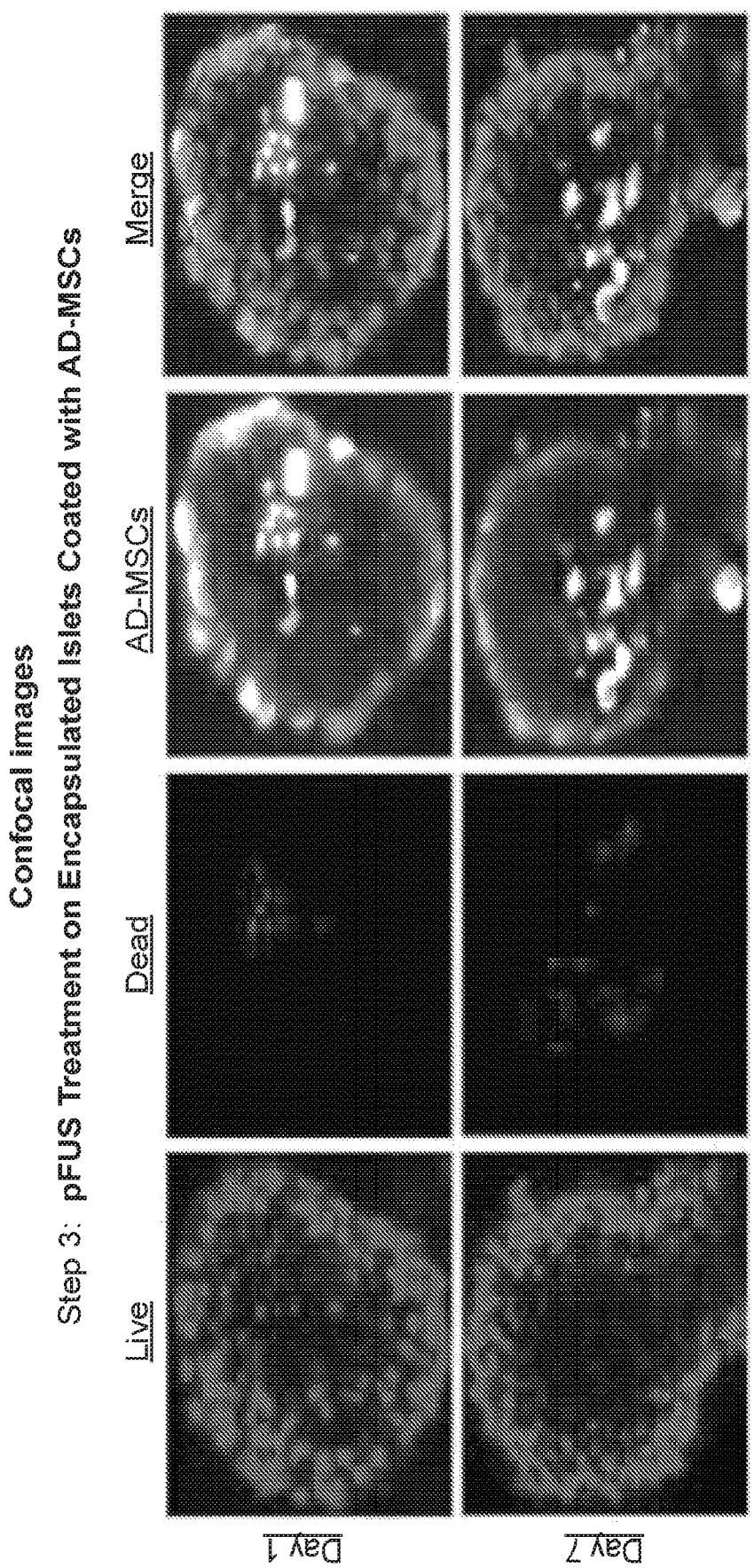
Figure 17B:
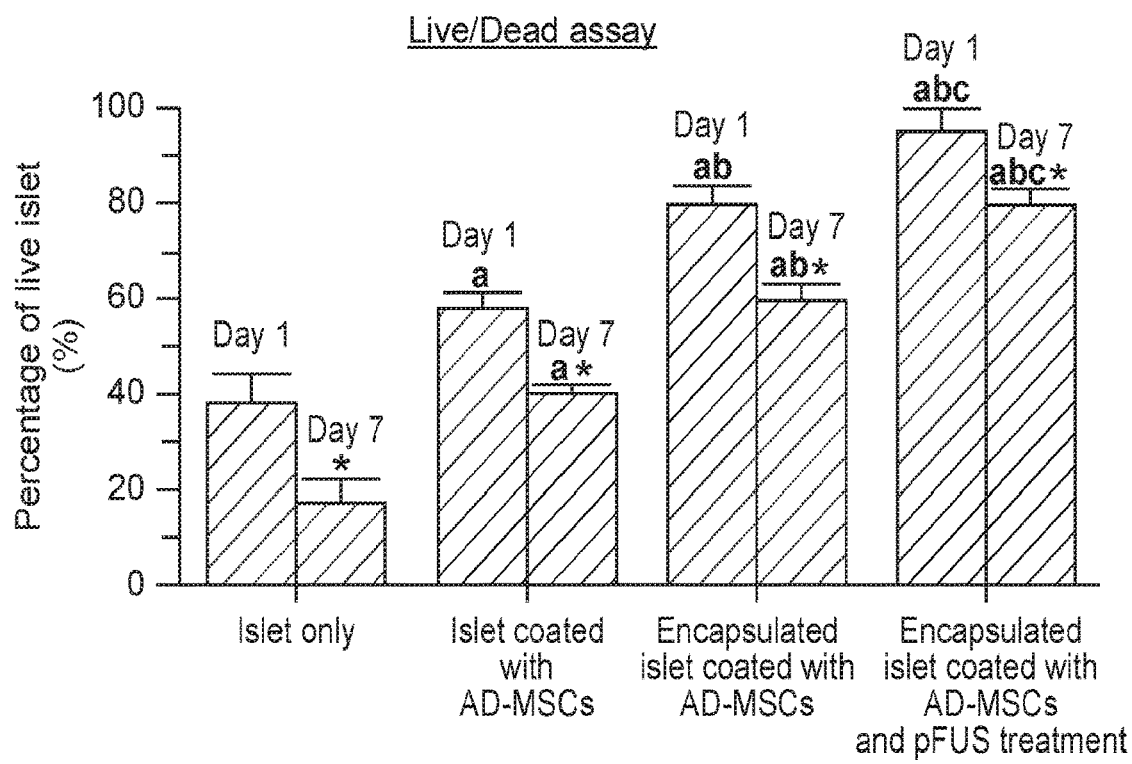
Figure 17C:
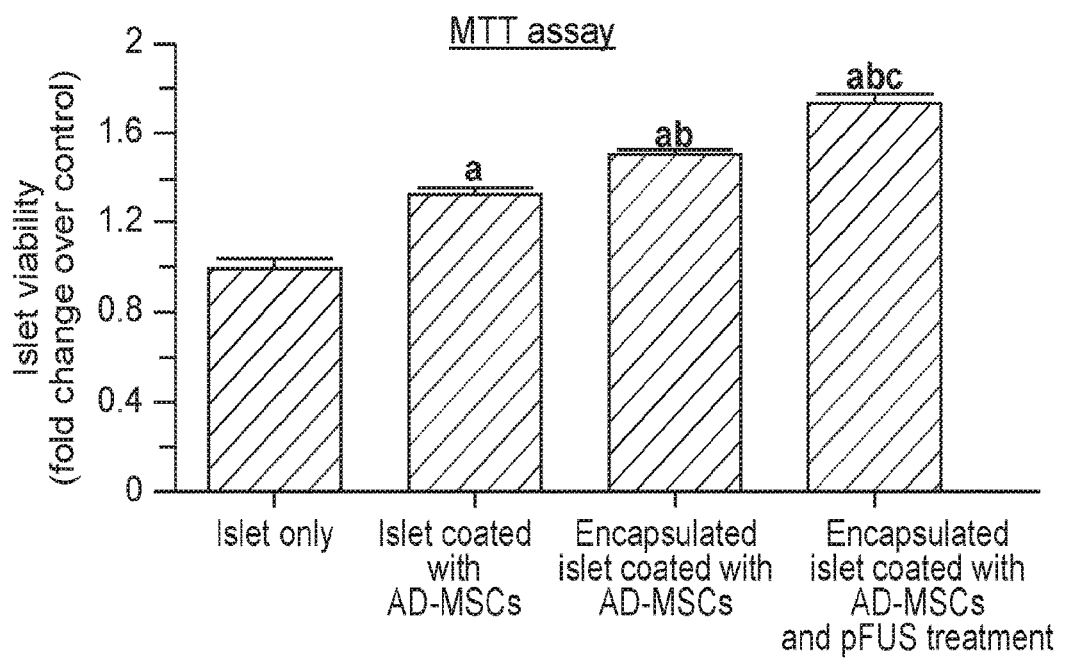

Step 1: AD-MSCs Coating on Islets: Results of live/dead assay at day 1 and 7 showed that the percentage of live islets was 38±6 and 17±5%, respectively for islet only. When islets were coated with AD-MSCs, islets were able to survive with a significantly higher degree of live islets compared to islets only at day 1 (58±3 vs 38±6%, P<0.05) and 7 (40±2 vs 17±5%, P<0.05; FIG. 17A-17B). MTT assay results also showed that, at day 7, relative to islets only, there was a significantly greater viability of islets when they were coated with AD-MSCs (1.33±0.03 vs 1.00±0.03-fold change, P<0.05; FIG. 17C). Using GSIS assay, islets indicated more responsiveness to high glucose challenge when they were coated with AD-MSCs compared to islets only (18.68±0.15 vs 12.36±0.77 ng/mL, P<0.05; FIG. 17D).

Step 2: Encapsulation of Islets Coated with AD-MSCs: Encapsulation of islet coated with AD-MSCs significantly altered islet viability post-encapsulation where the percentage of live islet was significantly higher compared to islets coated with AD-MSCs and islet only (80±4 vs 58±3 and 38±6% at day 1 and 85±1 vs 40±2 and 17±5% at day 7, P<0.05; FIGS. 17A-17B). MTT assay results, at day 7, relative to islets only, demonstrated that there was a significantly greater viability of islets when they were coated with AD-MSCs and encapsulated (1.50±0.02 vs 1.00±0.03-fold change, P<0.05; FIG. 17C). At day 7, encapsulated islets coated with AD-MSCs had a greater insulin secretory response to a high glucose challenge compared to islets coated with AD-MSCs and islets only (25.46±0.32 vs 18.68±0.15 and 12.360.77 ng/mL, respectively, P<0.05; FIG. 17D).

Step 3: pFUS Treatment on Encapsulated Islets Coated with AD-MSCs: When encapsulated islets coated with AD-MSCs were treated with pFUS, the amount of live cells significantly increased to 95±5 and 80±3% at day 1 and 7, respectively (P<0.05; FIGS. 17A-17B). MTT assay results showed that, at day 7, relative to islets only, there was a significantly greater viability of islets when they were coated with AD-MSCs, encapsulated and also treated with pFUS (FIG. 17C; 1.75±0.03 vs 1.00±0.03-fold change, P<0.05). Using a GSIS assay, islets were more responsive to glucose challenges when they were treated with pFUS. Compared to islets only, there was a significantly greater function of islets when they were coated with AD-MSCs, encapsulated and also treated with pFUS. At day 7, encapsulated islets coated with AD-MSCs which had been treated with pFUS had a greater insulin secretory response to high glucose challenges compared to islets only, islets coated with AD-MSCs and encapsulated islets coated with AD-MSCs (31.56±0.45 vs 12.36±0.77, 18.68±0.15, and 25.46±0.32 ng/mL, respectively, P<0.05; FIG. 17D).

Figure 18A:
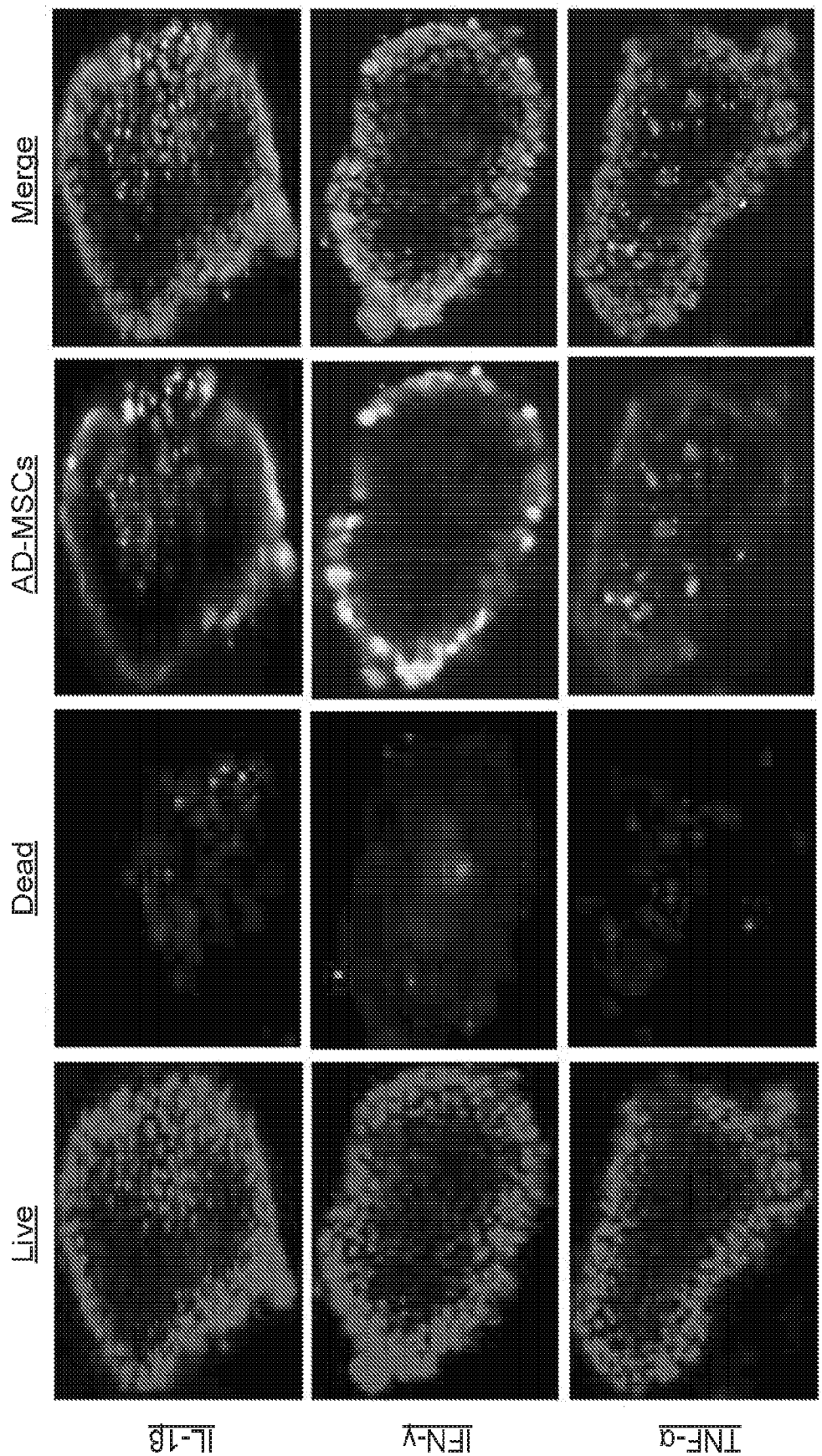
FIGS. 18A-18D. In vitro analysis of islet survival and function following exposure to pro-Inflammatory cytokines.
Figure 18A:
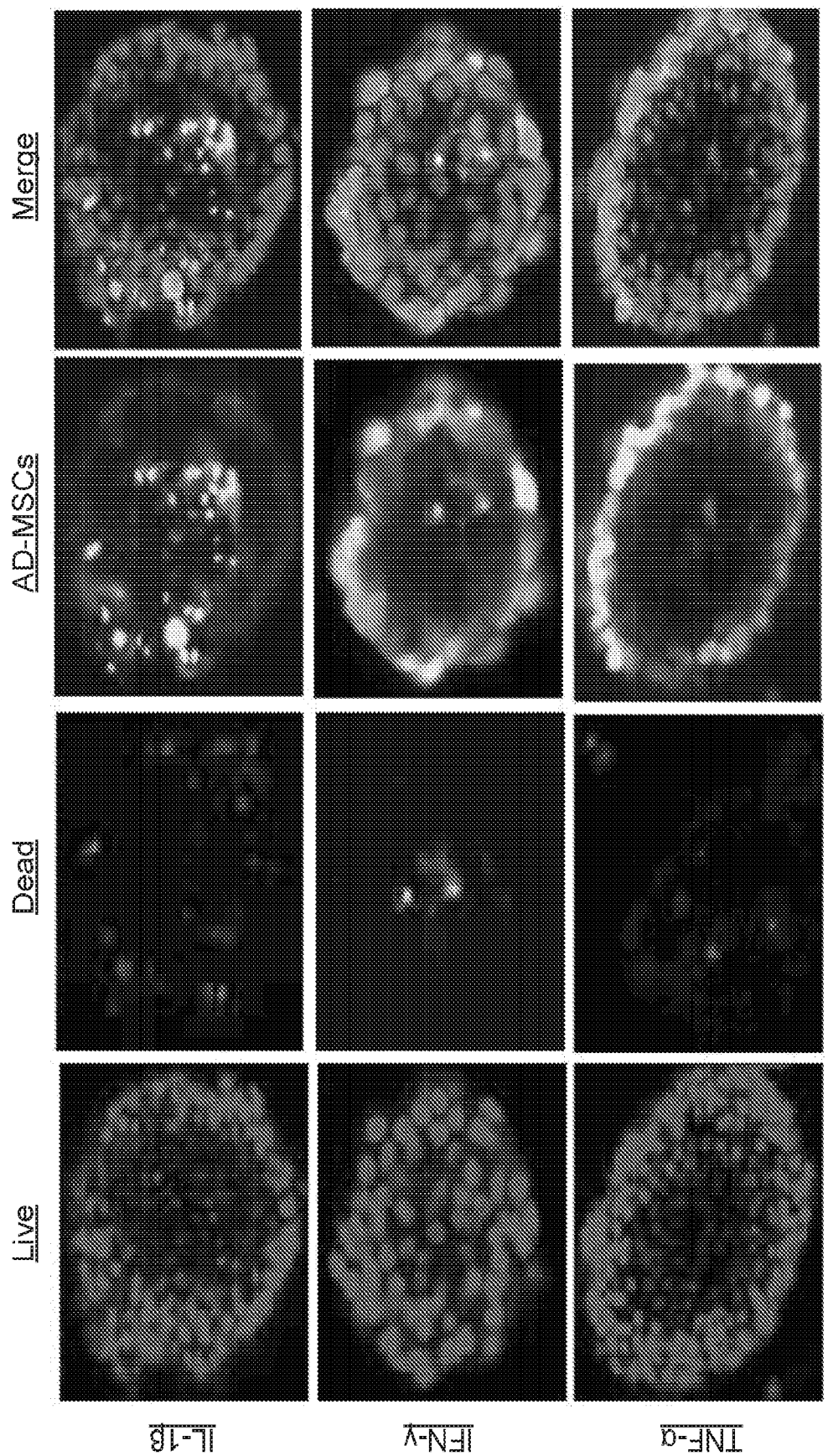
Figure 18B:
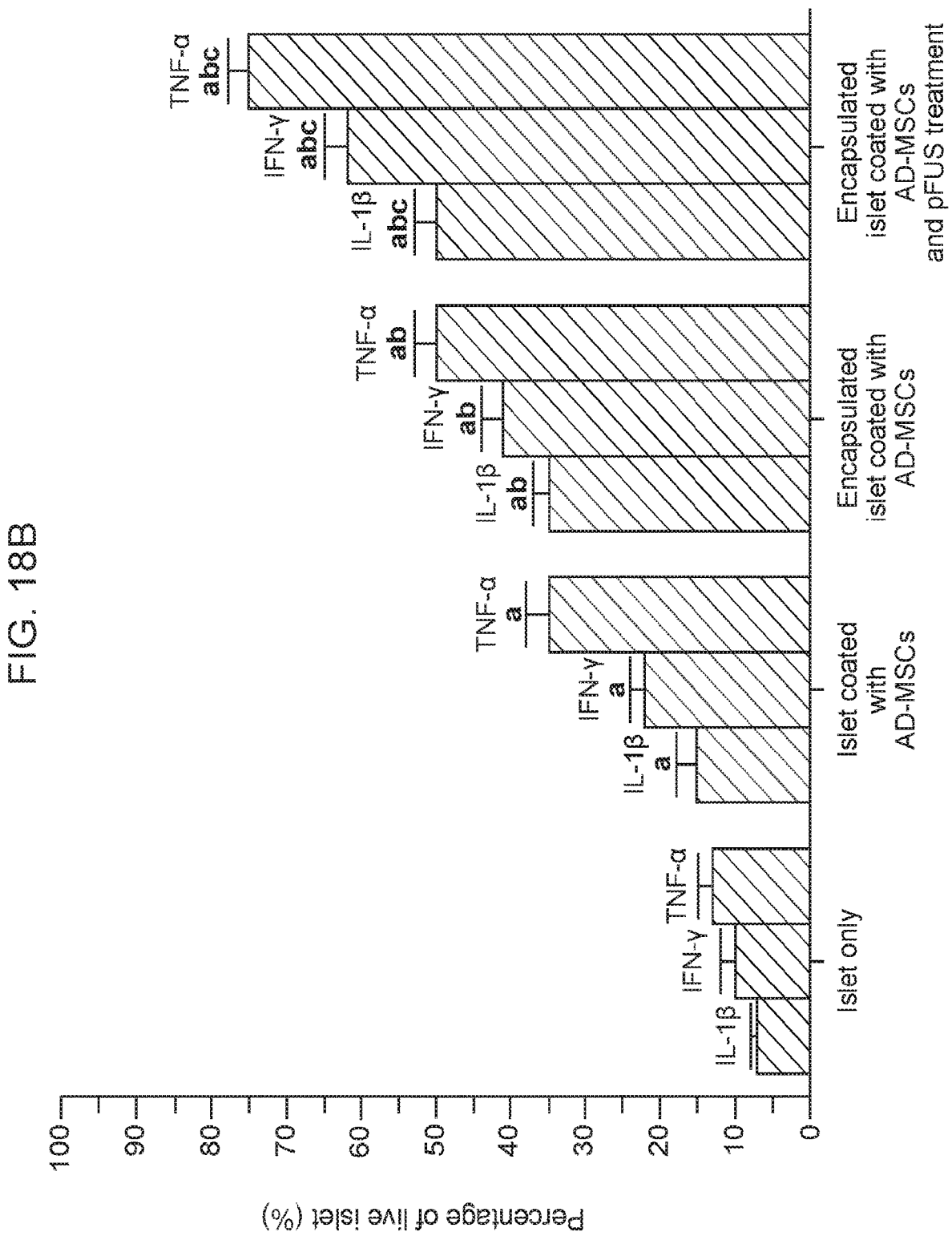
Figure 18C:
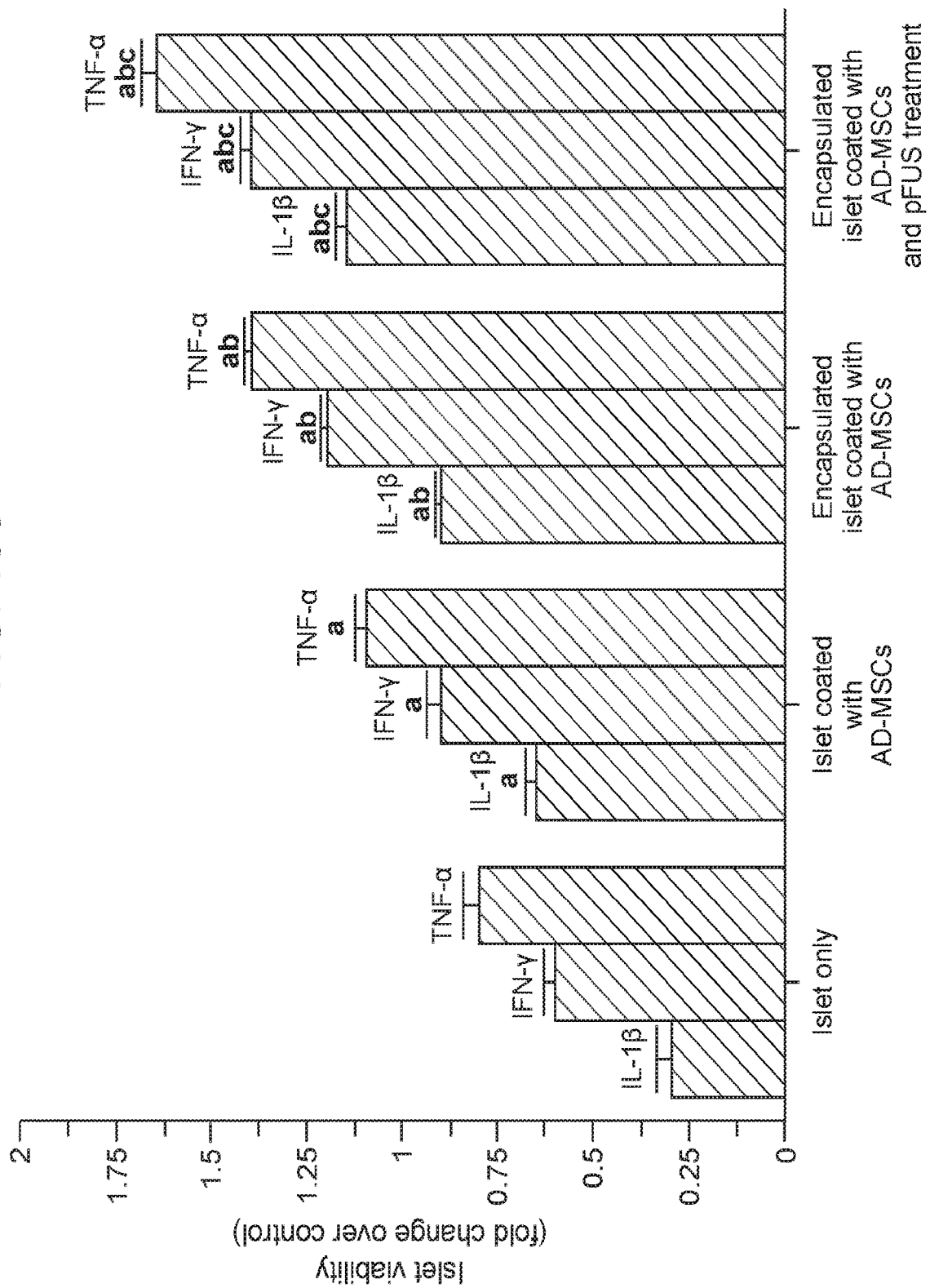
Figure 18D:
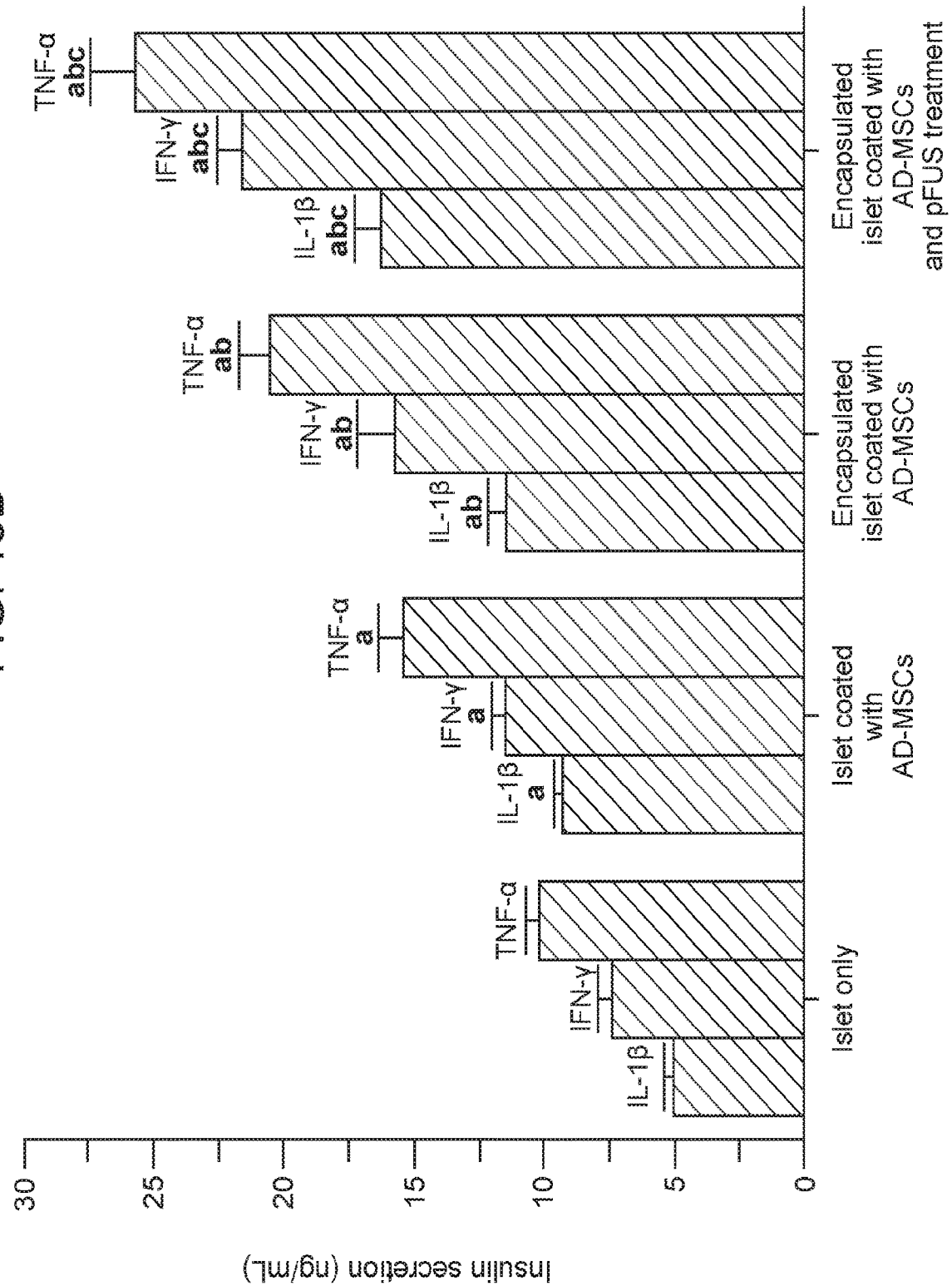

After exposure to pro-inflammatory cytokines including IL-1β or IFN-γ or TNF-α, the percentage of live islets was 7±1, 10±2, and 13±2%, respectively, for islets only. When islets were coated with AD-MSCs, encapsulated in alginate and treated with pFUS, they were able to maintain a higher level of viability compared to islets only at day 7 following exposure to IL-1β (15±3, 35±2, 50±3 vs 7±1%, P<0.05), IFN-γ (22±2, 41±3, 62±3 vs 10±2%, P<0.05) and TNF-α (35±3, 50±3, 75±3 vs 13±2%, P<0.05; FIG. 18A-18E). Similar results were obtained with MTT assays (i.e. viability of islets coated with AD-MSCs, encapsulated islets coated with AD-MSCs and encapsulated islets coated with AD-MSCs followed by pFUS treatment were significantly higher compared to islets only when islets exposed to IL-1β (0.65±0.03, 0.90±0.02 and 1.15±0.03 vs 0.30±0.04 fold change over control, P<0.05), IFN-γ (0.90±0.04, 1.20±0.02 and 1.40±0.03 vs 0.60±0.03 fold change over control, P<0.05) and TNF-α (1.10±0.03, 1.40±0.02, and 1.65±0.04 vs 0.80±0.04 fold change over control, P<0.05; FIG. 18F). Following GSIS assays, the amounts of insulin secreted from islets only was 5.1±0.3, 7.4±0.5, and 10.2±0.5 ng/mL when islets exposed to IL-1β, IFN-γ and TNF-α, respectively. However, AD-MSCs coating, co-encapsulation and pFUS treatment significantly elevated the insulin level to 9.3±0.4, 11.5±0.7 and 16.3±1 ng/mL, respectively, when islets exposed to IL-1β (P<0.05), 11.5±0.5, 15.7±1.5 and 21.6±1 ng/mL, respectively, when exposed to IFN-γ (P<0.05), and 15.4±1, 20.5±1.3, and 25.7±1.7 ng/mL, respectively, when exposed to TNF-α (P<0.05).

3. In Vivo Analysis of Islet Survival and Function 3.1. Metabolic Analysis

Figure 19B:
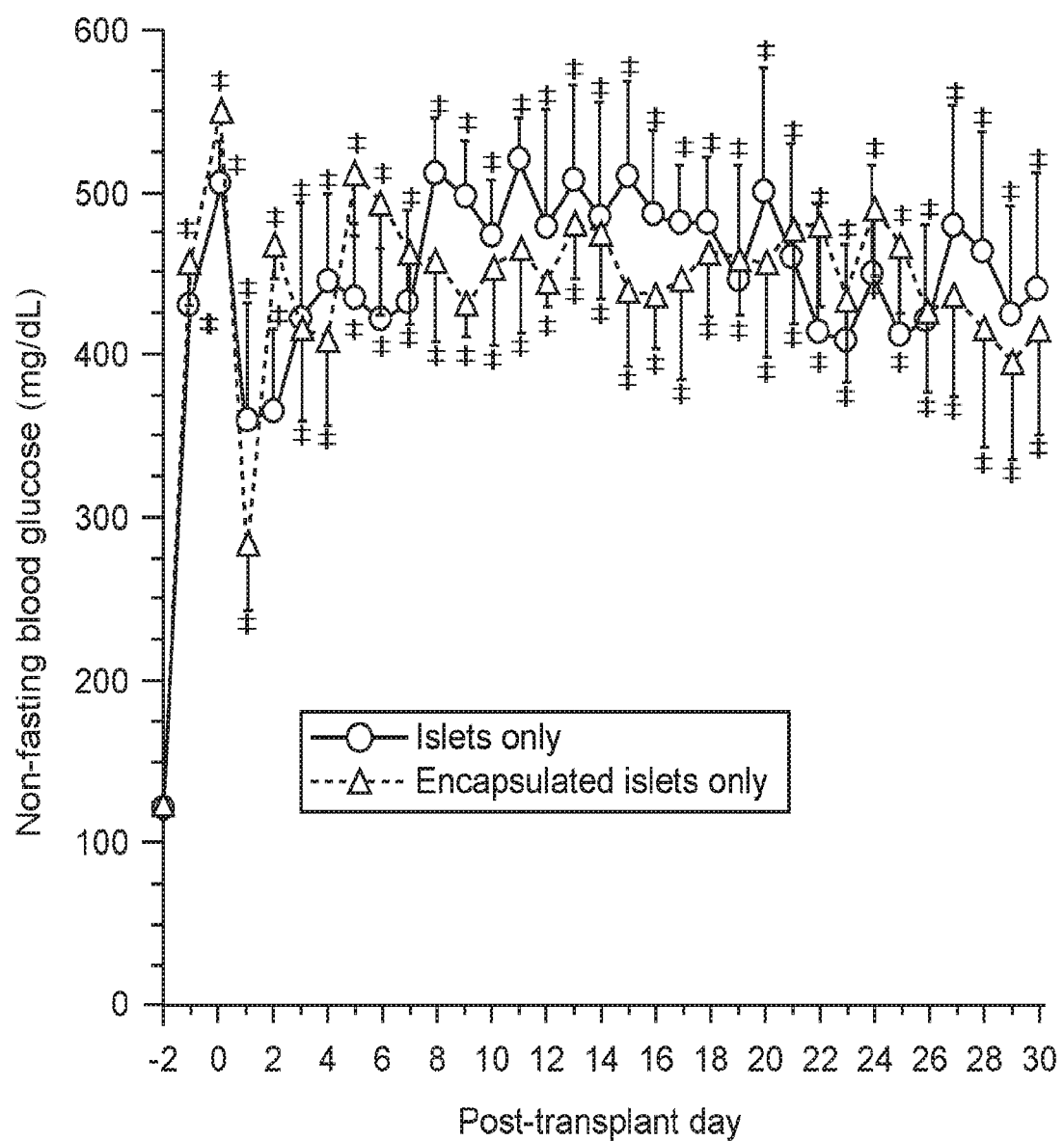
Figure 19C:
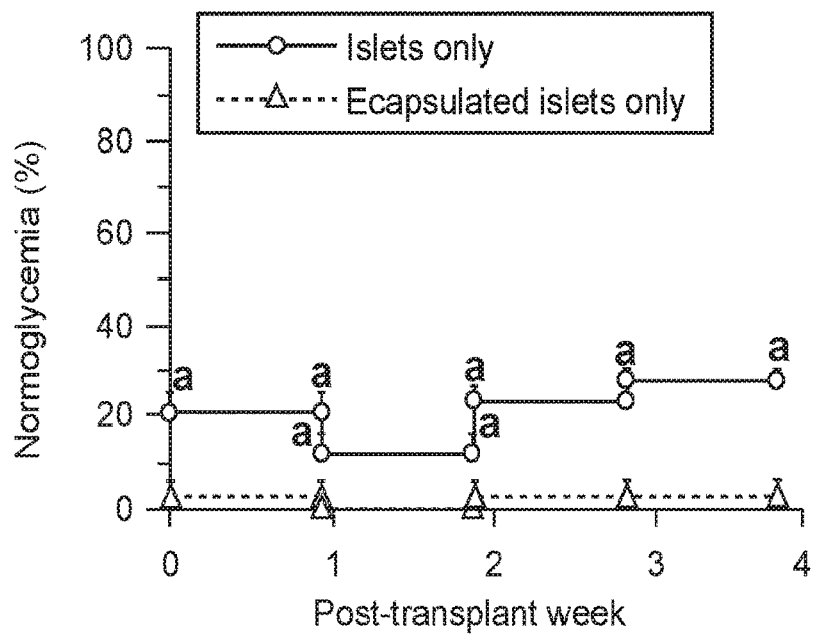
Figure 19D:
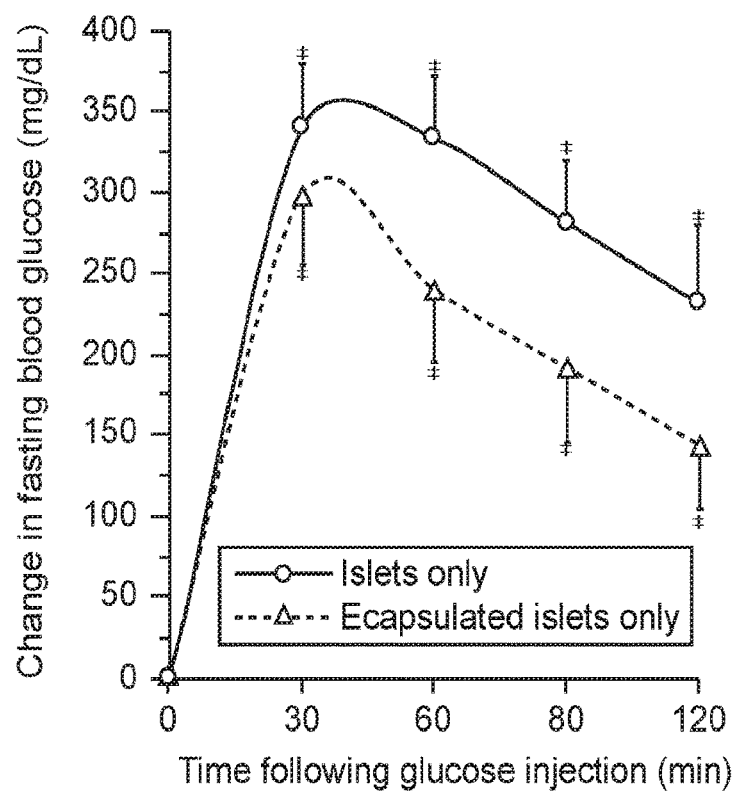
Figure 19E:
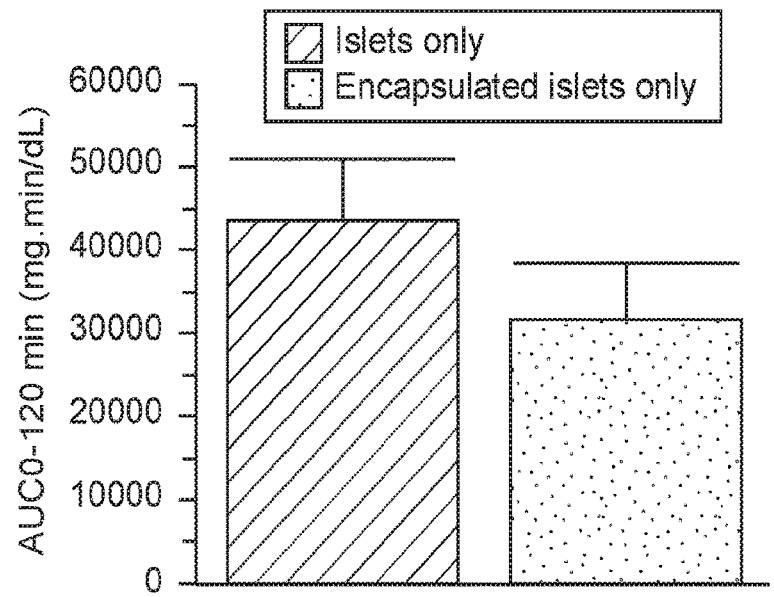
Figure 19F:
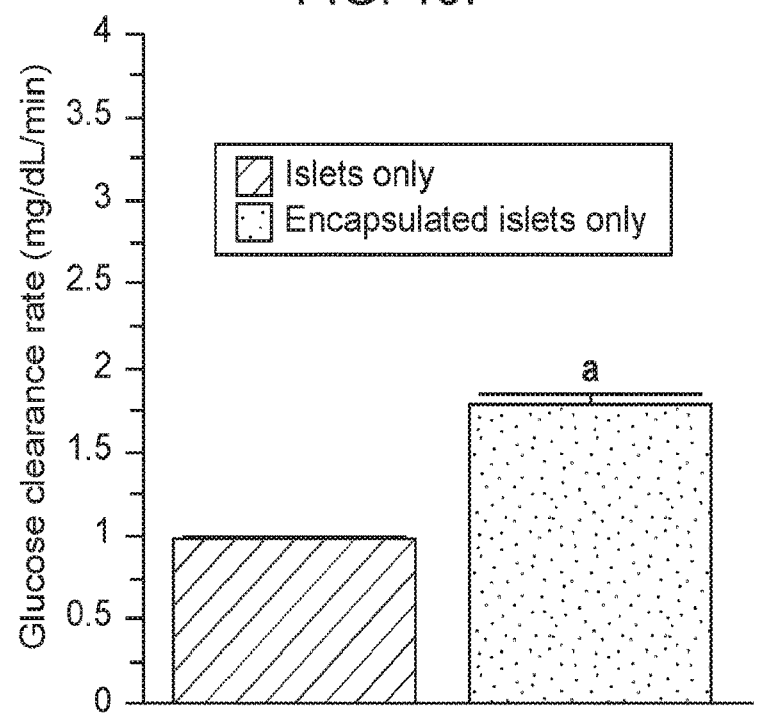
Figure 19G:
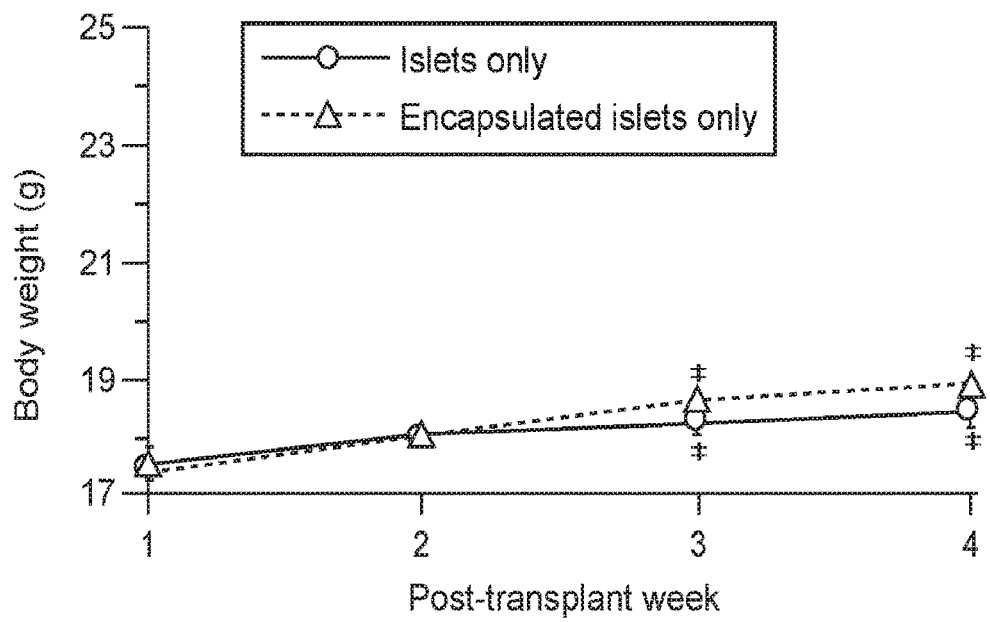

Following treatment with STZ, all animals became hyperglycemic with their BG values increasing from 116±10 mg/dL (baseline, day −2) to 535±20 mg/dL (post-STZ treatment, day 0; FIGS. 19B, 19H, 19N, 19T). Reversal of hyperglycemia was observed immediately in all groups that received islet transplants. Comparing BG values at day 1 post-transplant, values for mice transplanted with encapsulated islets only was similar to those mice transplanted with isles only (284±42 vs 382±65 mg/dL, P>0.05). This effect was sustained throughout the course of the study with mice transplanted with encapsulated islets only having no significant difference in BG values from day 1 to 30 compared to mice transplanted with islets only (P>0.05; FIG. 19B). The percentage of recipient mice which exhibited normoglycemia (normoglycemia %) in the first week following transplantation was 21±5% for those which were transplanted with islets only; this decreased to 12±5% at week 2 and then increased to 23±3% at week 3 and 28±3% at week 4 post-transplantation. In contrast, mice transplanted with encapsulated islets only remained diabetic from week 1 to 4 (P<0.05; FIG. 19C). Following intraperitoneal glucose tolerance tests (IPGTT), mice transplanted with encapsulated islets only showed a similar peak value (P>0.05; FIG. 19D) with no change in the area under the curve ($AUC_{0-120min}$ P>0.05; FIG. 19E) when compared to mice transplanted with islets only. However, the BG clearance rate (calculated from slope of BG change vs time from 30 to 90 min) was significantly higher for mice transplanted with encapsulated islets only when compared to mice transplanted with islets only (P<0.05; FIG. 19F). The body weight of all mice increased following transplantation. However, during the course of our study, the increase in body weight of mice transplanted with encapsulated islets only was not significantly different when compared to mice transplanted with islets only (P>0.05; FIG. 19G).

Figure 19H:
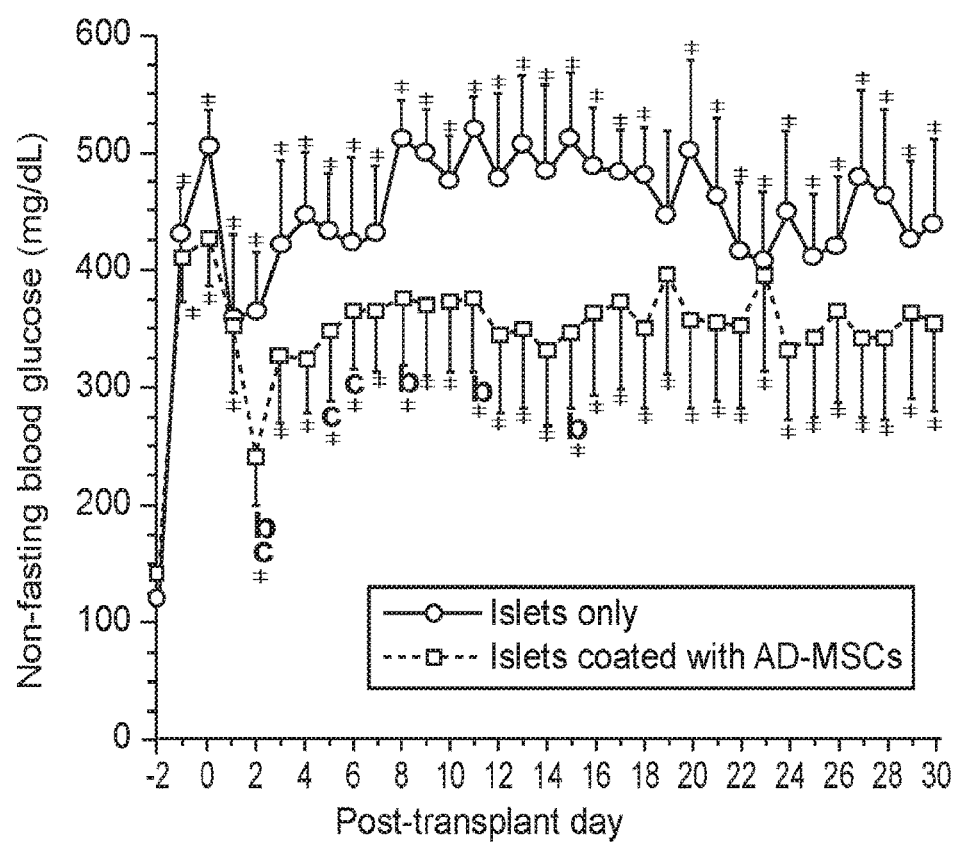
Figure 19I:
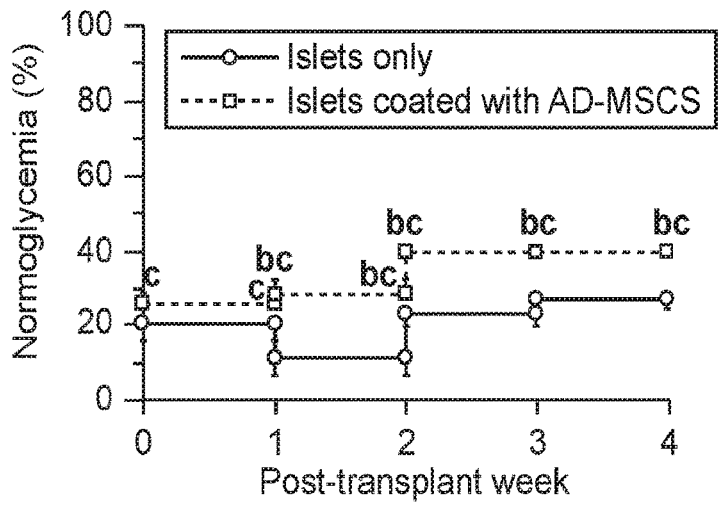
Figure 19J:
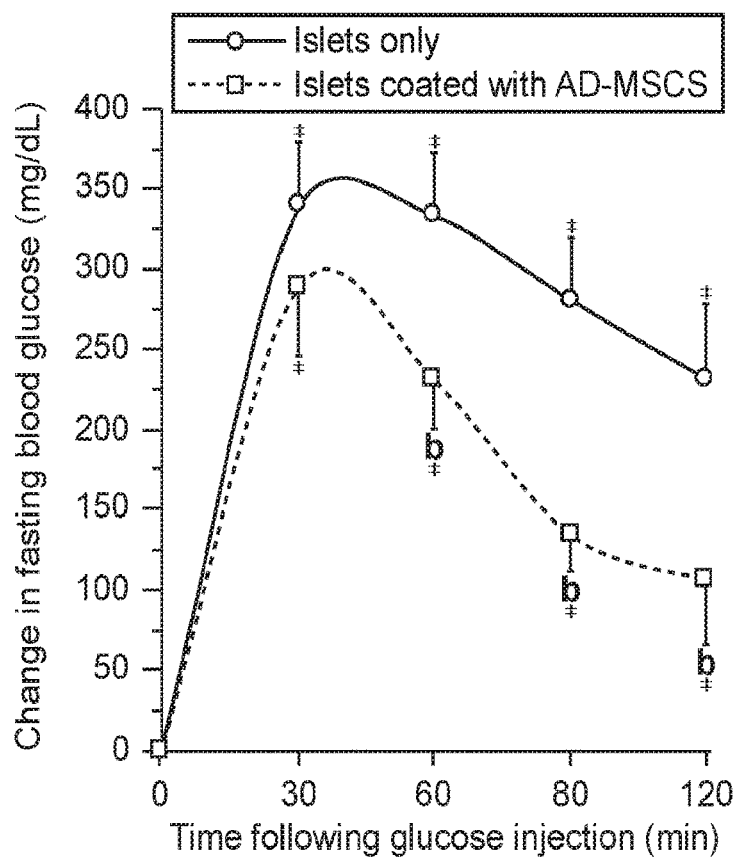
Figure 19K:
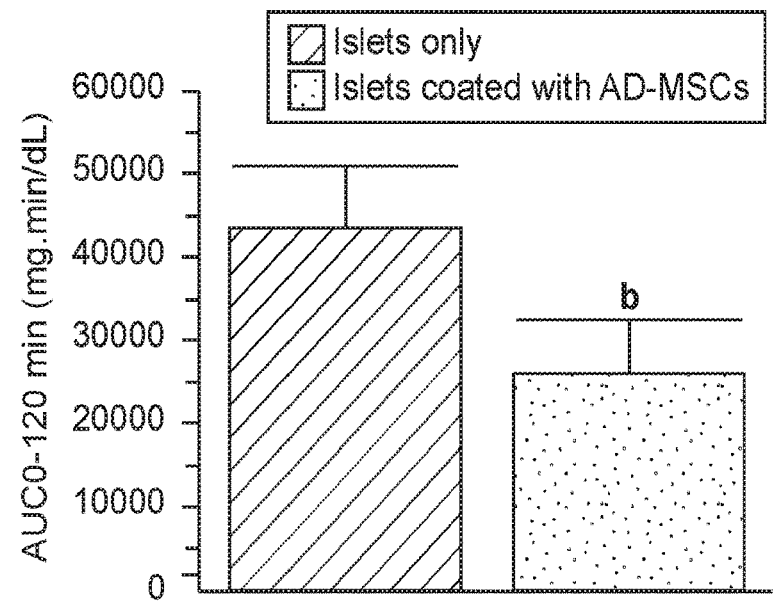
Figure 19L:
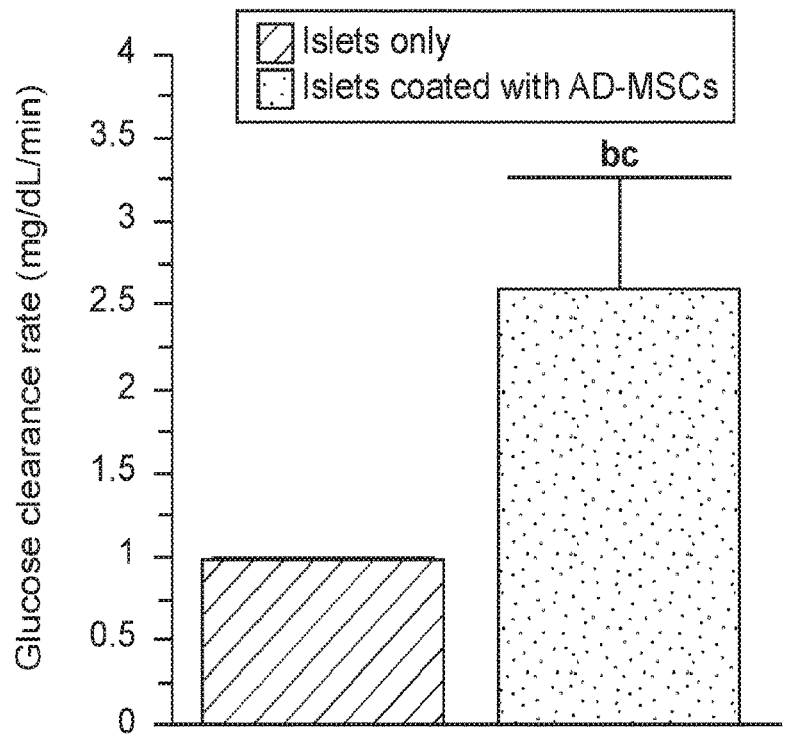
Figure 19M:
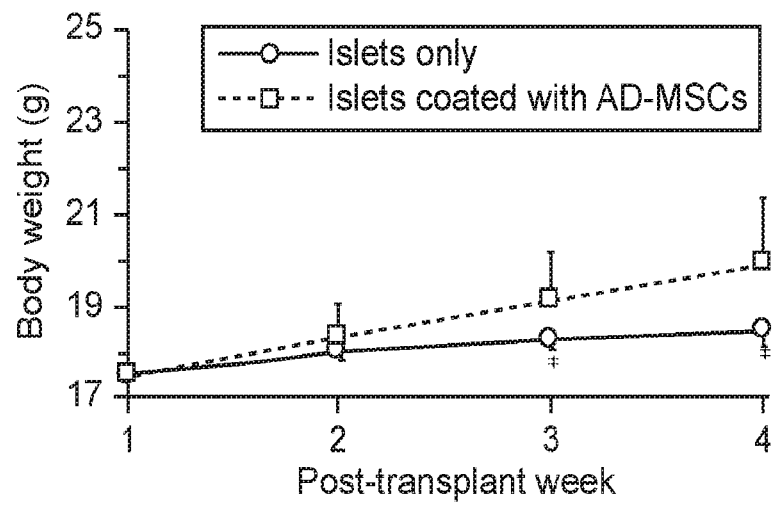

Step 1: AD-MSCs Coating on Islets: At day 2, 8, 11, and 15 post-transplantation, BG values for mice transplanted with islets coated with AD-MSCs was significantly lower than mice transplanted with islets only (P<0.05). Compared to mice transplanted with encapsulated islets only, at day 2, 5, and 6 post-transplantation, BG values for mice transplanted with islets coated with AD-MSCs was significantly lower (P<0.05). However, BG values from day 1-30 post-transplantation in mice transplanted with islets coated with AD-MSCs was significantly higher than their own baseline values pre-transplantation (P<0.05; FIG. 19H). The normoglycemia % for mice transplanted with islets coated with AD-MSCs was significantly higher compared to mice transplanted with islets only (except at week 1) or encapsulated islets only (P<0.05; FIG. 19I). Following IPGTT, mice transplanted with islets coated with AD-MSCs showed a significant decrease in BG values from 60-120 min when compared to mice transplanted with islets only (P<0.05; FIG. 19J). This caused a significant reduction in the $AUC_{0-120min}$ (P<0.05; FIG. 19K) and an increase in BG clearance rate compared to mice transplanted with islets only (P<0.05). Furthermore, compared to mice transplanted with encapsulated islets only, the BG clearance rate of mice transplanted with islets coated with AD-MSCs was significantly higher (P<0.05; FIG. 19L). From week 1 to 4 post-transplantation, the body weight of mice transplanted with islets coated with AD-MSCs increased, however, this increase was not significant (P>0.05). Although, the body weight of mice transplanted with islets coated with AD-MSCs was higher compared to mice transplanted with islets only or encapsulated islets only, these differences were also not significant (P>0.05; FIG. 19M).

Figure 19N:
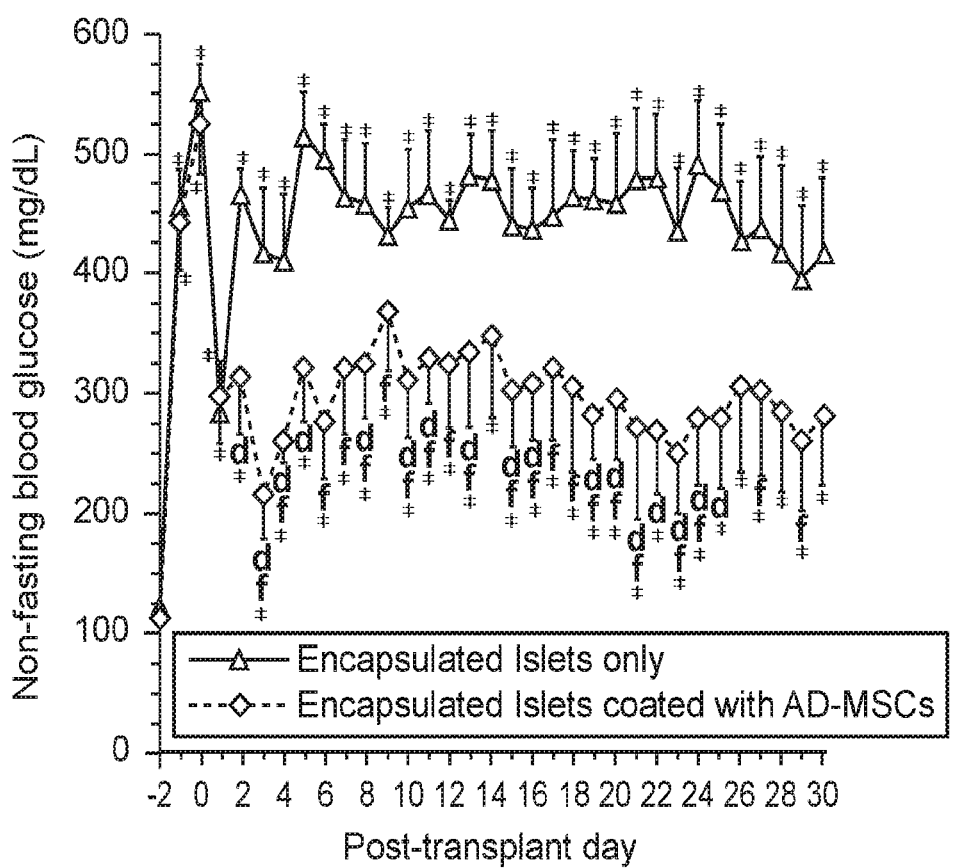
Figure 19O:
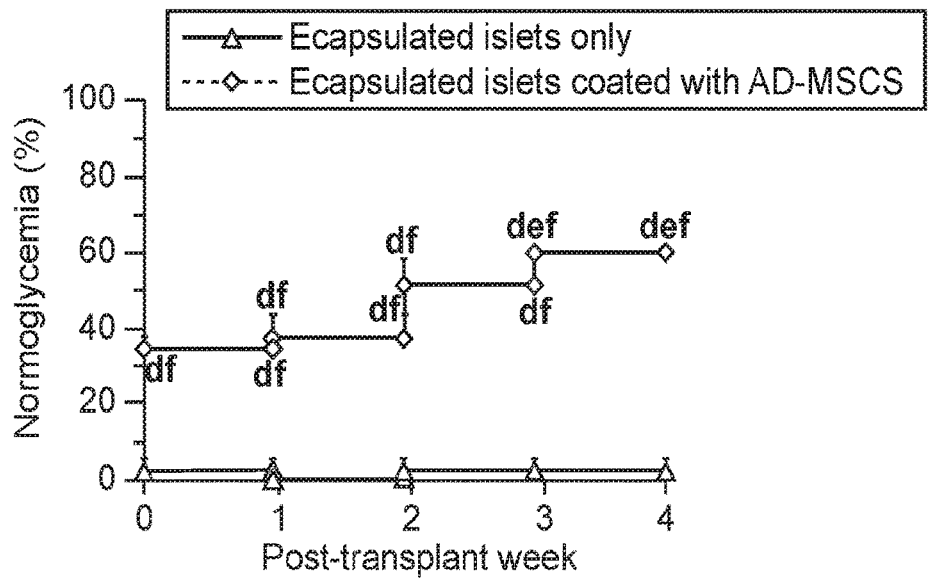
Figure 19P:
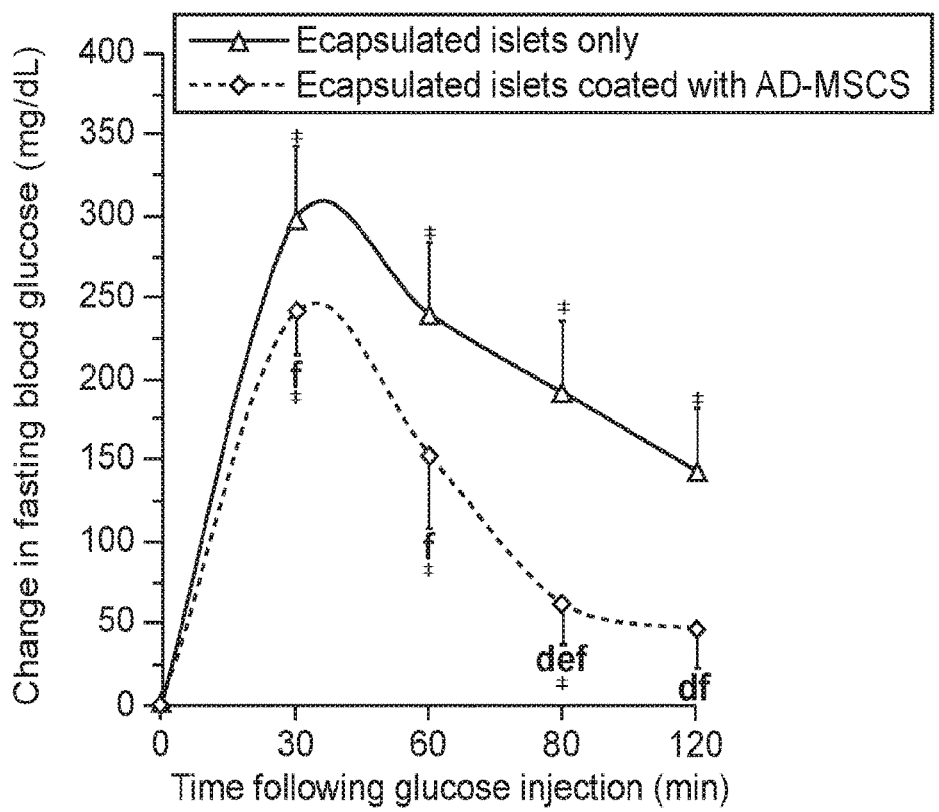
Figure 19Q:
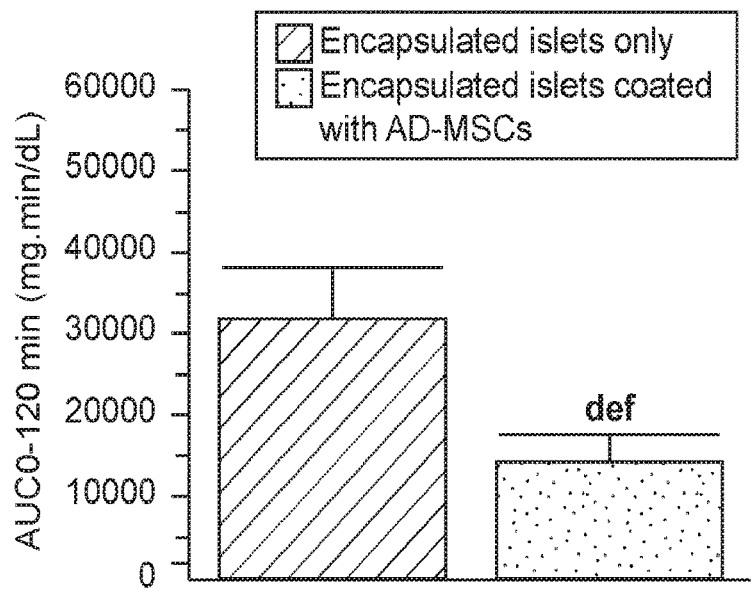
Figure 19R:
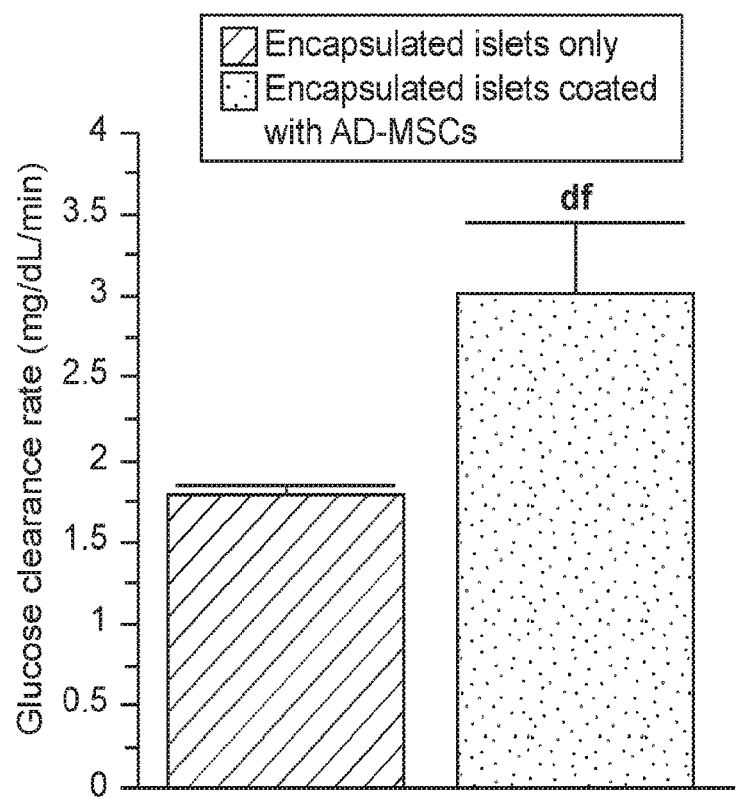
Figure 19S:
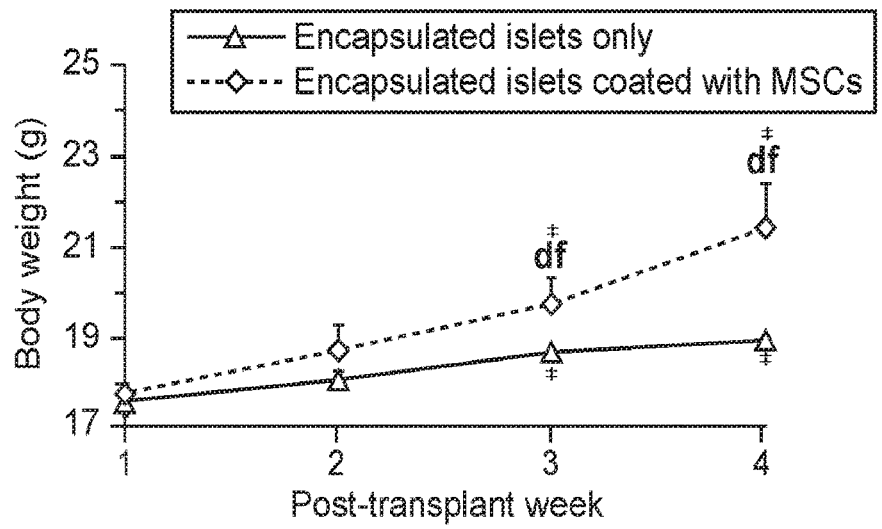

Step 2: Encapsulation of Islets Coated with AD-MSCs: At day 1 post-transplantation, BG values of mice transplanted with encapsulated islets coated with AD-MSCs was similar to mice transplanted with encapsulated islets only (298±72 vs 284±42 mg/dL, P>0.05). However, at day 2 post-transplantation, BG values for mice transplanted with encapsulated islets coated with AD-MSCs significantly decreased compared to mice transplanted with encapsulated islets only (313±70 vs 468±19 mg/dL; P<0.05). This effect was sustained throughout the course of our study with mice transplanted with encapsulated islets coated with AD-MSCs having significantly lower BG values from day 2 to 30 except at day 6, 7, 9, 12, 14, 17, 18, and 26-30 compared to mice transplanted with encapsulated islets only (P<0.05). Mice transplanted with encapsulated islets coated with AD-MSCs showed significantly lower BG values from day 2 to 30 except at day 1, 2, 5, 14, 22, 26, 28, and 30 compared to islets only. However, BG values in mice transplanted with encapsulated islets coated with AD-MSCs was still significantly higher compared to their own baseline values pre-transplantation (P<0.05; FIG. 19N). The normoglycemia % for encapsulated islets coated with AD-MSCs was significantly higher compared to mice transplanted with islets only or encapsulated islets only from week 1 to 4 and higher compared to mice transplanted with islets coated with AD-MSCs at week 4 (P<0.05; FIG. 19O). Following IPGTT testing, mice transplanted with encapsulated islets coated with AD-MSCs showed a significant decrease in BG values from 30 to 120 min compared to mice transplanted with islets only (P<0.05; FIG. 19P). The $AUC_{0-120min}$ for mice transplanted with encapsulated islets coated with AD-MSCs was significantly lower than mice transplanted with encapsulated islets only or islets coated with AD-MSCs or islets only (P<0.05; FIG. 19Q). Furthermore, mice transplanted with encapsulated islets coated with AD-MSCs had a significantly improved BG clearance rate compared to mice transplanted with islets only or encapsulated islets only (P<0.05; FIG. 19R). Comparing the body weight of mice transplanted with encapsulated islets only or islets only, mice transplanted with encapsulated islets coated with AD-MSCs had a significantly higher body weight at week 3 (P<0.05) and 4 (P<0.05; FIG. 19S).

Figure 19T:
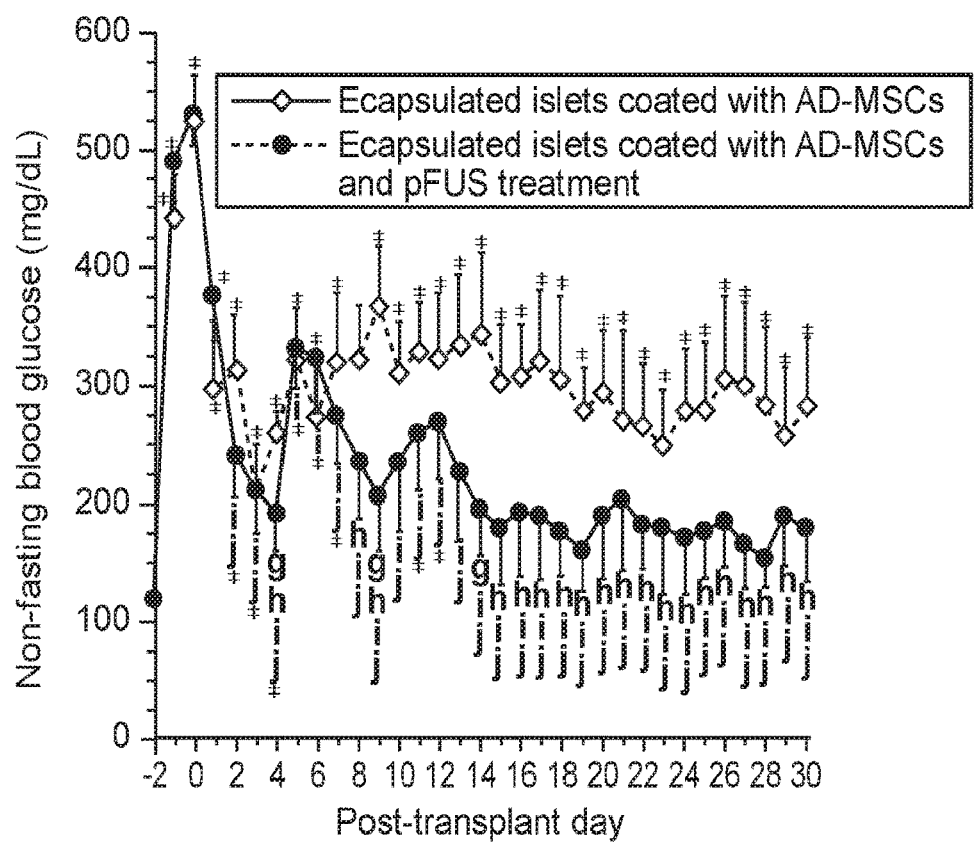
Figure 19U:
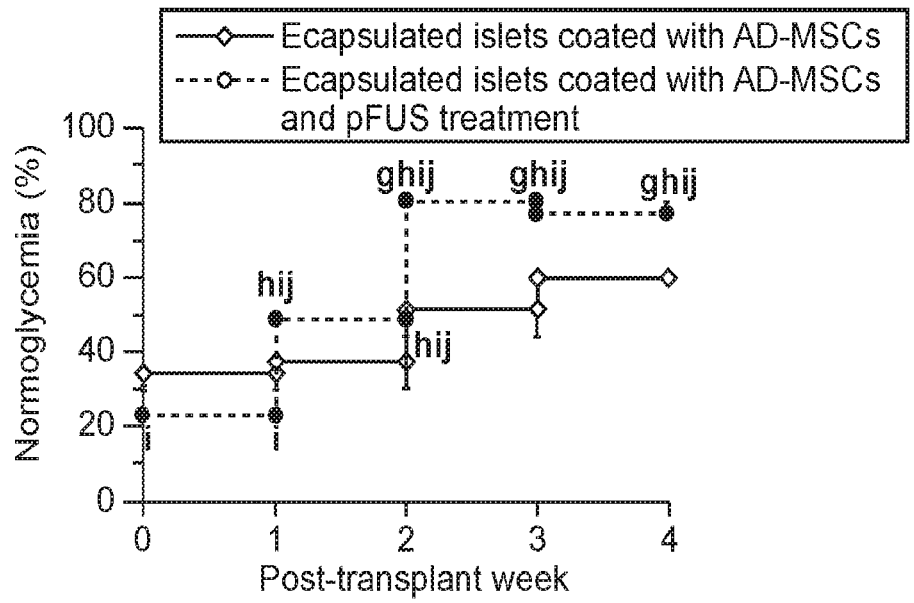
Figure 19V:
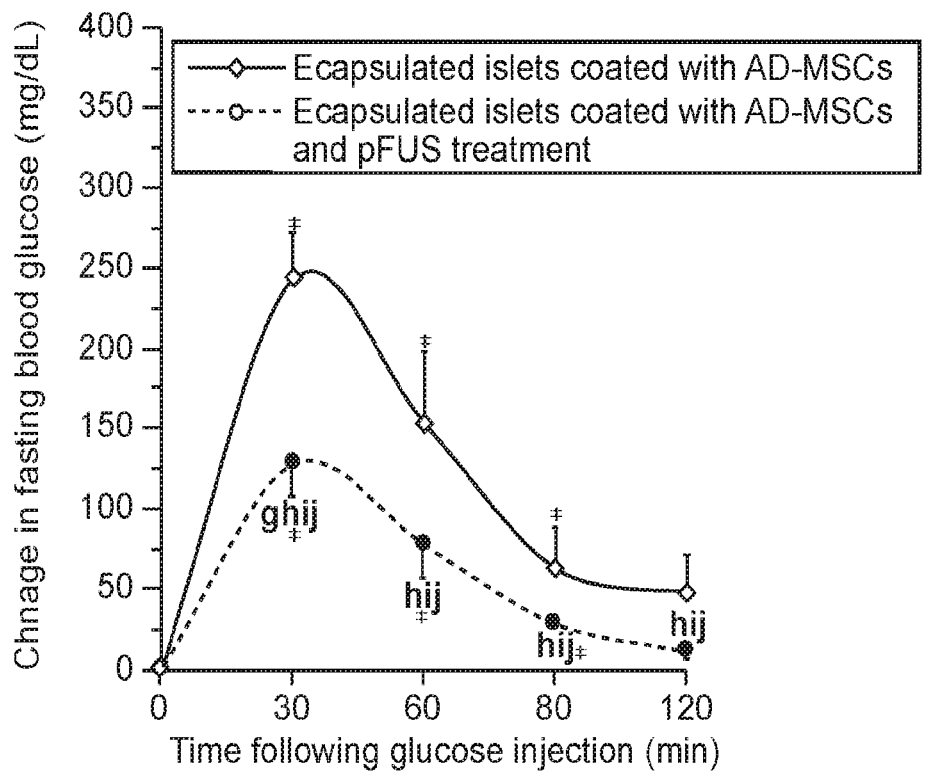
Figure 19W:
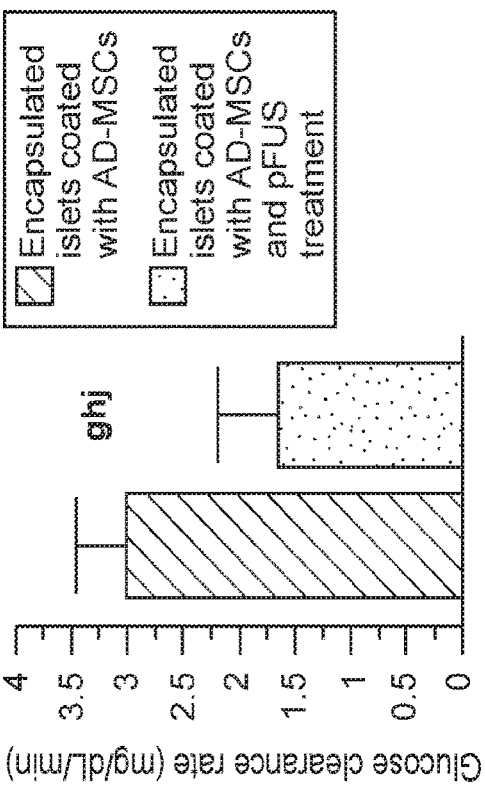
Figure 19X:
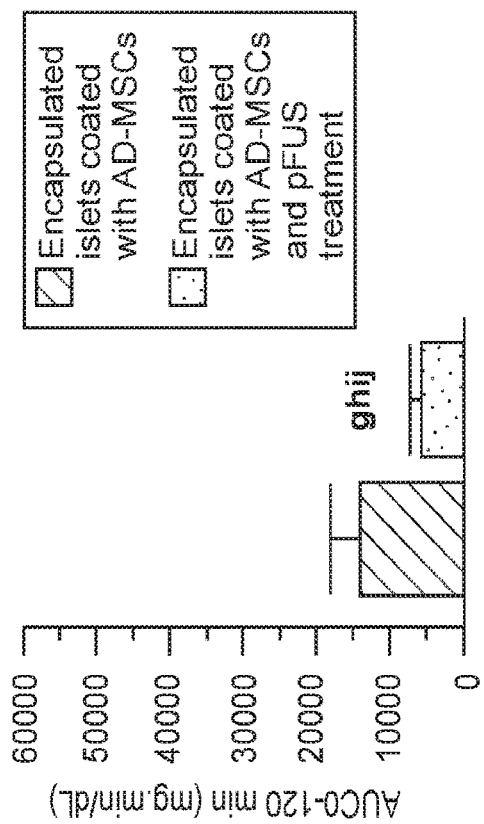
Figure 19Y:
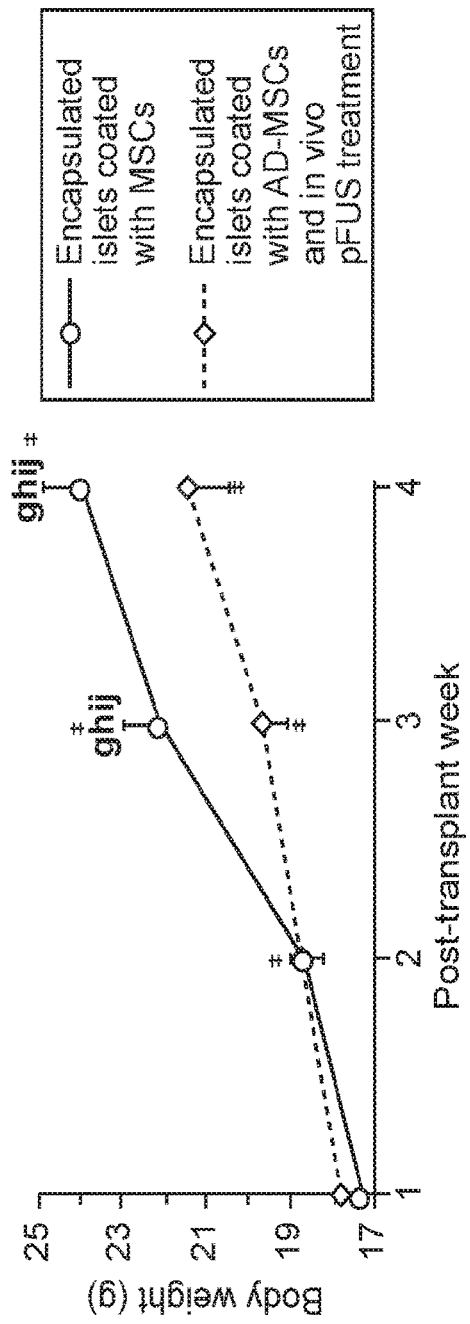

Step 3: pFUS Treatment on Encapsulated Islets Coated with AD-MSCs: pFUS treatment caused BG values to significantly decrease compared to the non-pFUS treated group (i.e. encapsulated islets coated with AD-MSCs receiving pFUS treatment vs. encapsulated islets coated with AD-MSCs) at day 4, 9, and 14 post-transplant (190±28 vs 260±18, 207±45 vs 369±50, and 196±39 vs 347±67, respectively, P<0.05). For pFUS treated mice, BG values were not significantly different compared to their own baseline (i.e. their pre-transplantation values) throughout the course of our study from day 1 to 30 except at day 1-7, and 11-12 (P<0.05). When compared with other tested groups, BG values for mice transplanted with encapsulated islets coated with AD-MSCs and treated with pFUS were significantly lower than mice transplanted with islets coated with AD-MSCs except at day 1-3, 5-7, 10-14, 20-21, encapsulated islets only except at day 1, and islets only except at day 1 and 5-6 (P<0.05; FIG. 19T). At week 2, a significantly higher normoglycemia % was achieved for pFUS treated mice compared to mice transplanted with islets only or encapsulated islets only or islets coated with AD-MSCs. However, from week 3 to 4, this effect was higher for pFUS treated mice compared to all other tested groups (P<0.05; FIG. 19U). Following IPGTT testing, mice transplanted with encapsulated islets coated with AD-MSCs and treated with pFUS showed a significant decrease in BG values at 30 min compared to mice transplanted with encapsulated islets coated with AD-MSCs (P<0.05). From 30 to 120 min, pFUS treated mice showed a significant decrease in BG values compared to mice transplanted with islets coated with AD-MSCs or encapsulated islets only or islets only (P<0.05; FIG. 19V). The $AUCoa20\sim m$ of mice transplanted with encapsulated islets coated with AD-MSCs and treated with pFUS was significantly lower compared to other tested groups (i.e. mice transplanted with encapsulated islets coated with AD-MSCs or islets coated with AD-MSCs or encapsulated islets only or islets only, P<0.05; FIG. 19W). Furthermore, mice transplanted with encapsulated islets coated with AD-MSCs which had been treated with pFUS showed a significantly enhanced BG clearance rate compared to mice transplanted with encapsulated islets coated with AD-MSCs or islets coated with AD-MSCs or islets only (P<0.05; FIG. 19X). Following pFUS treatment, the body weight of transplanted mice with encapsulated islets coated with AD-MSCs significantly increased (P<0.05). When compared to all other tested groups, the body weight of mice in the pFUS treated group was significantly higher at week 3 (P<0.05) and 4 (P<0.05; FIG. 18Y).

3.2. Histological and Molecular Analyses

Figure 20A:
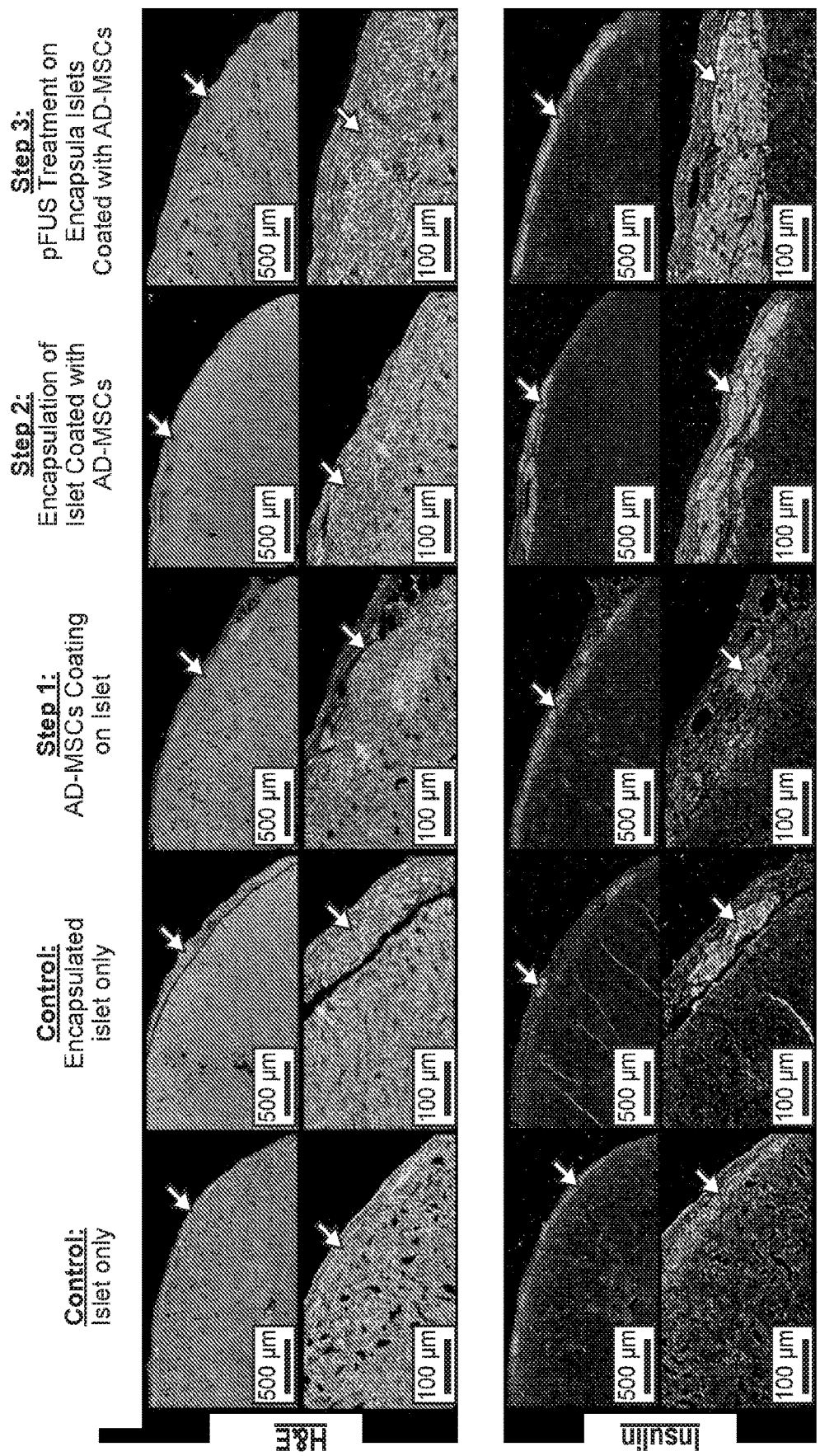
FIGS. 20A-20E. In vivo analysis of islet survival and function (Histological analysis)
Figure 20B:
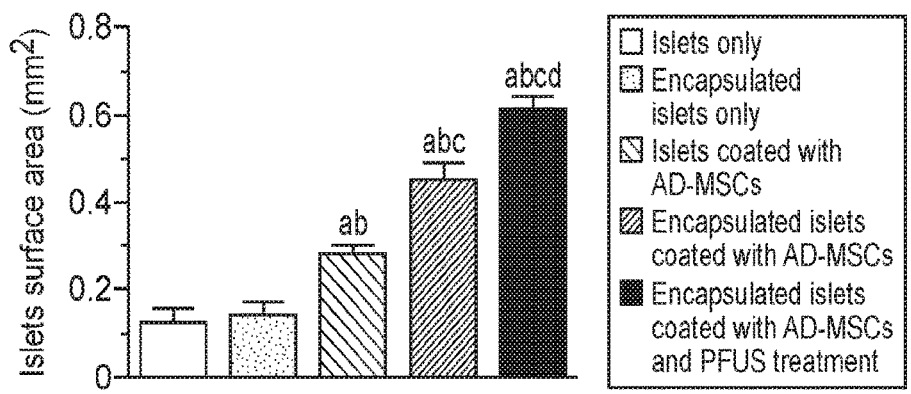
Figure 20C:
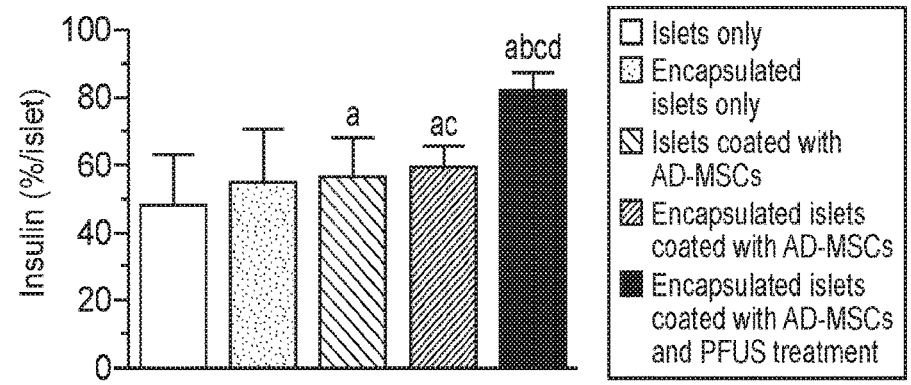
Figure 20D:
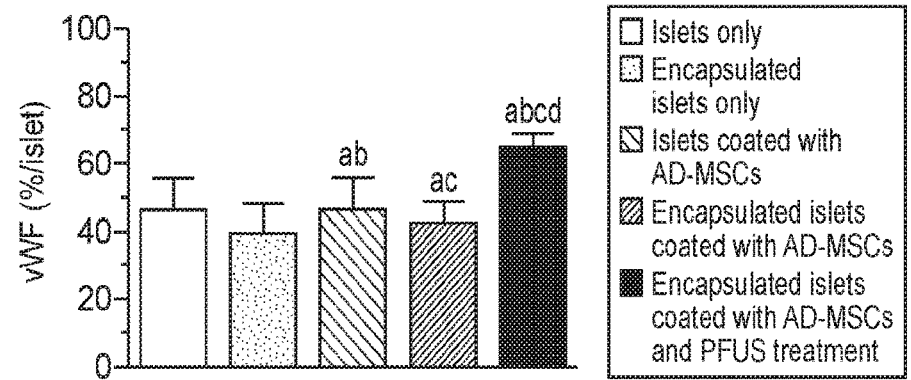
Figure 20E:
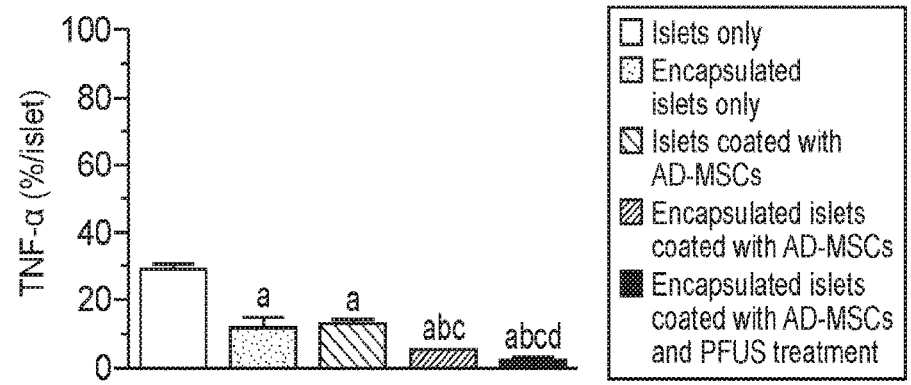

When tissues sections were stained using hematoxylin and eosin (H&E), insulin, and von Willebrand Factor (VWF), we found that encapsulation did not affect islet morphology (FIG. 20A) or islet number associated with the islet total surface area (0.13±0.03 vs 0.15±0.03 mm², P>0.05; FIG. 20B). Results showed that there was no significant difference in insulin (48.27±14.99 vs 55.05±15.77%/islet, P>0.05; FIG. 20C) and vWF (46.01±9.37 vs 39.45±8.37%/islet, P>0.05; FIG. 20D) expressions levels within islets, regardless of whether or not they were encapsulated. However, TNF-α expression was significantly reduced following encapsulation (29.33±1.48 vs 12.16±2.65%/islet for islets only vs encapsulated islets only, P<0.05; FIG. 20E).

Step 1: AD-MSCs Coating on Islets: In contrast to transplanted islets only or encapsulated islets only which had lost their spherical morphology with a more disorganized architecture, islets coated with AD-MSCs were more spherical (FIG. 20A) with a significantly higher total surface area compared to islets only (0.28±0.20 vs 0.13±0.03 mm², P<0.05) or encapsulated islets only (0.28±0.20 vs 0.15±0.03 mm², P<0.05; FIG. 20B). Islets coated with AD-MSCs showed a significant increase in insulin expression compared to islets only (56.54±11.66 vs 48.27±14.99, P<0.05; FIG. 20C). Furthermore, islets coated with AD-MSCs showed a significant increase in vWF expression compared to islets only (46.38±9.11 vs 46.01±9.37%/islet, P<0.05) or encapsulated islets only (46.38±9.11 vs 39.45±8.37%/islet, P<0.05; FIG. 20D). Decreased TNF-α expression was also noted for islets coated with AD-MSCs compared to islets only (13.60±0.77 vs 29.33±1.48%/islet, P<0.05; FIG. 20E).

Step 2: Encapsulation of Islets Coated with AD-MSCs: Encapsulation of islets coated with AD-MSCs resulted in islets retaining their spherical morphology (FIG. 20A), and enhancing their total surface area compared to islets only (0.45±0.04 vs 0.13±0.03 mm², P<0.05), encapsulated islets only (0.45±0.04 vs 0.15±0.03 mm², P<0.05) and islets coated with AD-MSCs (0.45±0.04 vs 0.28±0.20 mm², P<0.05; FIG. 20B). In this group, islets also showed elevated insulin expression compared to islets only (59.82±5.79 vs 48.27±14.99%/islet, P<0.05) or islets coated with AD-MSCs (59.82±5.79 vs 56.54±11.66%/islet, P<0.05; FIG. 20C). However, encapsulation of islets coated with AD-MSCs resulted in a significant decrease in vWF expression as compared to islets only (42.51±6.13 vs 46.01±9.37%/islet, P<0.05) or islets coated with AD-MSCs (42.51±6.13 vs 46.38±9.11%/islet, P<0.05; FIG. 20D). When TNF-α expression of islets was compared, encapsulated islets coated with AD-MSCs showed a significant decrease compared to islets only (5.55±0.24 vs 29.33±1.48%/islet, P<0.05), encapsulated islets only (5.55±0.24 vs 12.16±2.65%/islet, P<0.05) and islets coated with AD-MSCs (5.55±0.24 vs 13.60±0.77%/islet, P<0.05; FIG. 20E).

Step 3: pFUS Treatment on Encapsulated Islets Coated with AD-MSCs: Following pFUS treatment, islets had retained their native size and spherical morphology, and maintained their intrinsic architecture with β-cells (positive insulin staining) located in the center of the islets. Of note, islets which were treated with pFUS also subjectively demonstrated vascular regions within islets (FIGS. 20A-20B). However, compared to other experimental groups (i.e. islets only, encapsulated islets only, islets coated with AD-MSCs and encapsulated islets coated with AD-MSCs), pFUS treatment caused transplanted islets to show a significantly enhanced total surface area (0.61±0.03 vs 0.13±0.03, 0.28±0.2, and 0.45±0.04 $mm^2$, P<0.05; FIG. 20B), insulin (82.22±4.91 vs 48.26±14.99, 55.05±15.77, 56.53±11.66 and 59.82±5.78%/islet, P<0.05; FIG. 20C) and vWF (64.38±4.16 vs 46.01±9.37, 39.45±8.37, and 46.37±9.11 and 42.51±6.13%/islet, P<0.05; FIG. 20D) expression. Furthermore, in pFUS treated mice, islets had less inflammation as demonstrated by a reduction in the presence of TNF-α when compared to other mice (2.65±0.09 vs 29.33±1.48, 12.15±2.65, 13.60±0.77 and 5.55±0.24%/islet, P<0.05; FIG. 20E).

Figure 21A:
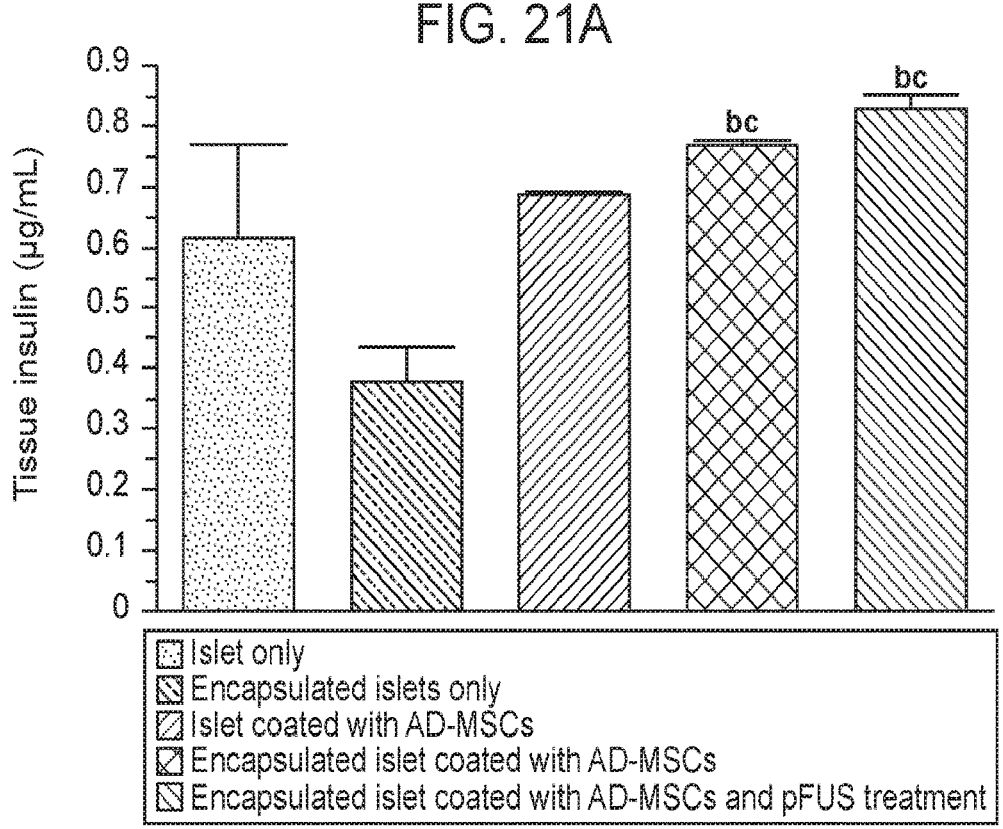
FIGS. 21A-21C. In vivo analysis of islet survival and function (Molecular Analysis): The level of insulin within (FIG. 21A) the kidney and (FIG. 21B) blood serum of mice transplanted with islets. The (FIG. 21C) cytokines expression profile in the kidney of mice transplanted with islets in following tested groups: islets only, encapsulated islets only, islets coated with AD-MSCs, encapsulated islets coated with AD-MSCs, and encapsulated islets coated with AD-MSCs and pFUS treatment. Significant differences: $^a$P<0.05: islets only vs. encapsulated islets only or islets coated with AD-MSCs or encapsulated islets coated with AD-MSCs or encapsulated islets coated with AD-MSCs and pFUS treatment; $^b$P<0.05: encapsulated islets only vs. islets coated with AD-MSCs or encapsulated islets coated with AD-MSCs or encapsulated islets coated with AD-MSCs and pFUS treatment; $^c$P<0.05: islets coated with AD-MSCs vs. encapsulated islets coated with AD-MSCs or encapsulated islets coated with AD-MSCs and pFUS treatment; $^d$P<0.05: encapsulated islets coated with AD-MSCs vs. encapsulated islets coated with AD-MSCs and pFUS treatment (One-way ANOVA post-hoc Tukey Test).
Figure 21B:
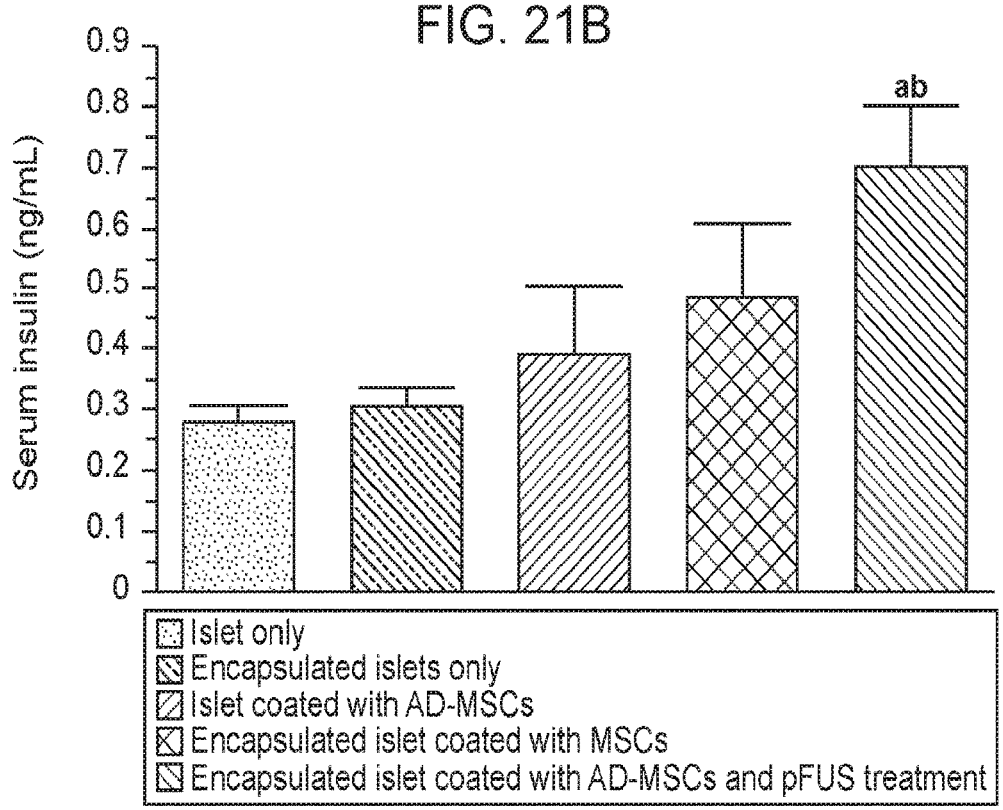
Figure 21C:
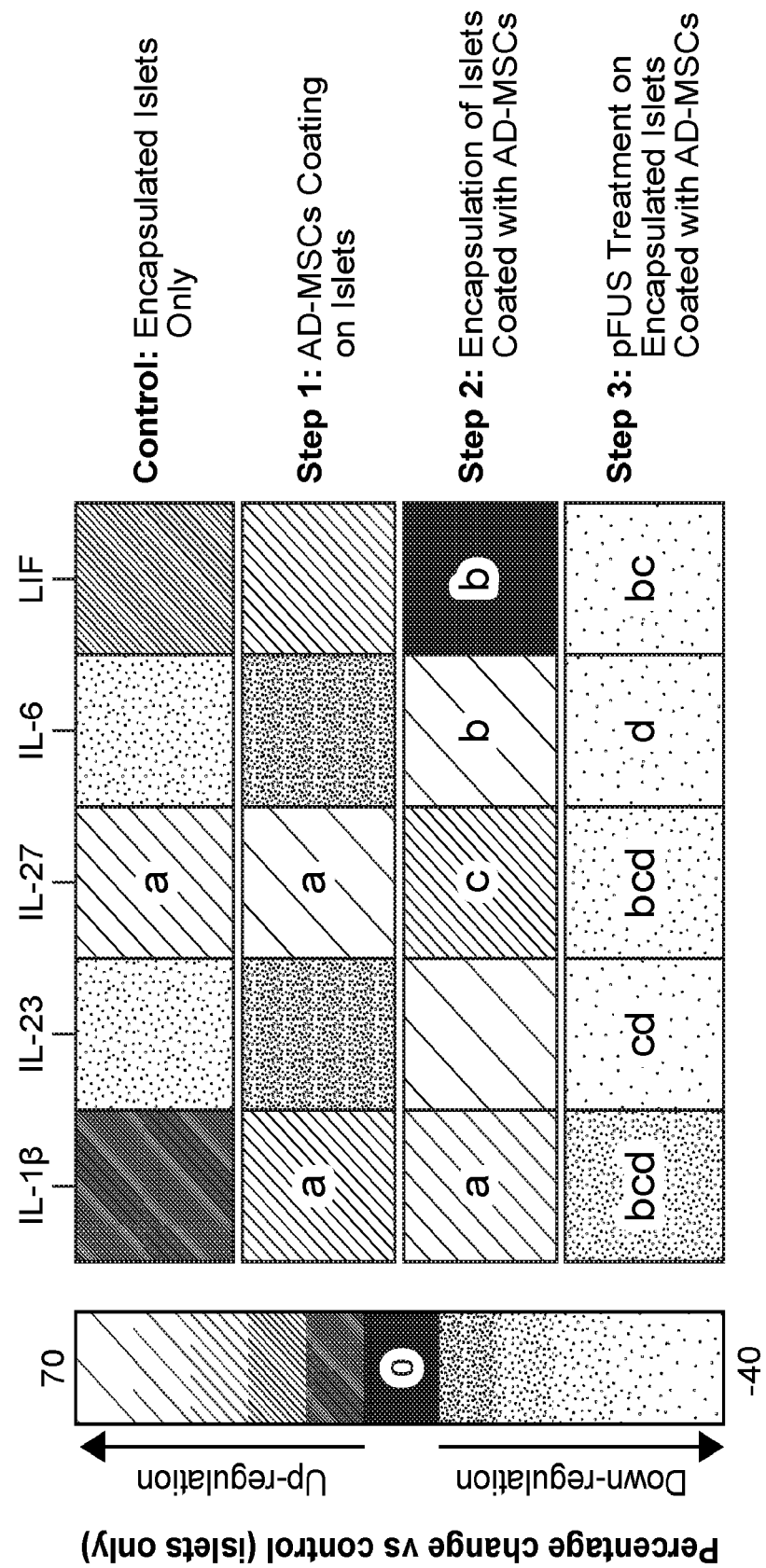

Analysis of the explanted kidneys showed that mice kidneys transplanted with encapsulated islets coated with AD-MSCs followed by pFUS treatment contained a significantly higher amount of insulin compared to mice kidneys transplanted with encapsulated islets only (0.83±0.03 vs 0.38±0.06 μg/mL, P<0.05) or islets coated with AD-MSCs (0.83±0.03 vs 0.69±0.01 μg/mL, P<0.05; FIG. 21A). Similarly, a significantly increase in blood serum insulin was found for pFUS treated mice compared to mice transplanted with islets only (0.70±0.10 vs 0.28±0.03 ng/mL, P<0.05) or encapsulated islets only (0.70±0.10 vs 0.30±0.03 ng/mL, P<0.05; FIG. 21B). We also analyzed cytokines expression in the kidneys and found that when pFUS is applied to encapsulated islets coated with AD-MSCs, pro-inflammatory cytokines were down-regulated compared to kidneys which were transplanted with either islets only, encapsulated islets only, islets coated with AD-MSCs or encapsulated islets coated with AD-MSCs. These cytokines were IL-1β (−11.49±0.70 vs 10.01±0.54, 29.32±2.20, 55.86±7.73%, P<0.05), IL-23 (−27.89±1.23 vs −6.17±0.25, and 64.28±13.98%, P<0.05), IL-27 (−20.62±2.49 vs 42.98±2.67, 49.28±2.47, and 24.50±1.75%, P<0.05), IL-6 (−24.65±1.06 vs 52.44±9.61%, P<0.05), and leukemia inhibitory factor (LIF: −29.98±7.03 vs 18.88±0.41 and 23.13±2.91%, P<0.05; FIG. 21C).

Discussion

In the present study, we demonstrated that we can promote the function and engraftment of pancreatic islets using a novel three-step approach. Here, we combined a cellular therapy shown to promote islet function (i.e. using AD-MSCs to coat islets; step 1) with a biocompatible biomaterial shown to protect transplanted islets (i.e. using alginate to encapsulate islets coated with AD-MSCs; step 2) and then we used a novel non-invasive technology, which employs soundwaves, to stimulate both islets and AD-MSCs (i.e. applying pFUS to encapsulated islets coated with AD-MSCs; step 3). In step 1, we co-cultured islets and AD-MSCs in a 1:500 ratio for 24 h to enable AD-MSCs to attach and uniformly coat islets. In step 2, islets coated with AD-MSCs were conformally encapsulated with an alginate layer measuring 50±11 μm to spatially localize AD-MSCs to islets as well as to provide a protective barrier to islets from any immune mediated attack. Finally, in step 3, encapsulated islets coated with AD-MSCs were treated with pFUS using the following parameters: 100 Hz PRF, 20% DC, 16.5 Vpk-pk and 1 min exposure time. This was done to enable soundwaves to increase the function and survival of islets either directly, or indirectly by stimulating AD-MSCs associated with the islets. Our in vitro and in vivo data both demonstrated an additive and synergistic effect on islet function and survival when these 3 steps were employed together.

Clinical studies have shown that islet transplantation can provide diabetic patients with long-term insulin independence and normalization of glycosylated hemoglobin (HbA1c) levels, while also preventing hypoglycemic episodes (29-32). However, despite more than 80% of patients becoming insulin-independent within the first year following islet transplantation, this number reduces over 5 years (33). Hence, islet transplantation is yet to reach its full clinical potential which, in part, can be attributed to islets being lost either immediately following their transplantation (i.e. failure of engraftment) or later on (i.e. as a result of autoimmune mediated cellular rejection). To address these shortcomings, in previous studies, we and others have examined the use of MSCs to help facilitate islet engraftment (34) as well as encapsulation to reduce the need for stringent immunosuppression to prevent graft rejection (35) However, by combining both of these approaches, this could potentially provide a complementary strategy to simultaneously address both the above issues.

Over the past decade, MSCs from different sources have been studied with islets. In in vitro studies where islets and MSCs are co-cultured together, and hence spatially constrained within a defined environment, MSCs have been shown to increase islet survival and function in both normal and adverse conditions (36-39). These beneficial effects of MSCs have also been seen when translated in vivo when islets and MSCs are co-transplanted together in a confined environment, such as the kidney subcapsular space (34). Here, MSCs have been shown to improve islet revascularization as well as suppress inflammatory responses (40, 41). However, during clinical islet transplantation, islets are infused into the portal vein, which results in them being randomly distributed throughout the liver. When MSCs are then also administered, they are given in another separate infusion that does not ensure co-engraftment of both the islets and MSCs at the same location. Furthermore, the much smaller MSCs (15-30 μm) can actually pass through the liver with most cells eventually ending up in the lung microcirculation (42, 43). If MSCs cannot be spatially located next to the islets, this will limit their therapeutic effect which is predominantly based on their ability to sense and modulate their surrounding microenvironment via their paracrine action (44). Given that MSCs, and in particular AD-MSCs, have such a prominent beneficial effect on islets, we decided to not only coat islets with these cells but also then encapsulate them together to prevent them from dissociating at the time of transplantation.

In a previous work, Duprez et al. (24) demonstrated that human bone marrow MSCs surrounded human islets before migrating towards their center and that the MSC coating was both dose- and time-dependent. They used islets and MSCs with the ratio of 1:100-500 and made comparisons between MSC coated islets; their data showed that with ratios of 1:100 (islet:MSCs) there was only a sporadic binding of MSCs to the islet surface, however when the ratio increased to >100 MSCs this resulted in a more uniform MSC coating. Indeed, this group found that a ratio of 1:500 islet:MSCs, and a coating time of 24 h, resulted in the optimal and uniform coating of islets with MSCs (24), and this was also verified by our studies using AD-MSCs. Once islets are coated with AD-MSCs, we found they exhibited an enhanced secretion of insulin in response to glucose challenges as well as improved survival in vitro which we attributed to the ability of AD-MSCs to secrete trophic and growth factors (37, 45) as well as increase the insulin sensitivity of islets (46).

In order to keep AD-MSCs together with islets, we conformally encapsulated islets coated with AD-MSCs in a thin layer of alginate (50±10 µm). While non-conformal encapsulation of islets have been extensively studied (i.e. using 500 µm capsules) these are not clinically translatable using the current approach for islet transplantation given that it increases the average diameter of conventional islet by approximately three fold which then results in an increase in the transplant volume by approximately 27 times, which can be difficult to accommodate in the host's liver (47, 48). Furthermore, this type of encapsulation predisposes islets to developing hypoxia given that the diffusion distance of oxygen through such thick capsules is hindered (47). Encapsulation also prevents the revascularization process which further exacerbates the hypoxia situation and also hinders the release of insulin compared to non-encapsulated islets (49). Hence, recent studies have been examining encapsulation techniques in which a very thin membrane, or conformal coating, can be applied to islets. By using conformal coating to minimize capsule thickness, this will help islets to better engraft in small spaces (i.e. the hepatic sinusoids) (50). Conformal coating can also help sustain islet function by facilitating the rapid diffusion of oxygen and nutrients through the thin coating, as well as the release of insulin from islets in response to glucose (51). Hence, in the present work we used an air flow technique which enabled us to uniformly coat islets with a 5011 µm layer of alginate which we confirmed with confocal microscopy. At this thickness, the alginate layer still allows for the diffusion of oxygen, nutrients, and glucose to islets while concomitantly protecting them from immune attack (52). Moreover, the alginate layer can prevent islet aggregation and preserve islet morphology (53) both of which have been shown to improve islet function (54). We chose alginate as our biomaterial for encapsulation given that it is one of the most widely investigated cell encapsulation biomaterials (55) and has been used in several clinical trials (56-59). Our results confirm that that islet survival and function can be improved in vitro following encapsulation and encapsulated islets retained their islet-like morphology in vivo. We also found a significant improvement in islet function and engraftment with encapsulated islets coated with AD-MSCs compared to when islets alone were encapsulated. This effect can be potentially due to the continuous exposure of the islets to the AD-MSCs as a result of encapsulation, which may confer an advantage for the lifetime of the graft.

One question that still needs to be addressed is how to stimulate islets, as well as other cellular therapies like AD-MSCs, after they have been given into living subjects. One approach to non-invasively stimulate these cells is to use soundwaves. The ability of soundwaves to propagate through tissue, and be focused at specific locations deep within the body, makes pFUS a very appealing non-invasive therapeutic strategy. Previous research has shown that pFUS is able to enhance the ability of beta cells to secrete insulin via a calcium dependent mechanism (60). Furthermore, given the ability of MSCs to be stimulated by their surrounding environment (i.e. hypoxia (61)), temperature (i.e. thermal shock (62)) and even chemicals (i.e. pharmacologic treatment or pro-inflammatory cytokine exposure (63, 64)), it is not surprising that soundwaves, at specific intensities, can physically stimulate AD-MSCs via a biomechanical effect. Stimulated MSCs have also been shown to upregulate Toll-like receptors (TLRs), which can increase their function to inflammatory milieu (65). Although future work will examine the specific mechanisms by which pFUS stimulates MSCs, we found that when encapsulated islets coated with AD-MSCs were stimulated with pFUS there was improved islet survival (i.e. enhanced percentage of live cells) and function (i.e. enhanced glucose stimulated insulin secretion).

Based on our in vitro data, we then examined whether this approach could be translated into an animal model. Hence, in diabetic animals we transplanted alginate encapsulated islets that had been coated with AD-MSCs and then used pFUS to stimulate these cells over 2 weeks (i.e. over the period of islet engraftment and when most islets are lost as a result of hypoxia, nutrient deprivation and inflammation). Interestingly we found that by using this combined three-step approach, we were able to restore glycemic control in animals faster and with less variability. These animals were also able to respond quicker and faster to intraperitoneal glucose challenges with transplanted islets also demonstrating improved revascularization (shown by an enhanced expression of vWF) and reduced evidence of surrounding inflammation (shown by a decreased expression of TNF-α on histology as well as down-regulation of pro-inflammatory cytokines IL-1β (66), IL-23 (67), IL-27 (68), and IL-6 (69) in the tissue lysate of the islet transplant. The ability of encapsulated islets coated with AD-MSCs to demonstrate increased vWF staining around the islets is in keeping these islets ability to secure a dedicated blood supply around their capsule given that vWF acts as a regulator of angiogenesis as well as controlling vessel proliferation and maturation (70). Of the pro-inflammatory cytokines which were down regulated, IL-1β is key given the upregulation of this specific one has been shown to be deleterious to transplanted islet survival and function via stimulation of insulin resistance in islets (71), inhibition of beta cell function (72), promotion of Fas-triggered apoptosis (72), and induction of nitric oxide (NO) synthase in beta cells and subsequent generation of toxic NO levels (73). Hence, taken together, these results demonstrate the ability of this approach to not only help islet engraftment at the site of transplantation but also that promote islet survival and function. Given our in vitro data, it is likely that pFUS is working to both stimulate islets directly as well as indirectly through the stimulation of AD-MSCs which are coated onto the surface of islets. In addition, the alginate capsule will likely also protect the transplanted islets from direct effects of inflammation as well as any host mediated response (74).

The clinical translation of this approach for patients with T1D treated with islet transplantation is feasible given that pFUS can be applied to patients using current clinically available equipment and AD-MSCs have already been used in multiple clinical trials (NCT03265613, NCT03691909, NCT02407470, NCT02145897). Although the acoustic parameters of pFUS to achieve the PNPs and intensities reported here would need to be modified accordingly, it should be noted that these values measured here are non-derated values given that the coupling medium (water) is non-attenuating, and the depth at which the pFUS was applied in the animals was non-significant for the frequency utilized. For humans, it will be necessary to utilize acoustic parameters that achieve the reported PNPs and intensities after deration. Derating the PNPs and intensities will be necessary because, for clinical treatment, the transducer will be coupled directly to the individual (via an acoustic coupling gel) and the acoustic pressure and intensities will be attenuated by the intervening tissue between the transducer and the target tissue region. Of note, clinical trials have also been carried out using encapsulated islets (58, 59), though none of these were able to achieve insulin independence (75). Clinical trials using encapsulated islets have lacked long-term efficacy, and although generally considered clinically safe, have not been encouraging overall (75). However, considering that clinical trials conducted with encapsulated islets were shown to be safe (59), we believe a similar evaluation in patients with our three-step approach using AD-MSCs, encapsulation and pFUS may provide therapeutic benefit.

In summary, we have demonstrated the usefulness of a three-step approach, i.e. islets coated with AD-MSCs, alginate encapsulation and pFUS treatment for islet transplantation. We have shown that our approach improves the overall survival and function of transplanted islets with a corresponding increase in angiogenesis and reduction in inflammation. Hence, this approach may overcome many of the hurdles currently faced by islet transplantation that have thus far limited it from reaching its full clinical potential.

REFERENCES

1. E. L. A. S, I. Mager, X. O. Breakefield, M. J. Wood, Extracellular vesicles: biology and emerging therapeutic opportunities. *Nat Rev Drug Discov* 12, 347-357 (2013).
2. C. Aguayo-Mazzucato, S. Bonner-Weir, Stem cell therapy for type 1 diabetes mellitus. *Nature Reviews Endocrinology* 6, 139 (2010).
3. E. A. Ryan et al., Clinical outcomes and insulin secretion after islet transplantation with the Edmonton protocol. *Diabetes* 50, 710-719 (2001).
4. M. Gillies, T. Mandel, The evolution of function and response to arginine challenge and pregnancy of portally and systemically placed islet cell grafts in streptozotocin diabetic mice. *Metabolism* 39, 1253-1258 (1990).
5. D. J. Van Der Windt, R. Bottino, A. Casu, N. Campanile, D. K. Cooper, Rapid loss of intraportally transplanted islets: an overview of pathophysiology and preventive strategies. *Xenotransplantation* 14, 288-297 (2007).
6. S. M. Watt et al., The angiogenic properties of mesenchymal stem/stromal cells and their therapeutic potential. *Br Med Bull* 108, 25-53 (2013).
7. H. Tao, Z. Han, Z. C. Han, Z. Li, Proangiogenic Features of Mesenchymal Stem Cells and Their Therapeutic Applications. *Stem Cells Int* 2016, 1314709 (2016).
8. P. R. Baraniak, T. C. McDevitt, Stem cell paracrine actions and tissue regeneration. *Regenerative medicine* 5, 121-143 (2010).
9. S. W. Schive et al., Human adipose-derived mesenchymal stem cells respond to short-term hypoxia by secreting factors beneficial for human islets in vitro and potentiate antidiabetic effect in vivo. *Cell medicine* 9, 103-116 (2017).
10. G. Cavallari et al., Mesenchymal stem cells and islet cotransplantation in diabetic rats: improved islet graft revascularization and function by human adipose tissue-derived stem cells preconditioned with natural molecules. *Cell transplantation* 21, 2771-2781 (2012).
11. S. Yamada et al., Trophic effect of adipose tissue-derived stem cells on porcine islet cells. *journal of surgical research* 187, 667-672 (2014).
12. Y. Ohmura et al., Combined transplantation of pancreatic islets and adipose tissue-derived stem cells enhances the survival and insulin function of islet grafts in diabetic mice. *Transplantation* 90, 1366-1373 (2010).
13. H. Wang et al., Autologous Mesenchymal Stem Cell and Islet Cotransplantation: Safety and Efficacy. *Stem Cells Transl Med* 7, 11-19 (2018).
14. C. Villa et al., Effects of composition of alginate-polyethylene glycol microcapsules and transplant site on encapsulated islet graft outcomes in mice. *Transplantation* 101, 1025 (2017).
15. L. S. del Burgo et al., 3D Printed porous polyamide macrocapsule combined with alginate microcapsules for safer cell-based therapies. *Scientific reports* 8, 8512 (2018).
16. M. Qi, Transplantation of encapsulated pancreatic islets as a treatment for patients with type 1 diabetes mellitus. *Advances in medicine* 2014 (2014).
17. N. Sakata et al., Encapsulated islets transplantation: past, present and future. *World journal of gastrointestinal pathophysiology* 3, 19 (2012).
18. V. Frenkel, Ultrasound mediated delivery of drugs and genes to solid tumors. *Advanced drug delivery reviews* 60, 1193-1208 (2008).
19. B. L. Furman, Streptozotocin-induced diabetic models in mice and rats. *Current protocols in pharmacology* 70, 5.47. 41-45.47. 20 (2015).
20. S. Merani, C. Toso, J. Emamaullee, A. Shapiro, Optimal implantation site for pancreatic islet transplantation. *British Journal of Surgery: Incorporating European Journal of Surgery and Swiss Surgery* 95, 1449-1461 (2008).
21. N. V. Evgenov, Z. Medarova, G. Dai, S. Bonner-Weir, A. Moore, In vivo imaging of islet transplantation. *Nature medicine* 12, 144 (2006).
22. J. C. Neuman, N. A. Truchan, J. W. Joseph, M. E. Kimple, A method for mouse pancreatic islet isolation and intracellular cAMP determination. *Journal of visualized experiments: JoVE* (2014).
23. J. H. Sung et al., Isolation and characterization of mouse mesenchymal stem cells. *Transplant Proc* 40, 2649-2654 (2008).
24. I. R. Duprez, U. Johansson, B. Nilsson, O. Korsgren, P. U. Magnusson,
Preparatory studies of composite mesenchymal stem cell islets for application in intraportal islet transplantation. *Upsala journal of medical sciences* 116, 8-17 (2011).
25. I. S. Castellanos, A. Jeremic, J. Cohen, V. Zderic, Ultrasound stimulation of insulin release from pancreatic beta cells as a potential novel treatment for type 2 diabetes. *Ultrasound in medicine & biology* 43, 1210-1222 (2017).
26. X. Zhou et al., Improved human bone marrow mesenchymal stem cell osteogenesis in 3D bioprinted tissue scaffolds with low intensity pulsed ultrasound stimulation. *Scientific reports* 6, 32876 (2016).

27. S. R. Burks et al., Pulsed focused ultrasound pretreatment improves mesenchymal stromal cell efficacy in preventing and rescuing established acute kidney injury in mice. *Stem Cells* 33, 1241-1253 (2015).
28. A. Molven et al., The Hypoglycemic Phenotype Is Islet Cell-Autonomous in Short-Chain Hydroxyacyl-CoA Dehydrogenase-Deficient Mice. *Diabetes* 65, 1672-1678 (2016).
29. E. A. Ryan et al., Five-year follow-up after clinical islet transplantation. *Diabetes* 54, 2060-2069 (2005).
30. A. M. Shapiro et al., Islet transplantation in seven patients with type 1 diabetes mellitus using a glucocorticoid-free immunosuppressive regimen. *N Engl J Med* 343, 230-238 (2000).
31. A. M. Shapiro, C. Ricordi, B. Hering, Edmonton's islet success has indeed been replicated elsewhere. *Lancet* 362, 1242 (2003).
32. S. Marzorati, A. Pileggi, C. Ricordi, Allogeneic islet transplantation. *Expert opinion on biological therapy* 7, 1627-1645 (2007).
33. A. M. Shapiro, M. Pokrywczynska, C. Ricordi, Clinical pancreatic islet transplantation. *Nat Rev Endocrinol* 13, 268-277 (2017).
34. G. Ren et al., Adipose tissue-derived mesenchymal stem cells rescue the function of islets transplanted in subtherapeutic numbers via their angiogenic properties. *Cell and tissue research* 376, 353-364 (2019).
35. B. P. Barnett et al., Magnetic resonance-guided, real-time targeted delivery and imaging of magnetocapsules immunoprotecting pancreatic islet cells. *Nature medicine* 13, 986-991 (2007).
36. T. Y. Yeung et al., Human mesenchymal stem cells protect human islets from pro-inflammatory cytokines. *PLoS One* 7, e38189 (2012).
37. S. H. Bhang et al., Mutual effect of subcutaneously transplanted human adipose-derived stem cells and pancreatic islets within fibrin gel. *Biomaterials* 34, 7247-7256 (2013).
38. S. Yamada et al., Trophic effect of adipose tissue-derived stem cells on porcine islet cells. *J Surg Res* 187, 667-672 (2014).
39. K.-S. Park et al., Trophic molecules derived from human mesenchymal stem cells enhance survival, function, and angiogenesis of isolated islets after transplantation. *Transplantation* 89, 509-517 (2010).
40. D. M. Berman et al., Mesenchymal stem cells enhance allogeneic islet engraftment in nonhuman primates. *Diabetes* 59, 2558-2568 (2010).
41. T. Ito et al., Mesenchymal stem cell and islet co-transplantation promotes graft revascularization and function. *Transplantation* 89, 1438-1445 (2010).
42. E. Eggenhofer et al., Mesenchymal stem cells are short-lived and do not migrate beyond the lungs after intravenous infusion. *Frontiers in immunology* 3, 297 (2012).
43. A. A. Arzouni, A. Vargas-Seymour, N. Nardi, A. J F King, P. M. Jones, Using mesenchymal stromal cells in islet transplantation. *Stem cells translational medicine* 7, 559-563 (2018).
44. C. L. Rackham, P. K. Dhadda, A. M. Le Lay, A. J. King, P. M. Jones, Preculturing islets with adipose-derived mesenchymal stromal cells is an effective strategy for improving transplantation efficiency at the clinically preferred intraportal site. *Cell medicine* 7, 37-47 (2014).
45. G. Cavallari et al., Mesenchymal stem cells and islet cotransplantation in diabetic rats: improved islet graft revascularization and function by human adipose tissue-derived stem cells preconditioned with natural molecules. *Cell Transplant* 21, 2771-2781 (2012).
46. A. K. Das et al., Intra-arterial allogeneic mesenchymal stem cells for critical limb ischemia are safe and efficacious: report of a phase I study. *World journal of surgery* 37, 915-922 (2013).
47. E. H. Jo, Y. H. Hwang, D. Y. Lee, Encapsulation of pancreatic islet with HMGB1 fragment for attenuating inflammation. *Biomaterials research* 19, 21 (2015).
48. J. Coelho, *Drug delivery systems: advanced technologies potentially applicable in personalised treatment* (Springer Science & Business Media, 2013).
49. V. Vaithilingam, B. E. Tuch, Islet transplantation and encapsulation: an update on recent developments. *The review of diabetic studies: RDS* 8, 51 (2011).
50. H. Zhu et al., Selection of implantation sites for transplantation of encapsulated pancreatic islets. *Tissue Engineering Part B: Reviews* 24, 191-214 (2018).
51. H. M. Tse, V. Kozlovskaya, E. Kharlampieva, C. S. Hunter, Minireview: directed differentiation and encapsulation of islet β-cells—recent advances and future considerations. *Molecular Endocrinology* 29, 1388-1399 (2015).
52. P. de Vos, M. Spasojevic, M. M. Faas, "Treatment of diabetes with encapsulated islets" in Therapeutic Applications of Cell Microencapsulation. (Springer, 2010), pp. 38-53.
53. A. Kerby, E. S. Jones, P. M. Jones, A. J. King, Co-transplantation of islets with mesenchymal stem cells in microcapsules demonstrates graft outcome can be improved in an isolated-graft model of islet transplantation in mice. *Cytotherapy* 15, 192-200 (2013).
54. G. Korbutt, A. Mallett, Z. Ao, M. Flashner, R. Rajotte, Improved survival of microencapsulated islets during in vitro culture and enhanced metabolic function following transplantation. *Diabetologia* 47, 1810-1818 (2004).
55. B. L. Strand, A. E. Coron, G. Skjak-Braek, Current and future perspectives on alginate encapsulated pancreatic islet. *Stem cells translational medicine* 6, 1053-1058 (2017).
56. G. Basta et al., Long-term metabolic and immunological follow-up of nonimmunosuppressed patients with type 1 diabetes treated with microencapsulated islet allografts: four cases. *Diabetes care* 34, 2406-2409 (2011).
57. R. Calafiore et al., Microencapsulated pancreatic islet allografts into nonimmunosuppressed patients with type 1 diabetes: first two cases. *Diabetes care* 29, 137-138 (2006).
58. B. E. Tuch et al., Safety and viability of microencapsulated human islets transplanted into diabetic humans. *Diabetes care* 32, 1887-1889 (2009).
59. D. Jacobs-Tulleneers-Thevissen et al., Sustained function of alginate-encapsulated human islet cell implants in the peritoneal cavity of mice leading to a pilot study in a type 1 diabetic patient. *Diabetologia* 56, 1605-1614 (2013).
60. I. S. Castellanos et al., Calcium-dependent ultrasound stimulation of secretory events from pancreatic beta cells. *Journal of therapeutic ultrasound* 5, 30 (2017).
61. F. R. Sharp et al., Hypoxic preconditioning protects against ischemic brain injury. *NeuroRx* 1, 26-35 (2004).
62. E. Creagh, D. Sheehan, T. Cotter, Heat shock proteins-modulators of apoptosis in tumour cells. *Leukemia* 14, 1161 (2000).
63. M. I. Niagara, H. K. Haider, S. Jiang, M. Ashraf, Pharmacologically preconditioned skeletal myoblasts are resistant to oxidative stress and promote angiomyogenesis via release of paracrine factors in the infarcted heart. Circulation research 100, 545-555 (2007).

64. G. Ren et al., Mesenchymal stem cell-mediated immunosuppression occurs via concerted action of chemokines and nitric oxide. *Cell stem cell* 2, 141-150 (2008).
65. G. Raicevic et al., Inflammation modifies the pattern and the function of Toll-like receptors expressed by human mesenchymal stromal cells. *Human immunology* 71, 235-244 (2010).
66. A. Schwarznau et al., IL-1β receptor blockade protects islets against pro-inflammatory cytokine induced necrosis and apoptosis. *Journal of cellular physiology* 220, 341-347 (2009).
67. A. M. Jackson et al., Gene expression changes in human islets exposed to type 1 diabetic serum. *Islets* 4, 312-319 (2012).
68. F.-C. Chou et al., Differential modulation of IL-12 family cytokines in autoimmune islet graft failure in mice. *Diabetologia* 60, 2409-2417 (2017).
69. J. M. Barra, H. M. Tse, Redox-dependent inflammation in islet transplantation rejection. *Frontiers in endocrinology* 9, 175 (2018).
70. A. M. Randi, M. A. Laffan, Von Willebrand factor and angiogenesis: basic and applied issues. *J Thromb Haemost* 15, 13-20 (2017).
71. C. Hajmrle et al., Interleukin-1 signaling contributes to acute islet compensation. *JCI insight* 1 (2016).
72. N. Giannoukakis, W. A. Rudert, M. Trucco, P. D. Robbins, Protection of human islets from the effects of interleukin-1β by adenoviral gene transfer of an IκB repressor. *Journal of Biological Chemistry* 275, 36509-36513 (2000).
73. A. Hoorens, G. Stangé, D. Pavlovic, D. Pipeleers, Distinction between interleukin-1-induced necrosis and apoptosis of islet cells. *Diabetes* 50, 551-557 (2001).
74. S. Hu, P. De Vos, Polymeric Approaches to Reduce Tissue Responses Against Devices Applied for Islet-Cell Encapsulation. *Frontiers in Bioengineering and Biotechnology* 7, 134 (2019).
75. V. Vaithilingam, S. Bal, B. E. Tuch, Encapsulated islet transplantation: where do we stand? *The review of diabetic studies: RDS* 14, 51 (2017).

What is claimed is:

1. A method of treating a subject for type 1 diabetes, the method comprising:
transplanting a therapeutically effective amount of a population of beta cells or islets to the subject at a transplantation site; and
administering a therapeutically effective amount of pulsed focused ultrasound (pFUS) therapy locally at the transplantation site to stimulate insulin secretion from beta cells in the transplanted population of beta cells or islets, the method further comprising transplanting stem cells, wherein the stem cells are transplanted in proximity to the population of beta cells or islets at the transplantation site.

2. The method of claim 1, further comprising administering a therapeutically effective amount of the pFUS therapy to the population of beta cells or islets before said transplanting the beta cells or islets.

3. The method of claim 1, further comprising administering a therapeutically effective amount of the pFUS therapy at the transplantation site before and/or after said transplanting the beta cells or islets to promote engraftment and revascularization of the population of beta cells or islets.

4. The method of claim 1, wherein the beta cells or islets are autologous, allogeneic, or xenogeneic, or comprise beta cells derived from stem cells or pancreatic progenitor cells.

5. The method of claim 1, where the stem cells are mesenchymal stem cells (MSCs).

6. The method of claim 5, further comprising administering a therapeutically effective amount of the pFUS therapy to the MSCs before, after, or before and after said transplanting the MSCs to stimulate paracrine secretion from the MSCs.

7. The method of claim 5, wherein the MSCs are from bone marrow (BM-MSCs), adipose tissue (AD-MSCs), or umbilical cord (UC-MSCs).

8. The method of claim 5, further comprising coculturing the beta cells or islets with the MSCs to coat the beta cells or islets with the MSCs; and transplanting the beta-cells or islets coated with the MSCs at the transplantation site.

9. The method of claim 8, wherein the beta cells or islets and the MSCs are cocultured together at a ratio ranging from about 1:100 to 1:2000 to allow the MSCs to attach to and coat the beta cells or islets.

10. The method of claim 1, further comprising encapsulating the beta cells or islets and the MSCs in a biocompatible conformal coating capable of allowing nutrients, oxygen, and glucose to diffuse into the beta cells or islets in vivo.

11. The method of claim 10, wherein the conformal coating has a thickness ranging from 25 μm to 100 μm.

12. The method of claim 10, wherein the conformal coating comprises a hydrogel.

13. The method of claim 12, wherein the hydrogel comprises alginate.

14. The method of claim 1, wherein the transplantation site is in a kidney, liver, omentum, peritoneum, or subcutaneous tissue of the subject.

* * * * *